(12) United States Patent
Allen et al.

(10) Patent No.: US 9,796,724 B2
(45) Date of Patent: *Oct. 24, 2017

(54) SUBSTITUTED PYRAZOLO[1,5-A]PYRIMIDINE COMPOUNDS AS TRK KINASE INHIBITORS

(71) Applicant: Array BioPharma, Inc., Boulder, CO (US)

(72) Inventors: Shelley Allen, Boulder, CO (US); Steven W. Andrews, Boulder, CO (US); Kevin Ronald Condroski, Boulder, CO (US); Julia Haas, Boulder, CO (US); Lily Huang, Boulder, CO (US); Yutong Jiang, Boulder, CO (US); Timothy Kercher, Boulder, CO (US); Jeongbeob Seo, Boulder, CO (US)

(73) Assignee: Array BioPharma, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/401,895

(22) Filed: Jan. 9, 2017

(65) Prior Publication Data

US 2017/0114069 A1  Apr. 27, 2017

Related U.S. Application Data

(63) Continuation of application No. 14/321,246, filed on Jul. 1, 2014, which is a continuation of application No. 13/382,858, filed as application No. PCT/US2010/041538 on Jul. 9, 2010, now Pat. No. 8,791,123.

(60) Provisional application No. 61/224,196, filed on Jul. 9, 2009, provisional application No. 61/346,767, filed on May 20, 2010.

(51) Int. Cl.
| | | |
|---|---|---|
| A01N 43/90 | (2006.01) |
| A61K 31/519 | (2006.01) |
| C07D 487/00 | (2006.01) |
| C07D 487/04 | (2006.01) |

(52) U.S. Cl.
CPC .......... C07D 487/04 (2013.01); A61K 31/519 (2013.01)

(58) Field of Classification Search
None
See application file for complete search history.

(56) References Cited

U.S. PATENT DOCUMENTS

| | | | |
|---|---|---|---|
| 5,844,092 A | 12/1998 | Presta et al. |
| 5,877,016 A | 3/1999 | Presta et al. |
| 5,910,574 A | 6/1999 | Presta et al. |
| 6,025,166 A | 2/2000 | Presta et al. |
| 6,027,927 A | 2/2000 | Presta et al. |
| 6,153,189 A | 11/2000 | Presta et al. |
| 7,384,632 B2 | 6/2008 | Devaux et al. |
| 7,491,794 B2 | 2/2009 | Blatt et al. |
| 7,550,470 B2 | 6/2009 | Fraley |
| 7,612,067 B2 | 11/2009 | Barbosa et al. |
| 7,615,383 B2 | 11/2009 | Devaux et al. |
| 8,106,167 B2 | 1/2012 | Wild, Jr. et al. |
| 8,114,989 B2 | 2/2012 | Wang et al. |
| 8,119,592 B2 | 2/2012 | Beigelman et al. |
| 8,148,107 B2 | 4/2012 | Macdonald et al. |
| 8,299,021 B2 | 10/2012 | Blatt et al. |
| 8,299,057 B2 | 10/2012 | Lombardi Borgia et al. |
| 8,338,417 B2 | 12/2012 | Li et al. |
| 8,450,322 B2 | 5/2013 | Andrews et al. |
| 8,513,263 B2 | 8/2013 | Haas et al. |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,691,221 B2 | 4/2014 | Pavone et al. |
| 8,791,123 B2* | 7/2014 | Allen ................... C07D 487/04 514/259.3 |
| 8,865,698 B2 | 10/2014 | Haas et al. |

(Continued)

FOREIGN PATENT DOCUMENTS

| | | |
|---|---|---|
| CN | 1938311 | 3/2007 |
| CN | 101119996 | 2/2008 |

(Continued)

OTHER PUBLICATIONS

Adriaenssens et al., "Nerve Growth Factor Is a Potential Therapeutic Target in Breast Cancer," Cancer Res., 2008, 68(2):346-351.

(Continued)

*Primary Examiner* — Jeffrey H Murray

(74) *Attorney, Agent, or Firm* — Fish & Richardson P.C.

(57) ABSTRACT

Compounds of Formula I:

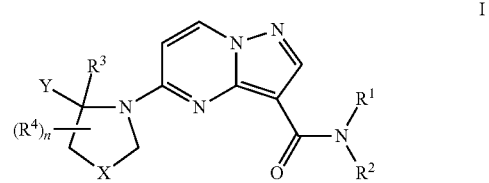

and salts thereof in which $R^1$, $R^2$, $R^3$, $R^4$, X, Y and n have the meanings given in the specification, are inhibitors of Trk kinases and are useful in the treatment of diseases which can be treated with a Trk kinase inhibitor such as pain, cancer, inflammation, neurodegenerative diseases and certain infectious diseases.

30 Claims, No Drawings

(56) References Cited

U.S. PATENT DOCUMENTS

| | | |
|---|---|---|
| 8,911,734 B2 | 12/2014 | Latham et al. |
| 8,912,194 B2 | 12/2014 | Ciomei |
| 8,933,084 B2 | 1/2015 | Andrews |
| 8,946,226 B2 | 2/2015 | Ciomei et al. |
| 9,102,671 B2 | 8/2015 | Molteni et al. |
| 9,127,013 B2 | 9/2015 | Haas et al. |
| 9,187,489 B2 | 11/2015 | Takeda et al. |
| 9,242,977 B2 | 1/2016 | Takeuchi et al. |
| 9,493,476 B2 | 11/2016 | Andrews et al. |
| 2006/0094699 A1 | 5/2006 | Kampen et al. |
| 2006/0128725 A1 | 6/2006 | Guzi |
| 2006/0211696 A1 | 9/2006 | Hibi et al. |
| 2007/0025540 A1 | 2/2007 | Travis |
| 2007/0042941 A1 | 2/2007 | Hirashima et al. |
| 2007/0082900 A1 | 4/2007 | Guzi et al. |
| 2009/0041717 A1 | 2/2009 | Macdonald et al. |
| 2010/0029633 A1 | 2/2010 | Allen et al. |
| 2010/0152219 A1 | 6/2010 | Block et al. |
| 2010/0297115 A1 | 11/2010 | Blaustein |
| 2011/0166122 A1 | 7/2011 | Andrews et al. |
| 2011/0195948 A1 | 8/2011 | Haas et al. |
| 2011/0268725 A1 | 11/2011 | Shelton |
| 2012/0108568 A1 | 5/2012 | Allen et al. |
| 2013/0203776 A1 | 8/2013 | Andrews et al. |
| 2013/0217662 A1 | 8/2013 | Andrews et al. |
| 2014/0194403 A1 | 7/2014 | Haas et al. |
| 2014/0227287 A1 | 8/2014 | Kamohara et al. |
| 2015/0005499 A1 | 1/2015 | Haas et al. |
| 2015/0031667 A1 | 1/2015 | Allen et al. |
| 2015/0051222 A1 | 2/2015 | Barbugian et al. |
| 2015/0166564 A1 | 6/2015 | Allen et al. |
| 2015/0218652 A1 | 8/2015 | Doebele et al. |
| 2015/0283132 A1 | 10/2015 | Lim et al. |
| 2015/0306086 A1 | 10/2015 | Wilcoxen |
| 2016/0000783 A1 | 1/2016 | Takeuchi et al. |
| 2016/0137654 A1 | 5/2016 | Arrigo et al. |
| 2016/0228441 A1 | 8/2016 | Haas et al. |
| 2016/0251357 A1 | 9/2016 | Andrews et al. |
| 2016/0272725 A1 | 9/2016 | Stransky et al. |
| 2017/0107232 A1 | 4/2017 | Andrews et al. |
| 2017/0112842 A1 | 4/2017 | Andrews et al. |
| 2017/0112849 A1 | 4/2017 | Andrews et al. |
| 2017/0114059 A1 | 4/2017 | Andrews et al. |
| 2017/0114067 A1 | 4/2017 | Haas et al. |
| 2017/0114068 A1 | 4/2017 | Andrews et al. |
| 2017/0119770 A1 | 5/2017 | Allen et al. |

FOREIGN PATENT DOCUMENTS

| | | |
|---|---|---|
| CN | 101208093 | 6/2008 |
| EP | 1873157 | 1/2008 |
| EP | 1948633 | 8/2011 |
| JP | 2004-087707 | 3/2004 |
| JP | 2004-277337 | 10/2004 |
| JP | 2005-008581 | 1/2005 |
| JP | 2007-504276 | 3/2007 |
| JP | 2007-514712 | 6/2007 |
| JP | 2008-523034 | 7/2008 |
| JP | 2008-285464 | 11/2008 |
| JP | 2009-502734 | 1/2009 |
| JP | 2009-511487 | 3/2009 |
| JP | 2009-541242 | 11/2009 |
| JP | 2010-508315 | 3/2010 |
| JP | 2011-520887 | 7/2011 |
| JP | 2012-506446 | 3/2012 |
| JP | 2012-507569 | 3/2012 |
| WO | WO 98/49167 | 11/1998 |
| WO | WO 2004/022561 | 3/2004 |
| WO | WO 2004/052286 | 6/2004 |
| WO | WO 2004/052315 | 6/2004 |
| WO | WO 2004/082458 | 9/2004 |
| WO | WO 2004/087707 | 10/2004 |
| WO | WO 2004/089415 | 10/2004 |
| WO | WO 2004/089471 | 10/2004 |
| WO | WO 2005/049033 | 6/2005 |
| WO | WO 2006/087538 | 8/2006 |
| WO | WO 2006/115452 | 11/2006 |
| WO | WO 2006/123113 | 11/2006 |
| WO | WO 2006/131051 | 12/2006 |
| WO | WO 2006/131952 | 12/2006 |
| WO | WO 2007/013673 | 2/2007 |
| WO | WO 2007/015824 | 2/2007 |
| WO | WO 2007/022999 | 3/2007 |
| WO | WO 2007/024680 | 3/2007 |
| WO | WO 2007/025090 | 3/2007 |
| WO | WO 2007/025540 | 3/2007 |
| WO | WO 2007/038314 | 4/2007 |
| WO | WO 2007/044410 | 4/2007 |
| WO | WO 2007/044449 | 4/2007 |
| WO | WO 2007/044893 | 4/2007 |
| WO | WO 2007/048066 | 4/2007 |
| WO | WO 2007/062805 | 6/2007 |
| WO | WO 2007/084815 | 7/2007 |
| WO | WO 2007/102679 | 9/2007 |
| WO | WO 2007/113000 | 10/2007 |
| WO | WO 2007/129161 | 11/2007 |
| WO | WO 2008/016131 | 2/2008 |
| WO | WO 2008/030579 | 3/2008 |
| WO | WO 2008/037477 | 4/2008 |
| WO | WO 2008/052734 | 5/2008 |
| WO | WO 2008/058126 | 5/2008 |
| WO | WO 2008/115974 | 9/2008 |
| WO | WO 2008/155421 | 12/2008 |
| WO | WO 2009/013126 | 1/2009 |
| WO | WO 2009/052145 | 4/2009 |
| WO | WO 2009/053442 | 4/2009 |
| WO | WO 2009/060197 | 5/2009 |
| WO | WO 2009/092049 | 7/2009 |
| WO | WO 2009/140128 | 11/2009 |
| WO | WO 2010/012733 | 2/2010 |
| WO | WO 2010/033941 | 4/2010 |
| WO | WO 2010/048314 | 4/2010 |
| WO | WO 2010/051549 | 5/2010 |
| WO | WO 2010/058006 | 5/2010 |
| WO | WO 2011/006074 | 1/2011 |
| WO | WO 2011/133637 | 10/2011 |
| WO | WO 2011/146336 | 11/2011 |
| WO | WO 2012/024650 | 2/2012 |
| WO | WO 2012/034091 | 3/2012 |
| WO | WO 2012/034095 | 3/2012 |
| WO | WO 2012/116217 | 8/2012 |
| WO | WO 2012/158413 | 11/2012 |
| WO | WO 2013/059740 | 4/2013 |
| WO | WO 2013/074518 | 5/2013 |
| WO | WO 03/080064 | 10/2013 |
| WO | WO 2013/174876 | 11/2013 |
| WO | WO 2013/183578 | 12/2013 |
| WO | WO 2014/036387 | 3/2014 |
| WO | WO 2014/047572 | 3/2014 |
| WO | WO 2014/078322 | 5/2014 |
| WO | WO 2014/078323 | 5/2014 |
| WO | WO 2014/078325 | 5/2014 |
| WO | WO 2014/078328 | 5/2014 |
| WO | WO 2014/078331 | 5/2014 |
| WO | WO 2014/078372 | 5/2014 |
| WO | WO 2014/078408 | 5/2014 |
| WO | WO 2014/078417 | 5/2014 |
| WO | WO 2014/078454 | 5/2014 |
| WO | WO 2015/017533 | 2/2015 |
| WO | WO 2015/112806 | 7/2015 |
| WO | WO 2015/124697 | 8/2015 |
| WO | WO 2015/175788 | 11/2015 |
| WO | WO 2016/027754 | 2/2016 |
| WO | WO 2016/196141 | 12/2016 |
| WO | WO 2016/196671 | 12/2016 |

OTHER PUBLICATIONS

American Cancer Society, "Sarcoma: Adult Soft Tissue Cancer," Jun. 2014, retrieved on Apr. 27, 2015, http://www.cancer.org/cancer/sarcoma-adultsofttissuecancer/detailedguide/sarcoma-adult-soft-tissue-cancer-key-statistics, 45 pages.

(56) References Cited

OTHER PUBLICATIONS

Asaumi et al., "Expression of neurotrophins and their receptors (TRK) during fracture healing," Bone, 2000, 26(6):625-633.
Bardelli, "Mutational analysis of the tyrosine kinome in colorectal cancers," Science, 2003, 300:949.
Brodeur, "Neuroblastoma: biological insights into a clinical enigma," Nat. Rev. Cancer, 2003, 3:203-216.
Brzezianska et al., "Rearrangements of NTRK1 oncogene in papillary thyroid carcinoma," Neuroendocrinology Letters, 2007, 28(3):221-229.
Burris et al., "Pharmacokinetics (PK) of LOXO-101 During the First-in-Human Phase I Study in Patients with Advanced Solid Tumors," Interim Update AACR Annual Meeting, Mar. 2015, Philadelphia, PA., 1 page.
Campos et al., "Enantioselective, palladium-catalyzed alpha-acylation of N-Boc-pyrrolidine," J. Am. Chem Soc., 2006, 128:3538-3539.
Caria et al., "Cytogenetic and molecular events in adenoma and well-differentiated thyroid follicular-cell neoplasia," Cancer Genet. Cytogenet., 2010, 203:21-29.
Chang-Qi et al., "Brain derived neurotrophic factor (BDNF) contributes to the pain hypersensitivity following surgical incision in the rats," Molecular Pain, 2008, 4:27.
Chinese Office Action in Chinese Patent Application No. CN 201180025013.9, dated Apr. 28, 2014, 11 pages.
Chinese Office Action in Chinese Patent Application No. CN201080040095.X, dated Feb. 27, 2015, 8 pages (English translation).
Cho et al., "Expression of mRNA for brain-derived neurotrophic factor in the dorsal root ganglion following peripheral inflammation," Brain Research, 1997, 749:358-362.
Colombian Office Action in Colombian Application No. CO 12-022-116-4, dated Feb. 14, 2014, 8 pages.
Colombian Office Action in Colombian Application No. CO 12-229421-4, dated Jan. 21, 2014, 6 pages.
Cruz, "Lung cancer: epidemiology, etiology and prevention," Clinics in Chest Medicine, 2011, 32(4): 1-61.
Dang et al., "Expression of nerve growth factor receptors is correlated with progression and prognosis of human pancreatic cancer," J. Gastroenterology and Hepatology, 2006, 21(5): 850-858.
Davidson et al., "Expression and activation of the nerve growth factor receptor TrkA in serous ovarian carcinoma," Clin. Cancer Res., 2003, 9(6):2248-2259.
Davies et al., "Resistance to ROS1 inhibition mediated by EGFR pathway activation in non-small cell lung cell," PLoS One, 2013, 8(12):e82236, 13 pages.
Delafoy et al., "Role of nerve growth factor in the trinitrobenzene sulfonic acid-induced colonic hypersensitivity," Pain, 2003, 105:489-497.
Di Mola et al., "Nerve growth factor and Trk high affinity receptor (TrkA) gene expression in inflammatory bowel disease," Gut, 2000, 46(5):670-678.
Dionne et al., "Cell cycle-independent death of prostate adenocarcinoma is induced by the trk tyrosine kinase inhibitor CEP-751 (KT6587)," Clin. Cancer Research, 1998, 4(8):1887-1898.
Doebele et al., "Phase II Trial of Stereotactic Body Radiation Therapy Combined with Erlotinib for Patients With Limited but Progressive Metastatic Non-Small-Cell Lung Cancer," J. Clin. Oncol., 2014, 32:9 pages.
Doebele et al., "An oncogenic NTRK fusion in a soft tissue sarcoma patient with response to the tropomyosin-related kinase (TRK) inhibitor LOXO-101," Cancer Discovery, Jul. 2015, 5(10):1049-1057.
Dolle et al., "Nerve growth factor-induced migration of endothelial cells," J. Pharmacol Exp Ther, 2005, 315(3):1220-1227.
Dou et al., "Increased nerve growth factor and its receptors in atopic dermatitis: an immunohistochemical study," Archives of Dermatological Research, 2006, 298(1):31-37.
Du et al., "Expression of NGF family and their receptors in gastric carcinoma: a cDNA microarray study," World Journal of Gastroenterology, http://www.wjgnet.com/1007-9327/full/v9/i7/1431.htm, Jul. 2003, 9(7):1431-1434.
Duranti et al., "Homologation of Mexiletine alkyl chanin and stereoselective blockade of skelatal muscle sodium channels," Euro. J. Med. Chem., 2000, 35:147-156.
Eguchi et al., "Fusion of ETV6 to neurotrophin-3 receptor TRKC in acute myeloid leukemia with t(12;15)(p13;q25)," Blood, 1999, 93(4):1355-1363.
European Search Report in European Application No. 13197815.7, dated Apr. 1, 2014, 5 pages.
Euthus et al., "ETV6-NTRK3—Trk-ing the primary event in human secretory breast cancer," Cancer Cell, 2002, 2(5):347-348.
Frattini et al., "The integrated landscape of driver genomic alterations in glioblastoma," Nature Genet., 2013, 45:1141-1149.
Freund-Michel and Frossard, "The nerve growth factor and its receptors in airway inflammatory diseases," Pharmacology & Therapeutics, 2008, 117(1):52-76.
Frey et al. "7-Aminopyrazolo[1,5-a]pyrimidines as potent multitargeted receptor tyrosine kinase inhibitors," J. Med. Chem, Jul. 2008, 51(13):3777-3787.
Greco et al., "Rearrangements of NTRK1 gene in papillary thyroid carcinoma," Molecular and Cellular Endocrinology, 2010, 321(1):44-49.
Gruber-Olipitz et al., "Neurotrophin 3/TrkC-regulated proteins in the human medulloblastoma cell line DAOY," J. Proteome Research, 2008, 7(5):1932-1944.
Gwak et al., "Attenuation of mechanical hyperalgesia following spinal cord injury by administration of antibodies to nerve growth factor in the rat." Neurosci. Lett., 2003, 336:117-120.
Hansen et al., "Autophagic cell death induced by TrkA receptor activation in human glioblastoma cells," J. of Neurochemistry, 2007, 103:259-275.
Harwood et al., "Experimental organic chemistry—Principles and practice," Experimental Chemistry—Organic Chemistry and Reaction, Jan. 1, 1989, 127-132.
Herzberg et al., "NGF involvement in pain induced by chronic constriction injury of the rat sciatic nerve," Neuroreport, 1997, 8:1613-1618.
Hong et al., "Clinical Safety and activity from a Phase 1 study of LOXO-101, a selective TRKA/B/C inhibitor, in solid-tumor patients with NTRK gene fusions," 2016 AACR Annual Meeting, Apr. 17, 2016, 32 pages.
Hu et al., "Decrease in bladder overactivity with REN1820 in rats with cyclophosphamide induced cystitis," J. Urology, 2005, 173(3):1016-1021.
Hu et al., "Identification of brain-derived neurotrophic factor as a novel angiogenic protein in multiple myeloma" Cancer Genetics and Cytogenetics, 2007, 178:1-10.
Igaz et al., "Biological and clinical significance of the JAK-STAT pathway; lessons from knockout mice," Inflamm Res., 2001, 50:435-441.
Ihle et al., "The Roles of Jaks and Stats in Cytokine Signaling," Canc. J. Sci. Am., 1998, 4(1):84-91.
International Preliminary Report on Patentability in International Application No. PCT/US2009/057729, dated Mar. 22, 2011, 7 pages.
International Preliminary Report on Patentability in International Application No. PCT/US2009/061519, dated Apr. 26, 2011, 6 pages.
International Preliminary Report on Patentability in International Application No. PCT/US2010/041538, dated Jan. 10, 2012, 7 pages.
International Preliminary Report on Patentability in International Application No. PCT/US2011/036452, dated Nov. 29, 2012, 6 pages.
International Search Report and Written Opinion in International Application No. PCT/US2009/0161519, dated Feb. 2, 2010, 8 pages.
International Search Report and Written Opinion in International Application No. PCT/US2009/057729, dated Feb. 4, 2010, 10 pages.

(56) References Cited

OTHER PUBLICATIONS

International Search Report and Written Opinion in International Application No. PCT/US2010/041538, dated Oct. 1, 2010, 10 pages.
International Search Report and Written Opinion in International Application No. PCT/US2015/060953, dated Feb. 8, 2016, 12 pages.
International Search Report and Written Opinion in International Application No. PCT/US2011/036452, dated Aug. 18, 2011, 9 pages.
Jaggar et al., "Inflammation of the rat urinary bladder is associated with a referred thermal hyperalgesia which is nerve growth factor dependent," Br. J. Anaesth, 1999, 83:442-448.
Japanese Office Action in Japanese Application No. JP 2013-511239, dated Mar. 4, 2015, 2 pages (English translation).
Jin et al., "TrkC plays an essential role in breast tumor growth and metastasis," Carcinogenesis, 2010, 31(11):1939-1947.
Jones et al., "Recurrent somatic alterations of FGFR1 and NTRK2 in pilocytic astrocytoma," Nature Genetics, 2013, 45:927-932.
Keysar et al., "A patient tumor transplant model of Squamous cell cancer identifies PI3K inhibitors as candidate therapeutics in defined molecular bins," Molecular Oncology, 2013, 7(4):776-790.
Kim et al., "NTRK1 fusion in glioblastoma multiforme," PloS One, 2014, 9(3):e91940.
Klijn et al., "A comprehensive transcriptional portrait of human cancer cell lines," Nat Biotechnol., 2015, 33(3):306-312.
Kolokythas et al., "Nerve growth factor and tyrosine kinase A receptor in oral squamous cell carcinoma: is there an association with perineural invasion?" J. Oral Maxillofacial Surgery, 2010, 68(6):1290-1295.
Kremer et al., "The safety and efficacy of a JAK inhibitor in patients with active rheumatoid arthritis: Results of a double-blind, placebo-controlled phase IIa trial of three dosage levels of CP-690,550 versus placebo," Arth. & Rheum., 2009, 60:1895-1905.
Kruettgen et al., "The dark side of the NGF family: neurotrophins in neoplasias," Brain Pathology, 2006, 16:304-310.
Lamb et al., "Nerve growth factor and gastric hyperalgesia in the rat," Neurogastrenterol. Motil., 2003, 15:355-361.
Leukemia, Wikipedia The Free Encyclopedia, Dec. 8, 2001, https://en.wikipedia.org/wiki/Leukemia, 15 pages.
Li et al., "Brain derived neurotrophic factor (BDNF) contributes to the pain hypersensitivity following surgical incision in the rats," Molecular Pain, 2008, 4(28):1-11.
Li et al., "Correlation of expressions of GFAP, NT-3, Trk and NCAM with neurotropic molecular mechanism and clinical factors in adenoid cystic carcinoma of salivary gland," Chinese Journal of Cancer Prevention and Treatment, 2009, 16(6): 428-430 (with English abstract).
Li et al., "Lumbar 5 ventral root transection-induced upregulation of nerve growth factor in sensory neurons and their target tissues: a mechanism in neuropathic pain," Mol. Cell. Neurosci., 2003, 23:232-250.
Linch et al., "Systemic treatment of soft-tissue sarcoma [mdash] gold standard and novel therapies," Nature Reviews Clinical Oncology, 2014, 11(4):187-202.
Lorigan et al., "Phase III trial of two investigational schedules of ifosfamide compared with standard-dose doxorubicin in advanced or metastatic soft tissue sarcoma: a European Organisation for Research and Treatment of Cancer Soft Tissue and Bone Sarcoma. Group Study," J. Clin Oncol., 2007, 25(21):3144-3150.
Lovly et al., "Inflammatory myofibroblastic tumors harbor multiple potentially actionable kinase fusions," Cancer Discov., 2014, 4(8):889-895.
Ma and Woolf, "The progressive tactile hyperalgesia induced by peripheral inflammation is nerve growth factor dependent," Neuroreport, 1997, 8:807-810.
Marchetti et al., "Frequent mutations in the neurotrophic tyrosine receptor kinase gene family in large cell neuroendocrine carcinoma of the lung," Human Mutation, 2008, 29(5):609-616.

Martin-Zanca et al., "A human oncogene formed by the fusion of truncated tropomyosin and protein tyrosine kinase sequences," Nature, 1986, 319:743-748.
Matayoshi, "Actions of brain-derived neurotrophic factor on spinal nociceptive transmission during inflammation in the rat," J. Physiol., 2005, 569:685-695.
McMahon et al., "The biological effects of endogenous nerve growth factor on adult sensory neurons revealed by a trkA-IgG fusion molecule," Nat. Med., 1995, 1:774-780.
McMahon., "VEGF Receptor Signaling in Tumor Angiogenesis," The Oncologist, 2000, 5(1): 3-10.
Mekinist, Highlights of Prescribing Information, Initial Approval 2013, revised Nov. 2015, Novartis Pharmaceuticals Corp., 27 pages.
Melo-Jorge et al., The Chagas' disease parasite Trypanosoma cruzi exploits nerve growth factor receptor TrkA to infect mammalian hosts Cell Host & Microbe, 2007, 1(4):251-261.
Meyer et al., "Remarkable leukemogenic potency and quality of a constitutively active neurotrophin receptor, deltaTrkA," Leukemia, 2007, 21:2171-2180.
Nagasubruamanian et al., "Brief Report: Infantile Fibrsarcoma With NTRK3-ETV6 Fusion Successfully Treated With the Tropomyosin-Related Kinase Inhibitor LOXO-101," Pediatric Blood & Cancer, 2016, DOI 10.1002, 3 pages.
Nakagawara, "Trk receptor tyrosine kinases a bridge between cancer and neural development," Cancer Letters, 2001, 169(2):107-114.
National Cancer Institute at the National Institutes of Health, posted on or before Jan. 5, 2000, retrieved on Jan. 13, 2015, http://www.cancer.gov/, 2 pages.
National Comprehensive Cancer Network, posted on or before Dec. 3, 1998, retrieved on Jan. 13, 2015, http://www.nccn.org/, 1 page.
NCT02122913, "Oral TRK Inhibitor LOXO-101 for Treatment of Advanced Adult Solid Tumors," ClinicalTrials.gov, First received Apr. 16, 2014, Last Updated Dec. 7, 2015, https://clinicaltrials.gov/ct2/show/NCT02122913.
NCT02050919, "Sorafenib Tosylate, Combination Chemotherapy, Radiation Therapy, and Surgery in Treating Patients With High-Risk Stage IIB-IV Soft Tissue Sarcoma," ClinicalTrials.gov, First received Jan. 29, 2014, Last Updated Dec. 16, 2015, https://www.clinicaltrials.gov/ct2/show/NCT02050919, 5 pages.
Ni et al., "siRNA interference with a proliferation-inducing ligand gene in the Sgr-7901 gastric carcinoma cell line," Asian Pacific Journal of Cancer Prevention, 2012, 13:1511-1514.
O'Shea, "Jaks, STATs, cytokine signal transduction, and immunoregulation: are we there yet?" Immunity, 1997, 7:1-11.
Papatsoris et al., "Manipulation of the nerve growth factor network in prostate cancer," Exper Opin Invest Drugs, 2007, 16(3):303-309.
Patani et al., "Bioisosterism: A rational approach in Drug Design," Chem Rev., Dec. 1996, 96(8):3147-3176.
Patapoutian et al., "Trk receptors: mediators of neurotrophin action," Current Opinion in Neurobiology, 2001, 11:272-280.
Perez-Pinera et al., "The Trk tyrosine kinase inhibitor K252a regulates growth of lung adenocarcinomas," Molecular and Cellular Biochemistry, 2007, 295(1&2):19-26.
Perrault et al., "The Synthesis of N-Aryl-5(S)-aminomethyl-2-oxazolidinone Antibacterials and Derivatives in One Step from Aryl Carbamates," Org. Process Res. Dev., 2003, 7:533-546.
Philippines Office Action in Philippines Application No. PH 1/2012/500048, dated May 30, 2014, 2 pages.
Pierottia and Greco, "Oncogenic rearrangements of the NTRK1/NGF receptor," Cancer Letters, 2006, 232:90-98.
Pinedo et al., "Translational Research: The Role of VEGF in Tumor Angiogenesis," The Oncologist, 2000, 5(1): 1-2.
Pinski et al., "Trk receptor inhibition induces apoptosis of proliferating but not quiescent human osteoblasts," Cancer Res, 2002, 62:986-989.
Pulciani et al., "Oncogenes in solid human tumours," Nature, 1982, 300(5892):539-542.
Ramer and Bisby, "Adrenergic innervation of rat sensory ganglia following proximal or distal painful sciatic neuropathy: distinct mechanisms revealed by anti-NGF treatment," Eur. J. Neurosci., 1999, 11:837-846.

(56) References Cited

OTHER PUBLICATIONS

Raychaudhuri et al., K252a, a high-affinity nerve growth factor receptor blocker, improves psoriasis: an in vivo study using the severe combined immunodeficient mouse-human skin model, J. Investigative Dermatology, 2004, 122(3):812-819.
Reuther et al., "Identification and characterization of an activating TrkA deletion mutation in acute myeloid leukemia," Mol. Cell. Biol. 2000, 20:8655-8666.
Ro et al., "Effect of NGF and anti-NGF on neuropathic pain in rats following chronic constriction injury of the sciatic nerve," Pain, 1999, 79:265-274.
Ross et al., "New routes to targeted therapy of intrahepatic cholangiocarcinomas revealed by next-generation sequencing," Oncologist, 2014, 19:235-242.
Rutkowski et al., "Treatment of advanced dermatofibrosarcoma protuberans with imatinib mesylate with or without surgical resection," J. Eur. Acad. Dermatol. Venereol., 2011, 25:264-270.
Santoro et al., "Doxorubicin versus CYVADIC versus doxorubicin plus ifosfamide in first-line treatment of advanced soft tissue sarcomas: a randomized study of the European Organization for Reasearh and Treatment of Cancer Soft Tissue and Bone Sarcoma. Group," J. Clin Oncol., 1995, 13(7):1537-1545.
Shelton et al., "Nerve growth factor mediates hyperalgesia and cachexia in auto-immune arthritis," Pain, 2005, 116:8-16.
Silverman, The Organic Chemistry of Drug Design and Drug Action, Second Edition, 2007, 20-21.
Sleijfer et al., "Prognastic and predictive factors for outcome to firs-line ifosfamide-containing chemotherapy for adult patients with advanced soft tissue sarcomas:an exploratory, retrospective analysis on large series from the European Organization for Research and Treatment of Cancer-Soft Tissue and Bone Sarcoma. Group," Eur J. Cancer, 2010, 46(1):72-83.
Sleijfer et al., "Using single-agent therapy in adult patients with advanced soft tissue sarcoma can still be considered standard care," Oncologist, 2005, 10(10):833-841.
Smith et al., "Annotation of human cancers with EGFR signaling-associated protein complexes using proximity ligation assays," Sci Signal, 2015, 8(359):ra4, 12 pages.
Sohrabji et al., "Estrogen-BDNF interactions: implications for neurodegenerative diseases," Frontiers in Neuroendocrinology, 2006, 27(4):404-414.
Stephens et al., "Trk receptors use redundant signal transduction pathways involving SHC and PLC-gamma 1 to mediate NGF responses," Neuron, Mar. 1994, 12(3):691-705.
Stransky et al., "The landscape of kinase fusions in cancer," Nature comm., 2014, 5:4846.
Tacconelli et al., "TrkA alternative splicing: a regulated tumor-promoting switch in human neuroblastoma," Cancer Cell, 2004, 6:347-360.
Tafinlar, Highlights of Prescribing Information, GlaxoSmithKline, Jan. 2014, 41 pages.
Taipale et al., "Chaperones as thermodynamic sensors of drug-target interactions reveal kinase inhibitor specifities in living cells," Nat Biotech, 2013, 31(7):630-637.
Taiwan Office Action in Taiwan Application No. 098135670, dated Jan. 20, 2014, 7 pages (with English Translation).
Taiwan Search Report in Taiwan Application No. 098132033, dated Dec. 13, 2013, 1 page (English translation only).
Theodosiou et al., "Hyperalgesia due to nerve damage: role of nerve growth factor," Pain, 1999, 81:245-255.
Thiele, "On Trk—the TrkB signal transduction pathway is an increasingly important target in cancer biology," Clinical Cancer Research, 2009, 105(19):5962-5967.
Thompson et al., "Brain-derived neurotrophic factor is an endogenous modulator of nociceptive responses in the spinal cord," Proc.Natl. Acad. Sci. USA, 1999, 96:7714-7718.
Truzzi et al., "Neurotrophins and their receptors stimulate melanoma cell proliferation and migration," J. Investigative Dermatology, 2008, 128(8):2031-2040.
Truzzi et al., "Neurotrophins in healthy and diseased skin ," Dermato-Endrocrinology, 2008, 3(1):32-36.
Vaishnavi et al., "TRKing Down an Old Oncogene in a New Era of Targeted Therapy," Cancer Discovery, Jan. 2015, 5(1):25-34.
Vaishnavi et al., Oncogenic and drug-sensitive NTRK1 rearrangements in lung cancer, Nature Med., 2013, 19:1469-1472.
Van Gurp et al., "Phase 1 dose-escalation study of CP-690 550 in stable renal allograft recipients: preliminary findings of safety, tolerability, effects on lymphocyte subsets and pharmacokinetics," Am. J. Transpl., 2008, 8:1711-1718.
Van Noesel et al., "Pediatric neuroblastomas: genetic and epigenetic 'danse macabre'," Gene, 2004, 325:1-15.
Wadhwa et al., "Expression of the neurotrophin receptors Trk A and Trk B in adult human astrocytoma and glioblastoma," Journal of Biosciences, 2003, 28(2):181-188.
Walch et al., "Role of neurotrophins and neurotrophins receptors in the in vitro invasion and heparanase production of human prostate cancer cells," Clin. Exp. Metastasis, 1999, 17:307-314.
Wang et al., "Trk kinase inhibitors as new treatments for cancer and pain," Expert Opin. Ther Patents, Mar. 2009, 19(3):305-319.
Wiesner et al., "Kinase fusions are frequent in Spitz tumours and spitzoid melanomas," Nature Comm., 2014, 5:3116.
Winski et al., "LOXO-101, a pan-TRK inhibitor, for the treatment of TRK-driven cancers," 26th EORTC-NCI-AACR Symposium on Molecular Targets and Cancer Therapeutics, Barcelona, Spain, 2014, 175.
Woolf et al., "Letter to Neuroscience: Nerve Growth Factor Contributes to the Generation of Inflammatory Sensory Hypersensitivity," Neuroscience, 1994, 62:627-331.
Wu et al., "The genomic landscape of diffuse intrinsic pontine glioma and pediatric non-brainstem high-grade glioma," Nature Genetics, 2014, 444-450.
Xalkori, Highlights of Prescribing Information, Pfizer Labs, Initial approval 2011, revised Mar. 2016, 20 pages.
Yilmaz et al., "Theraputic targeting of Trk supresses tumor proliferation and enhances cisplatin activity in HNSCC," Cancer Biology and Therapy, 2010, 10(6):644-653.
Zahn et al., "Effect of blockade of nerve growth factor and tumor necrosis factor on pain behaviors after plantar incision," J. Pain, 2004, 5:157-163.
Zelboraf, Highlights of Prescribing Information, Genentech USA, Initial Approval 2011, revised Aug. 2015, 18 pages.
Zhang et al., "Expression of nerve growth factor receptors and their prognostic value in human pancreatic cancer," Oncology Reports, 2005, 14:161-171.
Zheng et al., "Anchored multiplex PCR for targeted next-generation sequencing," Nature Med., Dec. 2014, 20(12):1479-1486.
U.S. Appl. No. 13/382,858, filed Jan. 6, 2012, Shelley Allen.
U.S. Appl. No. 14/321,246, filed Jul. 1, 2014, Shelley Allen.
U.S. Appl. No. 15/401,913, filed Jan. 9, 2017, Shelley Allen.
U.S. Appl. No. 13/698,922, filed Nov. 19, 2012, Steven W. Andrews.
U.S. Appl. No. 14/575,663, filed Dec. 18, 2014, Steven W. Andrews.
U.S. Appl. No. 15/350,888, filed Nov. 14, 2016, Steven W. Andrews.
U.S. Appl. No. 15/401,839, filed Jan. 9, 2017, Steven W. Andrews.
U.S. Appl. No. 15/401,952, filed Jan. 9, 2017, Steven W. Andrews.
U.S. Appl. No. 13/063,894, filed Mar. 14, 2011, Steven W. Andrews.
U.S. Appl. No. 13/614,968, filed Sep. 13, 2012, Steven W. Andrews.
U.S. Appl. No. 14/984,353, filed Dec. 30, 2015, Steven W. Andrews.
U.S. Appl. No. 15/401,792, filed Jan. 9, 2017, Steven W. Andrews.
U.S. Appl. No. 15/401,969, filed Jan. 9, 2017, Steven W. Andrews.
U.S. Appl. No. 13/125,263, filed Apr. 20, 2011, Julia Haas.
U.S. Appl. No. 13/943,590, filed Jul. 16, 2013, Julia Haas.
U.S. Appl. No. 14/490,460, filed Sep. 18, 2014, Julia Haas.
U.S. Appl. No. 14/596,611, filed Jan. 14, 2015, Julia Haas.
U.S. Appl. No. 14/846,166, filed Sep. 4, 2015, Julia Haas.
U.S. Appl. No. 15/399,389, filed Jan. 5, 2017, Julia Haas.
U.S. Appl. No. 14/943,014, filed Nov. 16, 2015, Alisha B. Arrigo.
U.S. Appl. No. 15/399,207, filed Jan. 5, 2017, Alisha B. Arrigo.
U.S. Appl. No. 15/335,378, filed Oct. 26, 2016, Nisha Nanda.

(56) References Cited

OTHER PUBLICATIONS

Albaugh et al., "Discovery of GNF-5837, a Selective TRK Inhibitor with Efficacy in Rodent Cancer Tumor Models," ACS Medicinal Chemistry Letters, 2012, 3(2):140-145.
Behrens et al., "Gö 6976 is a potent inhibitor of neurotrophin-receptor intrinsic tyrosine kinase," J Neurochem, Mar. 1999, 72:919-924.
Bensinger et al., "Transplantation of allogeneic peripheral blood stem cells mobilized by recombinant human granulocyte colony stimulating factor," Stem Cells, Jan. 1996;14(1):90-105.
Bensinger et al., "Transplantation of allogeneic peripheral blood stem cells mobilized by recombinant human granulocyte colony-stimulating factor [see comments].," Blood, Mar. 15, 1995;85(6):1655-8.
Bertrand et al., "The crystal structures of TrkA and TrkB suggest key regions for achieving selective inhibition," Journal of molecular biology, Oct. 26, 2012;423(3):439-53.
Branford, S., et al. "High frequency of point mutations clustered within the adenosine triphosphate-binding region of BCR/ABL in patients with chronic myeloid leukemia or Ph-positive acute lymphoblastic leukemia who develop imatinib (STI571) resistance," Blood, May 2002, 99, 3472-3475.
Bruse et al., "Improvements to Bead Based Oligonucleotide Ligation SNP Genotyping Assays," Biotechniques, Nov. 2008, 45:559-571.
Calero et al., "Sunitinib suppress neuroblastoma growth through degradation of MYCN and inhibition of angiogenesis," PLoS One, Apr. 23, 2014;9(4):e95628. doi: 10.1371/journal.pone.0095628. eCollection 2014.
Camoratto et al., "CEP-751 inhibits TRK receptor tyrosine kinase activity in vitro exhibits anti-tumor activity," Int. J Cancer, Aug. 1997, 72:673-679.
Carpinelli et al., "PHA-739358, a potent inhibitor of Aurora kinases with a selective target inhibition profile relevant to cancer," Mol Cancer Ther, Dec. 2007;6(12 Pt 1):3158-3168.
Cherry et al., "Recent kinase and kinase inhibitor X-ray structures: mechanisms of inhibition and selectivity insights," Curr Med Chem. Mar. 2004;11(6):663-73.
Choi et al., "(R)-2-Phenylpyrrolidine Substituted Imidazopyridazines: A New Class of Potent and Selective Pan-TRK Inhibitors," ACS medicinal chemistry letters, Mar. 19, 2015;6(5):562-7.
Croucher et al., "TrkB inhibition by GNF-4256 slows growth and enhances chemotherapeutic efficacy in neuroblastoma xenografts," Cancer Chemother Pharmacol. Jan. 2015;75(1):131-41. doi: 10.1007/s00280-014-2627-1. Epub Nov. 14, 2014.
Demaria et al., "Development of tumor-infiltrating lymphocytes in breast cancer after neoadjuvant paclitaxel chemotherapy," Clin Cancer Res, Oct. 2001;7(10):3025-30.
Drilon et al., "What hides behind the MASC: clinical response and acquired resistance to entrectinib after ETV6-NTRK3 identification in a mammary analogue secretory carcinoma (MASC)," Annals of Oncology., Feb. 15, 2016, 27(5):920-926.
Engman et al., "Syngeneic transplant in mantle cell lymphoma: a rare event and review of the literature," Clin Adv Hematol Oncol. May 2009;7(5):321-3.
Essand et al., "Genetically engineered T cells for the treatment of cancer," J Intern Med. Feb. 2013;273(2):166-81. doi: 10.1111/joim.12020.
Estrada-Bernal et al., "Abstract #: C65: TRK kinase domain mutations that induce resistance to a pan-TRK inhibitor," Poster, Presented at Proceedings of the AACR-NCI-EORTC International Conference: Molecular Targets and Cancer Therapeutics, Boston MA, Nov. 5-9, 2015; Mol Cancer Ther, Dec. 2015, 14(12)(Suppl. 2): 1 page.
Estrada-Bernal et al., "Abstract #: LB-118: Identification of TRKA and TRKB kinase domain mutations that induce resistance to a pan-TRK inhibitor," Poster, Presented at Proceedings of the 107th Annual Meeting of the American Association for Cancer Research, New Orleans LA, Apr. 16-20, 2016; Cancer Res, Jul. 2016, 76(14): 1 page.
Flannery et al., "Immunomodulation: NK cells activated by interferon-conjugated monoclonal antibody against human osteosarcoma," Eur J Cancer Clin Oncol. Jun. 1984;20(6):791-8.
Gaudet et al., "Allele-specific PCR in SNP genotyping," Methods Mol Biol. 2009;578:415-24. doi: 10.1007/978-1-60327-411-1__26.
GenBank Accession No. AAB33109.1, "trkB [*Homo sapiens*]," Jul. 27, 1995, 1 page.
GenBank Accession No. AAB33111.1, "trkC [*Homo sapiens*]," Jul. 27, 1995, 1 page.
GenBank Accession No. NM__002529, "High affinity nerve growth factor receptor isoform 2 precursor [*Homo sapiens*]," May 11, 2014, 4 pages.
GenBank Accession No. NM__001007792 "*Homo sapiens* neurotrophic tyrosine kinase, receptor, type 1 (NTRK1), transcript variant 3, mRNA," May 10, 2014, 5 pages.
GenBank Accession No. NP 001007793, "High affinity nerve growth factor receptor isoform 3 [*Homo sapiens*]," May 10, 2014, 3 pages.
GenBank Accession No. NP__002520 "High affinity nerve growth factor receptor isoform 2 precursor [*Homo sapiens*]," May 11, 2014, 4 pages.
GenBank Accession No. S76473.1, "trkB [human, brain, mRNA, 3194 nt]," Jul. 27, 1995, 2 pages.
GenBank Accession No. S76475.1, "trkC [human, brain, mRNA, 2715 nt]," Jul. 27, 1995, 2 pages.
Green & Wuts, eds, "Protective Groups in Organic Synthesis," John Wiley & Sons Inc, May 8, 1999.
Hamdouchi et al "Imidazo[1,2-b]pyridazines, novel nucleus with potent and broad spectrum activity against human picornaviruses: design, synthesis, and biological evaluation" J Med Chem., Sep. 25, 2003;46(20):4333-4341.
Harada et al., "Role and Relevance of TrkB Mutations and Expression in Non-Small Cell Lung Cancer," Clinical Cancer Research, Jan. 17, 2011, 17(9):2638-2645.
Hinrichs et al., "Exploiting the curative potential of adoptive T-cell therapy for cancer," Immunol Rev. Jan. 2014;257(1):56-71. doi: 10.1111/imr.12132.
Hobbs et al., "Effects of T-Cell Depletion on Allogeneic Hematopoietic Stem Cell Transplantation Outcomes in AML Patients," J Clin Med. Mar. 19, 2015;4(3):488-503. doi: 10.3390/jcm4030488.
Howell et al., "Dynamic allele-specific hybridization. A new method for scoring single nucleotide polymorphisms," Nat Biotechnol. Jan. 1999;17(1):87-8.
Huehls et al., "Bispecific T-cell engagers for cancer immunotherapy," Immunol Cell Biol. Mar. 2015;93(3):290-6. doi: 10.1038/icb.2014.93. Epub Nov. 4, 2014.
Imamura et al., "Allogeneic hematopoietic stem cell transplantation in adult acute lymphoblastic leukemia: potential benefit of medium-dose etoposide conditioning," Exp Hematol Oncol, Jul. 16, 2015;4:20. doi: 10.1186/s40164-015-0015-0. eCollection 2015.
International Preliminary Report on Patentability in International Application No. PCT/US2015/060953, dated May 16, 2017, 7 pages.
International Search Report and Written Opinion in International Application No. PGT/US2016/058951, dated Feb. 7, 2017, 20 pages.
Isdori et al., "Advancement in high dose therapy and autologous stem cell rescue in lymphoma," World J Stem Cells, Aug. 2015, 7(7):1039-1046.
Iyer et al., "AZ64 inhibits TrkB and enhances the efficacy of chemotherapy and local radiation in neuroblastoma xenografts," Cancer Chemother Pharmacol. Sep. 2012;70(3):477-86. doi: 10.1007/s00280-012-1879-x. Epub May 24, 2012.
Koboldt et al., "The next-generation sequencing revolution and its impact on genomics," Cell, Sep. 26, 2013;155(1):27-38. doi: 10.1016/j.cell.2013.09.006.

(56) References Cited

OTHER PUBLICATIONS

Lecht et al., "Angiostatic effects of K252a, a Trk inhibitor, in murine brain capillary endothelial cells," Mol Cell Biochem, Jun. 2010;339(1-2):201-13. doi: 10.1007/s11010-010-0386-9. Epub Feb. 11, 2010.
Li et al., "In vivo sensitized and in vitro activated B cells mediate tumor regression in cancer adoptive immunotherapy," J Immunol, Sep. 1, 2009;183(5):3195-203. doi: 10.4049/jimmunol.0803773. Epub Aug. 10, 2009.
Li et al., "Trk inhibitor attenuates the BDNF/TrkB-induced protection of neuroblastoma cells from etoposide in vitro and in vivo," Cancer Biol. Ther., Feb. 2015, 16(3):477-483.
Marras et al., "Genotyping SNPs with molecular beacons," Methods Mol Biol, 2003;212:111-28.
McCarthy et al., "Tropomyosin receptor kinase inhibitors: a patent update 2009-2013," Expert Opin Ther Pat. Jul. 2014;24(7):731-44. doi: 10.1517/13543776.2014.910195. Epub May 8, 2014.
Montagnoli et al., "Anti-proliferative effects of GW441756, a novel inhibitor of NGFreceptor tyrosine kinase a (TRKA), in human sarcoma," Italian Journal of Anatomy and Embryology, Nov. 11, 2010, 115:117.
Narayanan et al., "Discovery and preclinical characterization of novel small molecule TRK and ROS1 tyrosine kinase inhibitors for the treatment of cancer and inflammation," PLoS One, Dec. 26, 2013;8(12):e83380. doi: 10.1371/journal.pone.0083380. eCollection 2013.
Nollau et al., "Methods for detection of point mutations: performance and quality assessment. IFCC Scientific Division, Committee on Molecular Biology Techniques," Clin Chem. Jul. 1997;43(7):1114-28.
Obianyo et al., "Novel small molecule activators of the Trk family of receptor tyrosine kinases. Biochim Biophys Acta, 1834:2214-2218," Biochim Biophys Acta, Oct. 2013, 1834(10):2213-2218.
Olivier, "The Invader assay for SNP genotyping," Mutat Res, Jun. 3, 2005;573(1-2):103-10.
Pao, W., et al. "Acquired resistance of lung adenocarcinomas to gefitinib or erlotinib is associated with a second mutation in the EGFR kinase domain," PLoS Med, Feb. 2005, 2(3), e73.
Perales et al., "Fast Cars and No Brakes: Autologous Stem Cell Transplantation as a Platform for Novel Immunotherapies," Biol Blood Marrow Transplant, Jan. 2016;22(1):17-22. doi: 10.1016/j.bbmt.2015.10.014. Epub Oct. 17, 2015.
Ponsaerts et al., "Cancer immunotherapy using RNA-loaded dendritic cells," Clin. Exp. Immunol., Dec. 2003, 134:378-384.
Reungwetwattana et al., "Targeted therapies in development for non-small cell lung cancer," J Carcinog, Dec. 2013, 12:22, doi: 10.4103/1477-3163.123972. eCollection 2013.
Ricci et al., Neurotrophins and neurotrophin receptors in human lung cancer, Am. J. Respiratory Cell and Molecular Biology, Oct. 2001, 25(4): 439-446.
Richard et al., "Syngeneic stem cell transplant for spent-phase polycythaemia vera: eradication of myelofibrosis and restoration of normal haematopoiesis," Br. J Haematol., Apr. 2002, 117(1):245-246.
Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis," Acta Derm. Venereal., 2015, 95:542-548.
Russo et al., "Acquired Resistance to the Trk Inhibitor Entrectinib in Colorectal Cancer," Cancer Discovery, Jan. 1, 2016, 6(1):36-44.
Saragovi et al., "A TrkA-selective, fast internalizing nerve growth factor-antibody complex induces trophic but not neuritogenic signals," J Biol Chem, Dec. 25, 1998;273(52):34933-34940.
Shaw et al., "Ceritinib in ALK-rearranged non-small-cell lung cancer," N Engl J Med, Mar. 27, 2014;370(13):1189-97. doi: 10.1056/NEJMoa1311107.
Shaw et al., "Crizotinib in ROS1-rearranged non-small-cell lung cancer," N Engl J Med, Nov. 20, 2014;371(21):1963-71. doi: 10.1056/NEJMoa1406766. Epub Sep. 27, 2014.
Tahira et al., "dbQSNP: a database of SNPs in human promoter regions with allele frequency information determined by single-strand conformation polymorphism-based methods," Hum Mutat, Aug. 2005;26(2):69-77.
Thress et al., "Identification and preclinical characterization of AZ-23, a novel, selective, and orally bioavailable inhibitor of the Trk kinase pathway," Mol Cancer Ther, Jul. 2009;8(7):1818-27. doi: 10.1158/1535-7163.MCT-09-0036. Epub Jun. 9, 2009.
Turtle et al., "Artificial antigen-presenting cells for use in adoptive immunotherapy," Cancer J, Jul.-Aug. 2010;16(4):374-81. doi: 10.1097/PPO.0b013e3181eb33a6.
Wang et al., "Identification of 4-aminopyrazolylpyrimidines as potent inhibitors of Trk kinases," J Med Chem, Aug. 14, 2008;51(15):4672-84. doi: 10.1021/jm800343j. Epub Jul. 23, 2008.
Wang et al., "T cells sensitized with breast tumor progenitor cell vaccine have therapeutic activity against spontaneous HER2/neu tumors," Breast Cancer Res Treat, Jul. 2012;134(1):61-70. doi: 10.1007/s10549-011-1912-5. Epub Dec. 16, 2011.
Wei et al., "Abstract #2136: Entrectinib is Effective Against the Gatekeeper and Other Emerging Resistance Mutations in NTRK-, ROS1- and ALK-Rearranged Cancers," Poster, Presented at Proceedings of the 107th Annual Meeting of the American Association for Cancer Research, New Orleans LA, Apr. 16-20, 2016; Cancer Res, Jul. 2016, 76(14): 1 page.
Wittwer et al., "High-resolution genotyping by amplicon melting analysis using LCGreen," Clin Chem, Jun. 2003;49(6 Pt 1):853-60.
Woodward, "Bi-allelic SNP genotyping using the TaqMan® assay," Methods Mol Biol., 2014;1145:67-74. doi: 10.1007/978-1-4939-0446-4_6.
Yu et al., "Denaturing high performance liquid chromatography: high throughput mutation screening in familial hypertrophic cardiomyopathy and SNP genotyping in motor neurone disease," J Clin Pathol, May 2005;58(5):479-85.
Zage et al., "The selective Trk inhibitor AZ623 inhibits brain-derived neurotrophic factor-mediated neuroblastoma cell proliferation and signaling and is synergistic with topotecan," Cancer, Mar. 2011, 117(6): 1321-1391.
Zhang et al., "A novel multiplex tetra-primer ARMS-PCR for the simultaneous genotyping of six single nucleotide polymorphisms associated with female cancers," PLoS One, Apr. 17, 2013;8(4):e62126. doi: 10.1371/journal.pone.0062126. Print 2013.

* cited by examiner

SUBSTITUTED PYRAZOLO[1,5-A]PYRIMIDINE COMPOUNDS AS TRK KINASE INHIBITORS

This application is a continuation of U.S. application Ser. No. 14/321,246, filed Jul. 1, 2014, which is a continuation of U.S. application Ser. No. 13/382,858, filed Jan. 6, 2012, which is a national stage application filed under §371 of International Application No. PCT/US2010/041538, filed Jul. 9, 2010, which claims the benefit of U.S. Provisional Application No. 61/346,767, filed May 20, 2010 and U.S. Provisional Application No. 61/224,196, filed Jul. 9, 2009, the contents of each of which are hereby incorporated by reference in their entereties.

The present invention relates to novel compounds, to pharmaceutical compositions comprising the compounds, to processes for making the compounds and to the use of the compounds in therapy. More particularly, it relates to certain substituted pyrazolo[1,5-a]pyrimidine compounds which exhibit Trk family protein tyrosine kinase inhibition, and which are useful in the treatment of pain, cancer, inflammation, neurodegenerative diseases and certain infectious diseases.

The current treatment regimes for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Pataoutian, A. et al., *Current Opinion in Neurobiology*, 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *Neuroreport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448) and neuropathic pain animal models (Ramer, M. S. and Bisby, M. A. (1999) *Eur. J Neurosci.* 11, 837-846; Ro, L. S. et al. (1999); *Pain* 79, 265-274 Herzberg, U. et al. (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120). Additionally, recent literature indicates after inflammation, BDNF levels and TrkB signaling is increased in the dorsal root ganglion (Cho, L. et al. Brain Research 1997, 749, 358) and several studies have show antibodies that decrease signaling through the BDNF/TrkB pathway inhibit neuronal hypersensitization and the associated pain (Chang-Qi, L et al. Molecular Pain 2008, 4:27).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. In addition, activation of the BDNF/TrkB pathway has been implicated in numerous studies as a modulator of various types of pain including inflammatory pain (Matayoshi, S., *J. Physiol.* 2005, 569: 685-95), neuropathic pain (Thompson, S. W., *Proc. Natl. Acad. Sci. USA* 1999, 96:7714-18) and surgical pain (Li, C.-Q. et al., *Molecular Pain,* 2008, 4(28), 1-11). Because TrkA and TrkB kinases may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259) and colorectal cancer (Bardelli, A., *Science* 2003, 300, 949). In preclinical models of cancer, non-selective small molecule inhibitors of Trk A, B and C were efficacious in both inhibiting tumor growth and stopping tumor metastasis (Nakagawara, A. (2001) *Cancer Letters* 169:107-114; Meyer, J. et al. (2007) *Leukemia,* 1-10; Pierottia, M. A. and Greco A., (2006) *Cancer Letters* 232:90-98; Eric Adriaenssens, E. et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of Trk A, B and C. For example, inhibition of the neurotrophin/Trk pathway has been implicated in preclinical models of inflammatory lung diseases including asthma (Freund-Michel, V; Frossard, N.; *Pharmacology & Therapeutics* (2008), 117(1), 52-76), interstitial cystitis (Hu Vivian Y; et. al. *The Journal of Urology* (2005), 173(3), 1016-21), inflammatory bowel diseases including ulcerative colitis and Crohn's disease (Di Mola, F. F, et. al., *Gut* (2000), 46(5), 670-678) and inflammatory skin diseases such as atopic dermatitis (Dou, Y.-C.; et. al. *Archives of Dermatological Research* (2006), 298(1), 31-37), eczema and psoriasis (Raychaudhuri, S. P., et al., *J. Investigative Dermatology* (2004), 122(3), 812-819).

The neurotrophin/Trk pathway, particularly BDNF/TrkB, has also been implicated in the etiology of neurodegenerative diseases including multiple sclerosis, Parkinson's disease and Alzheimer's Disease (Sohrabji, Farida; Lewis, Danielle K., *Frontiers in Neuroendocrinology* (2006), 27(4), 404-414).

The TrkA receptor is also thought to be critical to the disease process in the infection of the parasitic infection of *Trypanosoma cruzi* (Chagas disease) in human hosts (de Melo-Jorge, M. et al. *Cell Host & Microbe* (2007), 1(4), 251-261).

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA and TrkC receptors has been observed in the bone forming area in mouse models of bone fracture (K. Asaumi, et al., Bone (2000) 26(6) 625-633). In addition, localization of NGF was observed in almost all bone forming cells (K. Asaumi, et al.). Recently, it was demonstrated that a pan-Trk inhibitor inhibits the tyrosine signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Several classes of small molecule inhibitors of Trk kinases said to be useful for treating pain or cancer are known (*Expert Opin. Ther. Patents* (2009) 19(3), 305-319).

Pyrazolo[1,5-a]pyrimidine compounds are known. For example, International patent application publication WO 2004/089415 discloses certain pyrazolo[1,5-a]pyrimidine-3-carboxamide compounds having a phenyl, thienyl or furyl group in the 5-position which are said to be 11-beta-hydroxysteroid dehydrogenase type 1 inhibitors useful in combination therapies.

European patent application publication No. EP 1948633A2 describes 5-phenyl-7-hydroxy-substituted pyrazolo[1,5-a]pyrimidine-3-carboxamide compounds as casein kinase II modulators for treating cancer.

PCT publication WO 2010/051549 describes pyrazolopyrimidine compounds having the general structure:

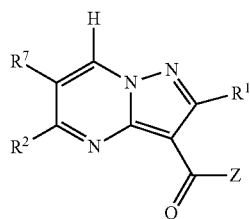

said to be inhibitors of Jak kinases.

It has now been found that certain pyrazolo[1,5-a]pyrimidine compounds bearing an aryl-substituted or heteroaryl-substituted heterocyclic group at the 5-position and a group having the formula C(=O)NR$^1$R$^2$ at the 3-position, wherein R$^1$ and R$^2$ are as defined herein, are inhibitors of Trk kinases, in particular inhibitors of TrkA and/or TrkB and/or TrkC, and are useful for treating disorders and diseases such as cancer and pain, including chronic and acute pain. Certain compounds which are inhibitors of TrkA and/or TrkB may be useful in the treatment of multiple types of pain including inflammatory pain, neuropathic pain, and pain associated with cancer, surgery, and bone fracture. In addition, compounds of the invention may be useful for treating cancer, inflammation, neurodegenerative diseases and certain infectious diseases.

In addition, compounds of the invention have been shown to be selective for the Trk family of kinases over closely related kinases. In particular, compounds of the invention are more selective for inhibiting TrkA kinase activity over inhibiting the activity of one or more members of the Jak kinase family (Jak1, Jak2, Jak3 and Tyk2). Inhibition of the Jak family of kinases has been postulated or demonstrated to result in several unwanted side effects including CD8 T and NK cell depletion (which can result in loss of tumor surveillance and increased infections), elevated cholesterol, neutropenia, thrombocytopenia, decreased reticulocytes (resulting in anemia) and bone marrow suppression (Igaz P. et al., *Inflamm. Res.,* 2001, 50:435-441; O'Shea J. J., Immunity, 1997, 7:1-11; Ihle J. N. et al., *Canc. J. Sci. Am.,* 1998, 4 suppl 1 S84-91; Gupta P. et al., *J. Clin. Pharm.* 2009; Kremer J. M. et al., *Arth. & Rheum.,* 2009, 60:1895-1905 and van Gurp E., et al., *Am. J. Transpl,* 2008, 8:1711-18). Accordingly, compounds of the invention may be more suitable as therapeutic treatments owing to their ability to inhibit the Trk family of kinases in preference over closely related kinases such as the Jak family of kinases, and therefore may avoid unwanted side effects in a mammal being treated with a compound of the invention.

Accordingly, one embodiment of this invention provides a compound of the general Formula I:

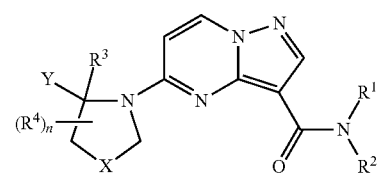

or a salt thereof, wherein:

R$^1$ is H or (1-6C alkyl);

R$^2$ is H, (1-6C)alkyl, -(1-6C)fluoroalkyl, -(1-6C)difluoroalkyl, -(1-6C)trifluoroalkyl, -(1-6C)chloroalkyl, -(2-6C)chlorofluoroalkyl, -(2-6C)difluorochloroalkyl, -(2-6C)chlorohydroxyalkyl, -(1-6C)hydroxyalkyl, -(2-6C)dihydroxyalkyl, -(1-6C alkyl)CN, -(1-6C alkyl)SO$_2$NH$_2$, -(1-6C alkyl)NHSO$_2$(1-3C alkyl), -(1-6C alkyl)NH$_2$, -(1-6C alkyl)NH(1-4C alkyl), -(1-6C alkyl)N(1-4C alkyl)$_2$, -(1-6C alkyl)NHC(=O)O(1-4C alkyl), -(1-6C alkyl)hetCyc$^1$, -(1-6C alkyl)hetAr$^1$, hetAr$^2$, hetCyc$^2$, —O(1-6C alkyl) which is optionally substituted with halogen, OH or (1-4C)alkoxy, —O(3-6C cycloalkyl), Cyc$^1$, -(1-6C alkyl)(3-6C cycloalkyl), -(1-6Calkyl)(1-4C alkoxy), -(1-6C hydroxyalkyl)(1-4C alkoxy), a bridged 7-membered cycloalkyl ring optionally substituted with (1-6C)hydroxyalkyl, or a bridged 7-8 membered heterocyclic ring having 1-2 ring nitrogen atoms;

or NR$^1$R$^2$ forms a 4-6 membered azacyclic ring optionally substituted with one or more substituents independently selected from (1-6C)alkyl, OH, CO$_2$H, (1-3C alkyl)CO$_2$H, —O(1-6C alkyl) and (1-6C)hydroxyalkyl;

hetCyc$^1$ is a 5-6 membered heterocyclic ring having 1-2 ring heteroatoms independently selected from N and O, wherein hetCyc$^1$ is optionally substituted with oxo, OH, halogen or (1-6C)alkyl;

hetCyc$^2$ is a 6 membered carbon-linked heterocyclic ring having 1-2 ring heteroatoms independently selected from N and O, wherein hetCyc$^2$ is optionally substituted with F, SO$_2$NH$_2$, SO$_2$(1-3C alkyl) or halogen;

hetAr$^1$ is a 5-membered heteroaryl ring having 1-2 ring heteroatoms independently selected from N and O and optionally substituted with (1-4C)alkyl;

hetAr$^2$ is a 5-6 membered heteroaryl ring having 1-2 ring nitrogen atoms and optionally substituted with one or more substituents independently selected from (1-4C)alkyl, (3-6C)cycloalkyl, halogen and OH;

Cyc¹ is a 3-6 membered cycloalkyl ring which is optionally substituted with one or more substituents independently selected from -(1-4C alkyl), —OH, —OMe, —CO₂H, -(1-4C alkyl)OH, halogen and CF₃;

Y is (i) phenyl optionally substituted with one or more substituents independently selected from halogen, (1-4C) alkoxy, —CF₃—CHF₂, —O(1-4C alkyl)hetCyc³, -(1-4C alkyl)hetCyc³, —O(1-4C alkyl)O(1-3C alkyl) and —O(3-6C dihydroxyalkyl), or (ii) a 5-6 membered heteroaryl ring having a ring heteroatom selected from N and S, wherein said heteroaryl ring is optionally substituted with one or more substituents independently selected from halogen, —O(1-4C alkyl), (1-4C)alkyl and NH₂, or (iii) a pyrid-2-on-3-yl ring optionally substituted with one or more substituents independently selected from halogen and (1-4C) alkyl;

hetCyc³ is a 5-6 membered heterocyclic ring having 1-2 ring heteroatoms independently selected from N and O and optionally substituted with (1-6C)alkyl;

X is null, —CH₂—, —CH₂CH₂—, —CH₂O— or —CH₂NR$^d$—;

R$^d$ is H or -(1-4C alkyl);

R³ is H or -(1-4C alkyl);

each R⁴ is independently selected from halogen, -(1-4C)alkyl, —OH, -(1-4C)alkoxy, —NH₂, —NH(1-4C alkyl) and —CH₂OH; and n is 0, 1, 2, 3, 4, 5 or 6.

In one embodiment of Formula I, X is selected from any of the values described above, other than null.

In one embodiment of Formula I, X is CH₂.

Compounds of Formula I include compounds of the general Formula Ia:

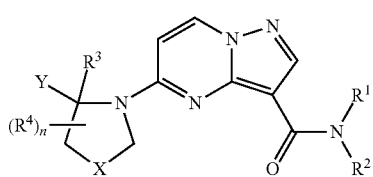

Ia or a salt thereof, wherein:

R¹ is H or (1-6C alkyl);

R² is H, (1-6C)alkyl, -(1-6C)fluoroalkyl, -(1-6C)hydroxyalkyl, -(2-6C)dihydroxyalkyl, -(1-6C alkyl)CN, -(1-6C alkyl)SO₂NH₂, -(1-6C alkyl)NHSO₂(1-3C alkyl), -(1-6C alkyl)NH₂, -(1-6C alkyl)NH(1-4C alkyl), -(1-6C alkyl)N(1-4C alkyl)₂, -(1-6C alkyl)hetCyc¹, -(1-6C alkyl)hetAr¹, hetAr², hetCyc², —O(1-6C alkyl), —O(3-6C cycloalkyl), Cyc¹, or a bridged 7-membered cycloalkyl ring, or NR¹R² forms a 4-6 membered azacyclic ring optionally substituted with one or more substituents independently selected from (1-6C)alkyl, OH, CO₂H and (1-3C alkyl) CO₂H;

hetCyc¹ is a 5-6 membered heterocyclic ring having 1-2 ring heteroatoms independently selected from N and O, wherein hetCyc¹ is optionally substituted with oxo;

hetCyc² is a 6 membered carbon-linked heterocyclic ring having 1-2 ring heteroatoms independently selected from N and O, wherein hetCyc² is optionally substituted with F, SO₂NH₂, or SO₂(1-3C alkyl);

hetAr¹ is a 5-membered heteroaryl ring having 1-2 ring heteroatoms independently selected from N and O and optionally substituted with (1-4C)alkyl;

hetAr² is a 5-6 membered heteroaryl ring having 1-2 ring nitrogen atoms and optionally substituted with one or more substituents independently selected from (1-4C)alkyl;

Cyc¹ is a 3-6 membered cycloalkyl ring which is optionally substituted with one or more substituents independently selected from -(1-4C alkyl), —OH, —OMe, —CO₂H and -(1-4C alkyl)OH;

Y is (i) phenyl optionally substituted with one or more substituents independently selected from halogen, (1-4C) alkoxy, —CF₃—CHF₂, —O(1-4C alkyl)hetCyc³ and —O(1-4C alkyl)O(1-3C alkyl), or (ii) a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl;

hetCyc³ is a 5-6 membered heterocyclic ring having 1-2 ring heteroatoms independently selected from N and O;

X is null, —CH₂—, —CH₂CH₂—, —CH₂O— or —CH₂NR$^d$—;

R$^d$ is H or -(1-4C alkyl);

R³ is H or -(1-4C alkyl);

each R⁴ is independently selected from halogen, -(1-4C) alkyl, —OH, -(1-4C)alkoxy, —NH₂, —NH(1-4C alkyl) and —CH₂OH; and n is 0, 1, 2, 3, 4, 5 or 6.

In one embodiment of Formula Ia, X is selected from any of the values described above, other than null.

In one embodiment of Formula Ia, X is CH₂.

In certain embodiments of Formula I, R¹ is hydrogen.

In certain embodiments of Formula I, R¹ is -(1-6C)alkyl. Examples include methyl, ethyl, propyl and isopropyl. A particular example is methyl.

In certain embodiments of Formula I, R² is H or -(1-6C) alkyl.

In certain embodiments, R² is hydrogen. In one embodiment, R² and R¹ are both hydrogen. In one embodiment, R² is hydrogen and R¹ is -(1-6C alkyl).

In certain embodiments, R² is selected from -(1-6C)alkyl, -(1-6C)fluoroalkyl, -(1-6C)difluoroalkyl, -(1-6C)trifluoroalkyl, -(1-6C)chloroalkyl, -(2-6C)chlorofluoroalkyl, -(2-6C) chlorohydroxyalkyl, -(1-6C alkyl)CN, -(1-6C alkyl) SO₂NH₂, and -(1-6C alkyl)NHSO₂(1-3C alkyl).

In certain embodiments, R² is -(1-6C)alkyl. In certain embodiments R² is selected from methyl, ethyl, propyl, isopropyl, butyl, isobutyl and tert-butyl. Particular examples include methyl, ethyl, isopropyl and tert-butyl. In one embodiment, R² is -(1-6C)alkyl and R¹ is hydrogen. In one embodiment, R² is -(1-6C)alkyl and R¹ is (1-6C alkyl).

In certain embodiments, R² is selected from -(1-6C) fluoroalkyl, -(1-6C)difluoroalkyl, -(1-6C)trifluoroalkyl, -(1-6C)chloroalkyl, -(2-6C)chlorofluoroalkyl, -(2-6C)chlorohydroxyalkyl, -(1-6C alkyl)CN, -(1-6C alkyl)SO₂NH₂, and -(1-6C alkyl)NHSO₂(1-3C alkyl).

In certain embodiments, R² is selected from -(1-6C) fluoroalkyl, -(1-6C alkyl)CN, -(1-6C alkyl)SO₂NH₂, and -(1-6C alkyl)NHSO₂(1-3C alkyl).

In certain embodiments, R² is -(1-6C)fluoroalkyl. A particular example is —C(CH₃)₂CH₂F. In one embodiment, R² is -(1-6C)fluoroalkyl and R¹ is hydrogen. In one embodiment, R² is -(1-6C)fluoroalkyl and R¹ is (1-6C alkyl).

In certain embodiments, R² is -(1-6C)difluoroalkyl. Examples include —CHF₂ and —CH₂CHF₂. In one embodiment, $R^2$ is -(1-6C)difluoroalkyl and $R^1$ is hydrogen. In one embodiment, $R^2$ is -(1-6C)difluoroalkyl and $R^1$ is (1-6C alkyl).

In certain embodiments, $R^2$ is -(1-6C)trifluoroalkyl. Examples include $CF_3$, $CH_2CF_3$ and $CH(CH_3)CF_3$. In one embodiment, $R^2$ is -(1-6C)trifluoroalkyl and $R^1$ is hydrogen. In one embodiment, $R^2$ is -(1-6C)trifluoroalkyl and $R^1$ is (1-6C alkyl).

In certain embodiments, $R^2$ is -(1-6C)chloroalkyl. An example includes $CH_2CH_2Cl$. In one embodiment, $R^2$ is -(1-6C)chloroalkyl and $R^1$ is hydrogen. In one embodiment, $R^2$ is -(1-6C)chloroalkyl and $R^1$ is (1-6C alkyl).

In certain embodiments, $R^2$ is -(1-6C)chlorofluoroalkyl. An example includes $CH_2CHFCH_2Cl$. In one embodiment, $R^2$ is -(1-6C)chlorofluoroalkyl and $R^1$ is hydrogen. In one embodiment, $R^2$ is -(1-6C)chlorofluoroalkyl and $R^1$ is (1-6C alkyl).

In certain embodiments, $R^2$ is -(1-6C)difluorochloroalkyl. An example includes —$CH_2CF_2CH_2Cl$. In one embodiment, $R^2$ is -(1-6C)difluorochloroalkyl and $R^1$ is H. In one embodiment, $R^2$ is -(1-6C)difluorochloroalkyl and $R^1$ is (1-6C alkyl).

In certain embodiments, $R^2$ is -(2-6C)chlorohydroxyalkyl. An example includes —$CH_2CH(OH)CH_2Cl$. In one embodiment, $R^2$ is -(2-6C)chlorohydroxyalkyl and $R^1$ is hydrogen. In one embodiment, $R^2$ is -(2-6C)chlorohydroxyalkyl and $R^1$ is (1-6C alkyl).

In certain embodiments, $R^2$ is selected from methyl, ethyl, propyl, isopropyl, isobutyl, tert-butyl, —$C(CH_3)_2CH_2F$, —$CHF_2$, —$CH_2CHF_2$, $CF_3$, $CH_2CF_3$, $CH(CH_3)CF_3$, $CH_2CH_2Cl$, $CH_2CHFCH_2Cl$, and —$CH_2CF_2CH_2Cl$.

In certain embodiments, $R^2$ is selected from methyl, ethyl, propyl, isopropyl, —$CF_3$ and —$CH_2CF_3$.

In certain embodiments, $R^2$ is -(1-6C)hydroxyalkyl or -(2-6C)dihydroxyalkyl.

In certain embodiments, $R^2$ is -(1-6C)hydroxyalkyl. Examples include —$CH_2CH_2OH$, —$CH_2CH_2CH_2OH$, —$CH_2CH_2CH_2CH_2OH$, —$CH_2CH(OH)CH_3$, —$C(CH_3)_2CH_2OH$, —$CH_2C(CH_3)_2OH$, —$CH(CH_3)CH_2OH$, —$CH_2C(CH_3)_2CH_2OH$, —$CH(CH_2OH)CH(CH_3)_2$, —$CH(CH_2CH_3)CH_2OH$, and —$CH(CH_2OH)C(CH_3)_3$. A particular example is —$CH_2CH_2OH$. In one embodiment, $R^2$ is -(1-6C)hydroxyalkyl and $R^1$ is hydrogen. In one embodiment, $R^2$ is -(1-6C)hydroxyalkyl and $R^1$ is -(1-6C alkyl).

In certain embodiments, $R^2$ is -(2-6C)dihydroxyalkyl. Examples include —$CH_2CH(OH)CH_2OH$, —$C(CH_3)(CH_2OH)_2$, —$CH(CH_2OH)_2$ and —$CH(CH_2OH)(CHOHCH_3)$. Particular examples include —$CH_2CH(OH)CH_2OH$ and —$C(CH_3)(CH_2OH)_2$. In one embodiment, $R^2$ is -(2-6C)dihydroxyalkyl and $R^1$ is hydrogen. In one embodiment, $R^2$ is -(2-6C)dihydroxyalkyl and $R^1$ is -(1-6C alkyl).

In certain embodiments, $R^2$ is -(1-6C alkyl)CN. Particular examples include —$CH_2CN$ and —$C(CH_3)_2CN$. In one embodiment, $R^2$ is -(1-6C alkyl)CN and $R^1$ is hydrogen. In one embodiment, $R^2$ is -(1-6C alkyl)CN and $R^1$ is (1-6C alkyl).

In certain embodiments, $R^2$ is -(1-6C alkyl)$SO_2NH_2$. A particular example is —$CH_2CH_2SO_2NH_2$. In one embodiment, $R^2$ is -(1-6C alkyl)$SO_2NH_2$ and $R^1$ is hydrogen. In one embodiment, $R^2$ is -(1-6C alkyl)$SO_2NH_2$ and $R^1$ is (1-6C alkyl).

In certain embodiments, $R^2$ is -(1-6C alkyl)$NHSO_2$(1-3C alkyl). Particular examples include —$CH_2CH_2NHSO_2CH_3$ and —$C(CH_3)_2CH_2NHSO_2CH_3$. In one embodiment, $R^2$ is -(1-6C alkyl)$NHSO_2$(1-3C alkyl) and $R^1$ is hydrogen. In one embodiment, $R^2$ is -(1-6C alkyl)$NHSO_2$(1-3C alkyl) and $R^1$ is (1-6C alkyl).

In certain embodiments, $R^2$ is selected from -(1-6C alkyl)$NH_2$, -(1-6C alkyl)NH(1-4C alkyl) and -(1-6C alkyl)N(1-4C alkyl)$_2$.

In certain embodiments, $R^2$ is -(1-6C alkyl)$NH_2$. Examples include —$CH_2C(CH_3)_2NH_2$ and —$CH_2CH_2CH_2NH_2$. A particular example is —$CH_2C(CH_3)_2NH_2$. In one embodiment, $R^2$ is -(1-6C alkyl)$NH_2$ and $R^1$ is hydrogen. In one embodiment, $R^2$ is -(1-6C alkyl)$NH_2$ and $R^1$ is (1-6C alkyl).

In certain embodiments, $R^2$ is -(1-6C alkyl)NH(1-4C alkyl). Examples include groups having the formula -(1-4C alkyl)$NHCH_3$. A particular value is —$C(CH_3)_2NHCH_3$. In one embodiment, $R^2$ is -(1-6C alkyl)NH(1-4C alkyl) and $R^1$ is hydrogen. In one embodiment, $R^2$ is -(1-6C alkyl)NH(1-4C alkyl) and $R^1$ is (1-6C alkyl).

In certain embodiments, $R^2$ is -(1-6C alkyl)N(1-4C alkyl)$_2$. Examples include groups having the formula -(1-4C alkyl)N($CH_3$)$_2$. A particular value is -(1-6C alkyl)$NMe_2$. In one embodiment, $R^2$ is -(1-6C alkyl)N(1-4C alkyl)$_2$ and $R^1$ is hydrogen. In one embodiment, $R^2$ is -(1-6C alkyl)N(1-4C alkyl)$_2$ and $R^1$ is (1-6C alkyl).

In certain embodiments, $R^2$ is -(1-6C alkyl)NHC(=O)O(1-4C alkyl). An example includes $CH_2CH_2CH_2NHC(=O)OC(CH_3)_3$. In one embodiment, $R^2$ is -(1-6C alkyl)NHC(=O)O(1-4C alkyl) and $R^1$ is hydrogen. In one embodiment, $R^2$ is -(1-6C alkyl)NHC(=O)O(1-4C alkyl) and $R^1$ is (1-6C alkyl).

In certain embodiments, $R^2$ is selected from -(1-6C alkyl)hetCyc$^1$ and -(1-6C alkyl)hetAr$^1$.

In certain embodiments, $R^2$ is -(1-6C alkyl)hetCyc$^1$. Examples of hetCyc$^1$ rings include morpholinyl, piperidinyl, piperazinyl and imidazolidinyl, each of which is optionally substituted with a substituent selected from oxo, OH, halogen, and (1-6C)alkyl. In certain embodiments hetCyc$^1$ is morpholinyl, piperidinyl, piperazinyl or imidazolidin-2-one optionally substituted with OH, halogen or (1-6C)alkyl. Examples of the -(1-6C)alkyl portion include methylene, ethylene, dimethylethylene, and the like.

Examples of $R^2$ when represented by -(1-6C alkyl)hetCyc$^1$ include the structures:

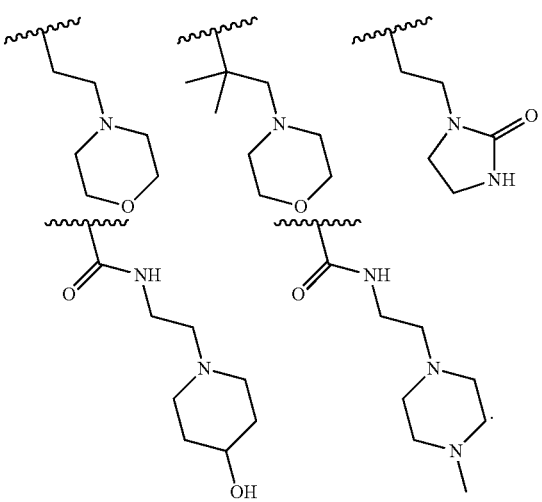

In certain embodiments, $R^2$ when represented by -(1-6C alkyl)hetCyc$^1$ includes the structures:

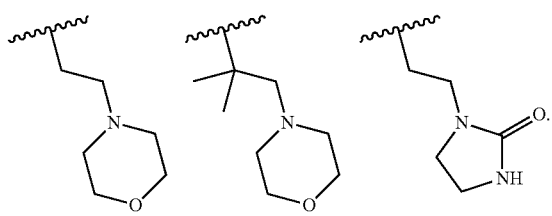 [SMILES: *CCN1CCOCC1 ; *C(C)(C)CN1CCOCC1 ; *CCN1CCNC1=O]

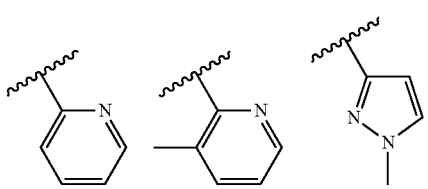

In certain embodiments hetCyc¹ is morpholinyl or imidazolidin-2-one.

In one embodiment, R² is -(1-6C alkyl)hetCyc¹ and R¹ is hydrogen. In one embodiment, R² is -(1-6C alkyl)hetCyc¹ and R¹ is (1-6C alkyl).

In certain embodiments, R² is -(1-6C alkyl)hetAr¹. Examples of hetAr¹ include furanyl, pyrazolyl, and imidazolyl rings which are optionally substituted with -(1-4C alkyl), for example methyl. Examples of the -(1-6C)alkyl portion include methylene, ethylene, dimethylmethylene, and the like. Examples of R² when represented by -(1-6C alkyl)hetAr¹ include the structures:

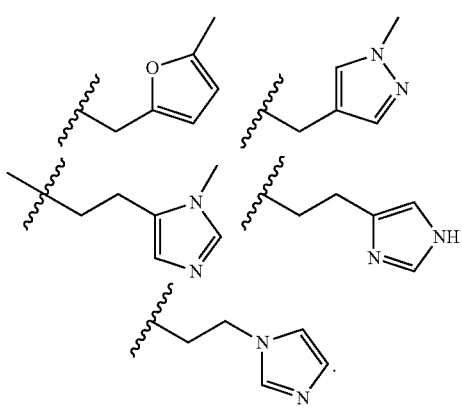

Particular values for R² when represented by -(1-6C alkyl)hetAr¹ include the structures:

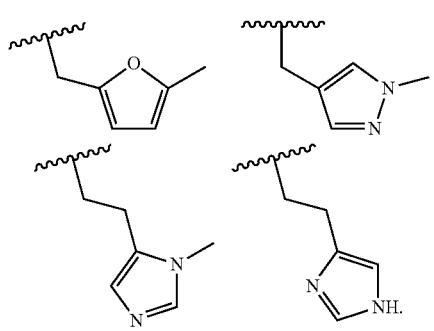

In one embodiment, R² is -(1-6C alkyl)hetAr¹ and R¹ is hydrogen. In one embodiment, R² is -(1-6C alkyl)hetAr¹ and R¹ is (1-6C alkyl).

In certain embodiments, R² is hetAr². Examples of hetAr² include pyridyl, pyrazolyl and imidazolyl rings optionally substituted with one or more substituents independently selected from (1-4C)alkyl, (3-6C)cycloalkyl, halogen and OH. Particular examples of hetAr² substituents include methyl, ethyl, isopropyl, cyclopropyl, fluoro and hydroxy. Particular examples of hetAr² include the structures:

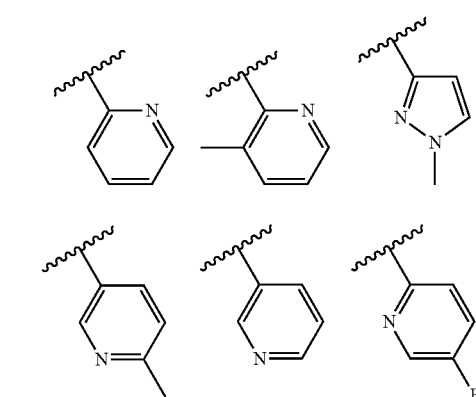

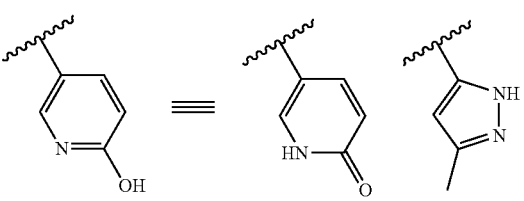

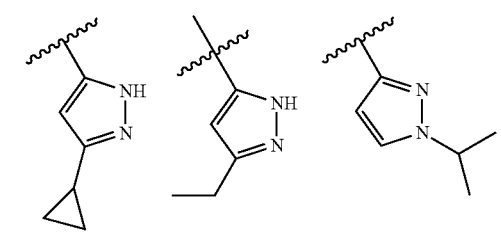

In certain embodiments hetAr² is a pyridyl or pyrazolyl ring optionally substituted with one or more substituents independently selected from -(1-4C)alkyl, for example one or more methyl groups, for example 1 or 2 methyl groups. Particular examples of hetAr² include the structures:

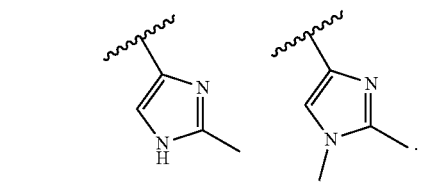

In one embodiment, R² is hetAr² and R¹ is hydrogen. In one embodiment, R² is hetAr² and R¹ is (1-6C alkyl).

In certain embodiments, R² is hetCyc². Examples of hetCyc² include piperidinyl and tetrahydropyranyl rings optionally substituted with F, SO₂NH₂ or SO₂(1-3C alkyl). Particular examples of R² when represented by hetCyc² include the structures:

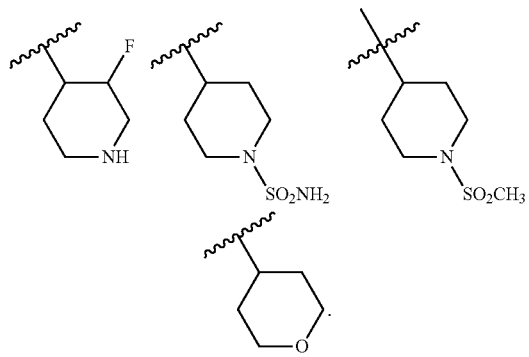

In one embodiment, $R^2$ is hetCyc² and $R^1$ is hydrogen. In one embodiment, $R^2$ is hetCyc² and $R^1$ is (1-6C alkyl).

In certain embodiments, $R^2$ is —O(1-6C alkyl) which is optionally substituted with halogen, OH or (1-4C)alkoxy. Examples include —OMe, —OEt, —OCH₂CH₂OC(CH₃)₃, —OCH₂CH₂Br, —OCH₂CH₂Cl and —OCH₂CH₂OH. In one embodiment, $R^2$ is —O(1-6C alkyl) which is optionally substituted with halogen, OH or (1-4C)alkoxy, and $R^1$ is hydrogen. In one embodiment, $R^2$ is —O(1-6C alkyl) which is optionally substituted with halogen, OH or (1-4C)alkoxy, and $R^1$ is (1-6C alkyl).

In certain embodiments, $R^2$ is —O(1-6C alkyl). Particular examples include OMe and OEt.

In certain embodiments, $R^2$ is —O(3-6C cycloalkyl). A particular example is cyclopropoxy. In one embodiment, $R^2$ is —O(3-6C cycloalkyl) and $R^1$ is hydrogen. In one embodiment, $R^2$ is —O(3-6C cycloalkyl) and $R^1$ is (1-6C alkyl).

In certain embodiments, $R^2$ is —O(1-6C alkyl) or —O(3-6C cycloalkyl)

In certain embodiments, $R^2$ is $Cyc^1$ or a bridged 7-membered cycloalkyl ring.

In certain embodiments, $R^2$ is $Cyc^1$, wherein $Cyc^1$ is a 3-6 membered cycloalkyl ring optionally substituted with one or more substituents independently selected from -(1-4C alkyl), —OH, —OMe, —CO₂H, -(1-4C alkyl)OH, halogen and CF₃. In one embodiment, $Cyc^1$ is optionally substituted with one or more substituents independently selected from methyl, —OH, —OMe, —CO₂H, CH₂OH, CH₂CH₂OH and CF₃. In certain embodiments, $R^2$ is $Cyc^1$, wherein the cycloalkyl ring is optionally substituted with one or more substituents independently selected from -(1-4C alkyl), —OH, —OMe, —CO₂H and -(1-4C alkyl)OH, such as one or more substituents independently selected from methyl, —OH, —CH₂OH and —CO₂H. In one embodiment, $Cyc^1$ is optionally substituted with one or more substituents independently selected from methyl, —OH, —CH₂OH and —CO₂H. In one embodiment, $Cyc^1$ is optionally substituted with one or two of said substituents.

Examples of $R^2$ when represented by $Cyc^1$ include the structures:

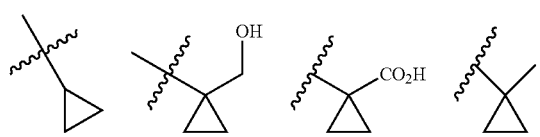

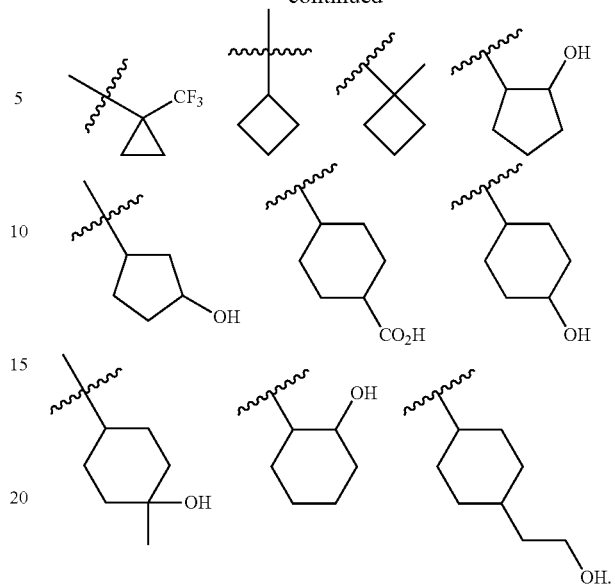

Particular examples of $R^2$ when represented by $Cyc^1$ include the structures:

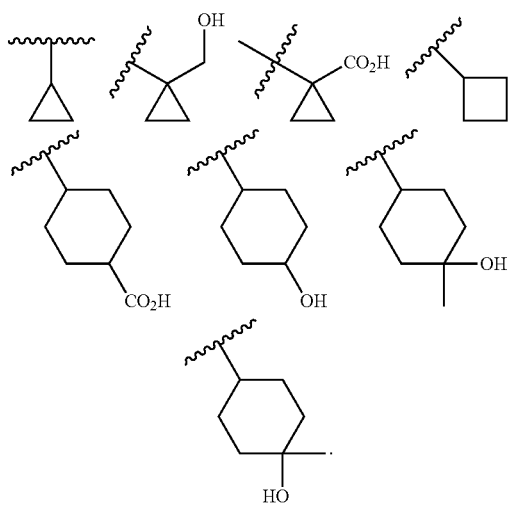

In one embodiment of Formula I, $Cyc^1$ is a 3, 4 or 5 membered cycloalkyl ring which is optionally substituted with one or more substituents independently selected from -(1-4C alkyl), —OH, —OMe, —CO₂H, -(1-4C alkyl)OH, halogen and CF₃.

In one embodiment of Formula I, $Cyc^1$ is a 3, 4 or 5 membered cycloalkyl ring which is optionally substituted with one or more substituents independently selected from -(1-4C alkyl), —OH, OMe, —CO₂H and -(1-4C alkyl)OH.

In one embodiment, $R^2$ is cyclopropyl.

In one embodiment $R_2$ is selected from the structures:

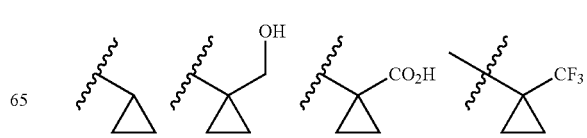

-continued

In one embodiment, $R^2$ is $Cyc^1$ and $R^1$ is hydrogen. In one embodiment, $R^2$ is $Cyc^1$ and $R^1$ is (1-6C alkyl).

In one embodiment, $R^2$ is a 3, 4 or 5 membered cycloalkyl ring which is optionally substituted with one or more substituents independently selected from -(1-4C alkyl), —OH, —OMe, —CO$_2$H, -(1-4C alkyl)OH, halogen and CF$_3$.

In one embodiment, $R^2$ is a 3, 4 or 5 membered cycloalkyl ring which is optionally substituted with one or more substituents independently selected from -(1-4C alkyl), —OH, OMe, —CO$_2$H and -(1-4C alkyl)OH.

In one embodiment, $R^2$ is a 3, 4 or 5 membered cycloalkyl ring which is optionally substituted with one or more substituents independently selected from methyl, —CO$_2$H, and CH$_2$OH.

In certain embodiments, $R^2$ is cyclopropyl optionally substituted with one or more substituents independently selected from -(1-4C alkyl), —OH, —OMe, —CO$_2$H, -(1-4C alkyl)OH, halogen and CF$_3$.

In certain embodiments, $R^2$ is cyclopropyl optionally substituted with one or more substituents independently selected from methyl, —CO$_2$H, and CH$_2$OH.

In certain embodiments, $R^2$ is cyclobutyl optionally substituted with one or more substituents independently selected from -(1-4C alkyl), —OH, —OMe, —CO$_2$H, -(1-4C alkyl)OH, halogen and CF$_3$. In certain embodiments, $R^2$ is cyclobutyl optionally substituted with one or more substituents independently selected from methyl, —OH, —OMe, —CO$_2$H, CH$_2$OH, CH$_2$CH$_2$OH and CF$_3$.

In certain embodiments, $R^2$ is cyclopentyl optionally substituted with one or more substituents independently selected from -(1-4C alkyl), —OH, —OMe, —CO$_2$H, -(1-4C alkyl)OH, halogen and CF$_3$. In certain embodiments, $R^2$ is cyclopentyl optionally substituted with one or more substituents independently selected from methyl, —OH, —OMe, —CO$_2$H, CH$_2$OH, CH$_2$CH$_2$OH and CF$_3$.

In certain embodiments, $R^2$ is cyclohexyl optionally substituted with one or more substituents independently selected from -(1-4C alkyl), —OH, —OMe, —CO$_2$H, -(1-4C alkyl)OH, halogen and CF$_3$. In certain embodiments, $R^2$ is cyclohexyl optionally substituted with one or more substituents independently selected from methyl, —OH, —OMe, —CO$_2$H, CH$_2$OH, CH$_2$CH$_2$OH and CF$_3$.

In certain embodiments, $R^2$ is -(1-6C alkyl)(3-6C cycloalkyl). Examples of the (1-6C alkyl) portion include methyl, ethyl, propyl and butyl. Examples of the cycloalkyl portion include cyclopropyl, cyclobutyl, cyclopentyl and cyclohexyl. In one embodiment, the cycloalkyl portion is cyclopropyl. Particular examples include the structures:

In one embodiment, $R^2$ is -(1-6C alkyl)(3-6C cycloalkyl) and $R^1$ is hydrogen. In one embodiment, $R^2$ is -(1-6C alkyl)(3-6C cycloalkyl) and $R^1$ is (1-6C alkyl).

In certain embodiments, $R^2$ is -(1-6Calkyl)(1-4C alkoxy). Examples include CH$_2$CH$_2$OCH$_3$ and CH(CH$_3$)CH$_2$OCH$_3$. In one embodiment, $R^2$ is -(1-6Calkyl)(1-4C alkoxy) and $R^1$ is hydrogen. In one embodiment, $R^2$ is -(1-6Calkyl)(1-4C alkoxy) and $R^1$ is (1-6C alkyl).

In certain embodiments, $R^2$ is -(1-6C hydroxyalkyl)(1-4C alkoxy). An example includes —CH$_2$CH(OH)CH$_2$OCH$_3$. In one embodiment, $R^2$ is -(1-6C hydroxyalkyl)(1-4C alkoxy) and $R^1$ is hydrogen. In one embodiment, $R^2$ is -(1-6C hydroxyalkyl)(1-4C alkoxy) and $R^1$ is (1-6C alkyl).

In certain embodiments, $R^2$ is a bridged 7-membered cycloalkyl ring. In certain embodiments, $R^2$ is a bridged 7-membered cycloalkyl ring optionally substituted with (1-6C)hydroxyalkyl. In certain embodiments, $R^2$ is a bridged 7-membered cycloalkyl ring optionally substituted with hydroxymethyl. Examples of $R^2$ include the structures:

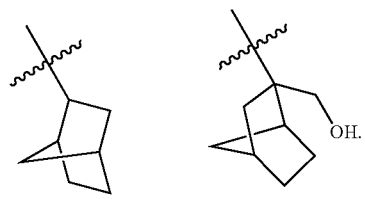 [SMILES: *C1CC2CCC1C2 ; *C1(CO)CC2CCC1C2]

A particular example or $R^2$ is the structure:

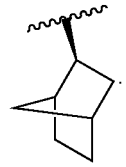 [SMILES: *[C@H]1CC2CCC1C2]

In one embodiment, $R^2$ is a bridged 7-membered cycloalkyl ring optionally substituted with (1-6C)hydroxyalkyl and $R^1$ is hydrogen. In one embodiment, $R^2$ is a bridged 7-membered cycloalkyl ring and $R^1$ is (1-6C alkyl).

In certain embodiments, $R^2$ is a bridged 7-8 membered heterocyclic ring having 1-2 ring nitrogen atoms. A particular example is the structure:

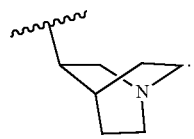 [SMILES: *C1CN2CCC1CC2]

In one embodiment, $R^2$ is a bridged 7-8 membered heterocyclic ring having 1-2 ring nitrogen atoms and $R^1$ is hydrogen. In one embodiment, $R^2$ is a bridged 7-8 membered heterocyclic ring having 1-2 ring nitrogen atoms and $R^1$ is (1-6C alkyl).

In certain embodiments, $NR^1R^2$ forms a 4-6 membered azacyclic ring optionally substituted with one or more substituents independently selected from (1-6C)alkyl, OH, CO$_2$H, (1-3C alkyl)CO$_2$H, —O(1-6C alkyl) and (1-6C) hydroxyalkyl. Examples include 4-6 membered azacyclic rings optionally substituted with one or more groups independently selected from methyl, OH, —C(=O)OH, —CH$_2$COOH, OMe, and —CH$_2$OH. In certain embodiments, the azacyclic ring is optionally substituted with one or two of said substituents. Particular examples include the structures:

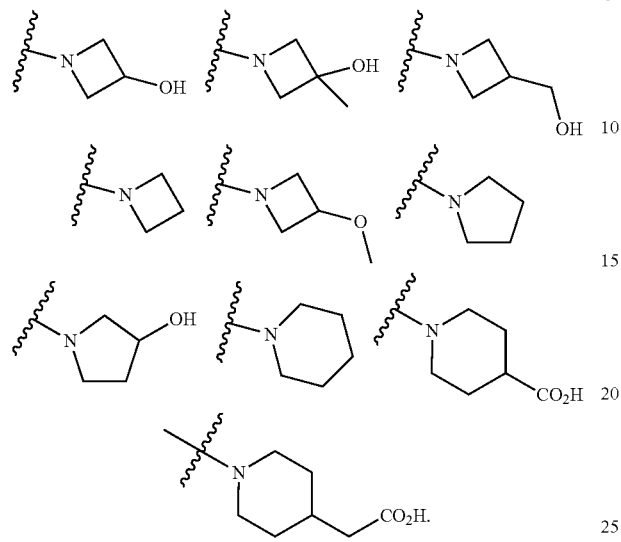

In certain embodiments, NR$^1$R$^2$ forms a 4-6 membered azacyclic ring optionally substituted with one or more substituents independently selected from -(1-6C)alkyl, —OH, —CO$_2$H and -(1-3C alkyl)CO$_2$H. Examples include 4-6 membered azacyclic rings optionally substituted with one or two groups independently selected from methyl, OH, —C(═O)OH and —CH$_2$COOH. Particular examples include the structures:

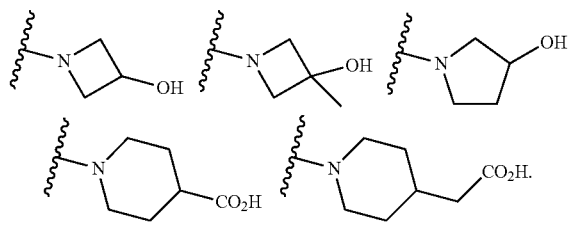

Compounds of Formula I also include compounds wherein:

R$^1$ is H or -(1-6C alkyl);

R$^2$ is H, -(1-6C)alkyl, -(1-6C)fluoroalkyl, -(1-6C)hydroxyalkyl, -(2-6C)dihydroxyalkyl, -(1-6C alkyl)CN, -(1-6C alkyl)SO$_2$NH$_2$, -(1-6C alkyl)NHSO$_2$(1-3C alkyl), -(1-6C alkyl)NH$_2$, -(1-6C alkyl)NH(1-4C alkyl), -(1-6C alkyl)N(1-4C alkyl)$_2$, -(1-6C alkyl)hetCyc$^1$, -(1-6C alkyl)hetAr$^1$, hetAr$^2$, —O(1-6C alkyl), —O(3-6C cycloalkyl), or a 3, 4 or 5 membered cycloalkyl ring optionally substituted with one or more substituents independently selected from -(1-4C alkyl), —OH, OMe, —CO$_2$H and -(1-4C alkyl)OH;

or NR$^1$R$^2$ forms a 4-6 membered azacyclic ring optionally substituted with one or more substituents independently selected from -(1-6C)alkyl, —OH, —CO$_2$H and -(1-3C alkyl)CO$_2$H;

and X, Y, R$^3$, R$^4$ and n are as defined for Formula I.

Compounds of Formula I also include compounds wherein:

R$^1$ is H or -(1-6C alkyl);

R$^2$ is H, -(1-6C)alkyl, -(1-6C)fluoroalkyl, -(1-6C)hydroxyalkyl, -(2-6C)dihydroxyalkyl, -(1-6C alkyl)CN, -(1-6C alkyl)SO$_2$NH$_2$, -(1-6C alkyl)NHSO$_2$(1-3C alkyl), -(1-6C alkyl)NH$_2$, -(1-6C alkyl)NH(1-4C alkyl), -(1-6C alkyl)N(1-4C alkyl)$_2$, -(1-6C alkyl)hetCyc$^1$, -(1-6C alkyl)hetAr$^1$, hetAr$^2$, hetCyc$^2$, —O(1-6C alkyl), —O(3-6C cycloalkyl), or a bridged 7-membered cycloalkyl ring, or NR$^1$R$^2$ forms a 4-6 membered azacyclic ring optionally substituted with one or more substituents independently selected from -(1-6C)alkyl, —OH, —CO$_2$H and -(1-3C alkyl)CO$_2$H; and and X, Y, R$^3$, R$^4$ and n are as defined for Formula I.

Referring now to the substituents on the ring at the 5-position of Formula I, wherein the 5-position is identified in the following structure:

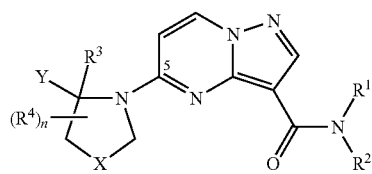

in one embodiment Y is phenyl optionally substituted with one or more substituents independently selected from halogen, (1-4C)alkoxy, —CF$_3$—CHF$_2$, —O(1-4C alkyl)hetCyc$^3$, -(1-4C alkyl)hetCyc$^3$, —O(1-4C alkyl)O(1-3C alkyl) and —O(3-6C dihydroxyalkyl).

In one embodiment, Y is phenyl optionally substituted with one or two of said substituents. In one embodiment Y is phenyl optionally substituted with one or more substituents independently selected from halogen, (1-4C)alkoxy, —O(1-4C alkyl)hetCyc$^3$, -(1-4C alkyl)hetCyc$^3$, —O(1-4C alkyl)O(1-3C alkyl) and —O(3-6C dihydroxyalkyl). In one embodiment, Y is phenyl optionally substituted with one or two of said substituents.

In one embodiment, Y is phenyl optionally substituted with one or more substituents independently selected from —F, —Cl, —OMe, —CF$_3$, —CHF$_2$, morpholinylethoxy, morpholinylethyl, —OCH$_2$CH$_2$OMe, 2,3-dihydroxypropoxy and 2,2-dimethyl-1,3-dioxolanyl. In one embodiment, Y is phenyl optionally substituted with one or two of said substituents.

The term "morpholinylethoxy" as used herein refers to a morpholinyl ring substituted at the nitrogen ring atom with an ethoxy group and can be represented by the structure:

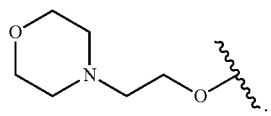 [SMILES: *OCCN1CCOCC1]

The term "morpholinylethyl" as used herein refers to a morpholinyl ring substituted at the nitrogen ring atom with an ethyl group and can be represented by the structure:

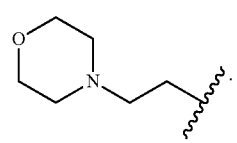 [SMILES: *CCN1CCOCC1]

Example of Y include phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluoro-phenyl, 2-difluoromethyl-5-fluorophenyl, 3-chloro-5-fluorophenyl, 3-fluoro-5-(2-morpholinylethoxy)phenyl, 3-fluoro-5-(2-morpholinylethyl)phenyl, 5-fluoro-2-(2-morpholinylethyl)phenyl, 3-fluoro-5-methoxyethoxyphenyl, 5-fluoro-2-methoxyethoxyphenyl, 3-fluoro-5-(2,3-dihydroxypropoxy)phenyl, 2-(2,3-dihydroxypropoxy)-5-fluorophenyl,

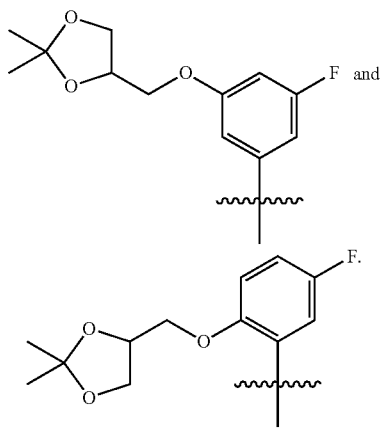

The terms "3-fluoro-5-(2-morpholinylethoxy)phenyl", "3-fluoro-5-(2-morpholinylethyl)phenyl" and "5-fluoro-2-(2-morpholinylethyl)phenyl" can be represented by the structures:

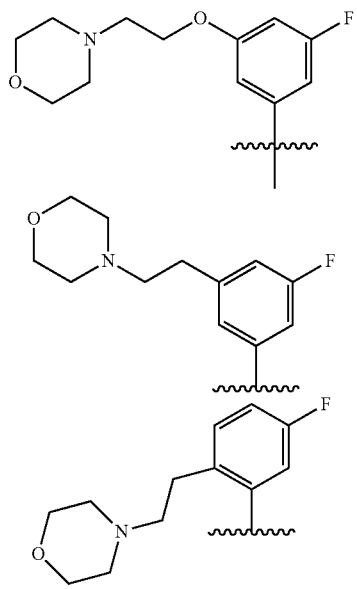

respectively.

In one embodiment, Y is fluorophenyl optionally substituted with a substituent selected from —O(1-4C alkyl)hetCyc³, -(1-4C alkyl)hetCyc³, —O(1-4C alkyl)O(1-3C alkyl) and —O(3-6C dihydroxyalkyl).

In one embodiment, Y is fluorophenyl substituted with a substituent selected from morpholinylethoxy, morpholinylethyl, —OCH₂CH₂OMe, 2,3-dihydroxypropoxy and 2,2-dimethyl-1,3-dioxolanyl.

In one embodiment, Y is selected from 3-fluoro-5-(2-morpholinylethoxy)phenyl, 5-fluoro-2-(2-morpholinoethoxy)phenyl, 3-fluoro-5-methoxyethoxyphenyl, 3-fluoro-5-(2-morpholinylethyl)phenyl, 5-fluoro-2-(2-morpholinylethyl)phenyl, 3-fluoro-5-(2,3-dihydroxypropoxy)phenyl, 2-(2,3-dihydroxypropoxy)-5-fluorophenyl,

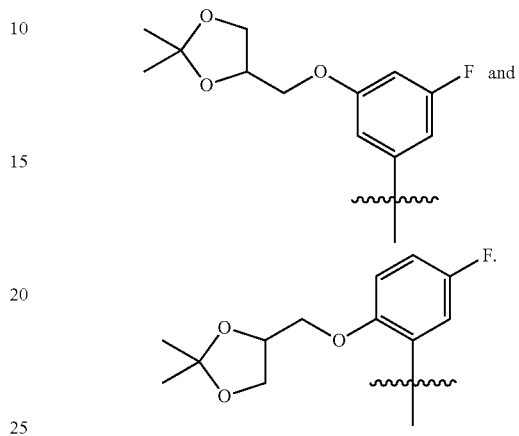

In one embodiment Y is phenyl optionally substituted with one or more substituents independently selected from halogen, -(1-4C)alkoxy, —CF₃, —CHF₂, —O(1-4C alkyl)hetCyc³ and —O(1-4C alkyl)O(1-3C alkyl).

In one embodiment, Y is phenyl optionally substituted with one or more substituents independently selected from —F, —Cl, —OMe, —CF₃, —CHF₂, morpholinylethoxy and —OCH₂CH₂OMe. In certain embodiments, Y is phenyl optionally substituted with one or two of said substituents. Particular values for Y include phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl, 3-chloro-5-fluorophenyl, 3-fluoro-5-(2-morpholinylethoxy)phenyl, 5-fluoro-2-(2-morpholinoethoxy)phenyl, 3-fluoro-5-methoxyethoxyphenyl and 5-fluoro-2-methoxyethoxyphenyl.

In one embodiment, Y is a 5-6 membered heteroaryl ring having a ring heteroatom selected from N and S, wherein said heteroaryl ring is optionally substituted with one or more substituents independently selected from halogen, —O(1-4C alkyl), (1-4C)alkyl and NH₂. Examples include pyridyl and thienyl groups optionally substituted with one or more substituents independently selected from halogen, —O(1-4C alkyl), (1-4C)alkyl and NH₂.

In certain embodiments, Y is pyridyl optionally substituted with one or more substituents independently selected from fluoro, chloro, methoxy, methyl, ethyl, and amino.

In certain embodiments Y is pyrid-2-yl, pyrid-3-yl, 5-fluoropyrid-3-yl, 2-methoxy-5-fluoropyridy-3-yl, 2-chloro-5-fluoropyridy-3-yl, 2-methyl-5-fluoropyrid-3-yl, 2-ethyl-5-fluoropyrid-3-yl or 2-amino-5-fluoropyrid-3-yl.

In certain embodiments, Y is pyridyl substituted with one or more substituents independently selected from halogen, (1-4C)alkyl and amino.

In certain embodiments, Y is pyridyl substituted with one or more substituents independently selected from halogen and (1-4C)alkyl.

In certain embodiments, Y is pyridyl substituted with one or more substituents independently selected from fluoro, chloro, methyl and ethyl.

In certain embodiments, Y is pyridyl substituted with one or more substituents independently selected from F, methyl and ethyl.

In certain embodiments, Y is 5-fluoropyrid-3-yl, 2-methyl-5-fluoropyrid-3-yl or 2-ethyl-5-fluoropyrid-3-yl.

In certain embodiments, Y is 5-fluoropyrid-3-yl.

In one embodiment, Y is a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl. Examples include pyridyl and thienyl groups optionally substituted with one or more substituents independently selected from halogen, —O(1-4C alkyl) and (1-4C)alkyl, for example one or more substituents independently selected from fluoro, methoxy and methyl. Particular values for Y include pyrid-2-yl, pyrid-3-yl, 5-fluoropyrid-3-yl, 2-methoxy-5-fluoropyridy-3-yl and 2-methyl-5-fluoropyridy-3-yl.

In one embodiment, Y is a pyrid-2-on-3-yl ring optionally substituted with one or more substituents independently selected from halogen and (1-4C)alkyl. Examples include pyrid-2-on-3-yl rings optionally substituted with one or more substituents independently selected from fluoro and methyl. In certain embodiments the pyrid-2-on-3-yl ring is optionally substituted with one or two of said substituents. In one embodiment, Y is 5-fluoropyridin-2(1H)-one optionally substituted with (1-4C)alkyl, for example methyl. Particular values for Y include the structures:

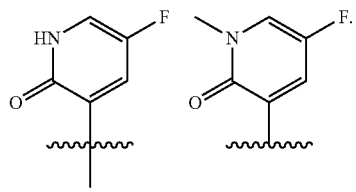

In one embodiment, the Y group has the absolute configuration shown in FIG. Ia:

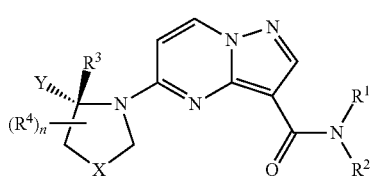

wherein $R^1$, $R^2$, $R^3$, $R^4$, X, Y and n are as defined herein.

With reference to the $R^3$ substituent, in one embodiment $R^3$ is H.

In one embodiment, $R^3$ is -(1-4C)alkyl, for example, methyl, ethyl, propyl, isopropyl or butyl. In one embodiment, $R^3$ is methyl.

With reference to the $R^4$ substituent, in one embodiment $R^4$ is halogen. Particular examples are fluoro and chloro.

In one embodiment, $R^4$ is -(1-4C)alkyl, such as methyl, ethyl, propyl, isopropyl, or butyl. A particular example is methyl.

In one embodiment, $R^4$ is —OH.

In one embodiment, $R^4$ is (1-4 C)alkoxy, for example —OMe and -OEt.

In one embodiment, $R^4$ is —NH$_2$.

In one embodiment, $R^4$ is —NH(1-4C alkyl), for example —NHMe, —NHEt, —NHPr, —NHiPr or —NHBu. A particular example is —NHMe.

In one embodiment, $R^4$ is CH$_2$OH.

In one embodiment, each $R^4$ is independently selected from —F, —Cl, —OH, —OMe, —NH$_2$, -Me, —CH$_2$OH and —NHMe.

In one embodiment, n is 0, 1, 2, 3 or 4. In one embodiment, n is 0, 1, 2 or 3. In one embodiment, n is 0, 1 or 2.

In one embodiment, n is 0.

In one embodiment, n is 1.

In one embodiment, n is 2.

With reference to the heterocyclic ring directly attached to the 5-position of Formula I, in certain embodiments, X is null, —CH$_2$— or —CH$_2$CH$_2$—.

In one embodiment X is null, such that the heterocyclic ring at the 5-position of Formula I has the structure:

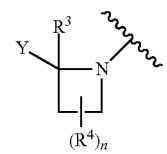

where $R^3$, $R^4$, Y and n are as defined herein. In one embodiment, Y is phenyl optionally substituted with one or more substituents independently selected from halogen, -(1-4C)alkoxy, —CF$_3$ and —CHF$_2$. In one embodiment, Y is phenyl, 3-fluorophenyl and 2,5-difluorophenyl. In one embodiment, Y is 5-6 membered heteroaryl ring having a ring heteroatom selected from N and S, wherein said heteroaryl ring is optionally substituted with one or more substituents independently selected from halogen, —O(1-4C alkyl) and (1-4C)alkyl, for example one or more halogen atoms. In one embodiment, Y is pyridyl. In one embodiment, $R^3$ is hydrogen. In another embodiment, $R^3$ is methyl. In one embodiment, n is 0. A particular example of the ring at the 5-position of Formula I when X is null includes the structures:

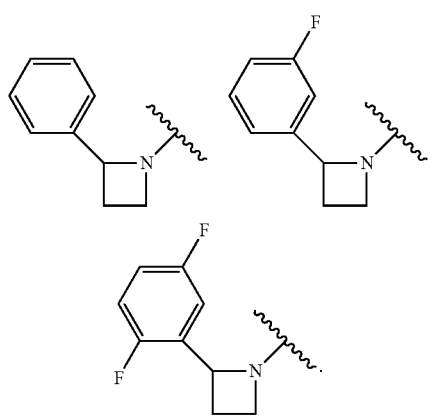

In one embodiment, X is CH$_2$, such that the heterocyclic ring at the 5-position of Formula I has the structure:

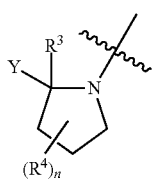

where R³, R⁴, Y and n are as defined herein. In one embodiment, X is CH₂, R³, R⁴ and n are as defined herein, and Y is phenyl optionally substituted with one or more substituents independently selected from —F, —Cl, —OMe, —CF₃, —CHF₂, morpholinylethoxy, morpholinylethyl, —OCH₂CH₂OMe, 2,3-dihydroxypropoxy and 2,2-dimethyl-1,3-dioxolanyl.

In one embodiment, X is CH₂, R³, R⁴ and n are as defined herein, and Y is phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl, 3-chloro-5-fluorophenyl, 3-fluoro-5-(2-morpholinylethoxy)phenyl, 3-fluoro-5-(2-morpholinylethyl)phenyl, 5-fluoro-2-(2-morpholinylethyl)phenyl, 3-fluoro-5-methoxyethoxyphenyl, 5-fluoro-2-methoxyethoxyphenyl, 3-fluoro-5-(2,3-dihydroxypropoxy)phenyl, 2-(2,3-dihydroxypropoxy)-5-fluorophenyl,

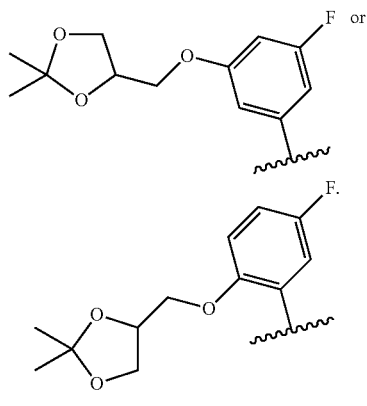

In one embodiment, X is CH₂, R³, R⁴ and n are as defined herein, and Y is fluorophenyl substituted with a substituent selected from morpholinylethoxy, —OCH₂CH₂OMe, 2,3-dihydroxypropoxy and 2,2-dimethyl-1,3-dioxolanyl.

In one embodiment, X is CH₂, Y and R⁴ are as defined herein, and R³ is hydrogen. In another embodiment, X is CH₂, Y and R⁴ are as defined herein, and R³ is methyl. In one embodiment, each R⁴ is independently selected from F, Cl, Me, OH, OMe, NH₂, NHMe, CH₂OH, CHF₂ and CF₃. In one embodiment, n is 0. In one embodiment, n is 1. In one embodiment, n is 2.

In one embodiment X is CH₂, R³, R⁴ and n are as defined herein, and Y is a 5-6 membered heteroaryl ring having a ring heteroatom selected from N and S, wherein said heteroaryl ring is optionally substituted with one or more substituents independently selected from halogen, —O(1-4C alkyl), (1-4C)alkyl and NH₂.

In one embodiment, X is CH₂, R³, R⁴ and n are as defined herein, and Y is pyrid-2-yl, pyrid-3-yl, 5-fluoropyrid-3-yl, 2-chloro-5-fluoropyridy-3-yl, 2-methyl-5-fluoropyrid-3-yl, or 2-ethyl-5-fluoropyrid-3-yl. In one embodiment, R³ is hydrogen. In another embodiment, R³ is methyl. In one embodiment, each R⁴ is independently selected from F, Cl, Me, OH, OMe, NH₂, NHMe, CH₂OH, CHF₂ and CF₃. In one embodiment, n is 0. In one embodiment, n is 1. In one embodiment, n is 2.

In one embodiment, X is CH₂, R³, R⁴ and n are as defined herein, and Y is pyridyl optionally substituted with one or more substituents independently selected from halogen and (1-4C)alkyl.

In one embodiment, X is CH₂, R³, R⁴ and n are as defined herein, and Y is pyridyl optionally substituted with one or more substituents independently selected from fluoro, methyl and ethyl.

In one embodiment, X is CH₂, R³, R⁴ and n are as defined herein, and Y is 5-fluoropyrid-3-yl, 2-methyl-5-fluoropyrid-3-yl, or 2-ethyl-5-fluoropyrid-3-yl. In one embodiment, R³ is hydrogen.

In one embodiment, X is CH₂, R³, R⁴ and n are as defined herein, and Y is a pyrid-2-on-3-yl ring optionally substituted with one or more substituents independently selected from halogen and (1-4C)alkyl.

In one embodiment, X is CH₂, R³, R⁴ and n are as defined herein, and Y is a pyrid-2-on-3-yl ring optionally substituted with one or more groups selected from methyl and fluoro. In one embodiment, Y is 5-fluoropyridin-2(1H)-one optionally substituted with methyl. In one embodiment, R³ is hydrogen. In another embodiment, R³ is methyl. In one embodiment, each R⁴ is independently selected from F, Cl, Me, OH, OMe, NH₂, NHMe, CH₂OH, CHF₂ and CF₃. In one embodiment, n is 0. In one embodiment, n is 1. In one embodiment, n is 2.

In one embodiment the ring at the 5-position of Formula I when X is CH₂ include the structures:

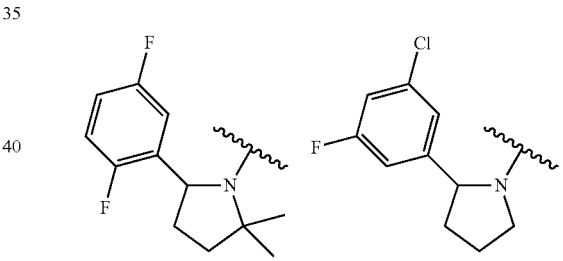

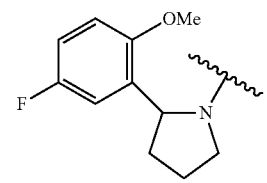

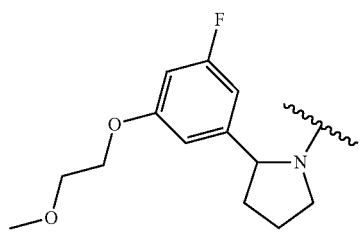

-continued
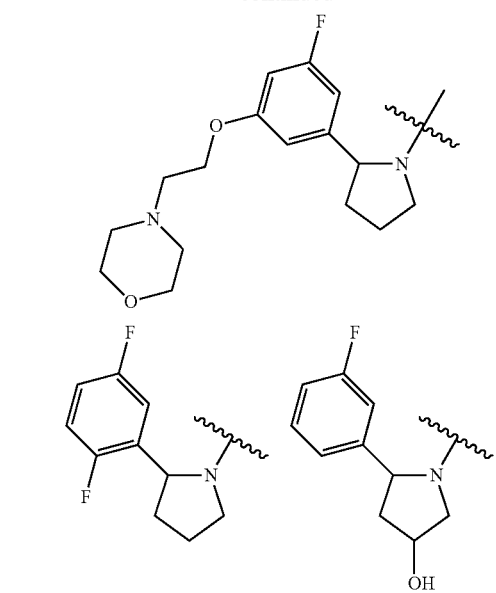
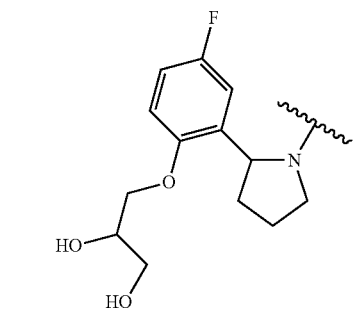
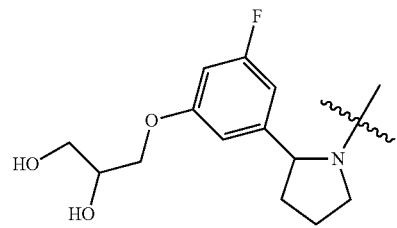
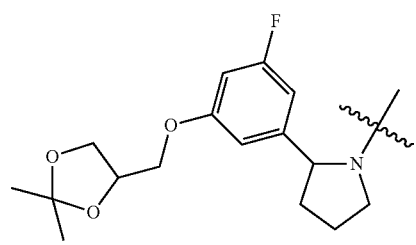
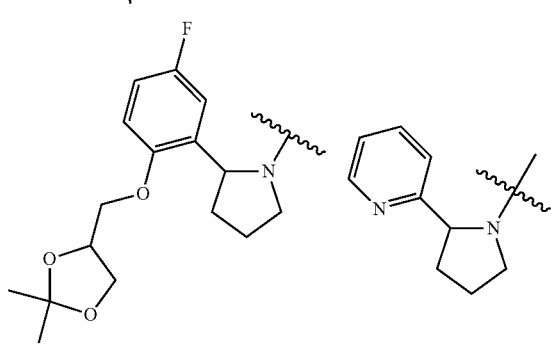
-continued
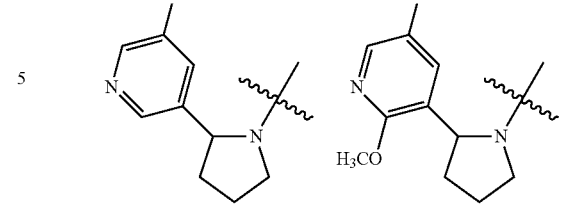
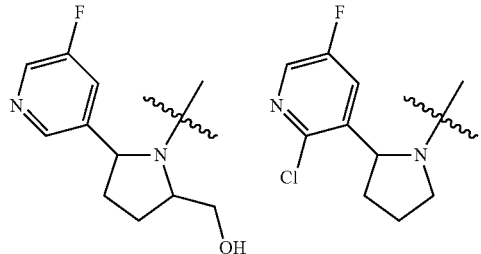
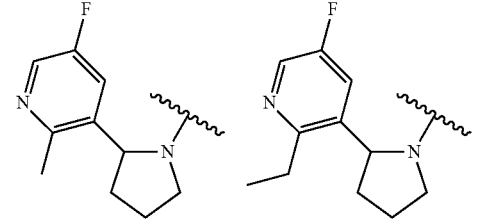
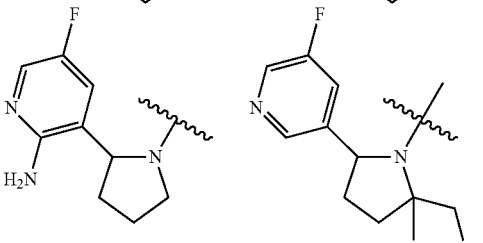
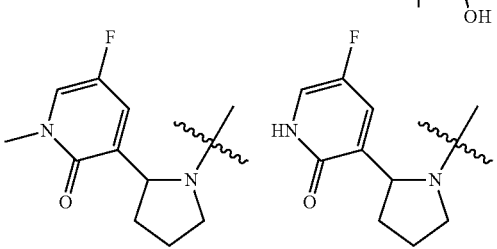
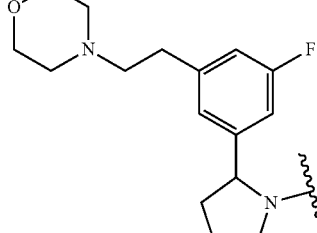
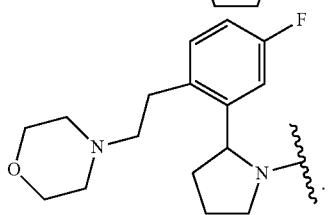
In one embodiment, X is CH$_2$, such that the heterocyclic ring at the 5-position of Formula I has the structure:

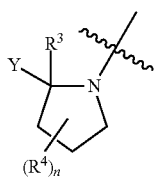

where $R^3$, $R^4$, Y and n are as defined herein. In one embodiment Y is phenyl optionally substituted with one or more substituents independently selected from halogen, -(1-4C)alkoxy, —$CF_3$—$CHF_2$, —O(1-4C alkyl)hetCyc$^3$ or —O(1-4C alkyl)O(1-3C alkyl). In one embodiment, Y is phenyl, 3-fluorophenyl, 2,5-difluorophenyl, 2-difluoromethyl-5-fluorophenyl, 2-trifluoromethyl-5-fluorophenyl, 2-chloro-5-fluorophenyl, 3-chloro-5-fluorophenyl, 2-methoxy-5-fluorophenyl, 3-fluoro-5-methoxyethoxyphenyl, 3-fluoro-5-(2-morpholinylethoxy)phenyl, 5-fluoro-2-(2-morpholinoethoxy)phenyl, or 5-fluoro-2-methoxyethoxyphenyl. In one embodiment, Y is a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl. In one embodiment, $R^3$ is hydrogen. In another embodiment, $R^3$ is methyl. In one embodiment, each $R^4$ is independently selected from F, Cl, Me, OH, OMe, $NH_2$, NHMe, $CH_2OH$, $CHF_2$ and $CF_3$. In one embodiment, Y is pyrid-2-yl, 5-fluoropyrid-3-yl or 2-methoxy-5-fluoropyridy-3-yl. In one embodiment, n is 0, 1 or 2.

Particular examples of the ring at the 5-position of Formula I when X is $CH_2$ include the structures:

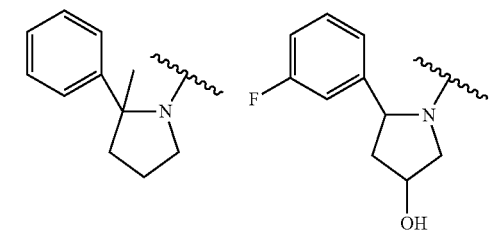

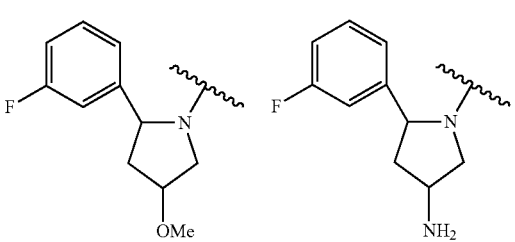

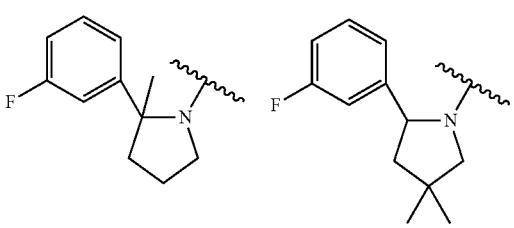

-continued

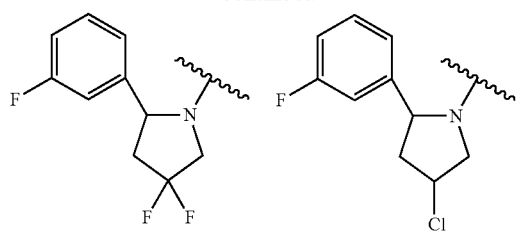

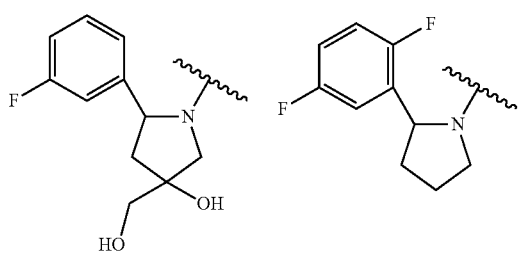

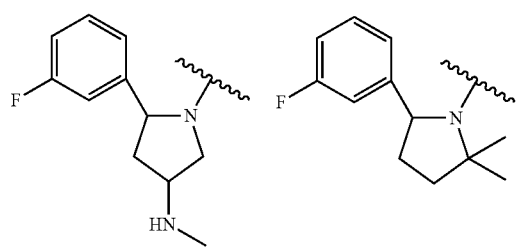

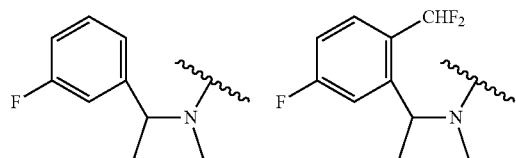

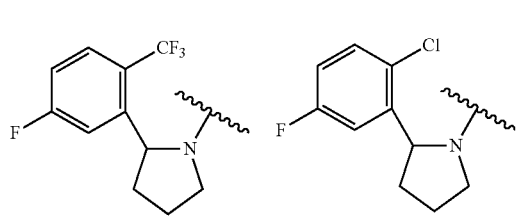

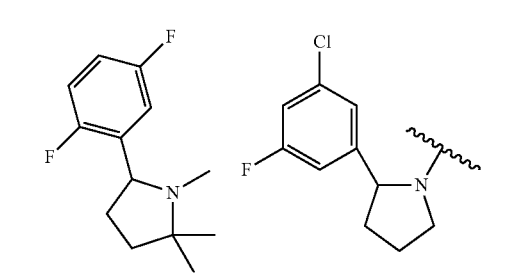

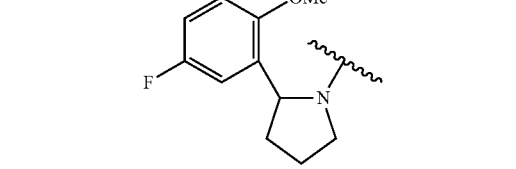

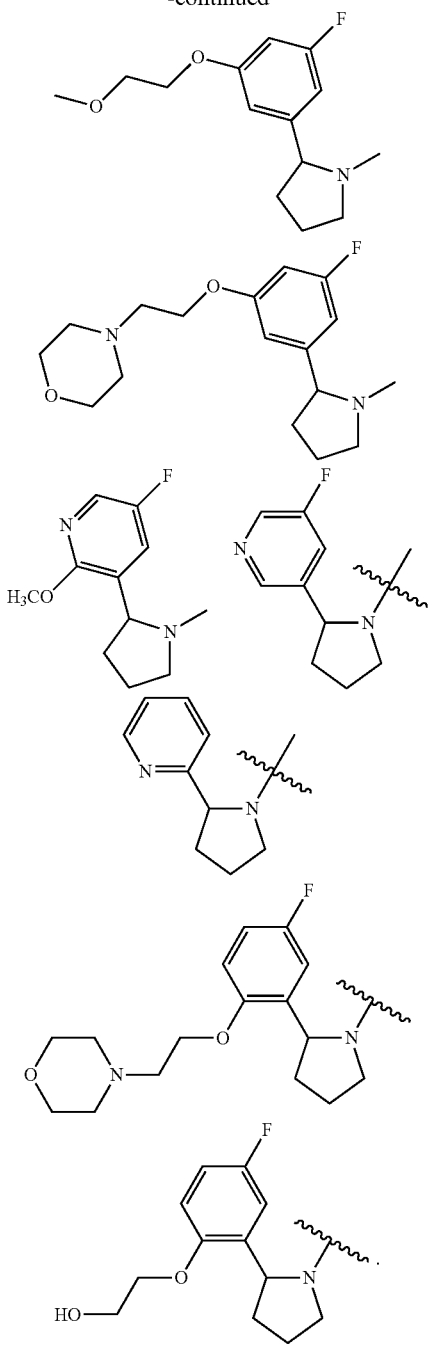

In one embodiment, X is —CH₂CH₂—, such that the heterocyclic ring at the 5-position of Formula I has the structure:

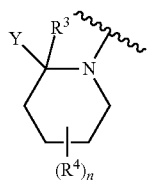

where $R^3$, $R^4$, Y and n are as defined herein. In one embodiment, Y is phenyl optionally substituted with one or more substituents independently selected from halogen, -(1-4C)alkoxy, —CF₃ and —CHF₂. In one embodiment, Y is phenyl or 3-fluorophenyl. In one embodiment, Y is a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl. In one embodiment, Y is pyridyl optionally substituted with one or more F atoms. In one embodiment, $R^3$ is hydrogen. In another embodiment, $R^3$ is methyl. In one embodiment, n is 0, 1 or 2. In one embodiment, n is 0. Particular examples of the ring at the 5-position of Formula I when X is —CH₂CH₂— include the structures:

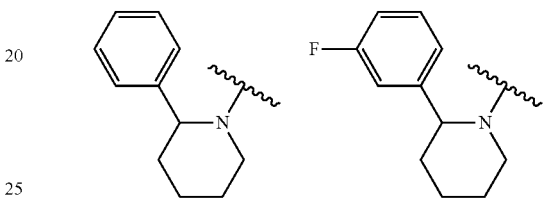

In one embodiment, X is —CH₂O—. In one embodiment, the heterocyclic ring at the 5-position of Formula I has the structure:

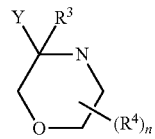

where $R^3$, $R^4$, Y and n are as defined herein. In one embodiment, Y is phenyl optionally substituted with one or more substituents independently selected from halogen, -(1-4C)alkoxy, —CF₃ and —CHF₂. In one embodiment, Y is phenyl optionally substituted with one or more substituents independently selected from —F and -(1-4C)alkoxy. In one embodiment, Y is phenyl, 3-fluorophenyl, 2,5-difluorophenyl, or 2-methoxyphenyl. In one embodiment, Y is a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl, for example one or more halogen atoms. In one embodiment, Y is pyrid-3-yl. In one embodiment, $R^3$ is hydrogen. In another embodiment, $R^3$ is methyl. In one embodiment, n is 0, 1 or 2. Particular examples of the ring at the 5-position of Formula I when X is —CH₂O— include the structures:

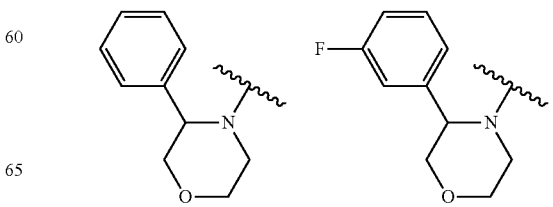

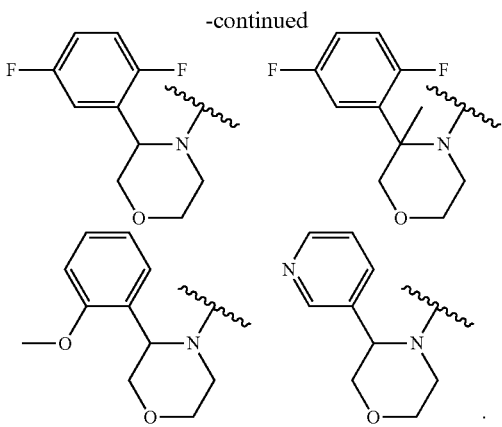

In one embodiment, X is —CH$_2$NR$^d$—. In one embodiment, the heterocyclic ring at the 5-position of Formula I has the structure:

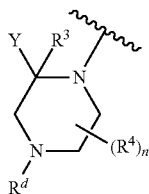

where R$^3$, R$^4$, Y, R$^d$ and n are as defined herein. In one embodiment, R$^d$ is H. In one embodiment, R$^d$ is -(1-4C)alkyl), for example methyl, ethyl, propyl, isopropyl, or butyl. A particular example is methyl. In one embodiment, Y is phenyl optionally substituted with one or more substituents independently selected from halogen, -(1-4C)alkoxy, —CF$_3$ and —CHF$_2$. In one embodiment, Y is a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl. In one embodiment, Y is pyridyl optionally substituted with one or more F atoms. In one embodiment, n is 0. Particular examples of the ring at the 5-position of Formula I when X is —CH$_2$NR$^d$— include the structures:

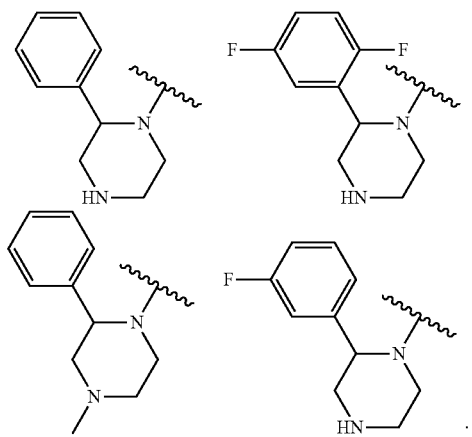

It will be appreciated that certain compounds according to the invention may contain one or more centers of asymmetry and may therefore be prepared and isolated as a mixture of isomers such as a racemic or diastereomeric mixture, or in an enantiomerically or diastereomerically pure form.

The compounds of Formula I also include compounds of Formula Ib

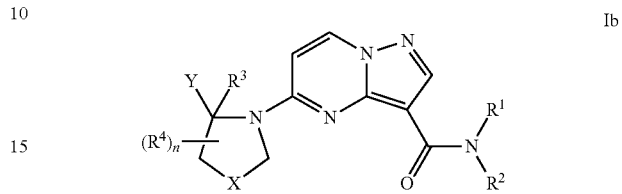

Ib and salts thereof, wherein:
R$^1$ is H;
R$^2$ is H, (1-6C)alkyl, (1-6C)fluoroalkyl, -(1-6C)hydroxyalkyl or -(2-6C)dihydroxyalkyl;
Y is (i) phenyl optionally substituted with one or more substituents independently selected from halogen, -(1-4C) alkoxy, —CF$_3$—CHF$_2$, —O(1-4C alkyl)hetCyc$^3$ and —O(1-4C alkyl)O(1-3C alkyl) or (ii) a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl;
hetCyc$^3$ is a 5-6 membered heterocyclic ring having 1-2 ring heteroatoms independently selected from N and O;
X is CH$_2$ or CH$_2$CH$_2$;
R$^3$ is H;
each R$^4$ is independently selected from halogen, -(1-4C) alkyl, —OH, -(1-4C)alkoxy, —NH$_2$, —NH(1-4C alkyl) and —CH$_2$OH; and
n is 0, 1, or 2.

In certain embodiments of Formula Ib, R$^2$ is H, (1-6C) alkyl, -(1-6C)hydroxyalkyl or -(2-6C)dihydroxyalkyl; Y is phenyl optionally substituted with one or more substituents independently selected from —F, —Cl, —OMe, —CF$_3$, —CHF$_2$, morpholinylethoxy and —OCH$_2$CH$_2$OMe; X is CH$_2$ and n is 0.

In certain embodiments of Formula Ib, R$^2$ is H, methyl, ethyl, isopropyl, tert-butyl, CH$_2$CH$_2$OH, or CH$_2$CH(OH)CH$_2$OH; Y is phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl, 3-chloro-5-fluorophenyl, 3-fluoro-5-(2-morpholinylethoxy) phenyl, 5-fluoro-2-(2-morpholinoethoxy)phenyl, 3-fluoro-5-methoxyethoxyphenyl or 5-fluoro-2-methoxyethoxyphenyl; X is CH$_2$; and n is 0.

In certain embodiments of Formula Ib, R$^2$ is H, (1-6C) alkyl, -(1-6C)hydroxyalkyl or -(2-6C)dihydroxyalkyl; Y is pyridyl optionally substituted with one or more substituents independently selected from F, OMe and Me; X is CH$_2$; and n is 0.

In certain embodiments of Formula Ib, R$^2$ is H, methyl, ethyl, isopropyl, tert-butyl, CH$_2$CH$_2$OH, or CH$_2$CH(OH)CH$_2$OH; Y is pyrid-2-yl, pyrid-3-yl, 5-fluoropyrid-3-yl, 2-methoxy-5-fluoropyridy-3-yl or 2-methyl-5-fluoropyridy-3-yl; X is CH$_2$; and n is 0.

Compounds of Formula I also include compounds of Formula Ic,

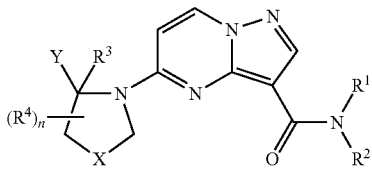

Ic and salts thereof, wherein:
NR¹R² forms a 4-6 membered azacyclic ring optionally substituted with one or more substituents independently selected from (1-6C)alkyl, OH, CO₂H and (1-3C alkyl)CO₂H;
X is CH₂ or CH₂CH₂;
Y is (i) phenyl optionally substituted with one or more substituents independently selected from halogen, (1-4C) alkoxy, —CF₃—CHF₂, —O(1-4C alkyl)hetCyc³ and —O(1-4C alkyl)O(1-3C alkyl) or (ii) a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl;
hetCyc³ is a 5-6 membered heterocyclic ring having 1-2 ring heteroatoms independently selected from N and O;
R³ is H;
each R⁴ is independently selected from halogen, -(1-4C)alkyl, —OH, -(1-4C)alkoxy, —NH₂, —NH(1-4C alkyl) and —CH₂OH; and
n is 0, 1, or 2.

In certain embodiments of Formula Ic, NR¹R² forms 4-6 membered azacyclic ring optionally substituted with one or two groups independently selected from methyl, OH, C(=O)OH or CH₂COOH; Y is phenyl optionally substituted with one or more substituents independently selected from —F, —Cl, —OMe, —CF₃, —CHF₂, morpholinylethoxy and —OCH₂CH₂OMe; X is CH₂; and n is 0.

In certain embodiments of Formula Ic, Y is phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl, 3-chloro-5-fluorophenyl, 3-fluoro-5-(2-morpholinylethoxy)phenyl, 5-fluoro-2-(2-morpholinoethoxy)phenyl, 3-fluoro-5-methoxyethoxyphenyl or 5-fluoro-2-methoxyethoxyphenyl; X is CH₂; n is 0; and NR¹R² forms 4-6 membered azacyclic ring selected from one of the following structures:

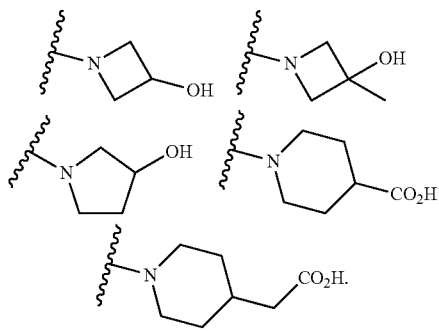

In certain embodiments of Formula Ic, NR¹R² forms 4-6 membered azacyclic ring optionally substituted with one or two groups independently selected from methyl, OH, C(=O)OH or CH₂COOH; Y is pyridyl optionally substituted with one or more substituents independently selected from F, OMe and Me; X is CH₂; and n is 0.

In certain embodiments of Formula Ic, Y is pyrid-2-yl, pyrid-3-yl, 5-fluoropyrid-3-yl, 2-methoxy-5-fluoropyridy-3-yl or 2-methyl-5-fluoropyridy-3-yl; X is CH₂; n is 0; and NR¹R² forms 4-6 membered azacyclic ring selected from one of the following structures:

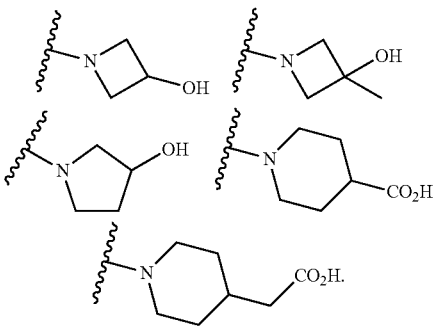

Compounds of Formula I also include compounds of Formula Id:

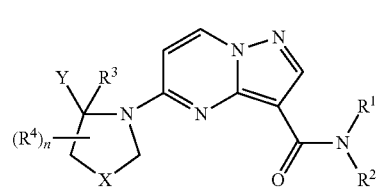

Id and salts thereof, wherein:
R¹ is H;
R² is Cyc¹ or a bridged 7-membered cycloalkyl ring, wherein Cyc¹ is a 3-6 membered cycloalkyl ring optionally substituted with one or more substituents independently selected from -(1-4C alkyl), —OH, —OMe, —CO₂H and -(1-4C alkyl)OH;
Y is (i) phenyl optionally substituted with one or more substituents independently selected from halogen, -(1-4C) alkoxy, —CF₃—CHF₂, —O(1-4C alkyl)hetCyc³ and —O(1-4C alkyl)O(1-3C alkyl) or (ii) a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl;
hetCyc³ is a 5-6 membered heterocyclic ring having 1-2 ring heteroatoms independently selected from N and O;
X is CH₂ or CH₂CH₂;
R³ is H;
each R⁴ is independently selected from halogen, -(1-4C)alkyl, —OH, -(1-4C)alkoxy, —NH₂, —NH(1-4C alkyl) and —CH₂OH; and
n is 0, 1, or 2.

In certain embodiments of Formula Id, R² is Cyc¹ which is optionally substituted with one or more substituents independently selected from methyl, —OH, —CH₂OH and —CO₂H; Y is phenyl optionally substituted with one or more substituents independently selected from —F, —Cl, —OMe, —CF₃, —CHF₂, morpholinylethoxy and —OCH₂CH₂OMe; X is CH₂; and n is 0.

In certain embodiments of Formula Id, Y is phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl, 3-chloro-5-fluorophenyl, 3-fluoro-5-(2-morpholinylethoxy) phenyl, 5-fluoro-2-(2-morpholinoethoxy)phenyl, 3-fluoro-5-methoxyethoxyphenyl or 5-fluoro-2-methoxyethoxyphenyl; X is $CH_2$, n is 0; and $R^2$ is selected from the structures:

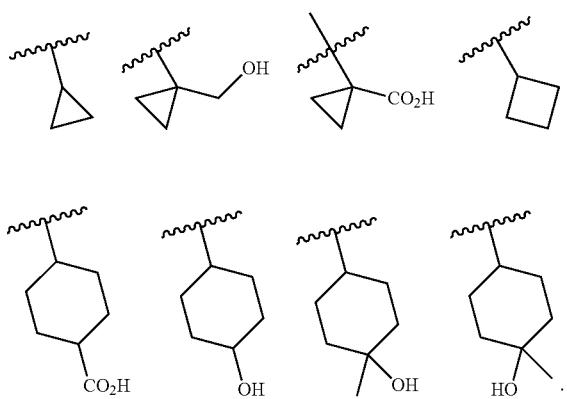

In certain embodiments of Formula Id, $R^2$ is cyclopropyl optionally substituted with one or two substituents independently selected from methyl, —OH, —$CH_2OH$ and —$CO_2H$; Y is phenyl optionally substituted with one or more substituents independently selected from —F, —Cl, —OMe, —$CF_3$, —$CHF_2$, morpholinylethoxy and —$OCH_2CH_2OMe$; X is $CH_2$; and n is 0.

In certain embodiments of Formula Id, $R^2$ is $Cyc^1$ which is optionally substituted with one or more substituents independently selected from methyl, —OH, —$CH_2OH$ and —$CO_2H$; Y is pyridyl optionally substituted with one or more substituents independently selected from F, OMe and Me; X is $CH_2$; and n is 0.

In certain embodiments of Formula Id, Y is pyrid-2-yl, pyrid-3-yl, 5-fluoropyrid-3-yl, 2-methoxy-5-fluoropyridy-3-yl or 2-methyl-5-fluoropyridy-3-yl; X is $CH_2$; n is 0; and $R^2$ is selected from the structures:

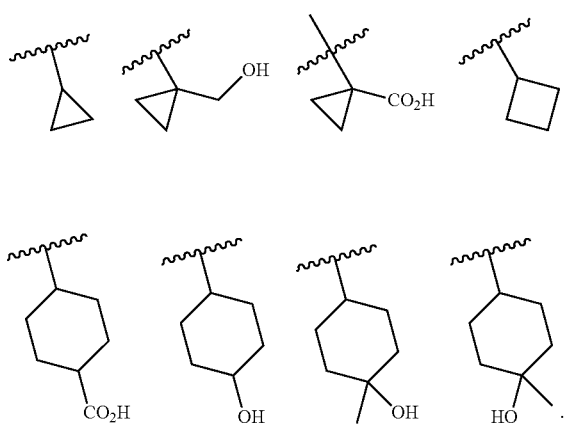

Compounds of Formula I also include compounds of Formula Ie

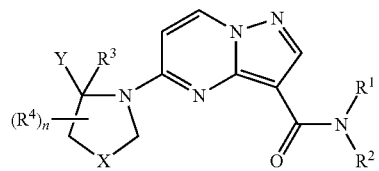

and salts thereof, wherein:

$R^1$ is H;

$R^2$ is -(1-6C alkyl)CN, -(1-6C alkyl)$SO_2NH_2$, -(1-6C alkyl)$NHSO_2$(1-3C alkyl), -(1-6C alkyl)$NH_2$, -(1-6C alkyl)NH(1-4C alkyl), or -(1-6C alkyl)N(1-4C alkyl)$_2$;

Y is (i) phenyl optionally substituted with one or more substituents independently selected from halogen, (1-4C) alkoxy, —$CF_3$—$CHF_2$, —O(1-4C alkyl)$hetCyc^3$ and —O(1-4C alkyl)O(1-3C alkyl), or (ii) a 5-6 membered heteroaryl ring having a ring heteroatom selected from N and S, wherein said heteroaryl ring is optionally substituted with one or more substituents independently selected from halogen and —O(1-4C alkyl);

$hetCyc^3$ is a 5-6 membered heterocyclic ring having 1-2 ring heteroatoms independently selected from N and O;

X is $CH_2$ or $CH_2CH_2$;

$R^3$ is H;

each $R^4$ is independently selected from halogen, -(1-4C) alkyl, —OH, -(1-4C)alkoxy, —$NH_2$, —NH(1-4C alkyl) and —$CH_2OH$; and n is 0, 1, or 2.

In certain embodiments of Formula Ie, Y is phenyl optionally substituted with one or more substituents independently selected from halogen, (1-4C)alkoxy, —$CF_3$—$CHF_2$, —O(1-4C alkyl)$hetCyc^3$ and —O(1-4C alkyl)O(1-3C alkyl); X is $CH_2$; and n is 0.

In certain embodiments of Formula Ie, Y is phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl, 3-chloro-5-fluorophenyl, 3-fluoro-5-(2-morpholinylethoxy) phenyl, 5-fluoro-2-(2-morpholinoethoxy)phenyl, 3-fluoro-5-methoxyethoxyphenyl or 5-fluoro-2-methoxyethoxyphenyl; X is $CH_2$; and n is 0.

In certain embodiments of Formula Ie, Y is a 5-6 membered heteroaryl ring having a ring heteroatom selected from N and S, wherein said heteroaryl ring is optionally substituted with one or more substituents independently selected from halogen and —O(1-4C alkyl); X is $CH_2$; and n is 0.

In certain embodiments of Formula Ie, Y is pyrid-2-yl, pyrid-3-yl, 5-fluoropyrid-3-yl, 2-methoxy-5-fluoropyridy-3-yl or 2-methyl-5-fluoropyridy-3-yl; X is $CH_2$ and n is 0.

Compounds of Formula I also include compounds of Formula If

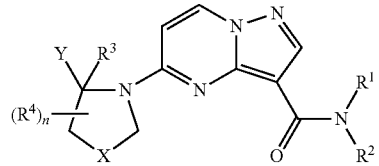

Compounds of Formula I also include compounds of Formula Ie and salts thereof, wherein:

R¹ is H;

R² is -(1-6C alkyl)hetCyc¹, -(1-6C alkyl)hetAr¹, hetAr² or hetCyc²;

hetCyc¹ is a 5-6 membered heterocyclic ring having 1-2 ring heteroatoms independently selected from N and O, wherein hetCyc¹ is optionally substituted with oxo;

hetCyc² is a 6 membered carbon-linked heterocyclic ring having 1-2 ring heteroatoms independently selected from N and O, wherein hetCyc² is optionally substituted with F, SO₂NH₂, or SO₂(1-3C alkyl);

hetAr¹ is a 5-membered heteroaryl ring having 1-2 ring heteroatoms independently selected from N and O and optionally substituted with (1-4C)alkyl;

hetAr² is a 5-6 membered heteroaryl ring having 1-2 ring nitrogen atoms and optionally substituted with one or more substituents independently selected from (1-4C)alkyl;

Y is (i) phenyl optionally substituted with one or more substituents independently selected from halogen, (1-4C)alkoxy, —CF₃—CHF₂, —O(1-4C alkyl)hetCyc³ and —O(1-4C alkyl)O(1-3C alkyl), or (ii) a 5-6 membered heteroaryl ring having a ring heteroatom selected from N and S, wherein said heteroaryl ring is optionally substituted with one or more substituents independently selected from halogen and —O(1-4C alkyl);

X is CH₂ or CH₂CH₂;

R³ is H;

each R⁴ is independently selected from halogen, -(1-4C)alkyl, —OH, -(1-4C)alkoxy, —NH₂, —NH(1-4C alkyl) and —CH₂OH; and n is 0, 1, or 2.

In certain embodiments of Formula If, R² is -(1-6C alkyl)hetAr¹ or hetAr²; Y is (i) phenyl optionally substituted with one or more substituents independently selected from halogen, (1-4C)alkoxy, —CF₃—CHF₂, —O(1-4C alkyl)het-Cyc³ and —O(1-4C alkyl)O(1-3C alkyl); X is CH₂; and n is 0.

In certain embodiments of Formula If, R² is -(1-6C alkyl)hetAr¹ or hetAr²; hetAr¹ is a furanyl, pyrazolyl, or imidazolyl ring optionally substituted with -(1-4C alkyl); hetAr² is a pyridyl or pyrazolo ring optionally substituted with one or more methyl groups; Y is phenyl, 3-fluorophenyl, 2,5-difluorophenyl, 2-methoxyphenyl, 2-chloro-5-fluorophenyl, 2-methoxy-5-fluorophenyl, 2-trifluoromethyl-5-fluorophenyl, 2-difluoromethyl-5-fluorophenyl, 3-chloro-5-fluorophenyl, 3-fluoro-5-(2-morpholinylethoxy)phenyl, 5-fluoro-2-(2-morpholinoethoxy)phenyl, 3-fluoro-5-methoxyethoxyphenyl or 5-fluoro-2-methoxyethoxyphenyl; X is CH₂ and n is 0.

In certain embodiments of Formula If, R² is -(1-6C alkyl)hetAr¹ or hetAr²; Y is a 5-6 membered heteroaryl ring having a ring heteroatom selected from N and S, wherein said heteroaryl ring is optionally substituted with one or more substituents independently selected from halogen and —O(1-4C alkyl); X is CH₂; and n is 0.

In certain embodiments of Formula If, R² is -(1-6C alkyl)hetAr¹ or hetAr²; hetAr¹ is a furanyl, pyrazolyl, or imidazolyl ring optionally substituted with -(1-4C alkyl); hetAr² is a pyridyl or pyrazolo ring optionally substituted with one or more methyl groups; Y is pyrid-2-yl, pyrid-3-yl, 5-fluoropyrid-3-yl, 2-methoxy-5-fluoropyridy-3-yl or 2-methyl-5-fluoropyridy-3-yl; X is CH₂; and n is 0.

In certain embodiments of Formula If, R² is -(1-6C alkyl)hetCyc¹ or hetCyc²; Y is (i) phenyl optionally substituted with one or more substituents independently selected from halogen, (1-4C)alkoxy, —CF₃—CHF₂, —O(1-4C alkyl)hetCyc³ and —O(1-4C alkyl)O(1-3C alkyl); X is CH₂; and n is 0.

In certain embodiments of Formula If, R² is -(1-6C alkyl)hetCyc¹ or hetCyc²; hetCyc¹ is a morpholinyl or imidazolidin-2-one ring; hetCyc² is a piperidinyl or tetrahydropyranyl ring optionally substituted with F, SO₂NH₂, or SO₂(1-3C alkyl); Y is phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl, 3-chloro-5-fluorophenyl, 3-fluoro-5-(2-morpholinylethoxy)phenyl, 5-fluoro-2-(2-morpholinoethoxy)phenyl, 3-fluoro-5-methoxyethoxyphenyl or 5-fluoro-2-methoxyethoxyphenyl; X is CH₂; and n is 0.

In certain embodiments of Formula If, R² is hetCyc²; hetCyc² is a piperidinyl or tetrahydropyranyl ring optionally substituted with F, SO₂NH₂, or SO₂(1-3C alkyl); Y is pyrid-2-yl, pyrid-3-yl, 5-fluoropyrid-3-yl, 2-methoxy-5-fluoropyridy-3-yl or 2-methyl-5-fluoropyridy-3-yl; X is CH₂; and n is 0.

The compounds of Formula I also include compounds of Formula Ig

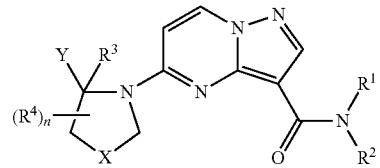

and salts thereof, wherein:

R¹ is H;

R² is —O(1-6C alkyl), —O(3-6C cycloalkyl);

Y is (i) phenyl optionally substituted with one or more substituents independently selected from halogen, -(1-4C)alkoxy, —CF₃—CHF₂, —O(1-4C alkyl)hetCyc³ and —O(1-4C alkyl)O(1-3C alkyl) or (ii) a 5-6 membered heteroaryl ring having a ring heteroatom selected from N and S, wherein said heteroaryl ring is optionally substituted with one or more substituents independently selected from halogen, —O(1-4C alkyl) and (1-4C)alkyl;

hetCyc³ is a 5-6 membered heterocyclic ring having 1-2 ring heteroatoms independently selected from N and O;

X is CH₂ or CH₂CH₂;

R³ is H;

each R⁴ is independently selected from halogen, -(1-4C)alkyl, —OH, -(1-4C)alkoxy, —NH₂, —NH(1-4C alkyl) and —CH₂OH; and n is 0, 1, or 2.

In certain embodiments of Formula Ig, R² is —O(1-6C alkyl), —O(3-6C cycloalkyl); Y is phenyl optionally substituted with one or more substituents independently selected from —F, —Cl, —OMe, —CF₃, —CHF₂, morpholinylethoxy and —OCH₂CH₂OMe; X is CH₂ and n is 0.

In certain embodiments of Formula Ig, R² is OMe, OEt or cyclopropoxy; Y is phenyl, 3-fluorophenyl, 2,5-difluorophenyl, 2-chloro-5-fluorophenyl, 2-methoxyphenyl, 2-methoxy-5-fluorophenyl, 2-trifluoromethyl-5-fluorophenyl, 2-difluoromethyl-5-fluorophenyl, 3-chloro-5-fluorophenyl, 3-fluoro-5-(2-morpholinylethoxy)phenyl, 5-fluoro-2-(2-morpholinoethoxy)phenyl, 3-fluoro-5-methoxyethoxyphenyl or 5-fluoro-2-methoxyethoxyphenyl; X is CH₂; and n is 0.

In certain embodiments of Formula Ig, R² is —O(1-6C alkyl), —O(3-6C cycloalkyl); Y is pyridyl optionally substituted with one or more substituents independently selected from F, OMe and Me; X is $CH_2$; and n is 0.

In certain embodiments of Formula Ig, $R^2$ is OMe, OEt or cyclopropoxy; Y is pyrid-2-yl, pyrid-3-yl, 5-fluoropyrid-3-yl, 2-methoxy-5-fluoropyridy-3-yl or 2-methyl-5-fluoropyridy-3-yl; X is $CH_2$; and n is 0.

The compounds of Formula I also include compounds of Formula Ih

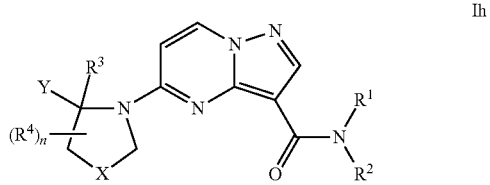

and salts thereof, wherein:

$R^1$ is H or -(1-6C alkyl);

$R^2$ is H, -(1-6C)alkyl, -(1-6C)fluoroalkyl, -(1-6C)hydroxyalkyl, -(2-6C)dihydroxyalkyl, -(1-6C alkyl)CN, -(1-6C alkyl)$SO_2NH_2$, -(1-6C alkyl)$NHSO_2$(1-3C alkyl), -(1-6C alkyl)$NH_2$, -(1-6C alkyl)NH(1-4C alkyl), -(1-6C alkyl)N(1-4C alkyl)$_2$, -(1-6C alkyl)hetCyc$^1$, -(1-6C alkyl)hetAr$^1$, hetAr$^2$, hetCyc$^2$, —O(1-6C alkyl), —O(3-6C cycloalkyl), or Cyc$^1$;

or $NR^1R^2$ forms a 4-6 membered azacyclic ring optionally substituted with one or more substituents independently selected from -(1-6C)alkyl, —OH, —$CO_2H$ and -(1-3C alkyl)$CO_2H$;

Cyc$^1$ is a 3, 4 or 5 membered cycloalkyl ring which is optionally substituted with one or more substituents independently selected from -(1-4C alkyl), —OH, OMe, —$CO_2H$ and -(1-4C alkyl)OH;

hetCyc$^1$ is a 5-6 membered heterocyclic ring having 1-2 ring heteroatoms independently selected from N and O, wherein hetCyc$^1$ is optionally substituted with oxo;

hetCyc$^2$ is a 6 membered carbon-linked heterocyclic ring having 1-2 ring heteroatoms independently selected from N and O, wherein hetCyc$^2$ is optionally substituted with F, $SO_2NH_2$, or $SO_2$(1-3C alkyl);

hetAr$^1$ is a 5-membered heteroaryl ring having 1-2 ring heteroatoms independently selected from N and O and optionally substituted with (1-4C)alkyl;

hetAr$^2$ is a 5-6 membered heteroaryl ring having 1-2 ring nitrogen atoms and optionally substituted with one or more substituents independently selected from (1-4C)alkyl;

X is $CH_2$;

Y is (i) fluorophenyl optionally substituted with a substituent selected from —O(1-4C alkyl)hetCyc$^3$, -(1-4C alkyl)hetCyc$^3$, —O(1-4C alkyl)O(1-3C alkyl) and —O(3-6C dihydroxyalkyl), (ii) pyridyl substituted with one or more substituents independently selected from F, methyl and ethyl, or (iii) 5-fluoropyridin-2(1H)-one optionally substituted with (1-4C)alkyl;

$R^3$ is H or -(1-4C alkyl);

each $R^4$ is independently selected from halogen, -(1-4C) alkyl, —OH, -(1-4C)alkoxy, —$NH_2$, —NH(1-4C alkyl) and —$CH_2OH$; and n is 0, 1, 2, 3, 4, 5 or 6.

In one embodiment of Formula Ih, Y is fluorophenyl optionally substituted with a substituent selected from —O(1-4C alkyl)hetCyc$^3$, -(1-4C alkyl)hetCyc$^3$, —O(1-4C alkyl)O(1-3C alkyl) and —O(3-6C dihydroxyalkyl).

In one embodiment of Formula Ih, Y is pyridyl substituted with one or more substituents independently selected from F, methyl and ethyl.

In one embodiment of Formula Ih, Y is 5-fluoropyridin-2(1H)-one optionally substituted with (1-4C)alkyl.

In one embodiment of Formula Ih, $R^2$ is a 3, 4 or 5 membered cycloalkyl ring which is optionally substituted with one or more substituents independently selected from -(1-4C alkyl), —OH, OMe, —$CO_2H$ and -(1-4C alkyl)OH.

In one embodiment of Formula Ih, $R^2$ is cyclopropyl optionally substituted with methyl, —$CO_2H$ or —$CH_2OH$.

In one embodiment of Formula Ih, $R^4$ is OH, F, methyl, or $CH_2OH$.

In one embodiment of Formula Ih, n is 0, 1 or 2.

In one embodiment of Formula Ih, $R^3$ is hydrogen.

In one embodiment of Formula Ih, $R^1$ is H; $R^2$ is a 3, 4 or 5 membered cycloalkyl ring which is optionally substituted with one or more substituents independently selected from -(1-4C alkyl), —OH, OMe, —$CO_2H$ and -(1-4C alkyl)OH; X is $CH_2$; Y is (i) fluorophenyl optionally substituted with a substituent selected from —O(1-4C alkyl)hetCyc$^3$, —O(1-4C alkyl)O(1-3C alkyl) and —O(3-6C dihydroxyalkyl), (ii) pyridyl substituted with one or more substituents independently selected from F, methyl and ethyl, or (iii) 5-fluoropyridin-2(1H)-one optionally substituted with (1-4C)alkyl; $R^3$ is H, and n is 0.

It will be appreciated that certain compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will also be appreciated that certain compounds of Formula I may be used as intermediates for further compounds of Formula I.

The compounds of Formula I include salts thereof. In certain embodiments, the salts are pharmaceutically acceptable salts. In addition, the compounds of Formula I include other salts of such compounds which are not necessarily pharmaceutically acceptable salts, and which may be useful as intermediates for preparing and/or purifying compounds of Formula I and/or for separating enantiomers of compounds of Formula I.

It will further be appreciated that the compounds of Formula I and their salts may be isolated in the form of solvates, and accordingly that any such solvate is included within the scope of the present invention.

Compounds of the invention may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1H$, $^2H$, $^3H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. The compounds according to the invention therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutics, research reagents, e.g., assay reagents, and diagnostic agents, e.g., in vivo imaging agents. All isotopic variations of the compounds of the present invention, whether radioactive or not, are intended to be encompassed within the scope of the present invention.

The term "(1-6C) alkyl" as used herein refers to saturated linear or branched-chain monovalent hydrocarbon radicals of one to six carbon atoms, respectively. Examples include, but are not limited to, methyl, ethyl, 1-propyl, 2-propyl, 1-butyl, 2-methyl-1-propyl, 2-butyl, 2-methyl-2-propyl, pentyl, and hexyl. The definition of "(1-6C) alkyl" likewise applies to the term "O-(1-6C) alkyl)".

The terms "(1-6C)fluoroalkyl", "(1-6C alkyl)CN", "(1-6C alkyl)SO$_2$NH$_2$", "(1-6C alkyl)NHSO$_2$(1-3C alkyl)", "(1-6C alkyl)NH$_2$", "(1-6C alkyl)NH(1-4C alkyl)", "(1-6C alkyl)N(1-4C alkyl)$_2$", "(1-6C alkyl)hetCyc$^1$" and "(1-6C alkyl) hetAr$^1$" as used herein refer to saturated linear or branched-chain monovalent hydrocarbon radicals of one to six carbon atoms, respectively, wherein one of the hydrogen atoms is replaced with a fluoro atom, or a CN, SO$_2$NH$_2$, NHSO$_2$(1-3C alkyl), NH$_2$, NH(1-4C alkyl), N(1-4C alkyl)$_2$, hetCyc$^1$ or hetAr$^1$ group, respectively.

The term "(1-6C)chloroalkyl" as used herein refers to saturated linear or branched-chain monovalent hydrocarbon radicals of one to six carbon atoms, respectively, wherein one of the hydrogen atoms is replaced with a chloro atom.

The term "(1-6C)hydroxyalkyl" as used herein refers to saturated linear or branched-chain monovalent hydrocarbon radicals of one to six carbon atoms, respectively, wherein one of the hydrogen atoms are replaced with a OH group.

The term "(2-6C)dihydroxyalkyl" as used herein refers to saturated linear or branched-chain monovalent hydrocarbon radicals of two to six carbon atoms, respectively, wherein two of the hydrogen atoms are replaced with a OH group, provided that two OH groups are not on the same carbon.

The term "(1-6C)difluoroalkyl" as used herein refers to saturated linear or branched-chain monovalent hydrocarbon radicals of one to six carbon atoms, respectively, wherein two of the hydrogen atoms are replaced with a fluoro atom.

The term "(1-6C)trifluoroalkyl" as used herein refers to saturated linear or branched-chain monovalent hydrocarbon radicals of one to six carbon atoms, respectively, wherein three of the hydrogen atoms are replaced with a fluoro atom.

The term "(2-6C)chlorofluoroalkyl" as used herein refers to saturated linear or branched-chain monovalent hydrocarbon radicals of two to six carbon atoms, respectively, wherein one of the hydrogen atoms is replaced with a chloro atom and one of the hydrogen atoms is replaced with a fluoro atom.

The term "(2-6C)difluorochloroalkyl" as used herein refers to saturated linear or branched-chain monovalent hydrocarbon radicals of two to six carbon atoms, respectively, wherein one of the hydrogen atoms is replaced with a chloro and two of the hydrogen atoms are replaced with a fluoro atom.

The term "(2-6C)chlorohydroxyalkyl" as used herein refers to a saturated linear or branched-chain monovalent hydrocarbon radicals of two to six carbon atoms, respectively, wherein one of the hydrogen atoms is replaced with a chloro and one of the hydrogen atoms is replaced with OH.

The term "(1-6C alkyl)NHC(=O)O(1-4C alkyl)" as used herein refers to saturated linear or branched-chain monovalent hydrocarbon radicals of one to six carbon atoms, respectively, wherein one of the hydrogen atoms is replaced with a —NHC(=O)O(1-4C alkyl) group.

The phrase "O(1-6C alkyl) which is optionally substituted with halogen, OH or (1-4C)alkoxy" as used herein refers to a saturated linear or branched-chain monovalent alkyl ether radical of one to six carbon atoms wherein the term "alkyl" is as defined herein and the radical is on the oxygen atom, and one of the hydrogen atoms on the carbon chain is optionally replaced with halogen, OH or (1-4C)alkoxy. Examples include methoxy, ethoxy, propoxy, isopropoxy, and butoxy radicals optionally substituted with halogen, OH or (1-4C)alkoxy.

The term "O(3-6C cycloalkyl)" as used herein refers to a cycloalkyl ether radical wherein the term "cycloalkyl" is a 3-6 membered carbocyclic ring and the radical is on the oxygen atom.

The term "-(1-6C alkyl)(3-6C cycloalkyl)" as used herein refers to a saturated linear or branched-chain monovalent hydrocarbon radical of one to six carbon atoms, respectively, wherein one of the hydrogen atoms is replaced with a 3-6 membered carbocyclic ring.

The term "-(1-6Calkyl)(1-4C alkoxy)" as used herein refers to a saturated linear or branched-chain monovalent hydrocarbon radical of one to six carbon atoms, respectively, wherein one of the hydrogen atoms is replaced with an (1-4C)alkoxy group.

The term "-(1-6C hydroxyalkyl)(1-4C alkoxy)" as used herein refers to a saturated linear or branched-chain monovalent hydrocarbon radical of one to six carbon atoms, respectively, wherein one of the hydrogen atoms is replaced with hydroxy (OH) group and one of the hydrogen atoms is replaced with an (1-4C)alkoxy group.

The term "halogen" includes fluoro, chloro, bromo and iodo.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) reacting a corresponding compound of Formula II

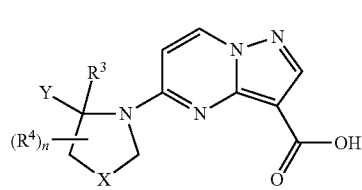

or a reactive derivative thereof with an amine having the formula HNR$^1$R$^2$; or (b) for compounds of Formula I where R$^1$ and R$^2$ are each hydrogen, reacting a compound of Formula III

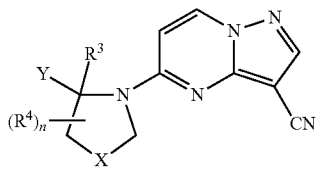

III with an inorganic acid; or (c) for a compound of Formula I where $R^2$ is (alkyl)NHSO$_2$((1-3C alkyl), reacting a compound having the formula IV

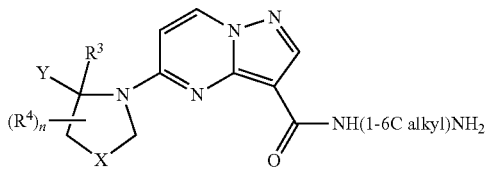

IV with -(1-3C alkyl)SO$_2$Cl; or (d) for compounds of Formula I wherein Y is 5-fluoropyridin-2(1H)-one, treating a corresponding compound having the formula VIII

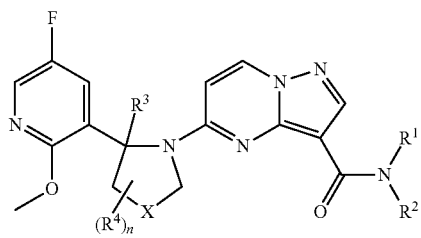

VIII with an acid at elevated temperatures; or (e) for a compound of Formula I wherein $R^2$ is CH$_2$CH(OH)CH$_2$OH, treating a corresponding compound having the formula IX

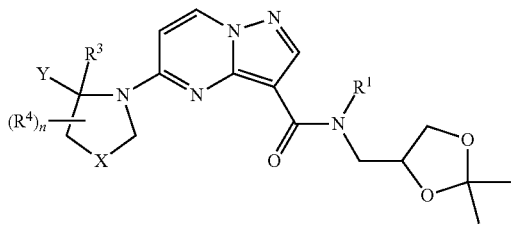

IX with an acid; or (f) for a compound of Formula I wherein Y is fluorophenyl substituted with —OCH$_2$CH(OH)CH$_2$OH, treating a corresponding compound having the formula X

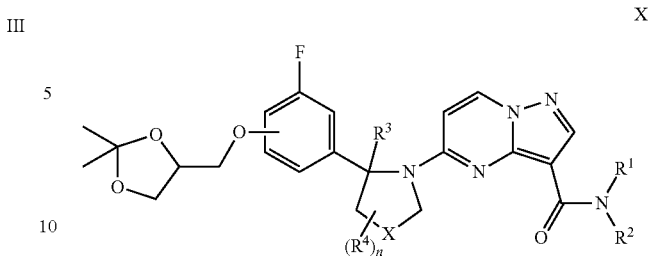

X with an acid; and removing or adding any protecting groups if desired, and forming a salt if desired.

Referring to method (a), the coupling of the compound of formula II with an amine having the formula HNR$^1$R$^2$ may be performed using conventional amide bond formation conditions, for example by reacting an amine with a reactive derivative of a carboxylic acid, for example an acid halide, such as an acid chloride. When reacting the acid form of a compound of Formula II, the reaction may be performed in the presence of a suitable coupling agent such as 2-(1H-7-Azabenzotriazol-1-yl)-1,1,3,3-tetramethyl uronium hexafluorophosphate methanaminium (HATU), O-Benzotriazole-N,N,N',N'-tetramethyl-uronium-hexafluoro-phosphate (HBTU), O-(Benzotriazol-1-yl)-N,N,N',N'-tetramethyl-uronium tetrafluoroborate (TBTU), N,N'-dicyclohexylcarbodiimide (DCC), 1-(3-dimethylaminopropyl)-3-ethylcarboiimide (DIEC) and any other amide coupling reagents well known to persons skilled in the art. Suitable bases include tertiary amine bases such as diisopropylethylamine (DIEA) and triethylamine. Suitable solvents include DMF and CH$_3$CN.

Referring to method (b), suitable acids include strong inorganic acids such as sulfuric acid.

Referring to methods (d), (e) and (f), suitable acids include inorganic acids such as hydrogen halides, for example HCl.

Compounds of formula II may be prepared by coupling a corresponding compound having formula IV

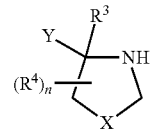

IV with a corresponding compound having formula V

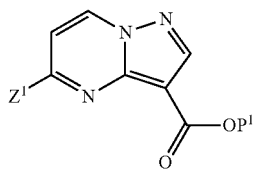

V where $Z^1$ is OH or a leaving group or atom and $P^1$ is H or a carboxyl protecting group. The leaving atom represented by $Z^1$ may be, for example, a halogen atom such as a chlorine atom. In this instance, the reaction is performed in the presence of a base, such as an amine base, for example diisopropylethylamine. The reaction is conveniently performed at elevated temperatures, for example at 100° C. Convenient solvents include alcohols such as butanol. When $Z^1$ is OH the reaction is performed in the presence of a coupling reagent. Suitable coupling reagents when $Z^1$ is OH include benzotriazolyloxy tris [dimethyl-amino] phosphonium hexafluorophosphate (BOP), HATU, HBTU or TBTU. The carboxyl protecting group may be any convenient carboxyl protecting group, for example as described in Greene & Wuts, eds., "Protecting Groups in Organic Synthesis", John Wiley & Sons, Inc. Examples of carboxyl protecting groups include (1-6C)alkyl groups, such as methyl, ethyl and t-butyl.

A compound of Formula V can be prepared by cyclizing a corresponding compound of Formula VI

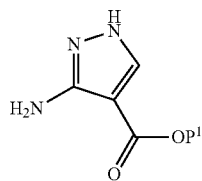

VI with (E)-ethyl 3-ethoxyacrylate to provide the compound of Formula V where $Z^1$ is OH as shown

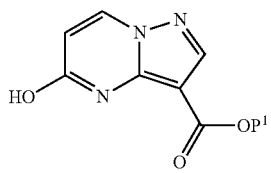

V or when $Z^1$ is a leaving group or atom, converting the hydroxy group into a leaving atom or group, for example by treating the compound of Formula V where $Z^1$ is OH with $POCl_3$.

Compounds of Formula I where the Y group has the absolute configuration shown in FIG. Ia:

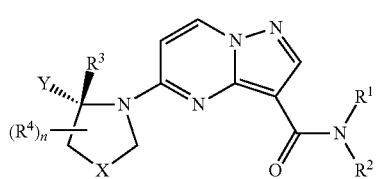

Ia are prepared by coupling a compound of Formula V with a corresponding compound having the formula IV-A

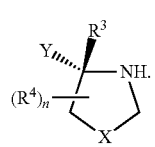

IV-A

The compound of Formula IV-A can be prepared by treating a compound of Formula VII

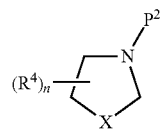

VII where $P^2$ is an amine protecting group, with an alkyl lithium base (for example sec-butyl lithium) in the presence of a chiral complexing agent (for example (−)-sparteine), followed by coupling with a compound having Y—$Z^2$ where $Z^2$ is a leaving group or atom, such as a halogen atom (for example bromine) in the presence of a palladium (II) catalyst and a ligand. Such enantioselective palladium-catalyzed reactions are described in Campos, et al., J. Am. Chem. Soc., 2006, 128:3538-3539. Suitable catalysts include $Pd(OAc)_2$. Suitable ligands include phosphine ligands such as $t-Bu_3P$—$HBF_4$. The amine protecting group may be any convenient amine protecting group, for example as described in Greene & Wuts, eds., "Protecting Groups in Organic Synthesis", John Wiley & Sons, Inc. Examples of amine protecting groups include acyl and alkoxycarbonyl groups, such as t-butoxycarbonyl (BOC).

The compounds of the formulas II, III, and IV are also believed to be novel and are provided as further aspects of the invention.

The ability of compounds of the invention to act as TrkA inhibitors may be demonstrated by the assays described in Examples A and B. The ability of compounds of the invention to act as TrkB inhibitors may be demonstrated by the assay described in Example B.

The selectivity of compounds of Formula I for TrkA versus one or more JAK kinases was determined using the assays describes in Examples C, D, E and F.

It was unexpectedly discovered that compounds of Formula I wherein X is $CH_2$ are particularly selective for inhibiting TrkA activity over inhibiting the activity of one or more JAK kinases, for example JAK2, as shown in Table 1. In one embodiment, compounds of Formula I are 10-30 fold more potent in inhibiting TrkA kinase activity over inhibiting Jak2 kinase activity. In one embodiment, compounds of Formula I are 30-100 fold more potent in inhibiting TrkA kinase activity over inhibiting Jak2 kinase activity. In one embodiment, compounds of Formula I are greater than 100 fold more potent in inhibiting TrkA kinase activity over inhibiting Jak2 kinase activity.

Additionally, it was unexpectedly discovered that compounds of Formula I wherein $R^2$ is a 3, 4 or 5 membered cycloalkyl ring which is optionally substituted with one or more substituents independently selected from -(1-4C alkyl), —OH, OMe, —$CO_2H$ and -(1-4C alkyl)OH are particularly selective for inhibiting TrkA activity over inhibiting the activity of one or more JAK kinases, for example JAK2, as shown in Table 1.

Additionally, it was unexpectedly discovered that compounds of Formula I wherein Y is (i) fluorophenyl optionally substituted with a substituent selected from —O(1-4C alkyl) hetCyc³, —O(1-4C alkyl)O(1-3C alkyl) and —O(3-6C dihydroxyalkyl), (ii) pyridyl substituted with one or more substituents independently selected from F, methyl and ethyl, or (iii) 5-fluoropyridin-2(1H)-one optionally substituted with (1-4C)alkyl, are particularly selective for inhibiting TrkA activity over inhibiting the activity of one or more JAK kinases, for example JAK2, as shown in Table 1.

Compounds of Formula I are useful for treating pain, including chronic and acute pain. Certain compounds which are inhibitors of TrkA and/or TrkB may be useful in the treatment of multiple types of pain including inflammatory pain, neuropathic pain, and pain associated with cancer, surgery, and bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress. The cause can usually be diagnosed and treated, and the pain is confined to a given period of time and severity. In some instances, it can become chronic.

In one embodiment, compounds of Formula I are useful for treating chronic pain. Chronic pain, as defined by the International Association for the Study of Pain, is widely believed to represent disease itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases.

In addition, compounds of Formula I may also be used to treat interstitial cystitis (IC), painful bladder syndrome (PBS), urinary incontinence, asthma, anorexia, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat or prevent said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

As used herein, the term treatment includes prophylaxis as well as treatment of a preexisting condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

Accordingly, another embodiment of this invention provides a method of treating pain in a mammal, comprising administering to said mammal one or more compounds of Formula I or a pharmaceutically acceptable salt thereof in an amount effective to treat or prevent said pain.

Another embodiment of this invention provides a method of treating inflammation in a mammal, comprising administering to said mammal one or more compounds of Formula I or a pharmaceutically acceptable salt thereof in an amount effective to treat or prevent said inflammation.

Another embodiment of this invention provides a method of treating a neurodegenerative disease in a mammal, comprising administering to said mammal one or more compounds of Formula I or a pharmaceutically acceptable salt thereof in an amount effective to treat or prevent said neurodegenerative disease.

Another embodiment of this invention provides a method of treating *Trypanosoma cruzi* infection in a mammal, comprising administering to said mammal one or more compounds of Formula I or a pharmaceutically acceptable salt thereof in an amount effective to treat or prevent said *Trypanosoma cruzi* infection.

The phrase "effective amount" means an amount of compound that, when administered to a mammal in need of such treatment, is sufficient to (i) treat or prevent a particular disease, condition, or disorder which can be treated with an inhibitor of TrkA and/or TrkB, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional drugs that work by the same or a different mechanism of action. Examples include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove, together with a pharmaceutically acceptable diluent or carrier.

According to another embodiment, the present invention provides a compound of Formula I or a pharmaceutically acceptable salt thereof, for use in the treatment of pain in a mammal.

In another embodiment, the present invention provides a compound of Formula I or a pharmaceutically acceptable salt thereof, for use in the treatment of inflammation in a mammal.

In another embodiment, the present invention provides a compound of Formula I or a pharmaceutically acceptable salt thereof, for use in the treatment of infectious diseases, for example *Trypanosoma cruzi* infection, in a mammal.

In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the treatment of a condition selected from pain, cancer, inflammation, neurodegenerative disease or *Trypanosoma cruzi* infection. In one embodiment, the condition is pain. In one embodiment, the condition is cancer. In one embodiment, the condition is inflammation. In one embodiment, the condition is a neurodegenerative disease. In one embodiment, the condition is *Trypanosoma cruzi* infection.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM, methylene chloride), toluene, dimethyl formamide (DMF) and dioxane were purchased from Aldrich in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assays

The ability of compounds of the invention to act as TrkA inhibitors may be demonstrated by the assays described in Examples A and B. The ability of compounds of the invention to act as TrkB inhibitors may be demonstrated by the assay described in Example B.

The selectivity of compounds of Formula I for inhibiting TrkA kinase activity over inhibiting one or more JAK kinases was determined using the assays describes in Examples C, D, E and F.

Example A

TrkA ELISA Assay

An enzyme-linked immunosorbant assay (ELISA) was used to assess TrkA kinase activity in the presence of inhibitors. Immulon 4HBX 384-well microtiter plates (Thermo part #8755) were coated with a 0.025 mg/mL solution of poly (Glu, Ala, Tyr; 6:3:1; Sigma P3899). Various concentrations of test compound, 2.5 nM TrkA (Invitrogen Corp., histidine-tagged recombinant human TrkA, cytoplasmic domain), and 500 µM ATP were incubated for 25 minutes at ambient temperature in the coated plates while shaking. The assay buffer consisted of 25 mM MOPS pH 7.5, 0.005% (v/v) Triton X-100 and 5 mM $MgCl_2$. The reaction mixture was removed from the plate by washing with PBS containing 0.1% (v/v) Tween 20. The phosphorylated reaction product was detected using 0.2 µg/mL of a phosphotyrosine specific monoclonal antibody (clone PY20) conjugated to horseradish peroxidase in conjunction with the TMB Peroxidase Substrate System (KPL). After the addition of 1M phosphoric acid, the chromogenic substrate color intensity was quantitated via absorbance at 450 nm. $IC_{50}$ values were calculated using either a 4 or 5-parameter logistic curve fit and are provided in Table 1.

Example B

TrkA and TrkB Omnia Assay

Trk enzymatic selectivity was assessed using Omnia™ Kinase Assay reagents from Invitrogen Corp. Enzyme (either TrkA or TrkB from Invitrogen Corp.) and test compound (various concentrations) were incubated for 10 minutes at ambient temperature in a 384-well white polypropylene plate (Nunc catalog#267462). Omnia Tyr Peptide #4 (for TrkA) or #5 (for TrkB), as well as ATP, were then added to the plate. Final concentrations were as follows: 20 nM enzyme, 500 µM of ATP for TrkA assay or 1 mM ATP for TrkB assay, 10 µM peptide substrate. The assay buffer consisted of 25 mM MOPS pH 7.5, 0.005% (v/v) Triton X-100 and 5 mM $MgCl_2$. The production of phosphorylated peptide was monitored continuously for 70 minutes using a Molecular Devices FlexStation II$^{384}$ microplate reader (excitation=360 nm; emission=485 nm). Initial rates were calculated from the progress curves. $IC_{50}$ values were calculated from these rates using either a 4 or 5-parameter logistic curve fit.

In each of TrkA and TrkB Omnia assays, compounds of the invention had an average $IC_{50}$ value below 1000 nM. Certain compounds had an average $IC_{50}$ value below 100 nM.

General JAK Kinase Enzyme Inhibition Assay Method

The assays described in Examples C, D, E and F for the determination of JAK1, JAK2, JAK3 and Tyk2 kinase activity, respectively, utilized the Omnia® Kinase fluorescence peptide substrate-based technology (Invitrogen). The specific components of the assay mixture are described in Examples C, D and E. In each of the assays described in Examples C, D and E, $Mg^{2+}$ is chelated upon phosphorylation of the Omnia peptide by the kinase to form a bridge between the chelation-enhanced fluorophore Sox and the phosphate, resulting in an increase in fluorescence emission at 485 nM when excited at 360 nM. The reactions were therefore read at excitation 360 nm and emission was measured at 485 nm every 50 seconds for 45 minutes using a PerkinElmer EnVision Multilabel Plate Reader.

The final buffer conditions for each of the JAK1, JAK2, JAK3 and Tyk2 assays were as follows: 25 mM HEPES, pH 7.4, 10 mM $MgCl_2$, 0.01% Triton X-100 and 1 mM DTT.

IC$_{50}$ Determinations

Compounds were prepared at 50× the final concentration in DMSO by conducting 3-fold serial dilutions from a 500-μM or 1000-μM intermediate dilution to give a 10-point dosing curve having a high dose of 10 or 20 μM. Two-μL aliquots of these were transferred to a fresh plate for a ten-fold intermediate dilution with assay buffer. Five-μL aliquots of the diluted compounds were then transferred to 20-μL of assay mixtures described in Examples C, D, E and F for a final concentration of DMSO of 2%. A standard or reference compound was typically included on each assay plate to validate that plate. For each plate, percent of control (POC) values were calculated for each well according to the following equation:

$$POC = \frac{\text{Sample} - \overline{X}_{min}}{\overline{X}_{max} - \overline{X}_{min}} \times 100,$$

where $\overline{X}_{max}$=Average Uninhibited Controls
$\overline{X}_{min}$=Average Background
IC$_{50}$'s were estimated from the POC's using a standard 4-parameter logistic model:

$$Y = A + \frac{B - A}{1 + \left(\frac{C}{X}\right)^D},$$

where A=Minimum Y (Bottom Asymptote)
B=Maximum Y (Top Asymptote)
C=EC$_{50}$
D=Slope Factor
X=Compound Concentration (nM)
Y=POC
The IC$_{50}$ is defined as the concentration of inhibitor at which the POC equals 50 for the fitted curve.

Example C

Jak1 Inhibition Assay

Compounds of Formula I were screened for their ability to inhibit Jak1 using the general enzyme inhibition assay method, in which the assay mixture contained 50 μM ATP, 8 μM Omnia® Y12 peptide (Catalog #IVGN KPZ3121C; Invitrogen Corporation, Carlsbad, Calif.) and 5 nM Jak1 in a total volume of 20 μL. GST-tagged human Jak1 kinase domain comprising amino acids 866-1154 was purchased from Invitrogen Corporation, Carlsbad, Calif. (catalog #IVGN PV4774). Results are shown in Table 2.

Example D

Jak2 Inhibition Assay

Compounds of Formula I were screened for their ability to inhibit Jak2 using the general enzyme inhibition assay method, in which the assay mixture contained 50 μM ATP, 10 μM Omnia® Y7 peptide (Catalog #IVGN KNZ3071C, Invitrogen Corporation, Carlsbad, Calif.) and 4 nM Jak2 in a total volume of 20 μL. Human Jak2 kinase domain comprising amino acids 808-1132 was purchased from Invitrogen Corporation, Carlsbad, Calif. (catalog #IVGN PV4210). Results are shown in Tables 1 and 2.

Example E

Jak3 Inhibition Assay

Compounds of Formula I were screened for their ability to inhibit Jak3 using the general enzyme inhibition assay method, in which the assay mixture contained 50 μM ATP, 10 μM Omnia® Y7 peptide (Catalog #IVGN KNZ3071C, Invitrogen Corporation, Carlsbad, Calif.) and 1.5 nM Jak3 in a total volume of 20 μL. GST-tagged human Jak3 kinase domain comprising amino acids 781-1124 was purchased from Invitrogen Corporation, Carlsbad, Calif. (catalog #IVGN PV3855). Results are shown in Table 2.

Example F

Tyk2 Inhibition Assay

Compounds of Formula I were screened for their ability to inhibit Tyk2 using the general enzyme inhibition assay method, in which the assay mixture contained 50 μM ATP, 8 μM Omnia® Y12 peptide (Catalog #IVGN KPZ3121C; Invitrogen Corporation, Carlsbad, Calif.) and 1 nM Tyk2 in a total volume of 20 μL. Human Tyk2 kinase domain, comprising amino acids 886 to 1187 with 10 additional histidine residues (histidine tag) on the carboxy terminus, was expressed and purified from bacculovirus in-house at Array BioPharma Inc. (Boulder, Colo.). The histidine tag was cleaved after purification using standard conditions. Results are shown in Table 2.

Table 1 provides IC$_{50}$ values for compounds of the invention when tested in the assays of Examples A and D. The Jak2 enzyme IC$_{50}$ was designated as >1000 nM when >50% inhibition was not observed at a 1000 nM concentration of test compound.

TABLE 1

| Example # | TrkA Enzyme IC$_{50}$ (nM) | Jak2 Enzyme IC$_{50}$ (nM) (% inhibition at 1000 nM) |
|---|---|---|
| 1 | 0.7 | >1000 (39.5) |
| 2 | 0.7 | >1000 (19.1) |
| 3 | 2.3 | >1000 (10.1) |
| 4 | 0.95 | >1000 (18.8) |
| 5 | 0.95 | >1000 (14.2) |
| 6 | 1.55 | >1000 (12.9) |
| 7 | 0.45 | 106.8 (90.0) |
| 8 | 1.1 | >1000 (25.7) |
| 9 | 3.45 | >1000 (4.6) |
| 10 | 1.05 | >1000 (47.5) |
| 11 | 777.1 | >1000 (10.1) |
| 12 | 238.25 | >1000 (4.5) |
| 13 | 0.5 | >1000 (41.4) |

TABLE 1-continued

| Example # | TrkA Enzyme IC$_{50}$ (nM) | Jak2 Enzyme IC$_{50}$ (nM) (% inhibition at 1000 nM) |
|---|---|---|
| 14 | 0.55 | 470 (66.7) |
| 15 | 0.6 | 156 (83.1) |
| 16 | 0.9 | >1000 (31.7) |
| 17 | 2.15 | >1000 (5.6) |
| 18 | 38.3 | >1000 (2.8) |
| 19 | 74.25 | >1000 (3.4) |
| 20 | 0.6 | 257 (78.9) |
| 21 | 2.95 | >1000 (5.8) |
| 22 | 2.1 | >1000 (9.8) |
| 23 | 1.1 | >1000 (10.1) |
| 24 | 3.6 | >1000 (11.5) |
| 25 | 0.4 | >1000 (19.4) |
| 26 | 1.3 | >1000 (9.9) |
| 27 | 214.5 | >1000 (1.3) |
| 28 | 2.8 | >1000 (5.0) |
| 29 | 1.3 | >1000 (13.2) |
| 30 | 1.95 | >1000 (25.7) |
| 31 | 10.6 | >1000 (5.1) |
| 32 | 5.3 | >1000 (8.6) |
| 33 | 1.5 | 23.4 (99.9) |
| 34 | 1.1 | 42.3 (96.9) |
| 35 | 1.2 | 278 (77.4) |
| 36 | 2.1 | >1000 (22.2) |
| 37 | 1.65 | >1000 (25.0) |
| 38 | 1.3 | >1000 (18.2) |
| 39 | 0.7 | >1000 (30.4) |
| 40 | 0.8 | >1000 (41.4) |
| 41 | 28.9 | >1000 (6.0) |
| 42 | 48.3 | >1000 (7.7) |
| 43 | 139 | >1000 (4.2) |
| 44 | 1.5 | 388 (71.5) |
| 45 | 1.4 | 195 (84.0) |
| 46 | 3.3 | >1000 (13.8) |
| 47 | 1.5 | >1000 (37.3) |
| 48 | 0.6 | 429 (72.7) |
| 49 | 4.2 | >1000 (17.2) |
| 50 | 1.23 | 418 (73.7) |
| 51 | 1.18 | 186 (82.5) |
| 52 | 7.4 | >1000 (9.4) |
| 53 | 10.4 | >1000 (8.7) |
| 54 | 2.25 | >1000 (23.0) |
| 55 | 1 | >1000 (24.1) |
| 56 | 2.4 | >1000 (28.0) |
| 57 | 3.93 | >1000 (9.7) |
| 58 | 9.4 | >1000 (4.7) |
| 59 | 16.95 | >1000 (14.5) |
| 60 | 2.25 | >1000 (21.1) |
| 61 | 1.95 | 699 (54.4) |
| 62 | 2.53 | >1000 (35.2) |
| 63 | 4.55 | >1000 (33.1) |
| 64 | 1.6 | 575 (60.3) |
| 65 | 0.6 | >1000 (34.1) |
| 66 | 0.57 | >1000 (24.7) |
| 67 | 5.1 | >1000 (22.3) |
| 68 | 6.6 | >1000 (23.0) |
| 69 | 60.3 | >1000 (6.0) |
| 70 | 23.95 | >1000 (9.0) |
| 71 | 8.65 | >1000 (6.2) |
| 72 | 44.35 | >1000 (11.7) |
| 73 | 48.55 | >1000 (4.9) |
| 74 | 12.6 | >1000 (12.2) |
| 75 | 6.95 | >1000 (15.1) |
| 76 | 90.05 | >1000 (4.8) |
| 77 | 5.37 | >1000 (15.3) |
| 78 | 34.85 | >1000 (5.8) |
| 79 | 1.3 | 698 (54.8) |
| 80 | 1.8 | 869 (50.7) |
| 81 | 1.15 | 666 (54.4) |
| 82 | 2.55 | >1000 (10.7) |
| 83 | 1.77 | >1000 (26.3) |
| 84 | 21.05 | >1000 (2.7) |
| 85 | 9.38 | >1000 (6.0) |
| 86 | 26.7 | >1000 (17.3) |
| 87 | 16.1 | >1000 (37.2) |
| 88 | 6.13 | >1000 (15.1) |
| 89 | 3.6 | >1000 (33.1) |

TABLE 1-continued

| Example # | TrkA Enzyme IC$_{50}$ (nM) | Jak2 Enzyme IC$_{50}$ (nM) (% inhibition at 1000 nM) |
|---|---|---|
| 90 | 0.95 | 472 (67.3) |
| 91 | 3.2 | >1000 (34.9) |
| 92 | 1013.3 | >1000 (0.5) |
| 93 | 5.1 | >1000 (34.7) |
| 94 | 568.2 | >1000 (4.4) |
| 95 | 5.4 | >1000 (19.2) |
| 96 | 342.5 | >1000 (4.8) |
| 97 | 6.2 | >1000 (6.8) |
| 98 | 9.0 | >1000 (23.7) |
| 99 | 7.0 | >1000 (45.8) |
| 100 | 4.7 | >1000 (13.8) |
| 101 | 11.7 | >1000 (26.2) |
| 102 | 5.2 | >1000 (17.3) |
| 103 | 87.8 | >1000 (4.5) |
| 104 | 83.1 | >1000 (6.1) |
| 105 | 25.4 | >1000 (18.7) |
| 106 | 7.7 | >1000 (8) |
| 107 | 16.4 | >1000 (7.1) |
| 108 | 1191.6 | >1000 (2.8) |
| 109 | 36.7 | >1000 (−0.3) |
| 110 | 37.2 | >1000 (−0.5) |
| 111 | 37.8 | >1000 (0.1) |
| 112 | 30.9 | >1000 (3.2) |
| 113 | 3.2 | >1000 (44.6) |
| 114 | 29.9 | >1000 (5) |
| 115 | 15.3 | >1000 (12.6) |
| 116 | 26.2 | >1000 (4.7) |
| 117 | 45.0 | >1000 (−1.4) |
| 118 | 22.5 | >1000 (−4.5) |
| 119 | 131.2 | >1000 (1.7) |
| 120 | 22.8 | >1000 (2.3) |
| 121 | 182.5 | >1000 (3.7) |
| 122 | 33.2 | >1000 (7.4) |
| 123 | 6.4 | >1000 (38.8) |
| 124 | 2.9 | 759 (53.3) |
| 125 | 12.8 | >1000 (6.1) |
| 126 | 218.5 | >1000 (−1) |
| 127 | 469.8 | >1000 (0.2) |
| 128 | 2595.0 | >1000 (1.2) |
| 129 | 8.0 | >1000 (25.2) |
| 130 | 1.7 | >1000 (27.9) |
| 131 | 5.0 | >1000 (14.6) |
| 132 | 44.4 | >1000 (3.7) |
| 133 | 16.0 | >1000 (14.4) |
| 134 | 7.4 | >1000 (3.3) |
| 135 | 142.2 | >1000 (−1) |
| 136 | 26.3 | >1000 (4.8) |
| 137 | 793.7 | >1000 (3.6) |
| 138 | 34.8 | >1000 (10) |
| 139 | 32.7 | >1000 (−0.4) |
| 140 | 0.9 | 76.7 (90.1) |
| 141 | 9.4 | >1000 (9.4) |
| 142 | 12.7 | >1000 (−0.9) |
| 143 | 8.0 | >1000 (7) |
| 144 | not tested | not tested |
| 145 | not tested | not tested |
| 146 | not tested | not tested |
| 147 | 30.8 | >1000 (0.9) |
| 148 | 1.1 | >1000 (44.3) |
| 149 | 6.1 | >1000 (10.2) |
| 150 | 5.7 | >1000 (8.9) |
| 151 | 1.4 | >1000 (35.6) |
| 152 | 18.1 | >1000 (7.6) |
| 153 | 2.1 | >1000 (33.8) |
| 154 | 1.3 | 524 (64.4) |
| 155 | 0.2 | >1000 (33.3) |
| 156 | 2.1 | >1000 (16.1) |
| 157 | 2.8 | >1000 (9.6) |
| 158 | 9.9 | >1000 (14.4) |
| 159 | 4.3 | >1000 (28.9) |
| 160 | 25.6 | >1000 (8.5) |
| 161 | 3.0 | >1000 (27.4) |
| 162 | 2.2 | 444 (66.2) |
| 163 | not tested | not tested |
| 164 | not tested | not tested |
| 165 | 1.1 | >1000 (26.8) |
| 166 | 2.4 | >1000 (13.8) |
| 167 | 2.2 | >1000 (9.8) |

TABLE 1-continued

| Example # | TrkA Enzyme IC$_{50}$ (nM) | Jak2 Enzyme IC$_{50}$ (nM) (% inhibition at 1000 nM) |
|---|---|---|
| 168 | 1.2 | >1000 (23.2) |
| 169 | 0.9 | 759 (51.9) |
| 170 | 11.6 | >1000 (0.7) |
| 171 | 4.7 | >1000 (7.8) |
| 172 | 2.5 | >1000 (11) |
| 173 | 1.5 | >1000 (5.4) |
| 174 | 16.3 | >1000 (6.4) |
| 175 | 12.2 | >1000 (3.8) |
| 176 | 27.2 | >1000 (6.3) |
| 177 | 1.8 | >1000 (26.2) |
| 178 | 2.5 | >1000 (16.9) |
| 179 | 8.5 | >1000 (−0.2) |
| 180 | 12.3 | >1000 (−0.8) |
| 181 | 17.1 | >1000 (5.2) |
| 182 | 11.3 | >1000 (21.2) |
| 183 | 6.9 | >1000 (−0.8) |
| 184 | 7.4 | >1000 (11.8) |
| 185 | 8.6 | >1000 (11.7) |
| 186 | 57.1 | >1000 (10.5) |
| 187 | 61.6 | >1000 (9.1) |
| 188 | 83.0 | >1000 (9.3) |
| 189 | 76.4 | >1000 (4.6) |
| 190 | 2.4 | >1000 (28.4) |
| 191 | 69.5 | >1000 (4.8) |
| 192 | 437.8 | >1000 (0.3) |
| 193 | 15.6 | >1000 (8.4) |
| 194 | 4.7 | >1000 (31.2) |
| 195 | 7.7 | >1000 (16.2) |
| 196 | 6.8 | >1000 (10.6) |
| 197 | 4.8 | >1000 (3.6) |
| 198 | 242.8 | >1000 (1.6) |
| 199 | 3.6 | >1000 (38.8) |
| 200 | 12.7 | >1000 (12.5) |
| 201 | 71.8 | >1000 (3.8) |
| 202 | 19.3 | >1000 (11.5) |
| 203 | not tested | not tested |
| 204 | 16.6 | >1000 (37) |
| 205 | 14.3 | >1000 (7.2) |
| 206 | 3.9 | >1000 (12.6) |
| 207 | 33.3 | >1000 (0.9) |
| 208 | 1.7 | >1000 (21.2) |
| 209 | 17.1 | >1000 (5.4) |
| 210 | 3.3 | >1000 (32.3) |
| 211 | 4.2 | >1000 (19.5) |
| 212 | 38.0 | >1000 (14.2) |
| 213 | 6.8 | >1000 (21.9) |
| 214 | 8.6 | >1000 (29.7) |
| 215 | 15.3 | >1000 (28.3) |
| 216 | 3.1 | 670 (54) |
| 217 | 5.8 | 551 (61.7) |
| 218 | 33.9 | >1000 (24.6) |
| 219 | 187.7 | >1000 (25.5) |
| 220 | 109.9 | >1000 (15.2) |
| 221 | 49.3 | >1000 (−1.2) |
| 222 | not tested | not tested |
| 223 | not tested | not tested |
| 224 | not tested | not tested |
| 225 | 52.4 | >1000 (2.7) |
| 226 | 10.5 | >1000 (100) |
| 227 | 12.3 | 445.8 (62.8) |
| 228 | 13.0 | >1000 (31.9) |
| 229 | 15.9 | >1000 (34.9) |
| 230 | 3.0 | 665.6 (53.3) |
| 231 | 8.7 | >1000 (26.6) |
| 232 | 4.5 | >1000 (31.9) |
| 233 | 75.9 | >1000 (6.7) |
| 234 | 10.7 | >1000 (5.3) |
| 235 | 2.8 | 311 (73.1) |
| 236 | 2.2 | 419 (69.1) |
| 237 | 2.1 | 616 (51.9) |
| 238 | 1.9 | 499 (58.9) |
| 239 | 10.1 | >1000 (15.5) |
| 240 | 11.3 | not tested |
| 241 | 21.8 | not tested |
| 242 | 8.9 | not tested |
| 243 | 9 | not tested |
| 244 | 38.2 | not tested |

Representative compounds of the invention were tested in the four Jak Kinase enzyme assays described in Examples C, D, E and F. The IC$_{50}$ values are shown in Table 2. These compounds were found to be even more selective for inhibiting TrkA kinase activity over inhibiting kinase activity of Jak1, Jak3 and Tyk2 than over inhibiting Jak2.

TABLE 2

| Ex # | TrkA IC$_{50}$ (nM) | Jak1 IC$_{50}$ (nM) (% inhibition at 1000 nM) | Jak2 IC$_{50}$ (nM) (% inhibition at 1000 nM) | Jak3 IC$_{50}$ (nM) (% inhibition at 1000 nM) | Tyk2 IC$_{50}$ (nM) (% inhibition at 1000 nM) |
|---|---|---|---|---|---|
| 30 | 1.9 | >1000 (13.4) | >1000 (30.4) | >1000 (2.9) | >1000 (11.3) |
| 52 | 7.4 | >1000 (8.6) | >1000 (13.0) | >1000 (0.8) | >1000 (13.8) |
| 140 | 0.9 | 546 (64.2) | 76.7 (98.5) | >1000 (20.2) | >1000 (34.8) |
| 93 | 5.1 | >1000 (19.7) | >1000 (42.2) | >1000 (10.6) | >1000 (17.2) |
| 106 | 7.6 | >1000 (8.2) | >1000 (21.0) | >1000 (9.7) | >1000 (14.8) |
| 114 | 17.1 | >1000 (10.9) | >1000 (15.6) | >1000 (8.5) | >1000 (11.4) |
| 181 | 29.8 | >1000 (12.8) | >1000 (18.1) | >1000 (8.9) | >1000 (10.7) |
| 91 | 3.2 | >1000 (20.3) | >1000 (42.1) | >1000 (8.3) | >1000 (14.8) |
| 123 | 6.3 | >1000 (22.0) | >1000 (49.1) | >1000 (8.9) | >1000 (14.4) |
| 124 | 2.9 | >1000 (36.4) | 759 (72.3) | >1000 (7.2) | >1000 (16.2) |
| 190 | 2.4 | >1000 (14.3) | >1000 (33.9) | >1000 (7.2) | >1000 (13.4) |
| 98 | 9.0 | >1000 (8.8) | >1000 (27.8) | >1000 (5.5) | >1000 (9.2) |
| 194 | 4.6 | >1000 (7.4) | >1000 (37.6) | >1000 (2.6) | >1000 (8.1) |

Preparation A

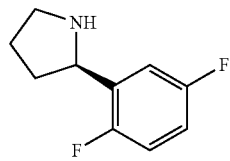 [SMILES: Fc1ccc(F)c([C@H]2CCCN2)c1]

(R)-2-(2,5-difluorophenyl)pyrrolidine

Step A: Preparation of (R)-tert-butyl 2-(2,5-difluorophenyl)pyrrolidine-1-carboxylate A solution of tert-butyl pyrrolidine-1-carboxylate (20 g, 116.8 mmol) and (−)-sparteine (32.9, 140 mmol) in MTBE (360 mL) was cooled to −78° C. and sec-BuLi (100 mL, 140 mmol, 1.4 M in cyclohexane) was introduced drop-wise via cannula, keeping the internal temperature under −70° C. The resulting solution was stirred for 3 hours at −78° C., followed by addition of a solution of ZnCl$_2$ (93.4 mL, 93.4 mmol, 1M in Et$_2$O) drop-wise with rapid stirring, keeping the internal temperature below −65° C. The resulting light suspension was stirred at −78° C. for 30 minutes and then warmed to ambient temperature. The resulting mixture was sequentially charged with 2-bromo-1,4-difluorobenzene (14.5 mL, 128 mmol), Pd(OAc)$_2$ (1.31 g, 5.8 mmol) and t-Bu$_3$P—HBF$_4$ (2.03 g, 7.0 mmol) in one portion. After stirring overnight at ambient temperature, concentrated NH$_4$OH (10.5 mL) was added and the reaction was stirred for 1 hour. The resulting slurry was filtered through Celite and the filter cake washed with Et$_2$O (1 L). The filtrate was washed with a 1M aqueous HCl solution (0.5 L) and brine. The organic layer was filtered and concentrated, and the crude product was purified by silica column chromatography, eluting with 5-10% EtOAc/hexanes to give product (R)-tert-butyl 2-(2,5-difluorophenyl)pyrrolidine-1-carboxylate as yellow oil (23.9 g, 72% yield).

Step B: Preparation of (R)-2-(2,5-difluorophenyl)pyrrolidine

To (R)-tert-butyl 2-(2,5-difluorophenyl)pyrrolidine-1-carboxylate (23.9 g, 84.4 mmol) was added 4N HCl in dioxane (56.2 mL). After stirring at ambient temperature for 2 hours, ether (200 mL) was added and the mixture was stirred for 10 minutes. The resulting slurry was filtered, yielding the title compound hydrochloride salt as a white solid (17.2 g). To obtain the free base, the HCl salt product was dispersed in a mixture of EtOAc (200 mL) and NaOH solution (100 mL, 2 N aq.) The layers were separated and the aqueous layer was extracted with EtOAc. The combined organic extracts were filtered and concentrated to give the desired product as a liquid (13.2 g, 85% yield).

The enantiomeric excess (% ee) of (R)-2-(2,5-difluorophenyl)pyrrolidine was determined as follows: To an ethanol solution of (R)-2-(2,5-difluorophenyl)pyrrolidine was added excess N-(2,4-dinitro-5-fluorophenyl)-L-alanine amide (FDAA, Marfey's reagent). The mixture was heated to reflux for approximately two minutes. After cooling to ambient temperature, the reaction mixture was diluted with acetonitrile and analyzed by HPLC (YMC ODS-AQ 4.6×50 mm 3 m 120A column; mobile phase: 5-95% solvent B in A; solvent A: H$_2$O/1% iPrOH/10 mM ammonium acetate, and solvent B: ACN/1% iPrOH/10 mM ammonium acetate; flow rate: 2 mL/min). The enantiomeric excess (ee %) was determined from the peak areas of the two diastereomeric derivatives formed. A 1:1 racemic standard was prepared according the same procedure described herein, replacing (R)-2-(2,5-difluorophenyl)pyrrolidine with (rac)-2-(2,5-difluorophenyl)pyrrolidine. The ee % of the title compound obtained as described above was determined to be >93%.

Preparation B

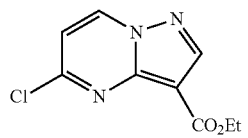 [SMILES: CCOC(=O)c1cnn2ccc(Cl)nc12]

Ethyl 5-chloropyrazolo[1,5-a]pyrimidine-3-carboxylate

Step A: Preparation of ethyl 5-hydroxypyrazolo[1,5-a]pyrimidine-3-carboxylate

Ethyl 3-amino-1H-pyrazole-4-carboxylate (25.0 g, 161 mmol) and (E)-ethyl 3-ethoxyacrylate (35.8 ml, 242 mmol) were mixed in DMF (537 mL). Cesium carbonate (78.7 g, 242 mmol) was added and the mixture heated to 110° C. for 15 hours. The reaction mixture was cooled to ambient temperature and acidified with HOAc to pH 4. The resultant precipitate was filtered and washed with water and EtOAc, yielding the title compound as a fluffy white solid. Additional material was obtained by an aqueous workup. The filtrate was concentrated to remove the DMF, was diluted in EtOAc (500 mL) and washed with H₂O. The resultant precipitate in the EtOAc layer was filtered and washed with water and EtOAc to obtain additional product. The solids were pooled and dried in vacuum to afford ethyl 5-hydroxypyrazolo[1,5-a]pyrimidine-3-carboxylate (33.3 g, 100% yield) as a fluffy white solid. MS (apci) m/z=206.2 (M–H).

Step B: Preparation of ethyl 5-chloropyrazolo[1,5-a]pyrimidine-3-carboxylate

Ethyl 5-hydroxypyrazolo[1,5-a]pyrimidine-3-carboxylate (22.7 g, 110 mmol) was suspended in phosphoryl trichloride (100 mL) and heated to reflux. After heating for 2 hours, the reaction mixture was cooled and concentrated to remove the excess POCl₃. The residue was diluted in DCM (100 mL) and slowly added to a flask containing ice water. The mixture was separated and the aqueous layer extracted with DCM. The combined organics were dried with MgSO₄, filtered and concentrated to afford ethyl 5-chloropyrazolo[1,5-a]pyrimidine-3-carboxylate (24.2 g, 97.6% yield) as a pale yellow solid. MS (apci) m/z=225.9 (M+H).

Preparation C

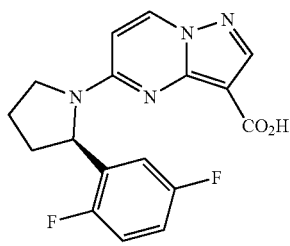 [SMILES: O=C(O)c1cnn2ccc(N3CCC[C@@H]3c3cc(F)ccc3F)nc12]

(R)-5-(2-(2,5-difluorophenyl)pyrrolidin-1-yl)pyrazolo[1,5-a]pyrimidine-3-carboxylic acid Step A: Preparation of (R)-ethyl 5-(2-(2,5-difluorophenyl)pyrrolidin-1-yl)pyrazolo[1,5-a]pyrimidine-3-carboxylate A mixture of ethyl 5-chloropyrazolo[1,5-a]pyrimidine-3-carboxylate (Preparation B, 2.00 g, 8.86 mmol), (R)-2-(2,5-difluorophenyl)pyrrolidine (Preparation A, 1.62 g, 8.86 mmol), diisopropylethylamine (3.09 mL, 17.7 mmol) and butan-1-ol (2.95 ml, 8.86 mmol) was heated at 100° C. for 15 hours. The reaction mixture was cooled to ambient temperature and was diluted with EtOAc (30 mL) and water (10 mL). Undissolved solid was filtered and washed with Et₂O to afford the title compound as a light orange solid (2.13 g). The organic layer was separated from the filtrate, washed with brine (10 mL) and dried over MgSO₄. The solution was filtered and concentrated to provide additional solid that was purified by silica chromatography using gradient elution with 50-100% EtOAc/hexanes. This afforded the title compound (0.50 g) as a light yellow solid. The combined yield was 2.63 g, 79.7%. MS (apci) m/z=373.1 (M+H).

Step B: Preparation of (R)-5-(2-(2,5-difluorophenyl)pyrrolidin-1-yl)pyrazolo[1,5-a]pyrimidine-3-carboxylic acid (R)-ethyl 5-(2-(2,5-difluorophenyl)pyrrolidin-1-yl)pyrazolo[1,5-a]pyrimidine-3-carboxylate (2.13 g, 5.72 mmol) was suspended in EtOH (28.6 mL) and heated at 90° C. for 20 min (homogeneous). 1M aq. LiOH (11.4 mL, 11.4 mmol) was added and the reaction mixture was heated for 15 hours at 90° C. After cooling, the reaction mixture was concentrated, diluted with water and washed with EtOAc to remove any unreacted starting material. The aqueous layer was then acidified to pH 1 using 2N HCl. After extracting with DCM and EtOAc, the combined organic fractions were dried with MgSO₄, filtered and concentrated to afford (R)-5-(2-(2,5-difluorophenyl)pyrrolidin-1-yl)pyrazolo[1,5-a]pyrimidine-3-carboxylic acid (1.82 g, 92.4%) as a light yellow solid. MS (apci) m/z=345.0 (M+H).

Preparation D

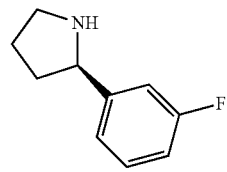 [SMILES: Fc1cccc([C@H]2CCCN2)c1]

(R)-2-(3-fluorophenyl)pyrrolidine

Prepared by the method of Preparation A, substituting 2-bromo-1,4-difluorobenzene with 1-bromo-3-fluorobenzene in Step A. MS (apci) m/z=166.0 (M+H). The ee % of the title compound was determined to be 94%.

Preparation E

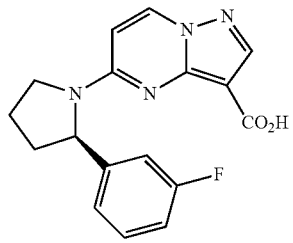 [SMILES: O=C(O)c1cnn2ccc(N3CCC[C@@H]3c3cccc(F)c3)nc12]

(R)-5-(2-(3-fluorophenyl)pyrrolidin-1-yl)pyrazolo[1,5-a]pyrimidine-3-carboxylic acid Step A: Preparation of (R)-ethyl 5-(2-(3-fluorophenyl)pyrrolidin-1-yl)pyrazolo[1,5-a]pyrimidine-3-carboxylate Prepared according to the method of Preparation C, substituting (R)-2-(2,5-difluorophenyl)pyrrolidine in Step A with (R)-2-(3-fluorophenyl)pyrrolidine. MS (apci) m/z=355.0 (M+H).

Step B: Preparation of (R)-5-(2-(3-fluorophenyl)pyrrolidin-1-yl)pyrazolo[1,5-a]pyrimidine-3-carboxylic acid (R)-ethyl 5-(2-(3-fluorophenyl)pyrrolidin-1-yl)pyrazolo[1,5-a]pyrimidine-3-carboxylate (0.76 g, 2.14 mmol) was suspended in EtOH (10.7 mL) and the mixture was heated at 90° C. for 20 minutes (homogeneous). 1M aqueous LiOH (4.29 ml, 4.29 mmol) was added and the reaction mixture was heated for 15 hours at 90° C. After cooling, the reaction mixture was concentrated, diluted with water and washed with EtOAc to remove any unreacted starting material. The aqueous layer was then acidified to pH 4 using 2N HCl. After extracting with DCM and EtOAc, the combined organic layers were dried with MgSO₄, filtered and concentrated to afford (R)-5-(2-(3-fluorophenyl)pyrrolidin-1-yl)pyrazolo[1,5-a]pyrimidine-3-carboxylic acid (0.60 g, 85.7% yield) as a glassy yellow solid. MS (apci) m/z=327.0 (M+H).

Preparation F

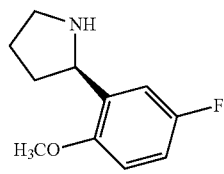 [SMILES: COc1ccc(F)cc1[C@H]1CCCN1]

(R)-2-(5-fluoro-2-methoxyphenyl)pyrrolidine

Prepared by the method of Preparation A, substituting 2-bromo-1,4-difluorobenzene with 2-bromo-4-fluoro-1-methoxybenzene in Step A. MS (apci) m/z=196.1 (M+H). The ee % of the title compound was determined to be >99%.

Preparation G

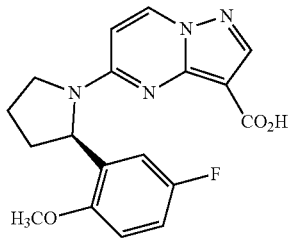 [SMILES: COc1ccc(F)cc1[C@H]1CCCN1c1ccn2ncc(C(=O)O)c2n1]

(R)-5-(2-(5-fluoro-2-methoxyphenyl)pyrrolidin-1-yl)pyrazolo[1,5-a]pyrimidine-3-carboxylic acid In a sealed tube, ethyl 5-chloropyrazolo[1,5-a]pyrimidine-3-carboxylate (Preparation B, 500 mg, 2.22 mmol), (R)-2-(5-fluoro-2-methoxyphenyl)pyrrolidine hydrochloride salt (513 mg, 2.22 mmol), and diisopropylethylamine (0.774 mL, 4.43 mmol) were combined in isopropanol (2 mL) and heated at 160° C. for 3 days. 2N NaOH (6 mL) and MeOH (5 mL) were added and the reaction mixture stirred at ambient temperature for 24 hours, followed by heating to 40° C. for 3 hours. The reaction was partially concentrated, treated with saturated aqueous NH₄Cl (10 mL) and the mixture extracted with EtOAc. The combined organic extracts were filtered, concentrated and the residue purified by reverse phase chromatography eluting with 0-60% acetonitrile/water to yield the title compound as a pink solid (254 mg, 32.2% yield). MS (apci) m/z=357.0 (M+H).

Preparation H

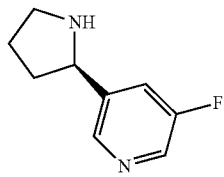 [SMILES: Fc1cncc([C@H]2CCCN2)c1]

(R)-3-fluoro-5-(pyrrolidin-2-yl)pyridine

Prepared by the method of Preparation A, substituting 2-bromo-1,4-difluorobenzene with 3-bromo-5-fluoropyridine in Step A. MS (apci) m/z=167.1 (M+H). The ee % of the title compound was determined to be 92%.

Preparation I

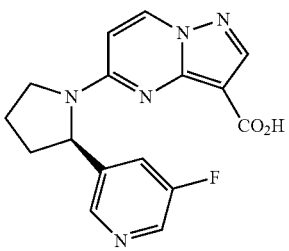 [SMILES: O=C(O)c1cnn2ccc(N3CCC[C@@H]3c3cncc(F)c3)nc12]

(R)-5-(2-(5-fluoropyridin-3-yl)pyrrolidin-1-yl)pyrazolo[1,5-a]pyrimidine-3-carboxylic acid Step A: Preparation of ethyl 5-(2-(5-fluoropyridin-3-yl)pyrrolidin-1-yl)pyrazolo[1,5-a]pyrimidine-3-carboxylate Ethyl 5-chloropyrazolo[1,5-a]pyrimidine-3-carboxylate (Preparation B; 0.50 g, 2.22 mmol), (R)-3-fluoro-5-(pyrrolidin-2-yl)pyridine dihydrochloride (0.53 g, 2.22 mmol) and diisopropylethylamine (1.46 mL, 8.86 mmol) were combined in isopropanol (2 mL) and heated at 95° C. for 70 hours. The crude product was purified by reverse phase chromatography, eluting with 0-50% acetonitrile/water to yield the title compound (540 mg, 68.6% yield). MS (apci) m/z=356.0 (M+H).

Step B: Preparation of 5-(2-(5-fluoropyridin-3-yl)pyrrolidin-1-yl)pyrazolo[1,5-a]pyrimidine-3-carboxylic acid Ethyl 5-(2-(5-fluoropyridin-3-yl)pyrrolidin-1-yl)pyrazolo[1,5-a]pyrimidine-3-carboxylate (0.540 g, 1.52 mmol) was dissolved in MeOH (20 mL) and treated with 1N NaOH (13 mL). After stirring for 5 days, citric acid (solid) was added to acidify the mixture to pH 4-5. Saturated aqueous NaCl (10 mL) was added and the reaction mixture extracted with DCM and EtOAc. The combined organic layers were combined to afford 5-(2-(5-fluoropyridin-3-yl)pyrrolidin-1-yl)pyrazolo[1,5-a]pyrimidine-3-carboxylic acid (0.49 g, 99% yield). MS (apci) m/z=328.0 (M+H).

Preparation J

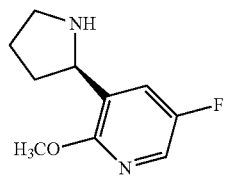 [SMILES: COc1ncc(F)cc1[C@H]1CCCN1]

(R)-5-fluoro-2-methoxy-3-(pyrrolidin-2-yl)pyridine

Step A: Preparation of 3-bromo-5-fluoro-2-methoxypyridine

3-Bromo-5-fluoropyridin-2(1H)-one (10.0 g, 52.1 mmol) and $Ag_2CO_3$ (10.0 g, 36.5 mmol) were combined in toluene (100 mL) and iodomethane (3.89 mL, 62.5 mmol) was added drop-wise. The reaction was stirred at ambient temperature overnight, filtered through Celite and the solids were washed with toluene. The filtrate was concentrated and the residue was purified on a silica gel column (5-25% EtOAc/hexanes) to afford 3-bromo-5-fluoro-2-methoxypyridine (4.70 g, 43.8%) as a clear oil.

Step B: Preparation of (R)-5-fluoro-2-methoxy-3-(pyrrolidin-2-yl)pyridine

Prepared by the method of Preparation A, substituting 2-bromo-1,4-difluorobenzene with 3-bromo-5-fluoro-2-methoxypyridine in Step A. MS (apci) m/z=197.1 (M+H). The ee % of the title compound was determined to be 98%.

Preparation K

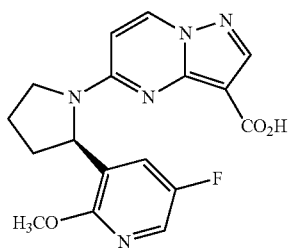 [SMILES: COc1ncc(F)cc1[C@H]1CCCN1c1ccn2ncc(C(=O)O)c2n1]

(R)-5-(2-(5-fluoro-2-methoxypyridin-3-yl)pyrrolidin-1-yl)pyrazolo[1,5-a]pyrimidine-3-carboxylic acid

Step A: Preparation of (R)-ethyl 5-(2-(5-fluoro-2-methoxypyridin-3-yl)pyrrolidin-1-yl)pyrazolo[1,5-a]pyrimidine-3-carboxylate Ethyl 5-chloropyrazolo[1,5-a]pyrimidine-3-carboxylate (Preparation B, 0.75 g, 3.32 mmol), (R)-5-fluoro-2-methoxy-3-(pyrrolidin-2-yl)pyridine dihydrochloride (0.984 g, 3.66 mmol), diisopropylethylamine (2.32 mL, 13.3 mmol) and n-butanol (1.11 mL) were heated at 90° C. for 48 hours. The reaction mixture was diluted with EtOAc and the mixture was washed with water, brine and saturated NaHCO$_3$. The organic layer was dried with MgSO$_4$, filtered and concentrated afford a dark orange oil. The oil was purified by silica chromatography, eluting with a 50-80% EtOAc/Hexane gradient, to afford (R)-ethyl 5-(2-(5-fluoro-2-methoxypyridin-3-yl)pyrrolidin-1-yl)pyrazolo[1,5-a]pyrimidine-3-carboxylate (0.72 g, 56.2%) as a yellow foam. MS (apci) m/z=386.0 (M+H).

Step B: (R)-5-(2-(5-fluoro-2-methoxypyridin-3-yl)pyrrolidin-1-yl)pyrazolo[1,5-a]pyrimidine-3-carboxylic acid To a suspension of (R)-ethyl 5-(2-(5-fluoro-2-methoxypyridin-3-yl)pyrrolidin-1-yl)pyrazolo[1,5-a]pyrimidine-3-carboxylate (0.72 g, 1.868 mmol) in MeOH (9.34 mL) was added 1N LiOH (3.74 ml, 3.74 mmol) and the reaction mixture heated to 70° C. for 15 hours. After cooling, the reaction mixture was concentrated and the resulting residue diluted in water. After acidifying with citric acid (solid), the aqueous layer was extracted with DCM. The combined organics were dried with MgSO$_4$, filtered and concentrated to afforded (R)-5-(2-(5-fluoro-2-methoxypyridin-3-yl)pyrrolidin-1-yl)pyrazolo[1,5-a]pyrimidine-3-carboxylic acid (0.67 g, 100%) as a yellow solid. MS (apci) m/z=357.9 (M+H).

Preparation L

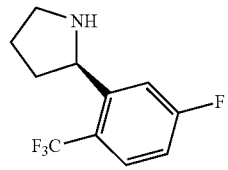 [SMILES: Fc1ccc(C(F)(F)F)c([C@H]2CCCN2)c1]

(R)-2-(5-fluoro-2-(trifluoromethyl)phenyl)pyrrolidine

Prepared by the method of Preparation A, substituting 2-bromo-1,4-difluorobenzene with 2-bromo-4-fluoro-1-(trifluoromethyl)benzene in Step A. MS (apci) m/z=234.1 (M+H). The ee % of the title compound was determined to be 90%.

Preparation M

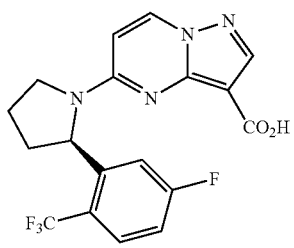 [SMILES: O=C(O)c1cnn2ccc(N3CCC[C@@H]3c3cc(F)ccc3C(F)(F)F)nc12]

(R)-5-(2-(5-fluoro-2-(trifluoromethyl)phenyl)pyrrolidin-1-yl)pyrazolo[1,5-a]pyrimidine-3-carboxylic acid Step A: Preparation of (R)-ethyl 5-(2-(5-fluoro-2-(trifluoromethyl)phenyl) pyrrolidin-1-yl)pyrazolo[1,5-a]pyrimidine-3-carboxylate Ethyl 5-chloropyrazolo[1,5-a]pyrimidine-3-carboxylate (Preparation B, 0.51 g, 2.26 mmol), (R)-2-(5-fluoro-2-(trifluoromethyl)phenyl)pyrrolidine hydrochloride (0.610 g, 2.26 mmol) and diisopropylethylamine (1.12 mL, 6.78 mmol) were suspended in isopropanol (2.5 mL) and heated to 120° C. for 24 hours. The reaction mixture was purified by reverse phase chromatography eluting with 0-75% acetonitrile/water to yield the title compound (0.92 g, 96.4% yield). MS (apci) m/z=423.0.0 (M+H).

Step B: Preparation of 5-(2-(5-fluoro-2-(trifluoromethyl)phenyl)pyrrolidin-1-yl)pyrazolo[1,5-a]pyrimidine-3-carboxylic acid (R)-ethyl 5-(2-(5-fluoro-2-(trifluoromethyl) phenyl)pyrrolidin-1-yl)pyrazolo[1,5-a]pyrimidine-3-carboxylate (0.92 g, 2.2 mmol) was combined with 1N NaOH (25 mL) and MeOH (40 mL). The reaction mixture was stirred at ambient temperature for 20 hours, followed by heating to 40° C. until complete. Citric acid (solid) was added until the mixture was pH 4-5. Brine (10 mL) was added and this was extracted with DCM and EtOAc. The combined organic layers were concentrated and the crude product was purified by reverse phase silica gel column chromatography eluting with 0-60% acetonitrile/water to yield 5-(2-(5-fluoro-2-(trifluoromethyl)phenyl)pyrrolidin-1-yl)pyrazolo[1,5-a]pyrimidine-3-carboxylic acid (0.45 g, 52%). MS (apci) m/z=395.0 (M+H).

Preparation N

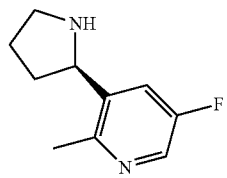

(R)-5-fluoro-2-methyl-3-(pyrrolidin-2-yl)pyridine

Step A: Preparation of 3-bromo-5-fluoro-2-methylpyridine 2,3-Dibromo-5-fluoropyridine (5.0 g, 19.6 mmol), Pd(PPh₃)₄ (1.13 g, 0.98 mmol) and methyl boronic acid (3.52 g, 58.9 mmol) were combined in dioxane (50 mL) then treated with $K_2CO_3$ (8.13, 58.9 mmol) and water (10 mL). The mixture was purged with $N_2$ then heated to 110° C. in a sealed vessel for 16 hours. The cooled mixture was partitioned between water (100 mL) and EtOAc (50 mL) and the layers separated. The aqueous layer was extracted with EtOAc (2×50 mL) and the combined organic phases were washed with brine (50 mL), dried over $Na_2SO_4$, filtered and concentrated. The residue was purified by silica gel column chromatography eluting with 1-3% EtOAc/hexanes to afford the product as a white solid (1.20 g, 32% yield). MS (apci) m/z=190.2 (M+).

Step B: Preparation of (R)-5-fluoro-2-methyl-3-(pyrrolidin-2-yl)pyridine

Prepared by the method of Preparation A, substituting 2-bromo-1,4-difluorobenzene with 3-bromo-5-fluoro-2-methylpyridine in Step A. MS (apci) m/z=181.1 (M+H).

Preparation O

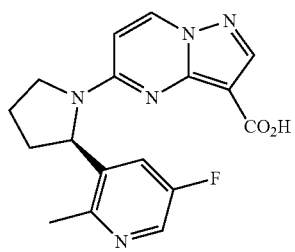 [SMILES: Cc1ncc(F)cc1[C@H]1CCCN1c1ccn2ncc(C(=O)O)c2n1]

(R)-5-(2-(5-fluoro-2-methylpyridin-3-yl)pyrrolidin-1-yl)pyrazolo[1,5-a]pyrimidine-3-carboxylic acid Step A: Preparation of (R)-ethyl 5-(2-(5-fluoro-2-methylpyridin-3-yl)pyrrolidin-1-yl)pyrazolo[1,5-a]pyrimidine-3-carboxylate To a solution of ethyl 5-hydroxypyrazolo[1,5-a]pyrimidine-3-carboxylate (Preparation B, Step A, 372 mg, 1.8 mmol) in DMF (10 mL) was added (benzotriazol-1-yloxy)tris(dimethylamino)phosphonium hexafluorophosphate (874 mg, 1.98 mmol). The mixture was stirred at ambient temperature for 10 minutes then treated with DIEA (1.57 mL, 8.99 mmol) and (R)-5-fluoro-2-methyl-3-(pyrrolidin-2-yl)pyridine dihydrochloride (455 mg, 1.80 mmol). After stirring at ambient temperature for 4 hours the mixture was partitioned between 10% citric acid (50 mL) and EtOAc (50 mL). The layers were separated and the aqueous layer was extracted with EtOAc (2×30 mL). The combined organic phases were washed successively with water (30 mL), saturated $NaHCO_3$ (30 mL), water (30 mL) and brine (2×30 mL), then dried over $Na_2SO_4$, filtered and concentrated. The residue was purified by silica gel column chromatography eluting with 1% MeOH/DCM to afford the product as white foam (480 mg, 72% yield). MS (apci) m/z=370.0 (M+H).

Step B: Preparation of (R)-5-(2-(5-fluoro-2-methylpyridin-3-yl)pyrrolidin-1-yl)pyrazolo[1,5-a]pyrimidine-3-carboxylic acid To a solution of (R)-ethyl 5-(2-(5-fluoro-2-methylpyridin-3-yl)pyrrolidin-1-yl)pyrazolo[1,5-a]pyrimidine-3-carboxylate (480 mg, 1.3 mmol) in a 1:1:1 mixture of THF:MeOH:water (30 mL) was added lithium hydroxide monohydrate (164 mg, 3.9 mmol). The mixture was stirred at ambient temperature for 16 hours then concentrated to 1/3 volume, acidified to pH 3 with 1N HCl and extracted with EtOAc (3×30 mL). The combined organic phases were washed with brine (20 mL), dried over $Na_2SO_4$, filtered and concentrated to afford the title product as a white solid (381 mg, 86% yield). MS (apci) m/z=342.0 (M+H).

Preparation P

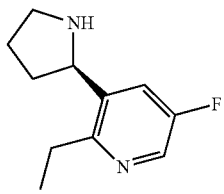

(R)-2-ethyl-5-fluoro-3-(pyrrolidin-2-yl)pyridine

Prepared by the method of Preparation N, substituting methyl boronic acid with ethyl boronic acid in Step A. MS (apci) m/z=195.1 (M+H).

Preparation Q

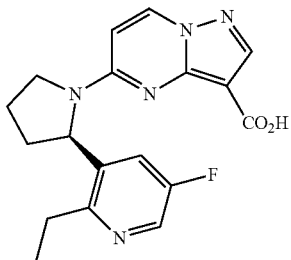 [SMILES: CCc1ncc(F)cc1[C@H]1CCCN1c1ccn2ncc(C(=O)O)c2n1]

(R)-5-(2-(2-ethyl-5-fluoropyridin-3-yl)pyrrolidin-1-yl)pyrazolo[1,5-a]pyrimidine-3-carboxylic acid Prepared by the method of Preparation O, substituting (R)-5-fluoro-2-methyl-3-(pyrrolidin-2-yl)pyridine dihydrochloride with (R)-2-ethyl-5-fluoro-3-(pyrrolidin-2-yl)pyridine dihydrochloride in Step A. MS (apci) m/z=356.0 (M+H).

Preparation R

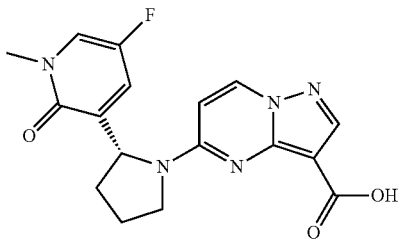 [SMILES: Cn1cc(F)cc([C@H]2CCCN2c2ccn3ncc(C(=O)O)c3n2)c1=O]

(R)-5-(2-(5-fluoro-1-methyl-2-oxo-1,2-dihydropyridin-3-yl)pyrrolidin-1-yl)pyrazolo[1,5-a]pyrimidine-3-carboxylic acid Step A: Preparation of (R)-ethyl 5-(2-(5-fluoro-2-oxo-1,2-dihydropyridin-3-yl)pyrrolidin-1-yl)pyrazolo[1,5-a]pyrimidine-3-carboxylate. To a mixture of (R)-ethyl 5-(2-(5-fluoro-2-methoxypyridin-3-yl)pyrrolidin-1-yl)pyrazolo[1,5-a]pyrimidine-3-carboxylate (1.0 g, 2.60 mmol, Preparation K, Step A) and AcOH (7.44 mL, 130 mmol) was added HBr (4.76 mL, 33 wt % in acetic acid, 26 mmol) at ambient temperature. The reaction mixture was heated at 90° C. for 2 hours. After cooling, the reaction mixture was diluted with EtOAc, washed with water, saturated $NaHCO_3$, and brine, dried with $MgSO_4$, filtered and concentrated. The crude material was purified by silica column chromatography, eluting with 2-3% MeOH/DCM to yield the title product (0.73 g, 76%). MS (apci) m/z=372.0 (M+H).

Step B: Preparation of (R)-ethyl 5-(2-(5-fluoro-1-methyl-2-oxo-1,2-dihydropyridin-3-yl)pyrrolidin-1-yl)pyrazolo[1,5-a]pyrimidine-3-carboxylate. To a suspension of (R)-ethyl 5-(2-(5-fluoro-2-oxo-1,2-dihydropyridin-3-yl)pyrrolidin-1-yl)pyrazolo[1,5-a]pyrimidine-3-carboxylate (0.73 g, 1.97 mmol) in DMF (10 mL) at 0° C. was added LiH (20 mg, 2.36 mmol). After stirring for 30 minutes, a solution of MeI (0.56 g, 3.93 mmol) in DMF (2 mL) was added and the reaction was stirred at ambient temperature for 17 hours. The reaction mixture was cooled to 0° C. and quenched with ice-water (30 mL). The mixture was extracted with EtOAc (3×), washed with water and brine, dried with $MgSO_4$, filtered and concentrated. The crude material was purified by silica column chromatography, eluting with 2.5% MeOH/DCM to yield the title product (0.64 g, 85%). MS (apci) m/z=386.0 (M+H).

Step C: Preparation of (R)-5-(2-(5-fluoro-1-methyl-2-oxo-1,2-dihydropyridin-3-yl)pyrrolidin-1-yl)pyrazolo[1,5-a]pyrimidine-3-carboxylic acid. Prepared by the method described in Preparation K, Step B using (R)-ethyl 5-(2-(5-fluoro-1-methyl-2-oxo-1,2-dihydropyridin-3-yl)pyrrolidin-1-yl)pyrazolo[1,5-a]pyrimidine-3-carboxylate to yield the title compound (0.571 g, 96% yield). MS (apci) m/z=358.0 (M+H).

Example 1

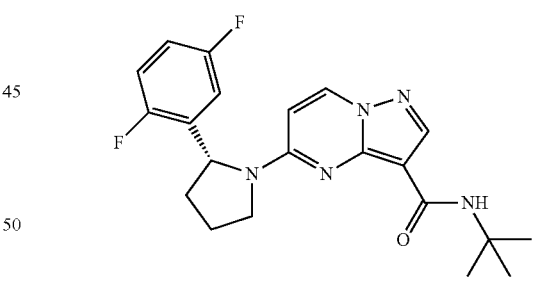

(R)—N-tert-butyl-5-(2-(2,5-difluorophenyl)pyrrolidin-1-yl)pyrazolo[1,5-a]pyrimidine-3-carboxamide To a solution of (R)-5-(2-(2,5-difluorophenyl)pyrrolidin-1-yl)pyrazolo[1,5-a]pyrimidine-3-carboxylic acid (Preparation C, 20.0 mg, 0.058 mmol) and HATU (24.3 mg, 0.064 mmol) in dry DMF (0.4 mL) was added tert-butyl amine (12.7 mg, 0.174 mmol) followed by diisopropylethylamine (22.5 mg, 0.174 mmol). The mixture was stirred under an atmosphere of N2 for 18 hours and was added to $H_2O$ (3 mL) and mixed. The mixture was extracted with EtOAc and combined extracts were washed with 1M HCl, $H_2O$, saturated $NaHCO_3$ and dried over $MgSO_4$. The solution was eluted through a SPE SiOH column eluting first with 50% EtOAc-hexanes then with EtOAc. The EtOAc pool was concentrated and the residual colorless glass was treated with hexanes give a white suspension. The hexanes were removed, and the solid was washed with hexanes and dried in vacuum to afford the title compound as a white solid (20 mg, 90%). MS (apci) m/z=400.1 (M+H).

Example 2

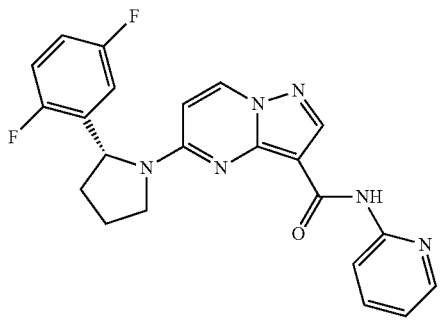 [SMILES: O=C(Nc1ccccn1)c1cnn2ccc(N3CCC[C@@H]3c3cc(F)ccc3F)nc12]

(R)-5-(2-(2,5-difluorophenyl)pyrrolidin-1-yl)-N-(pyridin-2-yl)pyrazolo[1,5-a]pyrimidine-3-carboxamide The title compound was prepared according to the procedure outlined for Example 1, using 2-aminopyridine (2 equivalents) heating at 90° C. for 7 hours. The crude material was purified out by $SiO_2$ column chromatography (50% EtOAc-hexanes) to give the title compound as a white solid (45% yield). MS (apci) m/z=421.1 (M+H).

Example 3

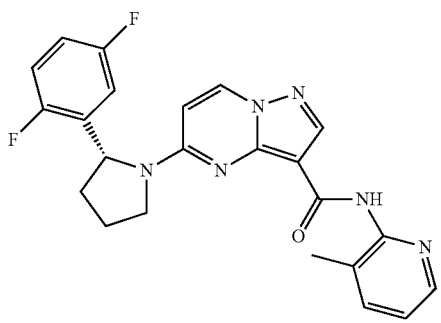 [SMILES: Cc1cccnc1NC(=O)c1cnn2ccc(N3CCC[C@@H]3c3cc(F)ccc3F)nc12]

(R)-5-(2-(2,5-difluorophenyl)pyrrolidin-1-yl)-N-(3-methylpyridin-2-yl)pyrazolo[1,5-a]pyrimidine-3-carboxamide To a suspension of (R)-5-(2-(2,5-difluorophenyl)pyrrolidin-1-yl)pyrazolo[1,5-a]pyrimidine-3-carboxylic acid (Preparation C, 25.0 mg, 0.072 mmol) in $CCl_4$ (1.0 mL) was added thionyl chloride (0.10 mL) and the mixture heated at reflux for 4 hours. The mixture was cooled to ambient temperature and was concentrated to a brittle foam. The foam was dissolved in pyridine (2 mL), 2-amino-3-methyl-pyridine (9.3 mg, 0.086 mmol) was added and the mixture was heated at 90° C. for 20 hours. The reaction was cooled to ambient temperature and the pyridine evaporated. The residue was partitioned into 1M NaOH and EtOAc, mixed and the EtOAc layer removed. The aqueous layer was extracted with EtOAc and combined EtOAc fractions were washed with $H_2O$, saturated NaCl and dried over $MgSO_4$. The solution was filtered and concentrated, and the resulting solid was washed with dry $Et_2O$ to afford the title compound as a white solid (7 mg, 29%). MS (apci) m/z=435.1 (M+H).

Example 4

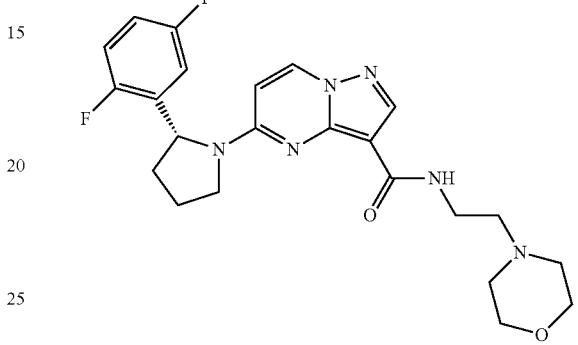

(R)-5-(2-(2,5-difluorophenyl)pyrrolidin-1-yl)-N-(2-morpholinoethyl)pyrazolo[1,5-a]pyrimidine-3-carboxamide The title compound was prepared according to the procedure outlined for Example 1 using 2-morpholinoethanamine (1.5 equiv). The combined EtOAc extracts were washed with 1M $Na_2CO_3$, $H_2O$, saturated NaCl and dried over $MgSO_4$. The solution was filtered through a SPE SiOH column eluting first with EtOAc and then with 10% MeOH/EtOAc. The MeOH/EtOAc pool was concentrated and the residual colorless glass was triturated with hexanes to give fine white precipitate. The solvent was decanted and the solid was washed with hexanes and dried in vacuum. This afforded the title compound as a white solid (79%). MS (apci) m/z=457.1 (M+H).

Example 5

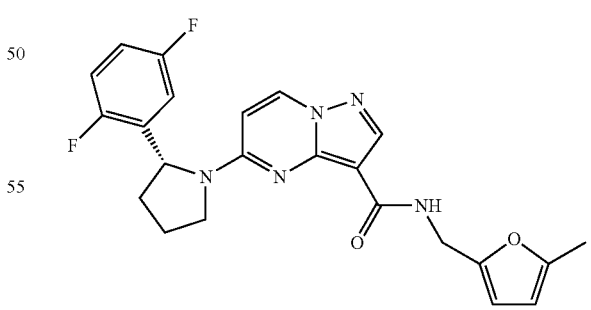

(R)-5-(2-(2,5-difluorophenyl)pyrrolidin-1-yl)-N-((5-methylfuran-2-yl)methyl)pyrazolo[1,5-a]pyrimidine-3-carboxamide The title compound was prepared according to the procedure outlined for Example 1 using (5-methylfuran-2-yl)

methanamine (1.5 equiv.) The dried EtOAc solution was filtered through a packed Celite plug and concentrated. The residual colorless glass was treated with Et$_2$O until dissolved then diluted with hexanes to give a white suspension. Solvents were decanted, the solid washed with hexanes and dried in vacuum. This provided the title compound as a white solid (43% yield). MS (apci) m/z=438.1 (M+H).

Example 6

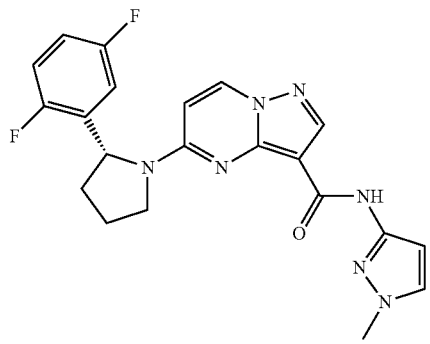 [SMILES: Cn1ccc(NC(=O)c2cnn3ccc(N4CCC[C@@H]4c4cc(F)ccc4F)nc23)n1]

(R)-5-(2-(2,5-difluorophenyl)pyrrolidin-1-yl)-N-(1-methyl-1H-pyrazol-3-yl)pyrazolo[1,5-a]pyrimidine-3-carboxamide The title compound was prepared according to the procedure outlined for Example 3 using 1-methyl-1H-pyrazol-3-amine (1.5 equiv.) at ambient temperature for 64 hours. The crude EtOAc solution was eluted through a SPE SiOH column (EtOAc elution) and concentrated. The residual white solid was washed with 10% Et$_2$O-hexanes and dried in vacuum to afford the title compound (47% yield). MS (apci) m/z=424.1 (M+H).

Example 7

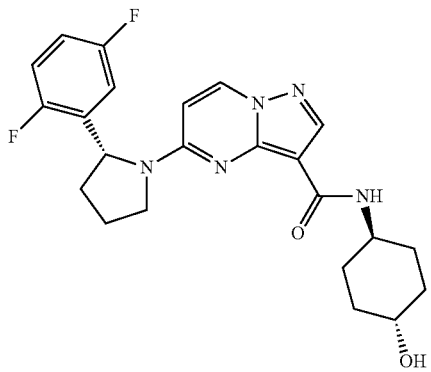 [SMILES: O=C(N[C@H]1CC[C@H](O)CC1)c1cnn2ccc(N3CCC[C@@H]3c3cc(F)ccc3F)nc12]

5-((R)-2-(2,5-difluorophenyl)pyrrolidin-1-yl)-N-((trans)-4-hydroxycyclohexyl)pyrazolo[1,5-a]pyrimidine-3-carboxamide The title compound was prepared according to the procedure outlined for Example 1 using trans-4-aminocyclohexanol (1.5 equiv). The combined EtOAc extracts were washed with 1M Na$_2$CO$_3$, H$_2$O, saturated NaCl and dried over MgSO$_4$. The solution was filtered through a Celite plug, concentrated and the residual colorless glass was treated with hexanes to give a white suspension. The hexanes were decanted and the solid washed with hexanes and dried in vacuum. This afforded the title compound as a white solid (86% yield). MS (apci) m/z=442.1 (M+H).

Example 8

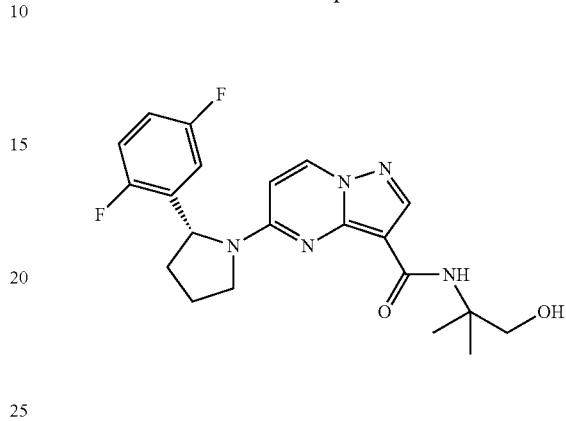

(R)-5-(2-(2,5-difluorophenyl)pyrrolidin-1-yl)-N-(1-hydroxy-2-methylpropan-2-yl)pyrazolo[1,5-a]pyrimidine-3-carboxamide The compound was prepared according to Example 3 using 2-amino-2-methylpropan-1-ol (4 equiv.). In this instance, the amine was added to the crude acid chloride in THF at 0° C. and the mixture was stirred for 15 hours during which time the temperature reached ambient temperature after 1-2 hours. The reaction mixture was partitioned into H$_2$O and 50% EtOAc-hexanes. The organic layer removed and the aqueous layer was extracted with 50% EtOAc-hexanes. The combined organic fractions were washed with 1M NaOH, H$_2$O and saturated NaCl. The solution was dried over MgSO$_4$ and eluted through a SPE SiOH column eluting first with 50% EtOAc-hexanes then with EtOAc. The EtOAc pool was concentrated and residual colorless glass was dissolved in Et$_2$O. Hexane was added and the resulting white suspension was concentrated to afford the title compound as a white solid (57% yield). MS (apci) m/z=416.1 (M+H).

Example 9

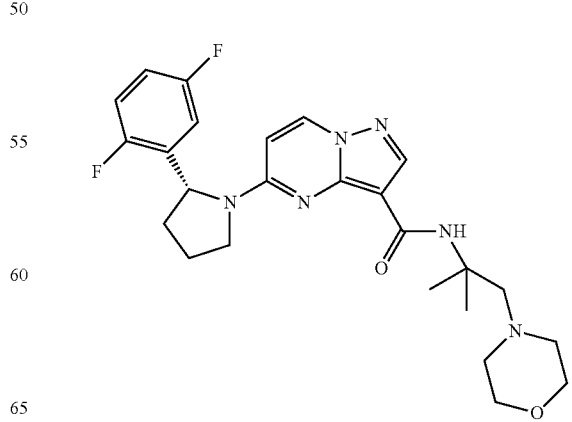

(R)-5-(2-(2,5-difluorophenyl)pyrrolidin-1-yl)-N-(2-methyl-1-morpholinopropan-2-yl)pyrazolo[1,5-a]pyrimidine-3-carboxamide The title compound was prepared according to Example 4 using 2-methyl-1-morpholinopropan-2-amine (1.5 equiv). The compound was isolated as a white solid after SiO₂ chromatography using EtOAc for elution (83% yield). MS (apci) m/z=485.2 (M+H).

Example 10

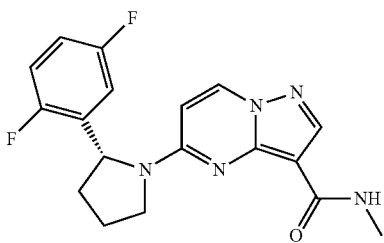 [SMILES: CNC(=O)c1cnn2ccc(N3CCC[C@@H]3c3cc(F)ccc3F)nc12]

(R)-5-(2-(2,5-difluorophenyl)pyrrolidin-1-yl)-N-methylpyrazolo[1,5-a]pyrimidine-3-carboxamide Prepared by the method as described in Example 1, substituting tert-butyl amine with methyl amine, to provide the final product as a white solid (34 mg, 83% yield). MS (apci) m/z=358.1 (M+H).

Example 11

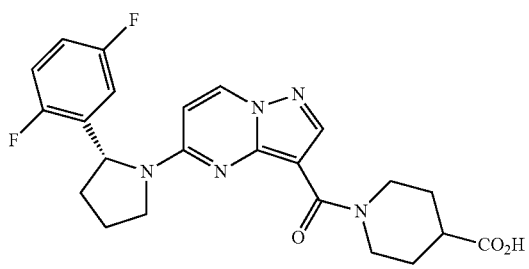 [SMILES: O=C(O)C1CCN(C(=O)c2cnn3ccc(N4CCC[C@@H]4c4cc(F)ccc4F)nc23)CC1]

(R)-1-(5-(2-(2,5-difluorophenyl)pyrrolidin-1-yl)pyrazolo[1,5-a]pyrimidine-3-carbonyl)piperidine-4-carboxylic acid Step A: Preparation of (R)-ethyl 1-(5-(2-(2,5-difluorophenyl)pyrrolidin-1-yl) pyrazole [1,5-a]pyrimidine-3-carbonyl)piperidine-4-carboxylate Prepared by the method as described in Example 1, substituting tert-butyl amine with ethyl piperidine-4-carboxylate. The crude material was purified by preparative TLC plate, eluting first with EtOAc and then 10% MeOH/EtOAc to afford the title compound (49 mg, 88% yield). MS (apci) m/z=484.1 (M+H).

Step B: (R)-1-(5-(2-(2,5-difluorophenyl)pyrrolidin-1-yl)pyrazolo[1,5-a]pyrimidine-3-carbonyl)piperidine-4-carboxylic acid (R)-ethyl 1-(5-(2-(2,5-di fluorophenyl)pyrrolidin-1-yl)pyrazolo[1,5-a]pyrimidine-3-carbonyl)piperidine-4-carboxylate (49 mg, 0.10 mmol) was dissolved in 1:1 THF/MeOH (1.0 mL) and 1M LiOH (0.20 mL, 0.20 mmol) was added. The mixture was stirred at ambient temperature for 2 hours and the reaction mixture was concentrated. The residue was diluted in water and the mixture acidified with 2N HCl. The mixture was extracted with DCM and EtOAc. The combined organics were washed with brine, dried with MgSO₄, filtered and concentrated. The residue was triturated with hexanes and the resulting white suspension was concentrated to afford the final product (43 mg, 92% yield) as a white solid. MS (apci) m/z=456.1 (M+H).

Example 12

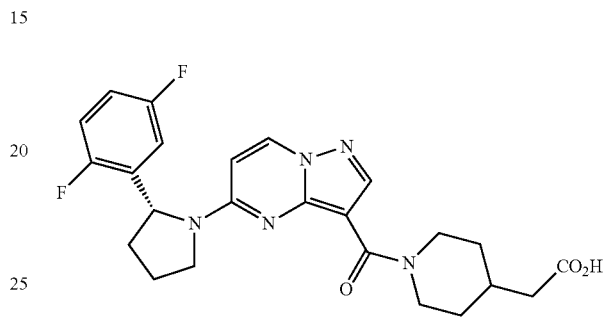

(R)-2-(1-(5-(2-(2,5-difluorophenyl)pyrrolidin-1-yl)pyrazolo[1,5-a]pyrimidine-3-carbonyl)piperidin-4-yl)acetic acid Step A: Preparation of (R)-ethyl 2-(1-(5-(2-(2,5-difluorophenyl)pyrrolidin-1-yl)pyrazolo[1,5-a]pyrimidine-3-carbonyl)piperidin-4-yl)acetate Prepared by the method as described in Example 11, substituting ethyl piperidine-4-carboxylate with ethyl 2-(piperidin-4-yl)acetate in step A (48 mg, 83% yield). MS (apci) m/z=498.1 (M+H).

Step B: Preparation of (R)-2-(1-(5-(2-(2,5-difluorophenyl)pyrrolidin-1-yl)pyrazolo[1,5-a]pyrimidine-3-carbonyl)piperidin-4-yl)acetic acid Prepared as described in Example 11 Step B to afford the final product (30 mg, 66% yield) as a white solid. MS (apci) m/z=470.1 (M+H).

Example 13

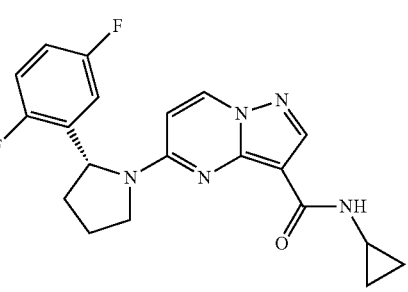

(R)—N-cyclopropyl-5-(2-(2,5-difluorophenyl)pyrrolidin-1-yl)pyrazolo[1,5-a]pyrimidine-3-carboxamide Prepared by the method as described in Example 1 substituting tert-butyl amine with cyclopropanamine. The crude material was purified by preparative TLC eluting with EtOAc then 10% MeOH/EtOAc to provide the final product as a white solid (28 mg, 63% yield). MS (apci) m/z=384.1 (M+H).

Example 14

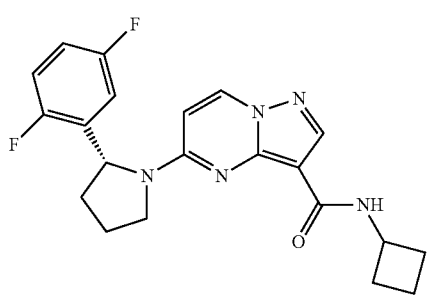 [SMILES: O=C(NC1CCC1)c1cnn2ccc(N3CCC[C@@H]3c3cc(F)ccc3F)nc12]

(R)—N-cyclobutyl-5-(2-(2,5-difluorophenyl)pyrrolidin-1-yl)pyrazolo[1,5-a]pyrimidine-3-carboxamide Prepared by the method as described in Example 1 substituting tert-butyl amine with cyclobutanamine, to provide the final product as a white solid (41 mg, 88% yield). MS (apci) m/z=398.1 (M+H).

Example 15

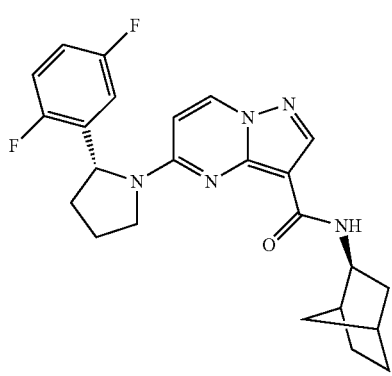 [SMILES: O=C(N[C@H]1CC2CCC1C2)c1cnn2ccc(N3CCC[C@@H]3c3cc(F)ccc3F)nc12]

N-((2S)-bicyclo[2.2.1]heptan-2-yl)-5-((R)-2-(2,5-difluorophenyl)pyrrolidin-1-yl)pyrazolo[1,5-a]pyrimidine-3-carboxamide Prepared by the method as described in Example 1, substituting tert-butyl amine with (2R)-bicyclo[2.2.1]heptan-2-amine. The crude material was purified by reverse phase chromatography eluting with 0-100% acetonitrile/water to yield the title compound as a white solid (47 mg, 92% yield.). MS (apci) m/z=438.2 (M+H).

Example 16

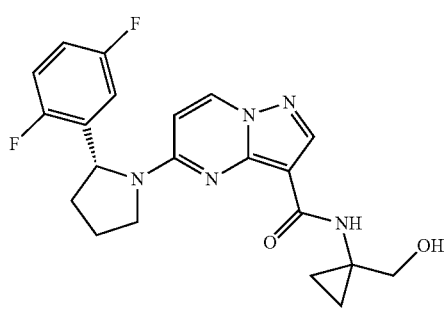 [SMILES: O=C(NC1(CO)CC1)c1cnn2ccc(N3CCC[C@@H]3c3cc(F)ccc3F)nc12]

(R)-5-(2-(2,5-difluorophenyl)pyrrolidin-1-yl)-N-(1-(hydroxymethyl)cyclopropyl)pyrazolo[1,5-a]pyrimidine-3-carboxamide Prepared by the method as described in Example 8, using (1-aminocyclopropyl)methanol (1.5 equiv.) the procedure described for Example 8. The title compound was obtained as a white solid (35% yield). MS (apci) m/z=414.1 (M+H).

Example 17

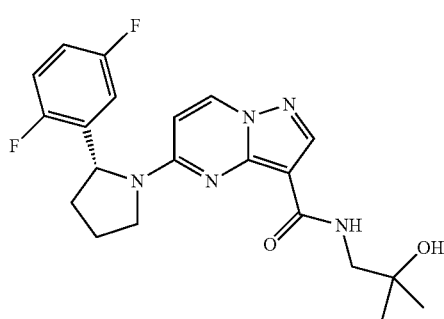 [SMILES: CC(C)(O)CNC(=O)c1cnn2ccc(N3CCC[C@@H]3c3cc(F)ccc3F)nc12]

(R)-5-(2-(2,5-difluorophenyl)pyrrolidin-1-yl)-N-(2-hydroxy-2-methylpropyl)pyrazolo[1,5-a]pyrimidine-3-carboxamide Prepared by the method as described in Example 8, using 1-amino-2-methylpropan-2-ol (4.0 equiv.). The title compound was obtained as a white solid (62% yield). MS (apci) m/z=416.1 (M+H).

Example 18

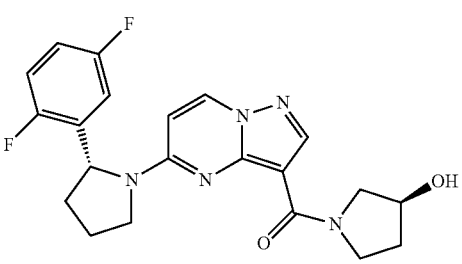 [SMILES: O=C(c1cnn2ccc(N3CCC[C@@H]3c3cc(F)ccc3F)nc12)N1CC[C@H](O)C1]

(5-((R)-2-(2,5-difluorophenyl)pyrrolidin-1-yl)pyrazolo[1,5-a]pyrimidin-3-yl)((S)-3-hydroxypyrrolidin-1-yl)methanone The title compound was prepared by the method as described in Example 1 using (S)-pyrrolidin-3-ol (2.0 equiv). The EtOAc pool was concentrated and the residual colorless glass was dissolved in EtOAc. Hexanes were added and resulting white suspension was concentrated to give the title compound as a white solid (42% yield). MS (apci) m/z=414.1 (M+H).

Example 19

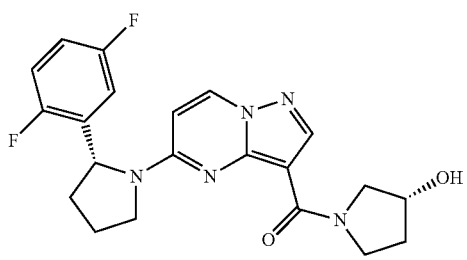 [SMILES: O=C(c1cnn2ccc(N3CCC[C@@H]3c3cc(F)ccc3F)nc12)N1CC[C@@H](O)C1]

(5-((R)-2-(2,5-difluorophenyl)pyrrolidin-1-yl)pyrazolo[1,5-a]pyrimidin-3-yl)((R)-3-hydroxypyrrolidin-1-yl)methanone Prepared by the method as described in Example 18 using (R)-pyrrolidin-3-ol (2.0 equiv.). The title compound was obtained as a white solid (99% yield). MS (apci) m/z=414.1 (M+H).

Example 20

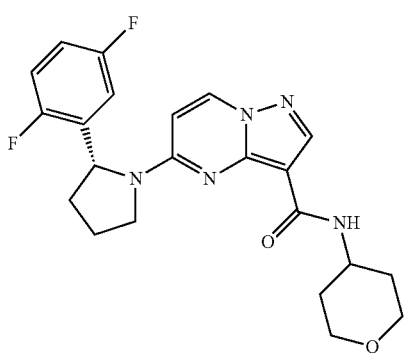 [SMILES: O=C(NC1CCOCC1)c1cnn2ccc(N3CCC[C@@H]3c3cc(F)ccc3F)nc12]

(R)-5-(2-(2,5-difluorophenyl)pyrrolidin-1-yl)-N-(tetrahydro-2H-pyran-4-yl)pyrazolo[1,5-a]pyrimidine-3-carboxamide The title compounding was prepared following the method of Example 1, using tetrahydro-2H-pyran-4-amine (2.0 equiv.). The EtOAc pool was concentrated and the residual colorless glass was dissolved in EtOAc. Hexanes were added and resulting white suspension was concentrated to give the title compound as a white solid (68% yield). MS (apci) m/z=428.1 (M+H).

Example 21

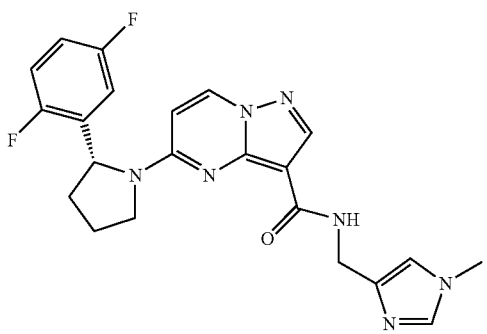 [SMILES: Cn1cnc(CNC(=O)c2cnn3ccc(N4CCC[C@@H]4c4cc(F)ccc4F)nc23)c1]

(R)-5-(2-(2,5-difluorophenyl)pyrrolidin-1-yl)-N-((1-methyl-1H-imidazol-4-yl)methyl)pyrazole[1,5-a]pyrimidine-3-carboxamide Prepared by the method described in Example 1 substituting tert-butyl amine with (1-methyl-1H-imidazol-4-yl)methanamine. The crude material was purified by reverse phase chromatography, eluting with 0-100% acetonitrile/water to yield the title compound as a white solid (22 mg, 43% yield.). MS (apci) m/z=438.1 (M+H).

Example 22

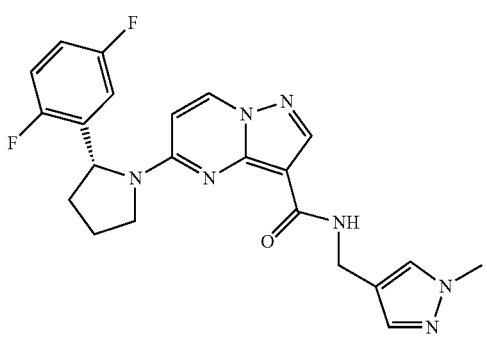 [SMILES: Cn1cc(CNC(=O)c2cnn3ccc(N4CCC[C@@H]4c4cc(F)ccc4F)nc23)cn1]

(R)-5-(2-(2,5-difluorophenyl)pyrrolidin-1-yl)-N-((1-methyl-1H-pyrazol-4-yl)methyl)pyrazolo[1,5-a]pyrimidine-3-carboxamide Prepared by the method described in Example 1 substituting tert-butyl amine with (1-methyl-1H-pyrazol-4-yl)methanamine. The crude material was purified by reverse phase chromatography, eluting with 0-100% acetonitrile/water to yield the title compound as a white solid (34 mg, 67% yield.). MS (apci) m/z=438.1 (M+H).

Example 23

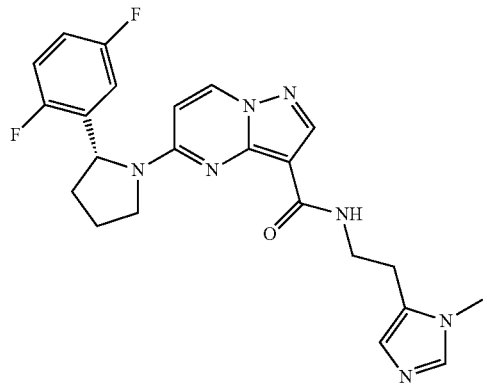 [SMILES: Cn1cncc1CCNC(=O)c1cnn2ccc(N3CCC[C@@H]3c3cc(F)ccc3F)nc12]

(R)-5-(2-(2,5-difluorophenyl)pyrrolidin-1-yl)-N-(2-(1-methyl-1H-imidazol-5-yl)ethyl)pyrazolo[1,5-a]pyrimidine-3-carboxamide Prepared by the method described in Example 1 substituting tert-butyl amine with 2-(1-methyl-1H-imidazol-5-yl)ethanamine. The crude material was purified by reverse phase chromatography, eluting with 0-100% acetonitrile/water to yield the title compound as a white solid (26 mg, 49% yield.). MS (apci) m/z=452.2 (M+H).

Example 24

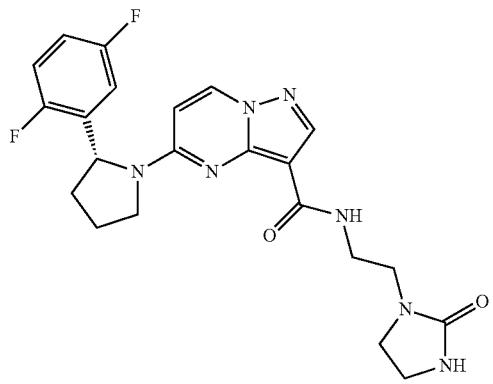 [SMILES: O=C(NCCN1CCNC1=O)c1cnn2ccc(N3CCC[C@@H]3c3cc(F)ccc3F)nc12]

(R)-5-(2-(2,5-difluorophenyl)pyrrolidin-1-yl)-N-(2-(2-oxoimidazolidin-1-yl)ethyl)pyrazole[1,5-a]pyrimidine-3-carboxamide Prepared by the method described in Example 1, substituting tert-butyl amine with 1-(2-aminoethyl)imidazolidin-2-one. The crude material was purified by reverse phase chromatography, eluting with 0-100% acetonitrile/water to yield the title compound as a white solid (23 mg, 43% yield.). MS (apci) m/z=456.1 (M+H).

Example 25

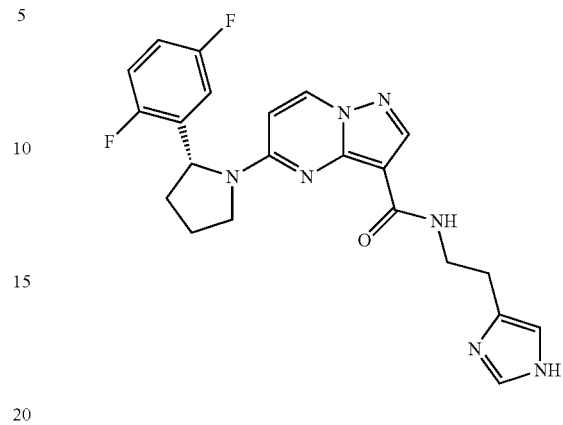

(R)—N-(2-(1H-imidazol-4-yl)ethyl)-5-(2-(2,5-difluorophenyl)pyrrolidin-1-yl)pyrazole[1,5-a]pyrimidine-3-carboxamide Prepared by the method described in Example 1, substituting tert-butyl amine with histamine. The crude material was purified by reverse phase chromatography, eluting with 0-100% acetonitrile/water to yield the title compound as a white solid (17 mg, 34% yield.). MS (apci) m/z=438.2 (M+H).

Example 26

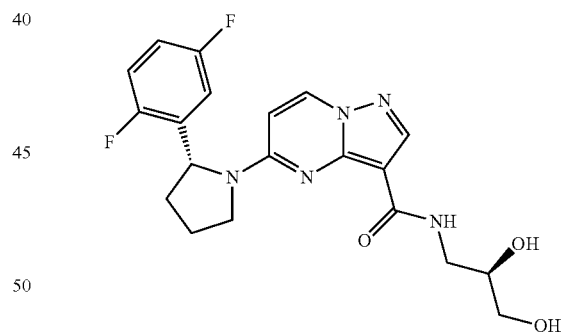

5-((R)-2-(2,5-difluorophenyl)pyrrolidin-1-yl)-N—((R)-2,3-dihydroxypropyl)pyrazolo[1,5-a]pyrimidine-3-carboxamide Prepared by the method described in Example 1, substituting tert-butyl amine with (R)-3-aminopropane-1,2-diol. The crude material was purified by preparative TLC using EtOAc then 10% MeOH/EtOAc for elution to afford the title compound (19 mg, 39% yield) as a white solid. MS (apci) m/z=418.1 (M+H).

Example 27

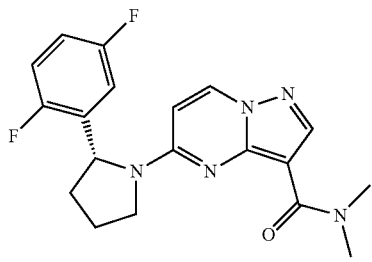 [SMILES: CN(C)C(=O)c1cnn2ccc(N3CCC[C@@H]3c3cc(F)ccc3F)nc12]

(R)-5-(2-(2,5-difluorophenyl)pyrrolidin-1-yl)-N,N-dimethylpyrazolo[1,5-a]pyrimidine-3-carboxamide Prepared by the method described in Example 1 substituting tert-butyl amine with dimethylamine. The crude material was purified by preparative TLC eluting with EtOAc then 10% MeOH/EtOAc to afford the title compound (7 mg, 19% yield) as a white solid. MS (apci) m/z=372.1 (M+H).

Example 28

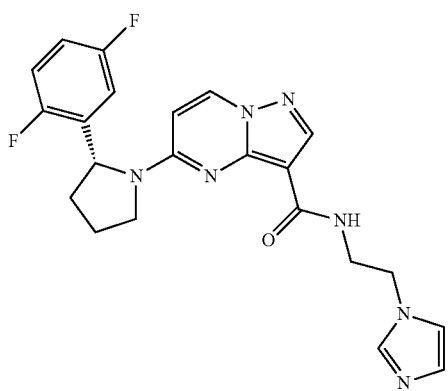 [SMILES: O=C(NCCn1ccnc1)c1cnn2ccc(N3CCC[C@@H]3c3cc(F)ccc3F)nc12]

(R)—N-(2-(1H-imidazol-1-yl)ethyl)-5-(2-(2,5-difluorophenyl)pyrrolidin-1-yl)pyrazolo[1,5-a]pyrimidine-3-carboxamide Prepared by the method described in Example 1 substituting tert-butyl amine with 2-(1H-imidazol-1-yl)ethanamine dihydrobromide. The crude material was purified by reverse phase chromatography eluting with 0-100% acetonitrile/water to yield the title compound as a white solid (25 mg, 57% yield.). MS (apci) m/z=438.1 (M+H).

Example 29

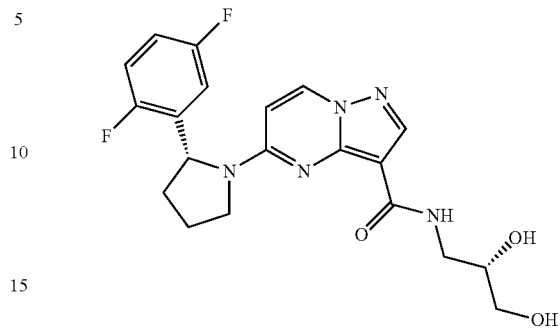

5-((R)-2-(2,5-difluorophenyl)pyrrolidin-1-yl)-N—((S)-2,3-dihydroxypropyl)pyrazolo[1,5-a]pyrimidine-3-carboxamide A mixture of (R)-5-(2-(2,5-difluorophenyl)pyrrolidin-1-yl)pyrazolo[1,5-a]pyrimidine-3-carboxylic acid (Preparation C, 400 mg, 1.16 mmol), HATU (486 mg, 1.28 mmol), and (S)-3-aminopropane-1,2-diol (318 mg, 3.49 mmol) in dry DMF (3.0 mL) was stirred for 1-2 minutes at ambient temperature. Diisopropylethylamine (DIEA) (0.62 mL, 3.49 mmol) was added and the reaction was flushed with $N_2$, sealed and stirred at ambient temperature for 18 hours. The reaction mixture was added to $H_2O$ (15 mL), mixed and extracted with EtOAc. The combined EtOAc extracts were washed with $H_2O$, saturated $NaHCO_3$ and dried over $MgSO_4$/activated carbon. The solution was eluted through a $SiO_2$ column eluting first with EtOAc then 10% MeOH/EtOAc. The 10% MeOH/EtOAc pool was concentrated and the residual, colorless glass was dissolved in a minimal amount of $CH_2Cl_2$. Hexane was added and the resulting white suspension was sonicated and concentrated to give the title product as a white solid (205 mg, 42%). MS (apci) m/z=418.1 (M+H).

Example 30

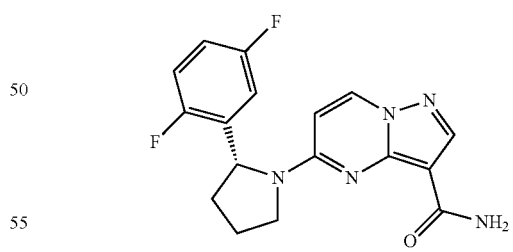

(R)-5-(2-(2,5-difluorophenyl)pyrrolidin-1-yl)pyrazolo[1,5-a]pyrimidine-3-carboxamide Step A: Preparation of 5-hydroxypyrazolo[1,5-a]pyrimidine-3-carbonitrile To a mixture of 5-amino-1H-pyrazole-4-carbonitrile (2.70 g, 25.0 mmol) and $Cs_2CO_3$ (16.3 g, 50.0 mmol) in dry DMF (70 mL) was added ethyl 3-ethoxyacrylate (5.41 g, 37.5 mmol) and the mixture was heated at 100° C. for 4 hours. The mixture was cooled to ambient temperature and the resultant slurry was poured into deionized H₂O (150 mL). The resulting aqueous solution was cooled on an ice bath and concentrated HCl was added slowly with mixing to pH=3.5. The resulting precipitate was collected, washed with H₂O followed by Et₂O. The solid was dried in vacuum to afford the product as a light beige powder (3.87 g, 97%). MS (apci) m/z=159.0 (M-1).

Step B: Preparation of (R)-5-(2-(2,5-difluorophenyl)pyrrolidin-1-yl)pyrazolo[1,5-a]pyrimidine-3-carbonitrile A flask was charged with the product from Step A (2.80 g, 17.5 mmol), benzotriazole-1-yl-oxy-tris-(dimethylamino)-phosphonium hexafluorophosphate (9.28 g, 21.0 mmol) and dry DMF (35 mL). The suspension was stirred at ambient temperature for 2 minutes and (R)-2-(2,5-difluorophenyl)pyrrolidine (Preparation A, 3.84 g, 21.0 mmol) and diisopropylethylamine (6.78 g, 62.5 mmol) were sequentially added (mild exotherm). The mixture was stirred at ambient temperature for 3 hours and poured into H₂O (175 mL). The mixture was extracted with 50% EtOAc-hexanes and the combined organic fractions were washed sequentially with 1M HCl, H₂O, 1M Na₂CO₃ and saturated NaCl. The solution was dried over MgSO₄/activated carbon and filtered through a short SiO₂ plug (350 mL course frit funnel, 1/4 full of SiO₂, capped with a layer of MgSO₄) using 50% EtOAc-hexanes for elution. The solution was concentrated to give the title compound as a brittle white foam that was crushed to a flowing white solid and dried in vacuum (5.50 g, 97%). MS (apci) m/z=326.2 (M+H).

Step C: Preparation of (R)-5-(2-(2,5-difluorophenyl)pyrrolidin-1-yl)pyrazolo[1,5-a]pyrimidine-3-carboxamide The product from Step B (3.00 g, 8.85 mmol) was added in small portions over 5 minutes to concentrated H₂SO₄ (30 mL) and the mixture was stirred at ambient temperature for 2 hours (homogeneous after 5 minutes). The solution was slowly added to chilled H₂O (300 mL) with stirring and the mixture was extracted with EtOAc. The combined EtOAc portions were washed with H₂O, 1M Na₂CO₃ and saturated NaCl. The EtOAc solution was dried over MgSO₄/activated carbon, filtered through a packed Celite pad and concentrated to give a white foam. The foam was dissolved in minimal CH₂Cl₂ and hexane was added to induce formation of a white precipitate. The mixture was concentrated to provide the title compound as a flowing white solid after drying in vacuum (2.80 g, 92%). MS (apci) m/z=344.1 (M+H).

Example 31

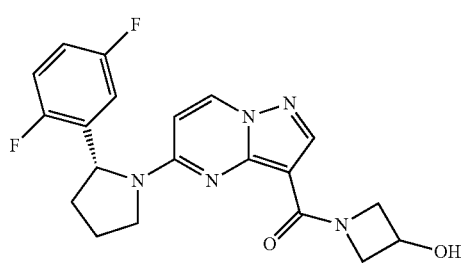 [SMILES: O=C(c1cnn2ccc(N3CCC[C@@H]3c3cc(F)ccc3F)nc12)N1CC(O)C1]

(R)-(5-(2-(2,5-difluorophenyl)pyrrolidin-1-yl)pyrazolo[1,5-a]pyrimidin-3-yl)(3-hydroxyazetidin-1-yl)methanone The title compound was prepared according to the method of Example 1, using azetidin-3-ol hydrochloride (2.0 equiv.). In this instance, the dried EtOAc solution was eluted through a SPE SiOH column eluting first with EtOAc then with 10% MeOH-EtOAc. The MeOH-EtOAc pool was concentrated to afford the title compound as a white solid (43% yield). MS (apci) m/z=400.0 (M+H).

Example 32

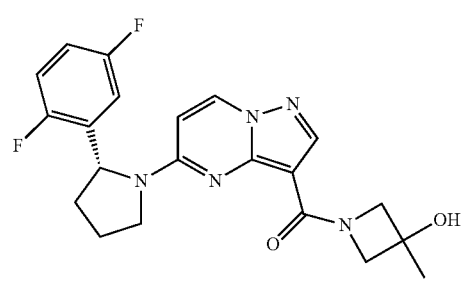 [SMILES: CC1(O)CN(C(=O)c2cnn3ccc(N4CCC[C@@H]4c4cc(F)ccc4F)nc23)C1]

(R)-(5-(2-(2,5-difluorophenyl)pyrrolidin-1-yl)pyrazolo[1,5-a]pyrimidin-3-yl)(3-hydroxy-3-methylazetidin-1-yl)methanone The title compound was prepared according to the method of Example 1, using 3-methyl-azetidin-3-ol trifluoroacetate (2.0 equiv.). The dried EtOAc solution was eluted through a SPE SiOH column eluting first with EtOAc then with 10% MeOH-EtOAc. The MeOH-EtOAc pool was concentrated to afford the title compound as a white solid (71% yield). MS (apci) m/z=414.1 (M+H).

Example 33

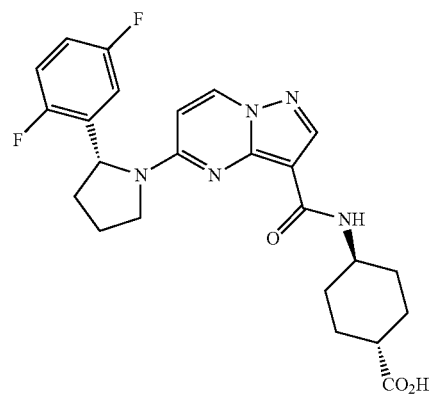 [SMILES: O=C(N[C@H]1CC[C@H](C(=O)O)CC1)c1cnn2ccc(N3CCC[C@@H]3c3cc(F)ccc3F)nc12]

Trans-4-(5-((R)-2-(2,5-difluorophenyl)pyrrolidin-1-yl)pyrazolo[1,5-a]pyrimidine-3-carboxamido)cyclohexanecarboxylic acid Step A: Preparation of (trans)-methyl 4-aminocyclohexanecarboxylate hydrochloride (Trans)-4-aminocyclohexanecarboxylic acid (200 mg, 1.40 mmol) was suspended in MeOH (5.5 mL) and cooled

85 to −10° C. To this was added SOCl$_2$ (204 μL, 2.79 mmol) dropwise and the mixture stirred for 15 minutes. The reaction mixture was warmed to ambient temperature for 15 minutes, followed by heating at reflux for 1 hour. After cooling, the mixture was concentrated to afford the title compound (260 mg, 96.1% yield). MS (apci) m/z=158.0 (M+H).

Step B: Preparation of (Trans)-methyl 4-(5-((R)-2-(2,5-difluorophenyl)pyrrolidin-1-yl)pyrazolo[1,5-a]pyrimidine-3-carboxamido)cyclohexanecarboxylate Prepared by the method described in Example 1 substituting tert-butyl amine with (trans)-methyl 4-aminocyclohexanecarboxylate hydrochloride. The crude material was purified by preparative TLC using EtOAc then 10% MeOH/EtOAc for elution to afford the title compound (38 mg, 91% yield) as a colorless oil. MS (apci) m/z=484.1 (M+H).

Step C: Preparation of (trans)-4-(5-((R)-2-(2,5-difluorophenyl)pyrrolidin-1-yl)pyrazolo[1,5-a] pyrimidine-3-carboxamido)cyclohexanecarboxylic acid Prepared by the method as described in Example 11, step B to afford the title compound (29 mg, 79% yield) as a white solid. MS (apci) m/z=4701 (M+H).

Example 34

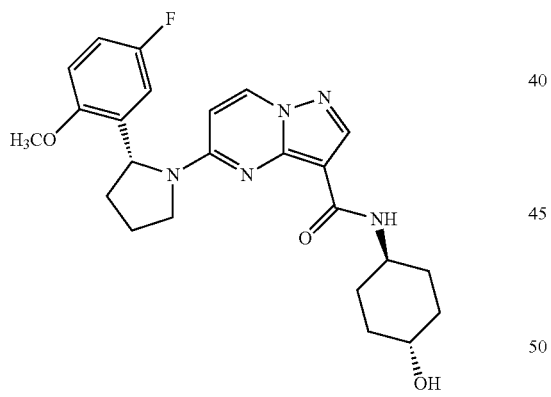

5-((R)-2-(5-fluoro-2-methoxyphenyl)pyrrolidin-1-yl)-N-((trans)-4-hydroxycyclohexyl)pyrazolo[1,5-a]pyrimidine-3-carboxamide Prepared by the method as described in Example 1 using (R)-5-(2-(5-fluoro-2-methoxyphenyl)pyrrolidin-1-yl)pyrazolo[1,5-a]pyrimidine-3-carboxylic acid (Preparation G) and (trans)-4-aminocyclohexanol. The crude material was purified by reverse phase chromatography, eluting with 0-60% acetonitrile/water to yield the title compound as a white solid (32 mg, 97% yield.). MS (apci) m/z=454.1 (M+H).

86

Example 35

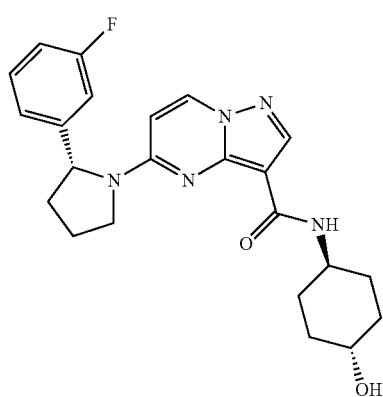 [SMILES: O=C(N[C@H]1CC[C@H](O)CC1)c1cnn2ccc(N3CCC[C@@H]3c3cccc(F)c3)nc12]

5-((R)-2-(3-fluorophenyl)pyrrolidin-1-yl)-N-((trans)-4-hydroxycyclohexyl)pyrazolo[1,5-a]pyrimidine-3-carboxamide Prepared by the method as described in Example 1 using (R)-5-(2-(3-fluorophenyl)pyrrolidin-1-yl)pyrazolo[1,5-a]pyrimidine-3-carboxylic acid (Preparation E) and (trans)-4-aminocyclohexanol to yield the title compound as a white solid (31 mg, 62% yield.). MS (apci) m/z=424.1 (M+H).

Example 36

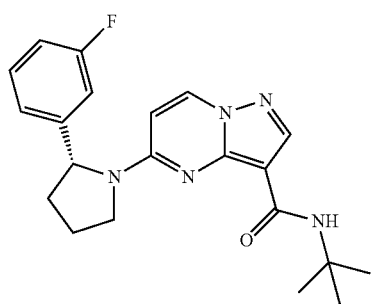 [SMILES: CC(C)(C)NC(=O)c1cnn2ccc(N3CCC[C@@H]3c3cccc(F)c3)nc12]

(R)—N-tert-butyl-5-(2-(3-fluorophenyl)pyrrolidin-1-yl)pyrazolo[1,5-a]pyrimidine-3-carboxamide Prepared by the method as described in Example 1 using (R)-5-(2-(3-fluorophenyl)pyrrolidin-1-yl)pyrazolo[1,5-a]pyrimidine-3-carboxylic acid (Preparation E) to yield the title compound as a white solid (33 mg, 74% yield.). MS (apci) m/z=382.1 (M+H).

Example 37

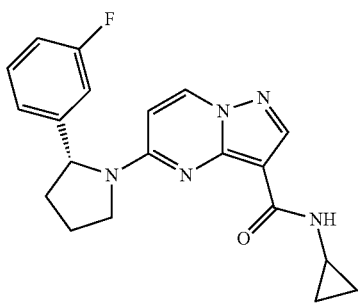 [SMILES: O=C(NC1CC1)c1cnn2ccc(N3CCC[C@@H]3c3cccc(F)c3)nc12]

(R)—N-cyclopropyl-5-(2-(3-fluorophenyl)pyrrolidin-1-yl)pyrazolo[1,5-a]pyrimidine-3-carboxamide Prepared by the method as described in Example 1 using (R)-5-(2-(3-fluorophenyl)pyrrolidin-1-yl)pyrazolo[1,5-a]pyrimidine-3-carboxylic acid (Preparation E) and cyclopropylamine to yield the title compound as a white solid (23 mg, 54% yield.). MS (apci) m/z=366.1 (M+H).

Example 38

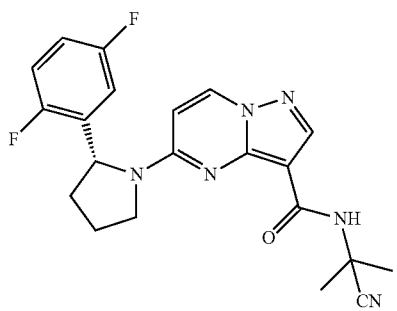 [SMILES: CC(C)(C#N)NC(=O)c1cnn2ccc(N3CCC[C@@H]3c3cc(F)ccc3F)nc12]

(R)—N-(2-cyanopropan-2-yl)-5-(2-(2,5-difluorophenyl)pyrrolidin-1-yl)pyrazolo[1,5-a]pyrimidine-3-carboxamide Prepared by the method described in Example 1 substituting tert-butyl amine with 2-amino-2-methylpropanenitrile. The crude material was purified by preparative TLC using EtOAc then 10% MeOH/EtOAc for elution to afford the title compound (15 mg, 41% yield) as a white solid. MS (apci) m/z=411.1 (M+H).

Example 39

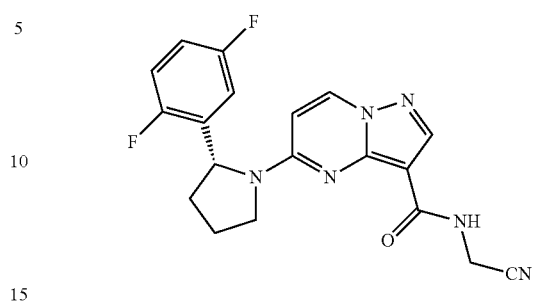

(R)—N-(cyanomethyl)-5-(2-(2,5-difluorophenyl)pyrrolidin-1-yl)pyrazolo[1,5-a]pyrimidine-3-carboxamide Prepared by the method described in Example 1 substituting tert-butyl amine with 2-aminoacetonitrile to provide the final product as a white solid (31 mg, 94% yield). MS (apci) m/z=383.0 (M+H).

Example 40

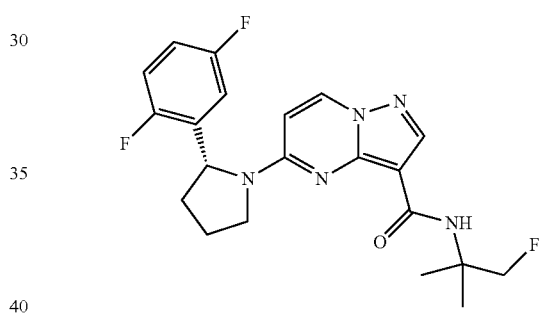

(R)-5-(2-(2,5-difluorophenyl)pyrrolidin-1-yl)-N-(1-fluoro-2-methylpropan-2-yl)pyrazolo[1,5-a]pyrimidine-3-carboxamide Prepared by the method described in Example 1 substituting tert-butyl amine with 1-fluoro-2-methylpropan-2-amine to provide the title compound as a white solid (31 mg, 84% yield). MS (apci) m/z=418.0 (M+H).

Example 41

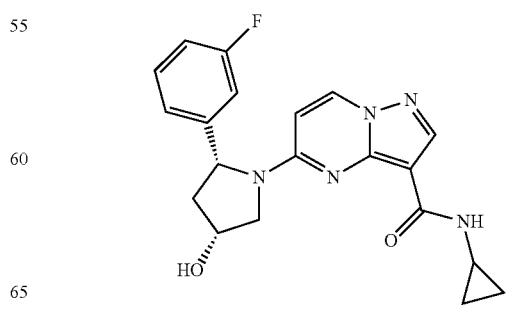

N-cyclopropyl-5-((2R,4R)-2-(3-fluorophenyl)-4-hydroxypyrrolidin-1-yl)pyrazolo[1,5-a]pyrimidine-3-carboxamide

Step A: Preparation of (R)-3-(tert-butyldimethylsilyloxy)-4-chlorobutanenitrile Tert-butyldimethylsilanecarbonitrile (20.0 g, 142 mmol), (R)-2-(chloromethyl)oxirane (13.1 g, 142 mmol) and tetrabutylammonium cyanide (0.380 g, 1.42 mmol) were mixed and heated at 100° C. for 15 hours. After cooling, the crude mixture was concentrated and the residue purified by silica chromatography eluting with 5% EtOAc/hexanes to afford (R)-3-(tert-butyldimethylsilyloxy)-4-chlorobutanenitrile (17.9 g, 54%) as a clear oil.

Step B: Preparation of (R)-3-(tert-butyldimethylsilyloxy)-5-(3-fluorophenyl)-3,4-dihydro-2H-pyrrole (3-fluorophenyl)magnesium bromide (203 mL, 102 mmol, 0.5 μM in ether) was slowly added via syringe to a solution of (R)-3-(tert-butyldimethylsilyloxy)-4-chlorobutanenitrile (9.50 g, 40.6 mmol) in MTBE (120 mL). The reaction was stirred for two hours and DME (35 mL) was slowly added over 15 minutes followed by EtOH (23 mL). After stirring overnight, brine (50 mL) and 1M NaOH (50 mL) were added and the reaction stirred for 1 hour. The reaction mixture was filtered through a pad of Celite and the collected solids were washed with EtOAc. The filtrate was washed with 1N NaOH and brine, filtered through phase-separator paper and concentrated to provide the title compound that was used directly in the next step. MS (apci) m/z=294.2 (M+H).

Step C: Preparation of (2R,4R)-4-(tert-butyldimethylsilyloxy)-2-(3-fluoro phenyl) pyrrolidine (R)-3-(tert-butyldimethylsilyloxy)-5-(3-fluorophenyl)-3,4-dihydro-2H-pyrrole (6.21 g, 21.2 mmol) was dissolved in methanol (100 mL) and AcOH (10 mL). The reaction was cooled to −78° C. and the sodium borohydride (2.00 g, 52.9 mmol) was slowly added in small portions. The reaction was allowed to warm to ambient temperature overnight. The reaction mixture was concentrated and the residue was diluted with EtOAc and 1N NaOH. Additional NaOH pellets were added to basify the aqueous layer. The organic layer was separated and the aqueous layer was extracted with EtOAc. The combined organic layers were dried with MgSO$_4$, filtered and concentrated. The residual oil was purified by silica chromatography eluting with 5% MeOH/EtOAc to afford (2R,4R)-4-(tert-butyldimethylsilyloxy)-2-(3-fluorophenyl)pyrrolidine (4.82 g, 77.1%) as a brown oil. MS (apci) m/z=296.1 (M+H).

Step D: Preparation of ethyl 5-((2R,4R)-4-(tert-butyldimethylsilyloxy)-2-(3-fluorophenyl)pyrrolidin-1-yl)pyrazolo[1,5-a]pyrimidine-3-carboxylate Prepared according to the method of Preparation C, using (2R,4R)-4-(tert-butyldimethylsilyloxy)-2-(3-fluorophenyl) pyrrolidine in Step A. MS (apci) m/z=485.1 (M+H).

Step E: Preparation of 5-((2R,4R)-2-(3-fluorophenyl)-4-hydroxypyrrolidin-1-yl)pyrazolo[1,5-a]pyrimidine-3-carboxylic acid Ethyl 5-((2R,4R)-4-(tert-butyldimethyl silyloxy)-2-(3-fluorophenyl)pyrrolidin-1-yl)pyrazolo[1,5-a]pyrimidine-3-carboxylate (205 mg, 0.422 mmol) was suspended in EtOH (2.0 mL) and 1M LiOH (0.845 ml, 0.845 mmol) was added. The mixture was heated at reflux for 4 hours and another portion of 1M LiOH (0.845 ml, 0.845 mmol) was added. The mixture was heated at reflux overnight, cooled to ambient temperature and concentrated. The residue was diluted in water and the mixture was treated with 2N HCl to achieve pH 1. The mixture was extracted with DCM and EtOAc and the combined extracts were dried with MgSO$_4$, filtered and concentrated to afford 5-((2R,4R)-2-(3-fluorophenyl)-4-hydroxypyrrolidin-1-yl)pyrazolo[1,5-a]pyrimidine-3-carboxylic acid (124 mg, 86%) as a light orange solid.

Step F: Preparation of N-cyclopropyl-5-((2R,4R)-2-(3-fluorophenyl)-4-hydroxypyrrolidin-1-yl)pyrazolo[1,5-a]pyrimidine-3-carboxamide Prepared by the method described in Example 1 using 5-((2R,4R)-2-(3-fluorophenyl)-4-hydroxypyrrolidin-1-yl) pyrazolo[1,5-a]pyrimidine-3-carboxylic acid and substituting tert-butyl amine with cyclopropylamine to provide the final product as a white solid (15 mg, 66% yield). MS (apci) m/z=382.1 (M+H).

Example 42

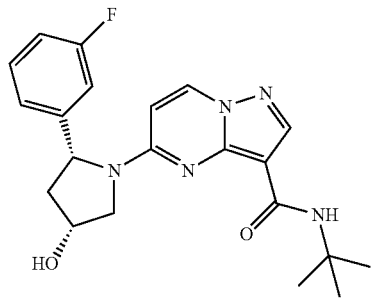 [SMILES: CC(C)(C)NC(=O)c1cnn2ccc(N3C[C@H](O)C[C@@H]3c3cccc(F)c3)nc12]

N-tert-butyl-5-((2R,4R)-2-(3-fluorophenyl)-4-hydroxypyrrolidin-1-yl)pyrazolo[1,5-a]pyrimidine-3-carboxamide Prepared by the method described in Example 1 using 5-((2R,4R)-2-(3-fluorophenyl)-4-hydroxypyrrolidin-1-yl) pyrazolo[1,5-a]pyrimidine-3-carboxylic acid and tert-butyl amine to provide the final product as a white solid (24 mg, 100% yield). MS (apci) m/z=398.1 (M+H).

Example 43

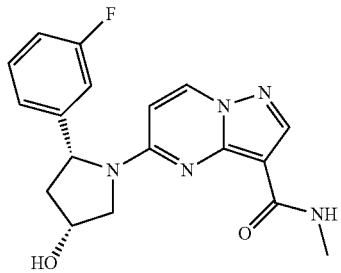 [SMILES: CNC(=O)c1cnn2ccc(N3C[C@H](O)C[C@@H]3c3cccc(F)c3)nc12]

5-((2R,4R)-2-(3-fluorophenyl)-4-hydroxypyrrolidin-1-yl)-N-methylpyrazolo[1,5-a]pyrimidine-3-carboxamide Prepared by the method described in Example 1 using 5-((2R,4R)-2-(3-fluorophenyl)-4-hydroxypyrrolidin-1-yl)pyrazolo[1,5-a]pyrimidine-3-carboxylic acid and methylamine to provide the final product as a white solid (9.4 mg, 45% yield). MS (apci) m/z=356.1 (M+H).

Example 44

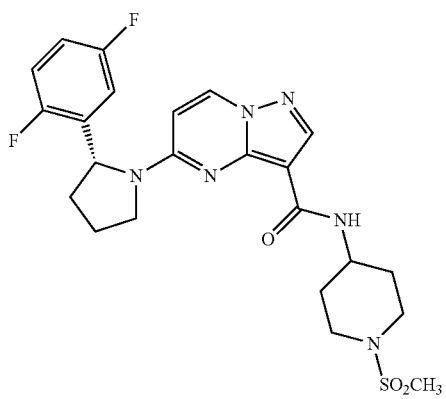 [SMILES: NS(=O)(=O)N1CCC(NC(=O)c2cnn3ccc(N4CCC[C@@H]4c4cc(F)ccc4F)nc23)CC1]

(R)-5-(2-(2,5-difluorophenyl)pyrrolidin-1-yl)-N-(1-(methylsulfonyl)piperidin-4-yl)pyrazolo[1,5-a]pyrimidine-3-carboxamide Prepared by the method described in Example 1 using 1-(methylsulfonyl)piperidin-4-amine hydrochloride (1.5 equiv.). The title compound was isolated as a white solid (83% yield) after purification by SiO₂ column (eluting with 50% EtOAc-hexanes, then EtOAc, and then 10% MeOH-EtOAc). MS (apci) m/z=505.0 (M+H).

Example 45

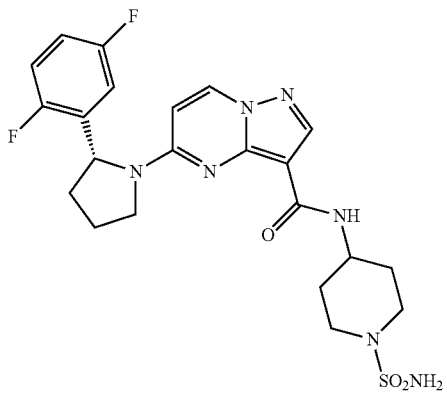

(R)-5-(2-(2,5-difluorophenyl)pyrrolidin-1-yl)-N-(1-sulfamoylpiperidin-4-yl)pyrazolo[1,5-a]pyrimidine-3-carboxamide Prepared by the method described in Example 1 using 4-aminopiperidine-1-sulfonamide (1.5 equiv.). The title compound was isolated as a white solid (80% yield) after SiO₂ column purification (eluting with 50% EtOAc-hexanes, then EtOAc, then 10% MeOH-EtOAc). MS (apci) m/z=506.0 (M+H).

Example 46

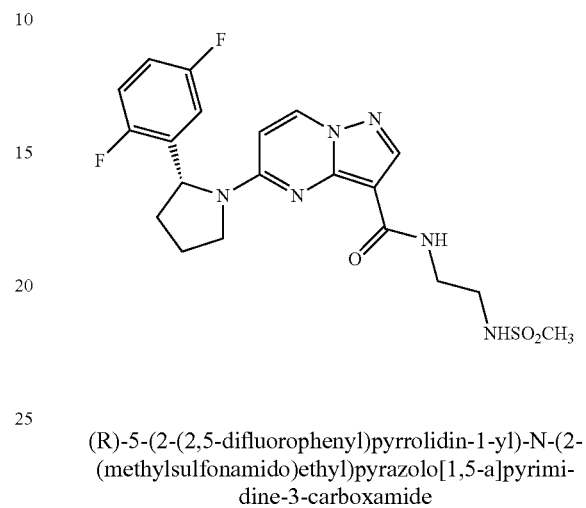

(R)-5-(2-(2,5-difluorophenyl)pyrrolidin-1-yl)-N-(2-(methylsulfonamido)ethyl)pyrazolo[1,5-a]pyrimidine-3-carboxamide Prepared by the method described in Example 1 using N-(2-aminoethyl)methanesulfonamide hydrochloride (2.0 equiv.). The title compound was isolated as a white solid (67% yield) after SiO₂ column purification (eluting with 50% EtOAc-hexanes, then EtOAc, then 10% MeOH-EtOAc). MS (apci) m/z=465.0 (M+H).

Example 47

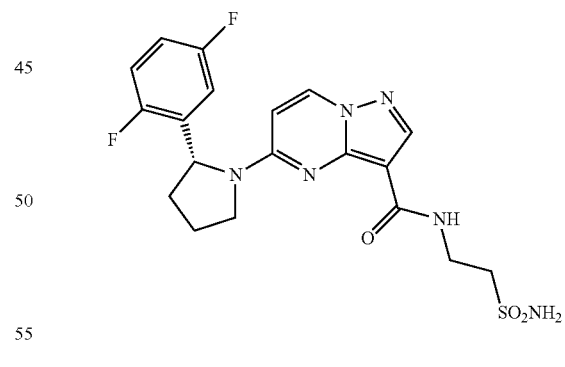

(R)-5-(2-(2,5-difluorophenyl)pyrrolidin-1-yl)-N-(2-sulfamoylethyl)pyrazolo[1,5-a]pyrimidine-3-carboxamide Prepared by the method described in Example 1 using 2-aminoethanesulfonamide (2.0 equiv.). The title compound was isolated as a white solid (67% yield) after SiO₂ column purification (eluting with 50% EtOAc-hexanes, then EtOAc, then 10% MeOH-EtOAc). MS (apci) m/z=451.0 (M+H).

Example 48

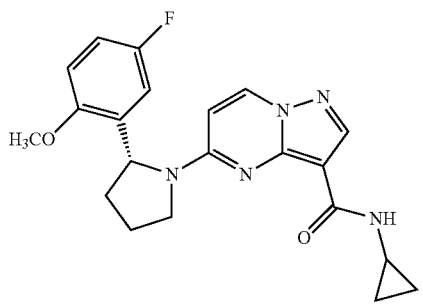 [SMILES: COc1ccc(F)cc1[C@H]1CCCN1c1ccn2ncc(C(=O)NC3CC3)c2n1]

(R)—N-cyclopropyl-5-(2-(5-fluoro-2-methoxyphenyl)pyrrolidin-1-yl)pyrazolo[1,5-a]pyrimidine-3-carboxamide Prepared by the method described in Example 1 using (R)-5-(2-(5-fluoro-2-methoxyphenyl)pyrrolidin-1-yl)pyrazolo[1,5-a]pyrimidine-3-carboxylic acid (Preparation G) and cyclopropylamine to yield the title compound as a white solid (19 mg, 68% yield). MS (apci) m/z=396.0 (M+H).

Example 49

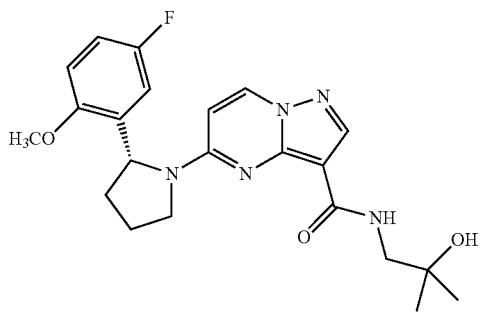 [SMILES: COc1ccc(F)cc1[C@H]1CCCN1c1ccn2ncc(C(=O)NCC(C)(C)O)c2n1]

(R)-5-(2-(5-fluoro-2-methoxyphenyl)pyrrolidin-1-yl)-N-(2-hydroxy-2-methylpropyl)pyrazolo[1,5-a]pyrimidine-3-carboxamide Prepared by the method described in Example 1 using (R)-5-(2-(5-fluoro-2-methoxyphenyl)pyrrolidin-1-yl)pyrazolo[1,5-a]pyrimidine-3-carboxylic acid (Preparation G) and 1-amino-2-methylpropan-2-ol to yield the title compound as a white solid (17 mg, 55% yield). MS (apci) m/z=428.1 (M+H).

Example 50

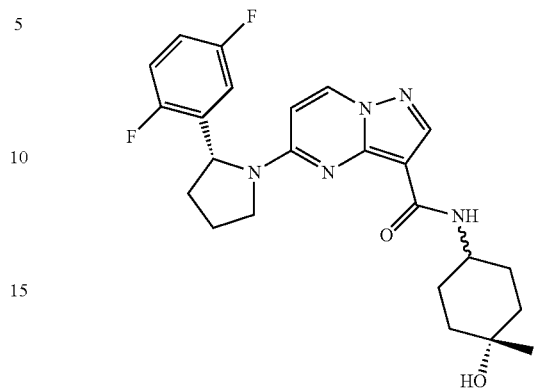

5-((R)-2-(2,5-difluorophenyl)pyrrolidin-1-yl)-N-(4-hydroxy-4-methyl cyclohexyl)pyrazolo[1,5-a]pyrimidine-3-carboxamide (Diastereomer 1)

Step A: Preparation of diastereomeric tert-butyl-4-hydroxy-4-methylcyclohexyl carbamates A solution of tert-butyl 4-oxocyclohexylcarbamate (1.20 g, 5.63 mmol) in dry THF (28.1 mL, 5.63 mmol) was cooled to −78° C. and 3.0 μM MeMgCl (5.72 mL, 17.2 mmol) was added. The reaction mixture was allowed to warm to ambient temperature and stirred for 48 hours. The reaction was quenched with saturated NH$_4$Cl (10 mL) and concentrated in vacuo. The residue was diluted in water and DCM and solid citric acid was added until the phases separated. The organic layer was removed and washed with saturated NaHCO$_3$, water and brine. The solution was dried with MgSO$_4$ filtered and concentrated to give a mixture of diastereomeric products as a white solid. The two diastereomers were separated using silica chromatography eluting with a gradient of 20-80% EtOAc/Hexanes: Minor isomer (45.1 mg, 7% yield), major isomer (113 mg, 18% yield). MS (apci) m/z=130.0 (M+H−Boc).

Step B: Preparation of 5-((R)-2-(2,5-difluorophenyl)pyrrolidin-1-yl)-N-(4-hydroxy-4-methylcyclohexyl)pyrazolo[1,5-a]pyrimidine-3-carboxamide (Diasteromer 1)

The minor isomer from Step A (45.1 mg, 0.197 mmol) was dissolved in DCM (1.0 mL) and 4N HCl in dioxane (492 μL, 1.97 mmol) was added. The reaction mixture was stirred at ambient temperature for 1 hour and was concentrated to afford 4-amino-1-methylcyclohexanol (minor isomer). The 4-amino-1-methylcyclohexanol was reacted with (R)-5-(2-(2,5-difluorophenyl)pyrrolidin-1-yl)pyrazolo[1,5-a]pyrimidine-3-carboxylic acid (Preparation C) according to the procedure outlined in Example 1 to provide the title product as a white solid (14 mg, 48% yield). MS (apci) m/z=456.1 (M+H).

Example 51

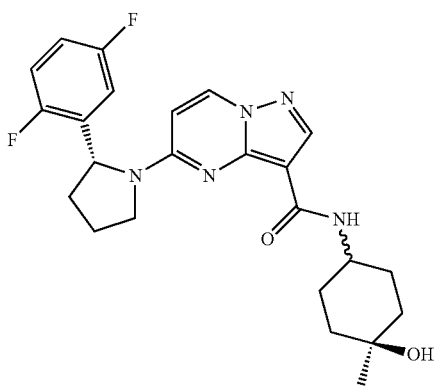

5-((R)-2-(2,5-difluorophenyl)pyrrolidin-1-yl)-N-(4-hydroxy-4-methylcyclohexyl)pyrazolo[1,5-a]pyrimidine-3-carboxamide (Diasteromer 2)

The major isomer from Step A in Example 50 (45.1 mg, 0.197 mmol) was dissolved in DCM (1.0 mL) and 4N HCl in dioxane (492 μL, 1.97 mmol) was added. The reaction mixture was stirred at ambient temperature for 1 hour and was concentrated to afford 4-amino-1-methylcyclohexanol (major isomer). The 4-amino-1-methylcyclohexanol was reacted with (R)-5-(2-(2,5-difluorophenyl)pyrrolidin-1-yl)pyrazolo[1,5-a]pyrimidine-3-carboxylic acid (Preparation C) according to the procedure outlined in Example 1 to provide the title product as a white solid (10.7 mg, 38% yield). MS (apci) m/z=456.1 (M+H).

Example 52

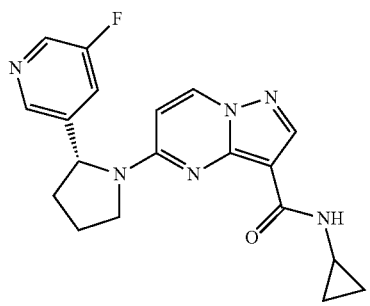 [SMILES: O=C(NC1CC1)c1cnn2ccc(N3CCC[C@@H]3c3cncc(F)c3)nc12]

(R)—N-cyclopropyl-5-(2-(5-fluoropyridin-3-yl)pyrrolidin-1-yl)pyrazolo[1,5-a]pyrimidine-3-carboxamide To a solution of (R)-5-(2-(5-fluoropyridin-3-yl)pyrrolidin-1-yl)pyrazolo[1,5-a]pyrimidine-3-carboxylic acid (Preparation I, 30.0 mg, 0.092 mmol) and HATU (52.1 mg, 0.137 mmol) in dry DMF (0.5 mL) was added cyclopropylamine (10.5 mg, 0.183 mmol) followed by diisopropylethylamine (35.5 mg, 0.275 mmol). The mixture was stirred under an atmosphere of N2 for 43 hours. The crude mixture was purified by reverse phase chromatography eluting with 0-50% acetonitrile/water to yield the title compound as a white solid (26 mg, 78% yield). MS (apci) m/z=367.0 (M+H).

Example 53

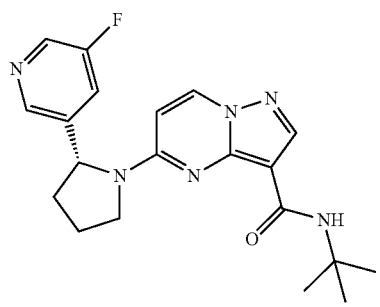 [SMILES: CC(C)(C)NC(=O)c1cnn2ccc(N3CCC[C@@H]3c3cncc(F)c3)nc12]

(R)—N-tert-butyl-5-(2-(5-fluoropyridin-3-yl)pyrrolidin-1-yl)pyrazolo[1,5-a]pyrimidine-3-carboxamide Prepared by the method as described in Example 1 using (R)-5-(2-(5-fluoropyridin-3-yl)pyrrolidin-1-yl)pyrazolo[1,5-a]pyrimidine-3-carboxylic acid (Preparation I) and 2-methylpropan-2-amine to yield the title compound as a white solid (23 mg, 67% yield). MS (apci) m/z=383.1 (M+H).

Example 54

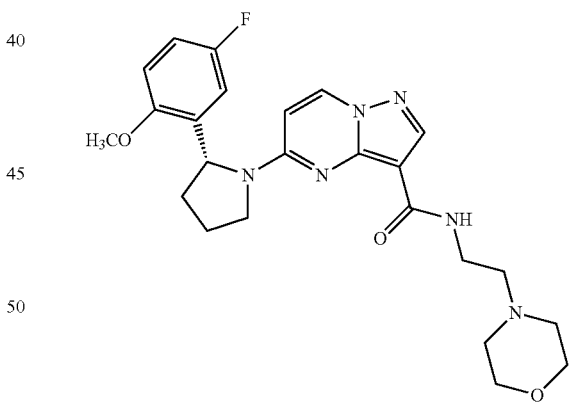

(R)-5-(2-(5-fluoro-2-methoxyphenyl)pyrrolidin-1-yl)-N-(2-morpholinoethyl)pyrazolo[1,5-a]pyrimidine-3-carboxamide Prepared by the method as described in Example 4, using (R)-5-(2-(5-fluoro-2-methoxyphenyl)pyrrolidin-1-yl)pyrazolo[1,5-a]pyrimidine-3-carboxylic acid (Preparation G) and 2-morpholinoethanamine (1.5 equiv.). The title compound was obtained as a white solid (65% yield). MS (apci) m/z=469.1 (M+H).

Example 55

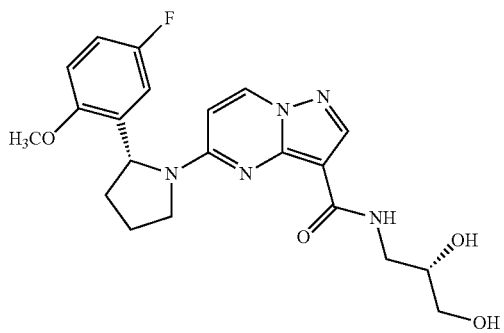 [SMILES: COc1ccc(F)cc1[C@H]1CCCN1c1ccn2ncc(C(=O)NC[C@H](O)CO)c2n1]

N—((S)-2,3-dihydroxypropyl)-5-((R)-2-(5-fluoro-2-methoxyphenyl)pyrrolidin-1-yl)pyrazolo[1,5-a]pyrimidine-3-carboxamide Prepared by the method of Example 1, using (R)-5-(2-(5-fluoro-2-methoxyphenyl)pyrrolidin-1-yl)pyrazolo[1,5-a]pyrimidine-3-carboxylic acid (Preparation G) and (S)-3-aminopropane-1,2-diol (2.0 equiv). The crude material was purified by $SiO_2$ column chromatography, eluting with EtOAc then 10% MeOH-EtOAc to afford the title compound as a white solid (53% yield). MS (apci) m/z=430.1 (M+H).

Example 56

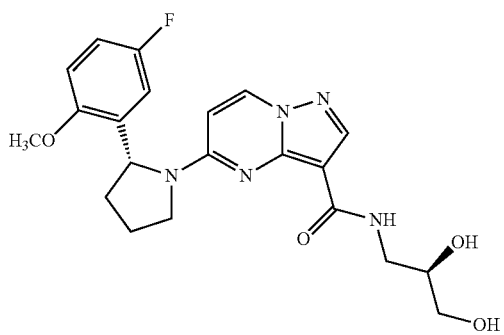 [SMILES: COc1ccc(F)cc1[C@H]1CCCN1c1ccn2ncc(C(=O)NC[C@@H](O)CO)c2n1]

N—((R)-2,3-dihydroxypropyl)-5-((R)-2-(5-fluoro-2-methoxyphenyl)pyrrolidin-1-yl)pyrazolo[1,5-a]pyrimidine-3-carboxamide Prepared by the method of Example 1, using (R)-5-(2-(5-fluoro-2-methoxyphenyl)pyrrolidin-1-yl)pyrazolo[1,5-a]pyrimidine-3-carboxylic acid (Preparation G) and (R)-3-aminopropane-1,2-diol (2.0 equiv). The crude material was purified by $SiO_2$ column chromatography, eluting with EtOAc then 10% MeOH-EtOAc to afford the title compound as a white solid (46% yield). MS (apci) m/z=430.1 (M+H).

Example 57

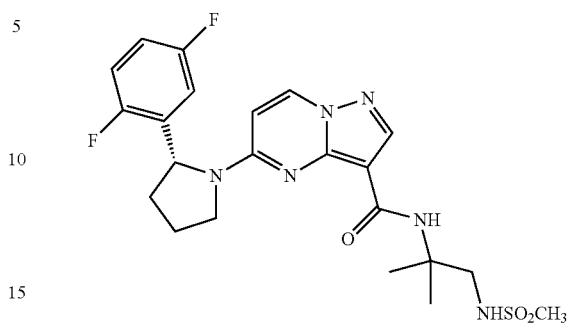

(R)-5-(2-(2,5-difluorophenyl)pyrrolidin-1-yl)-N-(2-methyl-1-(methylsulfonamido)propan-2-yl)pyrazolo[1,5-a]pyrimidine-3-carboxamide Step A: Preparation of tert-butyl 2-amino-2-methylpropylcarbamate Tert-butyl phenyl carbonate (0.421 mL, 2.270 mmol) was added to a solution of 2-methylpropane-1,2-diamine (200 mg, 2.270 mmol) in EtOH (4.5 mL) and the reaction mixture was heated at reflux overnight. The mixture was concentrated and the residue diluted in water. The mixture was acidified with 2N HCl to pH 4 and washed with DCM. The aqueous layer was treated with 1M NaOH (2 mL) and extracted with DCM. The combined organic layers were dried with $MgSO_4$, filtered and concentrated to afford tert-butyl 2-amino-2-methylpropylcarbamate (158 mg, 37% yield) as a colorless oil. MS (apci) m/z=188.9 (M+H).

Step B: Preparation of (R)-tert-butyl 2-(5-(2-(2,5-difluorophenyl)pyrrolidin-1-yl)pyrazolo[1,5-a]pyrimidine-3-carboxamido)-2-methylpropylcarbamate Prepared by the method described in Example 1 using tert-butyl 2-amino-2-methylpropylcarbamate to provide the title compound as a colorless oil (109 mg, 100% yield). MS (apci) m/z=515.2 (M+H).

Step C: Preparation of (R)—N-(1-amino-2-methylpropan-2-yl)-5-(2-(2,5-difluorophenyl)pyrrolidin-1-yl)pyrazolo[1,5-a]pyrimidine-3-carboxamide hydrochloride (R)-tert-butyl 2-(5-(2-(2,5-difluorophenyl)pyrrolidin-1-yl)pyrazolo[1,5-a]pyrimidine-3-carboxamido)-2-methylpropylcarbamate (109 mg, 0.212 mmol) was dissolved in DCM (1.0 mL) and 4N HCl in dioxane (0.530 mL, 2.12 mmol) was added. The mixture was stirred at ambient temperature for 4 hours and was concentrated afford the title compound (105 mg). MS (apci) m/z=415.2 (M+H).

Step D: Preparation of (R)-5-(2-(2,5-difluorophenyl)pyrrolidin-1-yl)-N-(2-methyl-1-(methylsulfonamido)propan-2-yl)pyrazolo[1,5-a]pyrimidine-3-carboxamide (R)—N-(1-amino-2-methylpropan-2-yl)-5-(2-(2,5-difluorophenyl)pyrrolidin-1-yl)pyrazolo[1,5-a]pyrimidine-3-carboxamide hydrochloride (24.0 mg, 0.0532 mmol) was dissolved in DCM (0.53 mL) and triethylamine (15.2 µL, 0.109 mmol) followed by MeSO₂Cl (4.34 µL, 0.0559 mmol) were added sequentially. The mixture was stirred at ambient temperature for 2 hours and was diluted with EtOAc. The mixture was washed with water and brine and was dried with MgSO₄. The solution was filtered and concentrated to afford the title compound (8.0 mg, 30% yield) as a white solid. MS (apci) m/z=493.1 (M+H).

Example 58

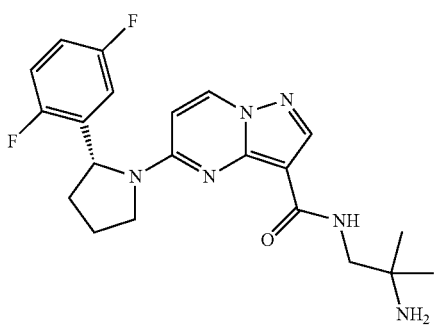 [SMILES: CC(C)(N)CNC(=O)c1cnn2ccc(N3CCC[C@@H]3c3cc(F)ccc3F)nc12]

(R)—N-(2-amino-2-methylpropyl)-5-(2-(2,5-difluorophenyl)pyrrolidin-1-yl)pyrazolo[1,5-a]pyrimidine-3-carboxamide Prepared by the method described in Example 1, using 2-methylpropane-1,2-diamine. The crude product was purified by reverse phase chromatography eluting with 0-100% acetonitrile/water to yield the title compound as a white solid (3.9 mg, 6.0% yield). MS (apci) m/z=415.1 (M+H).

Example 59

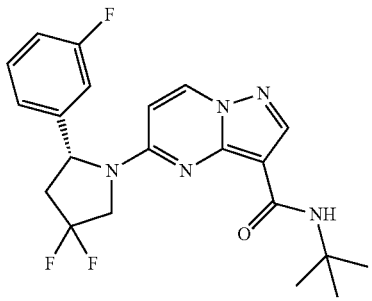 [SMILES: CC(C)(C)NC(=O)c1cnn2ccc(N3CC(F)(F)C[C@@H]3c3cccc(F)c3)nc12]

(R)—N-tert-butyl-5-(4,4-difluoro-2-(3-fluorophenyl)pyrrolidin-1-yl)pyrazolo[1,5-a]pyrimidine-3-carboxamide Step A: Preparation of (R)—N-tert-butyl-5-(2-(3-fluorophenyl)-4-oxopyrrolidin-1-yl)pyrazolo[1,5-a]pyrimidine-3-carboxamide N-tert-butyl-5-((2R,4R)-2-(3-fluorophenyl)-4-hydroxypyrrolidin-1-yl)pyrazolo[1,5-a]pyrimidine-3-carboxamide (Example 42, 10 mg, 0.025 mmol) and the Dess-Martin reagent (16 mg, 0.038 mmol) in DCM (2.0 mL) were stirred at ambient temperature overnight. 1N NaOH (2.5 mL) was added and the reaction stirred for 30 minutes. Brine (2.5 mL) was added and the reaction was filtered through a phase separator frit, washing with several portions of DCM. The DCM solution was concentrated and the residue purified by reverse phase chromatography (20-70% acetonitrile/water) to provide the title compound (2.7 mg, 27% yield) as a clear oil. MS (apci) m/z=396.0 (M+H).

Step B: Preparation of (R)—N-tert-butyl-5-(4,4-difluoro-2-(3-fluorophenyl)pyrrolidin-1-yl)pyrazolo[1,5-a]pyrimidine-3-carboxamide (R)—N-tert-butyl-5-(2-(3-fluorophenyl)-4-oxopyrrolidin-1-yl)pyrazolo[1,5-a]pyrimidine-3-carboxamide (1.40 mg, 3.54 µmol) and bis-(2-methoxyethyl)aminosulfur trifluoride (1.57 mg, 7.08 µmol) were mixed in DCM (2.0 mL) and the reaction was stirred at ambient temperature overnight. 1N NaOH (1.0 mL) was added and the reaction was stirred for 30 minutes. Brine (1.0 mL) was added and the mixture was filtered through a phase separator frit, washing with several portions of DCM. The DCM solution was concentrated and the residue purified by reverse phase chromatography (0-70% acetonitrile/water) to provide the title compound (1.30 mg, 88.0% yield) as a white solid. MS (apci) m/z=418.1 (M+H).

Example 60

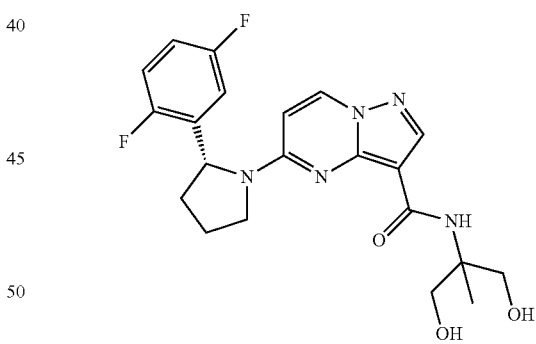

(R)-5-(2-(2,5-difluorophenyl)pyrrolidin-1-yl)-N-(1,3-dihydroxy-2-methylpropan-2-yl)pyrazolo[1,5-a]pyrimidine-3-carboxamide Prepared according to the method of Example 1, using 2-amino-2-methylpropane-1,3-diol (2.0 equiv). The crude material was purified by SiO₂ column chromatography, eluting with EtOAc and then 10% MeOH-EtOAc to provide the title compound as a white solid (54% yield). MS (apci) m/z=432.1 (M+H).

Example 61

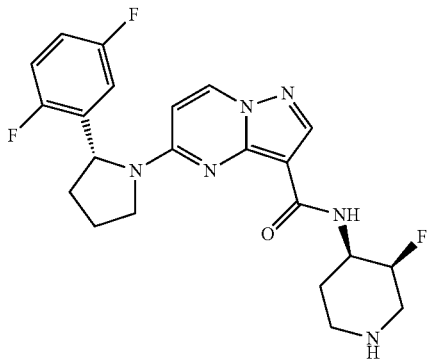 [SMILES: O=C(N[C@@H]1CCNC[C@@H]1F)c1cnn2ccc(N3CCC[C@@H]3c3cc(F)ccc3F)nc12]

5-((R)-2-(2,5-difluorophenyl)pyrrolidin-1-yl)-N-((3 S,4R)-3-fluoropiperidin-4-yl)pyrazolo[1,5-a]pyrimidine-3-carboxamide hydrochloride

Step A: Preparation of (3S,4R)-tert-butyl 4-(5-((R)-2-(2,5-difluorophenyl)pyrrolidin-1-yl)pyrazolo[1,5-a]pyrimidine-3-carboxamido)-3-fluoropiperidine-1-carboxylate Prepared according to the method of Example 1, using (3 S,4R)-tert-butyl 4-amino-3-fluoropiperidine-1-carboxylate (1.5 equiv). The title compound was obtained as a white solid (79% yield). MS (apci) m/z=545.21 (M+H).

Step B: Preparation of 5-((R)-2-(2,5-difluorophenyl)pyrrolidin-1-yl)-N-((3 S,4R)-3-fluoropiperidin-4-yl)pyrazolo[1,5-a]pyrimidine-3-carboxamide hydrochloride To a solution of the title compound from Step A (50.0 mg, 0.092 mmol) in EtOAc (1.5 mL) was added 4M HCl in dioxane (0.460 mL, 1.85 mmol) and the mixture was stirred at ambient temperature for 6 hours (white precipitate formed). The mixture was diluted with dry Et$_2$O (2 volumes) and sonicated to afford a fine white suspension. The solid was collected, washed with dry Et$_2$O and dried under vacuum to give the title compound as a white solid (42 mg, 95% yield). MS (apci) m/z=445.1 (M+H).

Example 62

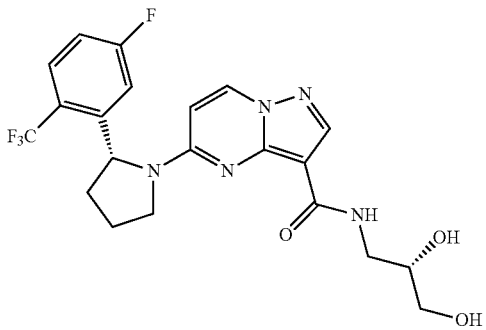 [SMILES: O=C(NC[C@H](O)CO)c1cnn2ccc(N3CCC[C@@H]3c3cc(F)ccc3C(F)(F)F)nc12]

N—((S)-2,3-dihydroxypropyl)-5-((R)-2-(5-fluoro-2-(trifluoromethyl)phenyl) pyrrolidin-1-yl)pyrazolo[1,5-a]pyrimidine-3-carboxamide Prepared by the method described in Example 1 using (R)-5-(2-(5-fluoro-2-(trifluoromethyl)phenyl)pyrrolidin-1-yl)pyrazolo[1,5-a]pyrimidine-3-carboxylic acid (Preparation M) and (S)-3-aminopropane-1,2-diol. The crude material was purified by reverse phase HPLC (0-60% acetonitrile/water) to provide the title compound (26 mg, 73% yield). MS (apci) m/z=468.1 (M+H).

Example 63

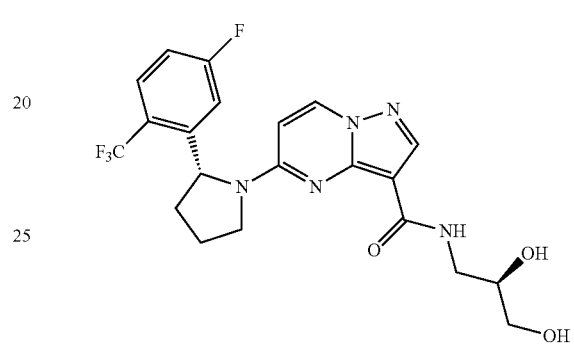

N—((R)-2,3-dihydroxypropyl)-5-((R)-2-(5-fluoro-2-(trifluoromethyl)phenyl) pyrrolidin-1-yl)pyrazolo[1,5-a]pyrimidine-3-carboxamide Prepared by the method described in Example 1 using (R)-5-(2-(5-fluoro-2-(trifluoromethyl)phenyl)pyrrolidin-1-yl)pyrazolo[1,5-a]pyrimidine-3-carboxylic acid (Preparation M) and (R)-3-aminopropane-1,2-diol. The crude material was purified by reverse phase HPLC (0-60% acetonitrile/water) to provide the title compound (34 mg, 73% yield). MS (apci) m/z=468.1 (M+H).

Example 64

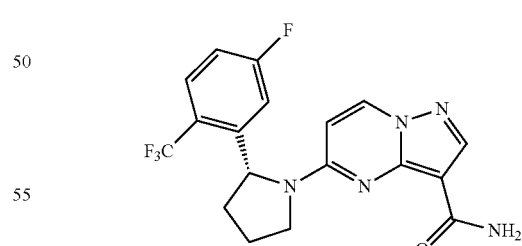

(R)-5-(2-(5-fluoro-2-(trifluoromethyl)phenyl)pyrrolidin-1-yl)pyrazolo[1,5-a]pyrimidine-3-carboxamide Prepared by the method described in Example 1 using (R)-5-(2-(5-fluoro-2-(trifluoromethyl)phenyl)pyrrolidin-1-yl)pyrazolo[1,5-a]pyrimidine-3-carboxylic acid (Preparation M) and ammonium chloride. The crude material was purified by reverse phase HPLC (0-60% acetonitrile/water) to yield the title compound (23 mg, 78% yield.). MS (apci) m/z=394.0 (M+H).

Example 65

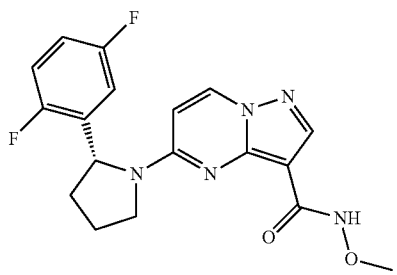 [SMILES: CONC(=O)c1cnn2ccc(N3CCC[C@@H]3c3cc(F)ccc3F)nc12]

(R)-5-(2-(2,5-difluorophenyl)pyrrolidin-1-yl)-N-methoxypyrazolo[1,5-a]pyrimidine-3-carboxamide Prepared by the method described in Example 1 using O-methylhydroxylamine hydrochloride (2.0 equiv). The title compound was obtained as a white solid (53% yield). MS (apci) m/z=374.1 (M+H).

Example 66

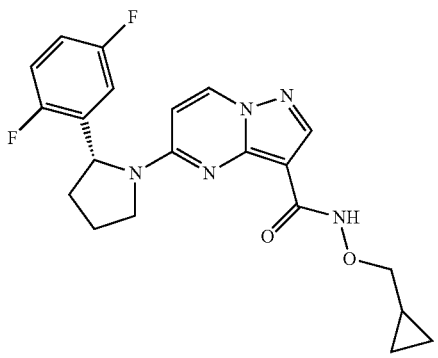 [SMILES: O=C(NOCC1CC1)c1cnn2ccc(N3CCC[C@@H]3c3cc(F)ccc3F)nc12]

(R)—N-(cyclopropylmethoxy)-5-(2-(2,5-difluorophenyl)pyrrolidin-1-yl)pyrazolo[1,5-a]pyrimidine-3-carboxamide Prepared by the method described in Example 1 using O-(cyclopropylmethyl)hydroxylamine (2.0 equiv). The title compound was obtained as a white solid (31% yield). MS (apci) m/z=414.1 (M+H).

Example 67

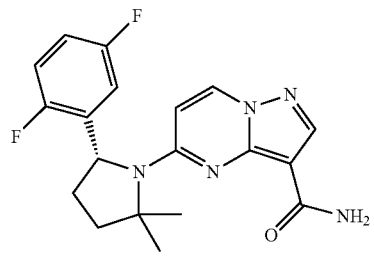 [SMILES: CC1(C)CC[C@H](c2cc(F)ccc2F)N1c1ccn2ncc(C(N)=O)c2n1]

(R)-5-(5-(2,5-difluorophenyl)-2,2-dimethylpyrrolidin-1-yl)pyrazolo[1,5-a]pyrimidine-3-carboxamide Step A: Preparation of (R)-tert-butyl 5-(2,5-difluorophenyl)-2,2-dimethyl pyrrolidine-1-carboxylate Prepared by the method described in Preparation A, Step A substituting tert-butyl pyrrolidine-1-carboxylate with tert-butyl 2,2-dimethylpyrrolidine-1-carboxylate to provide the title compound as a white solid (640 mg, 37% yield). MS (apci) m/z=212.1 (M+H−Boc).

Step B: Preparation of (R)-5-(2,5-difluorophenyl)-2,2-dimethylpyrrolidine hydrochloride Prepared by the method as described in Preparation A, Step B, using (R)-tert-butyl 5-(2,5-difluorophenyl)-2,2-dimethyl pyrrolidine-1-carboxylate to afford the title compound (420 mg, 97% yield). MS (apci) m/z=212.1 (M+H).

Step C: Preparation of (R)-ethyl 5-(5-(2,5-difluorophenyl)-2,2-dimethylpyrrolidin-1-yl)pyrazolo[1,5-a]pyrimidine-3-carboxylate A sealed pressure tube was charged with (R)-5-(2,5-difluoro phenyl)-2,2-dimethylpyrrolidine HCl salt (300 mg, 1.21 mmol), diisopropylethylamine (423 µl, 2.42 mmol), ethyl 5-chloropyrazolo[1,5-a]pyrimidine-3-carboxylate (273 mg, 1.21 mmol) and isopropanol (2.0 mL). The tube was sealed and the mixture was heated at 160° C. for 3 days. Additional ethyl 5-chloropyrazolo[1,5-a]pyrimidine-3-carboxylate (273 mg, 1.21 mmol) was added and the reaction was heated at 160° C. 2 days. The reaction mixture was concentrated and the residue purified by reverse phase HPLC (eluting with 0-60% acetonitrile/H$_2$O) to provide the title compound (136 mg, 28%) as a beige solid. MS (apci) m/z=401.1 (M+H).

Step D: Preparation of (R)-5-(5-(2,5-difluorophenyl)-2,2-dimethylpyrrolidin-1-yl)pyrazolo[1,5-a]pyrimidine-3-carboxylic acid (R)-ethyl 5-(5-(2,5-difluorophenyl)-2,2-dimethylpyrrolidin-1-yl)pyrazolo[1,5-a]pyrimidine-3-carboxylate (136 mg, 0.340 mmol) was dissolved in MeOH (5.0 mL) and 1N NaOH (3.40 mL, 3.40 mmol) was added. The reaction was stirred at ambient temperature for 5 days and then heated at reflux for 4 hours. The reaction mixture was cooled, poured onto a mixture of brine (10 mL) and 2N HCl (5 mL) and extracted with DCM. The combined organic extracts were filtered through PS paper and concentrated to provide the title compound (123 mg, 97% yield) as a beige solid. MS (apci) m/z=373.0 (M+H).

Step E: Preparation of (R)-5-(5-(2,5-difluorophenyl)-2,2-dimethylpyrrolidin-1-yl)pyrazolo[1,5-a]pyrimidine-3-carboxamide Prepared by the method described in Example 1 using (R)-5-(5-(2,5-difluorophenyl)-2,2-dimethylpyrrolidin-1-yl)pyrazolo[1,5-a]pyrimidine-3-carboxylic acid and ammonium chloride. The crude material was purified by reverse phase HPLC (0-70% acetonitrile/water) to provide the title compound (8.5 mg, 33% yield.). MS (apci) m/z=372.1 (M+H).

Example 68

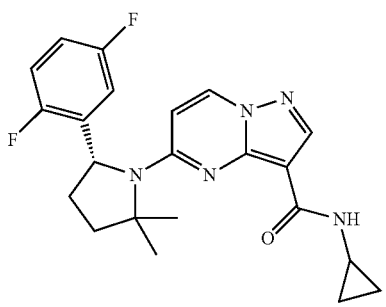 [SMILES: CC1(C)CC[C@H](c2cc(F)ccc2F)N1c1ccn2ncc(C(=O)NC3CC3)c2n1]

(R)—N-cyclopropyl-5-(5-(2,5-difluorophenyl)-2,2-dimethylpyrrolidin-1-yl)pyrazolo[1,5-a]pyrimidine-3-carboxamide Prepared by the method described in Example 1 using (R)-5-(5-(2,5-difluorophenyl)-2,2-dimethylpyrrolidin-1-yl)pyrazolo[1,5-a]pyrimidine-3-carboxylic acid and cyclopropylamine in Step D. The crude material was purified by reverse phase HPLC (0-75% acetonitrile/water) to provide the title compound (11 mg, 39% yield.). MS (apci) m/z=412.1 (M+H).

Example 69

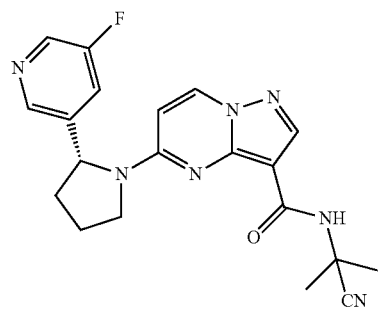 [SMILES: CC(C)(C#N)NC(=O)c1cnn2ccc(N3CCC[C@@H]3c3cncc(F)c3)nc12]

(R)—N-(2-cyanopropan-2-yl)-5-(2-(5-fluoropyridin-3-yl)pyrrolidin-1-yl)pyrazolo[r 15-a]pyrimidine-3-carboxamide Prepared by the method described in Example 1 using (R)-5-(2-(5-fluoropyridin-3-yl)pyrrolidin-1-yl)pyrazolo[1,5-a]pyrimidine-3-carboxylic acid (Preparation I) and 2-amino-2-methylpropanenitrile to yield the title compound as a white solid (21 mg, 57% yield). MS (apci) m/z=394.1 (M+H).

Example 70

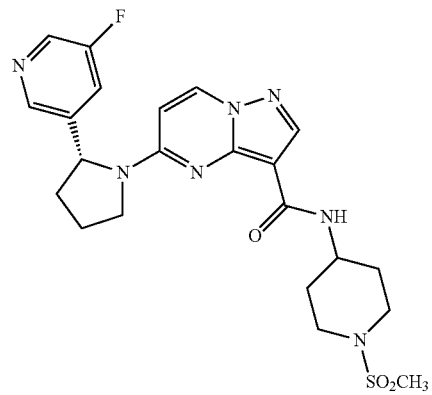 [SMILES: CS(=O)(=O)N1CCC(NC(=O)c2cnn3ccc(N4CCC[C@@H]4c4cncc(F)c4)nc23)CC1]

(R)-5-(2-(5-fluoropyridin-3-yl)pyrrolidin-1-yl)-N-(1-(methylsulfonyl)piperidin-4-yl)pyrazolo[1,5-a]pyrimidine-3-carboxamide Prepared by the method as described in Example 1 using (R)-5-(2-(5-fluoropyridin-3-yl)pyrrolidin-1-yl)pyrazolo[1,5-a]pyrimidine-3-carboxylic acid (Preparation I) and 1-(methylsulfonyl)piperidin-4-amine to yield the title compound as a white solid (44 mg, 100% yield). MS (apci) m/z=488.1 (M+H).

Example 71

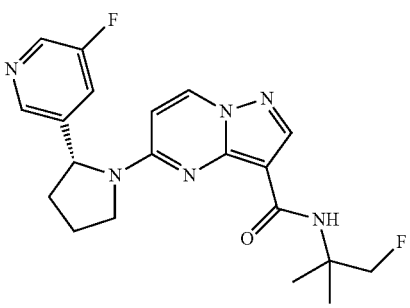 [SMILES: CC(C)(CF)NC(=O)c1cnn2ccc(N3CCC[C@@H]3c3cncc(F)c3)nc12]

(R)—N-(1-fluoro-2-methylpropan-2-yl)-5-(2-(5-fluoropyridin-3-yl)pyrrolidin-1-yl)pyrazolo[1,5-a]pyrimidine-3-carboxamide Prepared by the method described in Example 1 using (R)-5-(2-(5-fluoropyridin-3-yl)pyrrolidin-1-yl)pyrazolo[1,5-a]pyrimidine-3-carboxylic acid (Preparation I) and 1-fluoro-2-methylpropan-2-amine to yield the title compound as a white solid (37 mg, 100% yield). MS (apci) m/z=401.0 (M+H).

Example 72

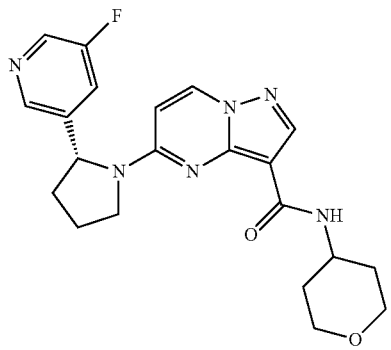 [SMILES: O=C(NC1CCOCC1)c1cnn2ccc(N3CCC[C@@H]3c3cncc(F)c3)nc12]

(R)-5-(2-(5-fluoropyridin-3-yl)pyrrolidin-1-yl)-N-(tetrahydro-2H-pyran-4-yl)pyrazolo[1,5-a]pyrimidine-3-carboxamide Prepared by the method as described in Example 1 using (R)-5-(2-(5-fluoropyridin-3-yl)pyrrolidin-1-yl)pyrazolo[1,5-a]pyrimidine-3-carboxylic acid (Preparation I) and tetrahydro-2H-pyran-4-amine to yield the title compound as a white solid (34 mg, 90% yield). MS (apci) m/z=411.1 (M+H).

Example 73

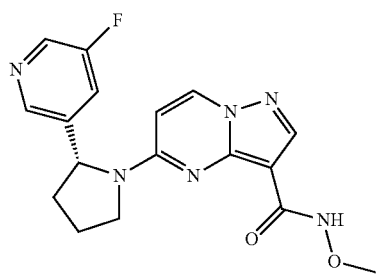 [SMILES: CONC(=O)c1cnn2ccc(N3CCC[C@@H]3c3cncc(F)c3)nc12]

(R)-5-(2-(5-fluoropyridin-3-yl)pyrrolidin-1-yl)-N-methoxypyrazolo[1,5-a]pyrimidine-3-carboxamide Prepared by the method as described in Example 1 using (R)-5-(2-(5-fluoropyridin-3-yl)pyrrolidin-1-yl)pyrazolo[1,5-a]pyrimidine-3-carboxylic acid (Preparation I) and O-methylhydroxylamine to yield the title compound as a white solid (15 mg, 35% yield). MS (apci) m/z=357.0 (M+H).

Example 74

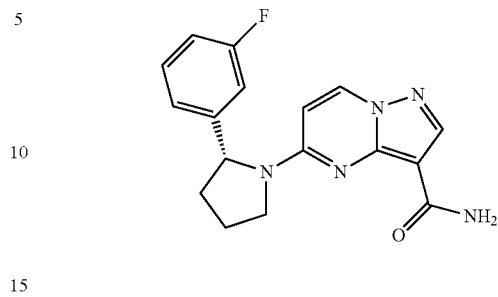

(R)-5-(2-(3-fluorophenyl)pyrrolidin-1-yl)pyrazolo[1,5-a]pyrimidine-3-carboxamide To a suspension of (R)-5-(2-(3-fluorophenyl)pyrrolidin-1-yl)pyrazolo[1,5-a]pyrimidine-3-carboxylic acid (Preparation E, 50.0 mg, 0.153 mmol) in CCl$_4$ (1.0 mL) was added thionyl chloride (182 mg, 1.53 mmol) and the mixture was heated at reflux for 4 hours (homogeneous after 5 minutes). The mixture was cooled to ambient temperature and was concentrated to give a brittle foam. The foam was dissolved in dry THF (2 mL) and dimethylaminopyridine (DMAP) (3.74 mg, 0.031 mmol) was added. Anhydrous ammonia was bubbled into the mixture with stirring for 5 minutes. The reaction vessel was sealed and the reaction was stirred at ambient temperature for 18 hours. The mixture was added to H$_2$O (4 mL) and extracted with EtOAc. The combined extracts were washed with 1M Na$_2$CO$_3$, H$_2$O and saturated NaCl. The solution was dried over MgSO$_4$/activated carbon and filtered through a SiO$_2$ plug (EtOAc then 10% MeOH/EtOAc for elution). The solution was concentrated to give the title compound as a white solid (38 mg, 76%). MS (apci) m/z=326.0 (M+H).

Example 75

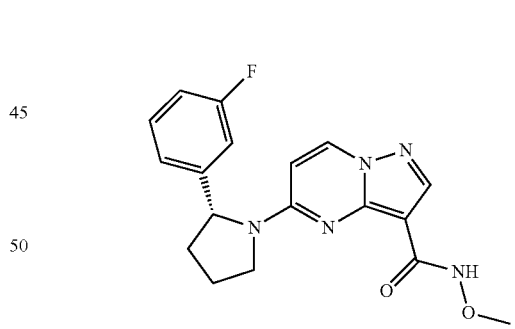

((R)-5-(2-(3-fluorophenyl)pyrrolidin-1-yl)-N-methoxypyrazolo[1,5-a]pyrimidine-3-carboxamide To a suspension of (R)-5-(2-(3-fluorophenyl)pyrrolidin-1-yl)pyrazolo[1,5-a]pyrimidine-3-carboxylic acid (Preparation E, 50.0 mg, 0.153 mmol) in CCl$_4$ (1.5 mL) was added thionyl chloride (182 mg, 1.53 mmol) and mixture heated at reflux for 4 hours (homogeneous). The mixture was cooled to ambient temperature and was concentrated to a brittle beige foam. DMAP (3.7 mg, 0.031 mmol), methylhydroxyl amine HCl (38.4 mg, 0.460 mmol) and dry THF (2 mL) were added and mixed. Diisopropylethylamine (79.2 mg, 0.613 mmol) was added, and the reaction flushed with N₂ and stirred at ambient temperature for 18 hours. The mixture was diluted with H₂O (4 mL) and extracted with EtOAc and the combined extracts were washed with 1M Na₂CO₃, H₂O and saturated NaCl. The solution was dried over MgSO₄/activated carbon and filtered through a SiO₂ plug eluting with EtOAc. The mixture was concentrated to give a white foam that was dissolved in minimal CH₂Cl₂ and treated with dry hexanes to give a fine white suspension. The mixture was concentrated to give the title compound as white solid (42 mg, 77%). MS (apci) m/z=356.0 (M+H).

Example 76

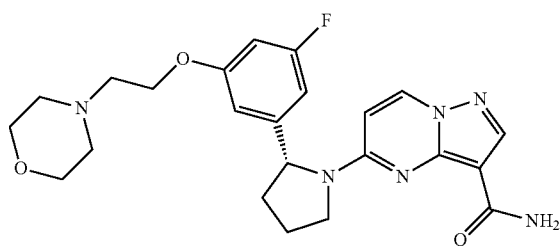 [SMILES: NC(=O)c1cnn2ccc(N3CCC[C@@H]3c3cc(F)cc(OCCN4CCOCC4)c3)nc12]

(R)-5-(2-(3-fluoro-5-(2-morpholinoethoxy)phenyl) pyrrolidin-1-yl)pyrazolo[1,5-a]pyrimidine-3-carboxamide Step A: Preparation of (R)-tert-butyl 2-(3-fluoro-5-hydroxyphenyl)pyrrolidine-1-carboxylate Prepared by the method as described in Preparation A, Step A, substituting 2-bromo-1,4-difluorobenzene with 3-bromo-5-fluorophenyl acetate to afford the title compounds (10.3 g, 62% yield). MS (apci) m/z=182.1 (M+H–Boc).

Step B: Preparation of (R)-3-fluoro-5-(pyrrolidin-2-yl)phenol hydrochloride

To a solution of (R)-tert-butyl 2-(3-fluoro-5-hydroxyphenyl)pyrrolidine-1-carboxylate (10.3 g, 36.5 mmol) in DCM (20 mL) was added 4N HCl in dioxane (36.5 mL, 146 mmol) and the mixture was stirred at ambient temperature for 15 hours. The resulting precipitate was filtered and washed with DCM to afford (R)-3-fluoro-5-(pyrrolidin-2-yl)phenol hydrochloride (5.81 g, 73.3% yield).

Step C: Preparation of (R)-ethyl 5-(2-(3-fluoro-5-hydroxyphenyl)pyrrolidin-1-yl)pyrazolo[1,5-a]pyrimidine-3-carboxylate Prepared by the method as described in Preparation C, Step A, using (R)-2-(2,5-difluorophenyl)pyrrolidine and (R)-3-fluoro-5-(pyrrolidin-2-yl)phenol hydrochloride. The crude material was purified by reverse phase HPLC (0-60% acetonitrile/water) to provide yield the title compound (775 mg, 94% yield). MS (apci) m/z=370.9 (M+H).

Step D: Preparation of (R)-ethyl 5-(2-(3-fluoro-5-(2-morpholinoethoxy) phenyl)pyrrolidin-1-yl)pyrazolo[1,5-a]pyrimidine-3-carboxylate (R)-ethyl 5-(2-(3-fluoro-5-hydroxyphenyl)pyrrolidin-1-yl)pyrazolo[1,5-a]pyrimidine-3-carboxylate (167 mg, 0.451 mmol), 4-(2-chloroethyl)morpholine hydrochloride (168 mg, 0.902 mmol), and K₂CO₃ (312 mg, 2.25 mmol) were suspended in DMF (5 mL) and stirred at ambient temperature for 15 hours. The crude reaction mixture was purified by reverse phase HPLC (0-60% acetonitrile/water) to provide the title compound (218 mg, 100% yield). MS (apci) m/z=484.1 (M+H).

Step E: Preparation of (R)-5-(2-(3-fluoro-5-(2-morpholinoethoxy)phenyl) pyrrolidin-1-yl)pyrazolo[1,5-a]pyrimidine-3-carboxylic acid Prepared using the hydrolysis conditions described in Preparation C, Step B. The crude material was purified by reverse phase HPLC (0-40% acetonitrile/water) to yield the title compound (208 mg, 94% yield). MS (apci) m/z=456.1 (M+H).

Step F: Preparation of (R)-5-(2-(3-fluoro-5-(2-morpholinoethoxy)phenyl) pyrrolidin-1-yl)pyrazolo[1,5-a]pyrimidine-3-carboxamide Prepared by the method described in Example 1 using (R)-5-(2-(3-fluoro-5-(2-morpholinoethoxy)phenyl) pyrrolidin-1-yl)pyrazolo[1,5-a]pyrimidine-3-carboxylic acid ammonium chloride to yield the title compound as a white solid (19 mg, 69% yield.). MS (apci) m/z=455.1 (M+H).

Example 77

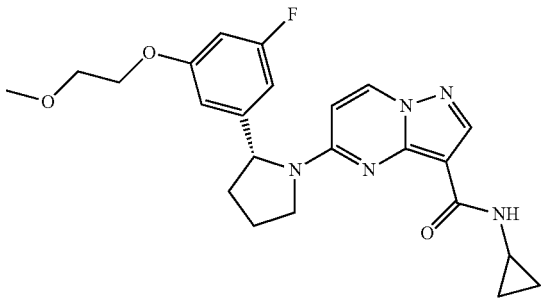 [SMILES: COCCOc1cc(F)cc([C@H]2CCCN2c2ccn3ncc(C(=O)NC4CC4)c3n2)c1]

(R)—N-cyclopropyl-5-(2-(3-fluoro-5-(2-methoxyethoxy)phenyl)pyrrolidin-1-yl)pyrazole[1,5-a]pyrimidine-3-carboxamide Step A: Preparation of (R)-ethyl 5-(2-(3-fluoro-5-(2-methoxyethoxy)phenyl)pyrrolidin-1-yl)pyrazolo[1,5-a]pyrimidine-3-carboxylate (R)-ethyl 5-(2-(3-fluoro-5-hydroxyphenyl)pyrrolidin-1-yl)pyrazolo[1,5-a]pyrimidine-3-carboxylate (Example 76 Step B, 174 mg, 0.470 mmol), 1-bromo-2-methoxyethane (196 mg, 1.41 mmol), and K₂CO₃ (325 mg, 2.35 mmol) were suspended in DMF (5 mL) and stirred at ambient temperature for 15 hours. The crude reaction mixture was purified by reverse phase HPLC (0-60% acetonitrile/water) to provide yield the title compound (183 mg, 91% yield). MS (apci) m/z=429.0 (M+H).

Step B: Preparation of (R)-5-(2-(3-fluoro-5-(2-methoxyethoxy)phenyl)pyrrolidin-1-yl)pyrazolo[1,5-a]pyrimidine-3-carboxylic acid (R)-ethyl 5-(2-(3-fluoro-5-(2-methoxy ethoxy)phenyl) pyrrolidin-1-yl)pyrazolo[1,5-a]pyrimidine-3-carboxylate (178 mg, 0.415 mmol) was suspended in a mixture of 1N NaOH (5 mL) and MeOH (5 mL). The reaction mixture was stirred at ambient temperature until complete and quenched with 2N HCl (25 mL). The mixture was extracted with ethyl acetate and the combined organic fractions were concentrated to give the title compound (177 mg, 100% yield). MS (apci) m/z=401.0 (M+H).

Step C: Preparation of (R)—N-cyclopropyl-5-(2-(3-fluoro-5-(2-methoxyethoxy) phenyl)pyrrolidin-1-yl) pyrazolo[1,5-a]pyrimidine-3-carboxamide Prepared by the method described in Example 1 using (R)-5-(2-(3-fluoro-5-(2-methoxyethoxy)phenyl)pyrrolidin-1-yl)pyrazolo[1,5-a]pyrimidine-3-carboxylic acid and cyclopropylamine to yield the title compound as a white solid (16 mg, 52% yield). MS (apci) m/z=440.1 (M+H).

Example 78

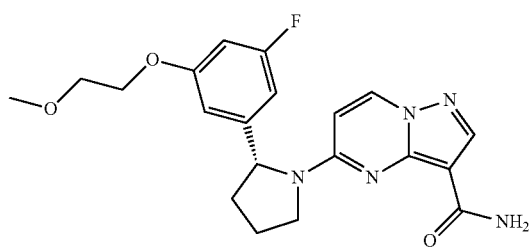 [SMILES: COCCOc1cc(F)cc([C@H]2CCCN2c2ccn3ncc(C(N)=O)c3n2)c1]

(R)-5-(2-(3-fluoro-5-(2-methoxyethoxy)phenyl)pyrrolidin-1-yl)pyrazolo[1,5-a]pyrimidine-3-carboxamide Prepared by the method described in Example 77 using ammonium chloride in Step C. The crude material was purified by reverse phase HPLC (0-60% acetonitrile/water) to provide the title compound (16 mg, 53% yield.). MS (apci) m/z=400.1 (M+H).

Example 79

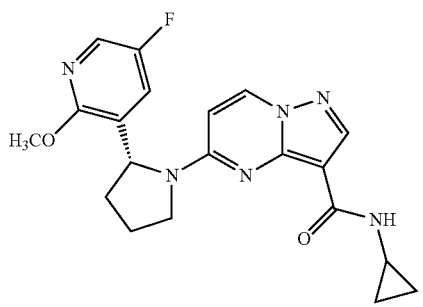

(R)—N-cyclopropyl-5-(2-(5-fluoro-2-methoxypyridin-3-yl)pyrrolidin-1-yl)pyrazolo[1,5-a]pyrimidine-3-carboxamide Prepared by the method described in Example 1 using (R)-5-(2-(5-fluoro-2-methoxypyridin-3-yl)pyrrolidin-1-yl) pyrazolo[1,5-a]pyrimidine-3-carboxylic acid (Preparation K) and cyclopropanamine. The combined organic extracts were concentrated and the residue was purified by reverse phase HPLC (0-70% acetonitrile/water) to provide the title compound (19 mg, 57% yield.). MS (apci) m/z=397.0 (M+H).

Example 80

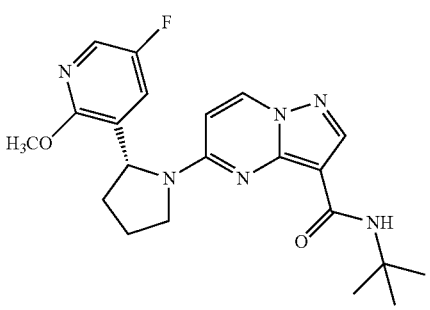 [SMILES: COc1ncc(F)cc1[C@H]1CCCN1c1ccn2ncc(C(=O)NC(C)(C)C)c2n1]

(R)—N-tert-butyl-5-(2-(5-fluoro-2-methoxypyridin-3-yl)pyrrolidin-1-yl)pyrazolo[1,5-a]pyrimidine-3-carboxamide Prepared by the method described in Example 1 using (R)-5-(2-(5-fluoro-2-methoxypyridin-3-yl)pyrrolidin-1-yl) pyrazolo[1,5-a]pyrimidine-3-carboxylic acid (Preparation K). The combined organic extracts were concentrated and the residue was purified by reverse phase HPLC (0-80% acetonitrile/water) to provide the title compound (23 mg, 68% yield). MS (apci) m/z=413.0 (M+H).

Example 81

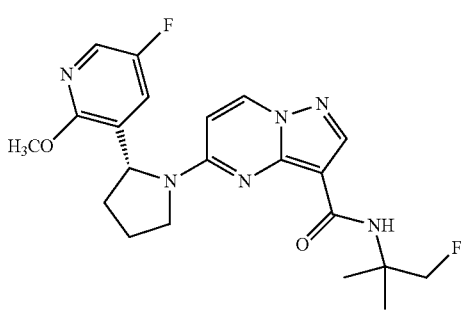 [SMILES: COc1ncc(F)cc1[C@H]1CCCN1c1ccn2ncc(C(=O)NC(C)(C)CF)c2n1]

(R)-5-(2-(5-fluoro-2-methoxypyridin-3-yl)pyrrolidin-1-yl)-N-(1-fluoro-2-methylpropan-2-yl)pyrazolo[1,5-a]pyrimidine-3-carboxamide Prepared by the method described in Example 1 using (R)-5-(2-(5-fluoro-2-methoxypyridin-3-yl)pyrrolidin-1-yl) pyrazolo[1,5-a]pyrimidine-3-carboxylic acid (Preparation K) and 1-fluoro-2-methylpropan-2-amine. The combined organic extracts were concentrated and the residue was purified by reverse phase HPLC (0-90% acetonitrile/water) to provide the title compound (28 mg, 78% yield). MS (apci) m/z=431.0 (M+H).

Example 82

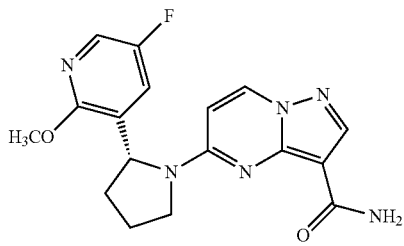 [SMILES: COc1ncc(F)cc1[C@H]1CCCN1c1ccn2ncc(C(N)=O)c2n1]

(R)-5-(2-(5-fluoro-2-methoxypyridin-3-yl)pyrrolidin-1-yl)pyrazolo[1,5-a]pyrimidine-3-carboxamide Prepared by the method described in Example 1 using (R)-5-(2-(5-fluoro-2-methoxypyridin-3-yl)pyrrolidin-1-yl)pyrazolo[1,5-a]pyrimidine-3-carboxylic acid (Preparation K) and 7N $NH_3$ in MeOH. The combined organic extracts were concentrated and the residue was purified by reverse phase HPLC (0-80% acetonitrile/water) to provide the title compound (15 mg, 38% yield). MS (apci) m/z=357.0 (M+H).

Example 83

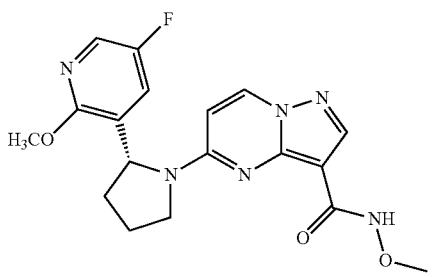 [SMILES: CONC(=O)c1cnn2ccc(N3CCC[C@@H]3c3cc(F)cnc3OC)nc12]

(R)-5-(2-(5-fluoro-2-methoxypyridin-3-yl)pyrrolidin-1-yl)-N-methoxypyrazolo[1,5-a]pyrimidine-3-carboxamide Prepared by the method described in Example 1 using (R)-5-(2-(5-fluoro-2-methoxypyridin-3-yl)pyrrolidin-1-yl)pyrazolo[1,5-a]pyrimidine-3-carboxylic acid (Preparation K) and O-methylhydroxylamine. The combined organic extracts were concentrated and the residue was purified by reverse phase HPLC (0-80% acetonitrile/water) to yield the title compound (29 mg, 67% yield). MS (apci) m/z=387.0 (M+H).

Example 84

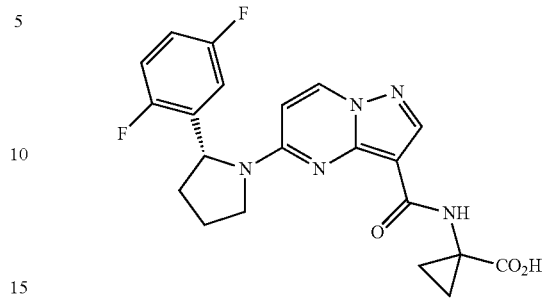

(R)-1-(5-(2-(2,5-difluorophenyl)pyrrolidin-1-yl)pyrazolo[1,5-a]pyrimidine-3-carboxamido)cyclopropanecarboxylic acid Step A: Preparation of (R)-ethyl 1-(5-(2-(2,5-difluorophenyl)pyrrolidin-1-yl)pyrazolo[1,5-a]pyrimidine-3-carboxamido)cyclopropanecarboxylate Using ethyl 1-aminocyclopropanecarboxylate hydrochloride (2.0 equiv) in the procedure described for the synthesis of Example 1, the title compound was obtained as a white solid (61% yield). MS (apci) m/z=456.1 (M+H).

Step B: Preparation of (R)-1-(5-(2-(2,5-difluorophenyl)pyrrolidin-1-yl)pyrazolo[1,5-a]pyrimidine-3-carboxamido)cyclopropanecarboxylic acid To a solution of the above ester (39 mg, 0.086 mmol) in 2:1 THF-MeOH (1.5 mL) was added 1M aq. LiOH (0.257 mL, 257 mmol) and the mixture was stirred at ambient temperature for 18 hours. The mixture was concentrated and the residual solid was dissolved in $H_2O$ (3 mL). The solution was treated with 1M HCl to pH=3. The resulting precipitate was collected, washed with water and dried in vacuum to yield the title compound as a white solid (31 mg, 83%). MS (apci) m/z=428.0 (M+H).

Example 85

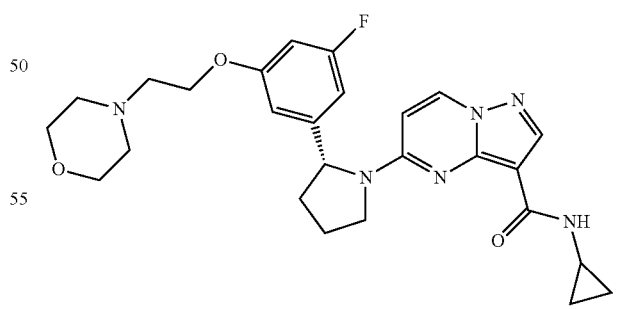

(R)—N-cyclopropyl-5-(2-(3-fluoro-5-(2-morpholinoethoxy)phenyl)pyrrolidin-1-yl)pyrazolo[1,5-a]pyrimidine-3-carboxamide Prepared by the method described in Example 76, substituting ammonium chloride with cyclopropylamine in Step F. The crude material was purified by reverse phase HPLC (0-60% acetonitrile/water) to provide the title compound (30 mg, 99% yield.). MS (apci) m/z=495.1 (M+H).

Example 86

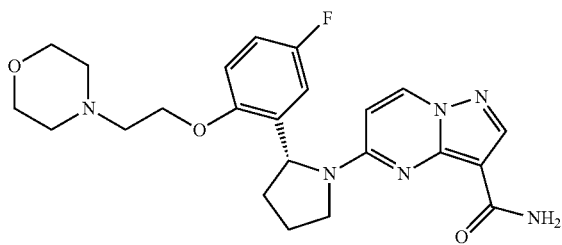 [SMILES: NC(=O)c1cnn2ccc(N3CCC[C@@H]3c3cc(F)ccc3OCCN3CCOCC3)nc12]

(R)-5-(2-(5-fluoro-2-(2-morpholinoethoxy) phenyl) pyrrolidin-1-yl)pyrazolo[1,5-a]pyrimidine-3-carboxamide Step A: Preparation of (R)-tert-butyl 2-(2-acetoxy-5-fluorophenyl)pyrrolidine-1-carboxylate Prepared by the method as described in Preparation A, Step A, substituting 2-bromo-1,4-difluorobenzene with 2-bromo-4-fluorophenyl acetate to afford the title compound (5.75 g, 35% yield). MS (apci) m/z=224.1 (M+H−Boc).

Step B: Preparation of (R)-4-fluoro-2-(pyrrolidin-2-yl)phenol hydrochloride

Prepared according to the procedure outlined for Example 76, Step B, to afford the title compound (2.64 g, 59.3% yield). MS (apci) m/z=182.1 (M+H).

Step C: Preparation of (R)-ethyl 5-(2-(3-fluoro-5-hydroxyphenyl)pyrrolidin-1-yl)pyrazolo[1,5-a]pyrimidine-3-carboxylate Prepared by the method as described in Preparation C, Step A, using ethyl 5-chloropyrazolo[1,5-a]pyrimidine-3-carboxylate and (R)-4-fluoro-2-(pyrrolidin-2-yl)phenol hydrochloride. The crude material was purified by reverse phase HPLC (0-65% acetonitrile/water) to provide the title compound (686 mg, 84% yield). MS (apci) m/z=371.0 (M+H).

Step D: Preparation of (R)-ethyl 5-(2-(3-fluoro-5-(2-morpholinoethoxy) phenyl)pyrrolidin-1-yl)pyrazolo[1,5-a]pyrimidine-3-carboxylate Prepared according to the procedure described in Example 76, Step D, using (R)-ethyl 5-(2-(3-fluoro-5-hydroxyphenyl)pyrrolidin-1-yl)pyrazolo[1,5-a]pyrimidine-3-carboxylate. The crude reaction mixture was purified by reverse phase HPLC (0-60% acetonitrile/water) to provide the title compound (250 mg, 96% yield). MS (apci) m/z=484.1 (M+H).

Step E: Preparation of (R)-5-(2-(5-fluoro-2-(2-morpholinoethoxy) phenyl) pyrrolidin-1-yl)pyrazolo[1, 5-a]pyrimidine-3-carboxylic acid hydrochloride To a solution of (R)-ethyl 5-(2-(3-fluoro-5-(2-morpholinoethoxy) phenyl)pyrrolidin-1-yl)pyrazolo[1,5-a]pyrimidine-3-carboxylate (250 mg, 535 mmol) in MeOH (10 ml) was added 1N NaOH (aqueous, 6 mL). The reaction was stirred at ambient temperature for 1 week, then concentrated, treated with 4N HCl in dioxane (5 ml) and concentrated. The crude material was purified by reverse phase HPLC (0-50% acetonitrile/water) to yield the title compound. MS (apci) m/z=456.1 (M+H).

Step F: Preparation of (R)-5-(2-(5-fluoro-2-(2-morpholinoethoxy) phenyl) pyrrolidin-1-yl)pyrazolo[1, 5-a]pyrimidine-3-carboxamide Prepared by the method described in Example 76, Step F, using ((R)-5-(2-(5-fluoro-2-(2-morpholinoethoxy) phenyl) pyrrolidin-1-yl)pyrazolo[1,5-a]pyrimidine-3-carboxylic acid hydrochloride and ammonium chloride to yield the title compound as a white solid (42.2 mg, 91% yield.). MS (apci) m/z=455.1 (M+H).

Example 87

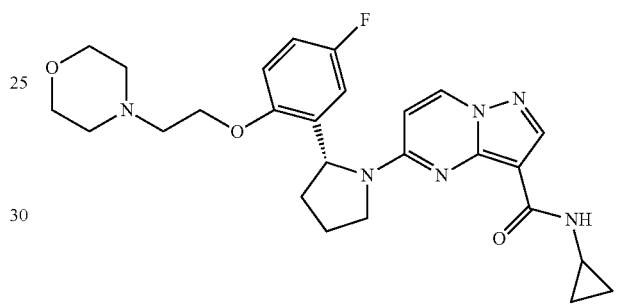

(R)—N-cyclopropyl-5-(2-(5-fluoro-2-(2-morpholinoethoxy)phenyl) pyrrolidin-1-yl)pyrazolo[1,5-a]pyrimidine-3-carboxamide Prepared by the method described in Example 76, Step F using ((R)-5-(2-(5-fluoro-2-(2-morpholinoethoxy)phenyl) pyrrolidin-1-yl)pyrazolo[1,5-a]pyrimidine-3-carboxylic acid hydrochloride and cyclopropylamine to yield the title compound as a white solid (35.4 mg, 70% yield.). MS (apci) m/z=495.1 (M+H).

Example 88

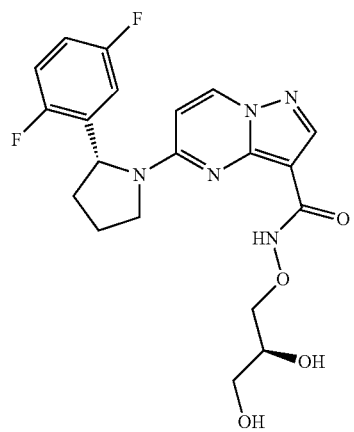 [SMILES: O=C(NOC[C@@H](O)CO)c1cnn2ccc(N3CCC[C@@H]3c3cc(F)ccc3F)nc12]

5-((R)-2-(2,5-difluorophenyl)pyrrolidin-1-yl)-N—((S)-2,3-dihydroxypropoxy)pyrazolo[1,5-a]pyrimidine-3-carboxamide Step A: Preparation of 5-((R)-2-(2,5-difluorophenyl)pyrrolidin-1-yl)-N—(((S)-2,2-dimethyl-1,3-dioxolan-4-yl)methoxy)pyrazolo[1,5-a]pyrimidine-3-carboxamide To a suspension of (R)-5-(2-(2,5-difluorophenyl)pyrrolidin-1-yl)pyrazolo[1,5-a]pyrimidine-3-carboxylic acid (Preparation C, 100 mg, 0.290 mmol) in $CCl_4$ (1.5 mL) was added thionyl chloride (0.10 mL, 1.37 mmol) and the mixture was heated at reflux for 2.5 hours. The mixture was cooled to ambient temperature and was concentrated to give a residual brittle foam. The foam was dissolved in dry THF (2.0 mL) and the solution was sequentially treated with DMAP, DIEA and (S)—O-((2,2-dimethyl-1,3-dioxolan-4-yl)methyl)hydroxylamine (85.5 mg, 0.581 mmol). The reaction was stirred at ambient temperature for 4.5 hours and was concentrated to approx. 0.5 mL. The mixture was diluted with $H_2O$ (5 mL) and extracted with 50% EtOAc-hexanes. The combined extracts were washed with 1M HCl, $H_2O$, 1M $Na_2CO_3$ and saturated NaCl. The solution was dried over $MgSO_4$ and activated carbon, then filtered through a short $SiO_2$ plug, eluting first with 50% EtOAc-hexanes then 10% MeOH-EtOAc. The MeOH-EtOAc pool was concentrated to give a colorless foam. The foam was dissolved in minimal $CH_2Cl_2$ and treated with hexanes to give a white suspension. The suspension was concentrated to afford the title compound as white solid that was dried in vacuum (137 mg, 100%). MS (apci) m/z=474.1 (M+H).

Step B: Preparation of 5-((R)-2-(2,5-difluorophenyl)pyrrolidin-1-yl)-N—((S)-2,3-dihydroxypropoxy)pyrazolo[1,5-a]pyrimidine-3-carboxamide To a solution of 5-((R)-2-(2,5-difluorophenyl)pyrrolidin-1-yl)-N—(((S)-2,2-dimethyl-1,3-dioxolan-4-yl)methoxy)pyrazolo[1,5-a]pyrimidine-3-carboxamide (135 mg, 0.285 mmol) in THF (4.0 mL) was added 6M HCl (1.0 mL) dropwise and the mixture was stirred at ambient temperature for 1.5 hours. The reaction mixture was concentrated to approximately 1 mL and was diluted with $H_2O$ (5 mL). The resulting milky white mixture was extracted with EtOAc and the combined extracts were washed with 1M $Na_2CO_3$ and saturated NaCl. The EtOAc solution was dried over $MgSO_4$ and filtered through a packed Celite pad capped with a layer of $MgSO_4$. The solution was concentrated to give a colorless foam that was dissolved in minimal $CH_2Cl_2$ and treated with hexanes to give a white suspension. The suspension was concentrated to give the title compound as a white solid that was dried in vacuum (102 mg, 82%). MS (apci) m/z=434.0 (M+H).

Example 89

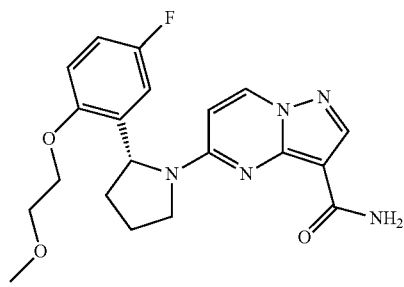 [SMILES: COCCOc1ccc(F)cc1[C@H]1CCCN1c1ccn2ncc(C(N)=O)c2n1]

(R)-5-(2-(5-fluoro-2-(2-methoxyethoxy)phenyl)pyrrolidin-1-yl)pyrazolo[1,5-a]pyrimidine-3-carboxamide Step A: Preparation of (R)-methyl 5-(2-(5-fluoro-2-(2-methoxyethoxy)phenyl) pyrrolidin-1-yl)pyrazolo[1,5-a]pyrimidine-3-carboxylate Prepared by the method described in Example 86, Step D, substituting 4-(2-chloroethyl)morpholine hydrochloride with 1-bromo-2-methoxyethane to afford the title compound (209 mg, 80% yield). MS (apci) m/z=415.0 (M+H).

Step B: Preparation of (R)-5-(2-(5-fluoro-2-(2-methoxyethoxy)phenyl) pyrrolidin-1-yl)pyrazolo[1,5-a]pyrimidine-3-carboxylic acid Prepared from (R)-methyl 5-(2-(5-fluoro-2-(2-methoxyethoxy)phenyl) pyrrolidin-1-yl)pyrazolo[1,5-a]pyrimidine-3-carboxylate by the method described in Example 77, Step B to afford the title compound (163 mg, 84% yield). MS (apci) m/z=401.0 (M+H).

Step C: Preparation (R)-5-(2-(5-fluoro-2-(2-methoxyethoxy)phenyl) pyrrolidin-1-yl)pyrazolo[1,5-a]pyrimidine-3-carboxamide Prepared by the method described in Example 76, Step F using (R)-5-(2-(5-fluoro-2-(2-methoxyethoxy)phenyl) pyrrolidin-1-yl)pyrazolo[1,5-a] pyrimidine-3-carboxylic acid and ammonium chloride to yield the title compound as a white solid (32.6 mg, 55% yield.). MS (apci) m/z=400.1 (M+H).

Example 90

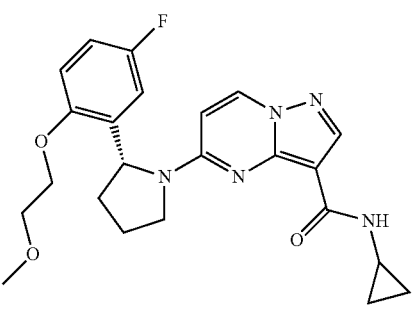 [SMILES: COCCOc1ccc(F)cc1[C@H]1CCCN1c1ccn2ncc(C(=O)NC3CC3)c2n1]

(R)—N-cyclopropyl-5-(2-(5-fluoro-2-(2-methoxy-ethoxy)phenyl) pyrrolidin-1-yl)pyrazolo[1,5-a]pyrimidine-3-carboxamide Prepared by the method described in Example 89, Step C substituting ammonium chloride with cyclopropylamine to yield the title compound as a white solid (7.9 mg, 12% yield.). MS (apci) m/z=495.1 (M+H).

Example 91

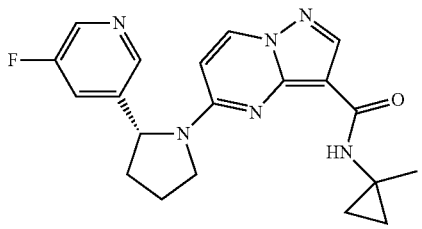 [SMILES: CC1(NC(=O)c2cnn3ccc(N4CCC[C@@H]4c4cncc(F)c4)nc23)CC1]

(R)-5-(2-(5-fluoropyridin-3-yl)pyrrolidin-1-yl)-N-(1-methylcyclopropyl)pyrazolo[1,5-a]pyrimidine-3-carboxamide Step A: Preparation of tert-butyl 1-methylcyclopropylcarbamate Diphenylphosphoryl azide (2.63 mL, 12.2 mmol) was added to a mixture of 1-methylcyclopropanecarboxylic acid (1.22 g, 12.2 mmol) and TEA (1.70 mL, 12.2 mmol) in anhydrous tert-BuOH (25 mL, 12.2 mmol) under nitrogen, followed by heating first at 50° C. for 15 minutes, then at 100° C. for 16 hours. After cooling to ambient temperature, the reaction was concentrated. The crude material was taken up in ether (50 mL), washed with saturated NaHCO₃ and water (50 mL each), and dried (MgSO₄), giving the crude product as white solid (0.81 g, 38% yield), which was used directly in the next step without further purification.

Step B: Preparation of 1-methylcyclopropanamine hydrochloride

A solution of 1-methylcyclopropylcarbamate (250 mg, 1.46 mmol) in HCl (4N dioxane, 3.65 mL, 14.6 mmol) was stirred at ambient temperature for 1 hour. It was then concentrated, triturated with ether, and filtered, giving the product as white solid (78 mg, 50%).

Step C: Preparation of (R)-5-(2-(5-fluoropyridin-3-yl)pyrrolidin-1-yl)-N-(1-methylcyclopropyl)pyrazolo[1,5-a]pyrimidine-3-carboxamide To a DMF (0.6 mL) solution of (R)-5-(2-(5-fluoropyridin-3-yl)pyrrolidin-1-yl)pyrazolo[1,5-a]pyrimidine-3-carboxylic acid (Preparation I, 10.5 mg, 0.0321 mmol) and HATU (14.6 mg, 0.0385 mmol) was added 1-methylcyclopropanamine hydrochloride (4.14 mg, 0.0385 mmol) and DIEA (0.0168 mL, 0.0962 mmol). After stirring for 10 minutes, the reaction mixture was directly purified by reverse-phase chromatography (5 to 50% acetonitrile/water) to yield the final product as white solid (10 mg, 82%). LCMS (apci) m/z=381.1 (M+H).

Example 92

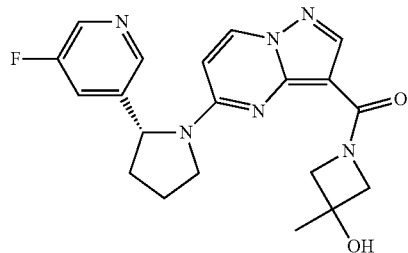 [SMILES: CC1(O)CN(C(=O)c2cnn3ccc(N4CCC[C@@H]4c4cncc(F)c4)nc23)C1]

(R)-(5-(2-(5-fluoropyridin-3-yl)pyrrolidin-1-yl)pyrazolo[1,5-a]pyrimidin-3-yl)(3-hydroxy-3-methylazetidin-1-yl)methanone Step A: Preparation of 3-methylazetidin-3-ol 2,2,2-trifluoroacetate To a solution of 1-benzhydryl-3-methylazetidin-3-ol (0.46 g, 1.82 mmol) in EtOH (15 mL) was added TFA (0.14 mL, 1.82 mmol) and Pd(OH)₂/C (0.127 g, 0.182 mmol). The reaction was subjected to hydrogenation (50 psi) on a Parr shaker at ambient temperature overnight. The reaction mixture was filtered, concentrated and triturated with Et₂O. The fine white solid was filtered to yield the product as a TFA salt.

Step B: Preparation of (R)-(5-(2-(5-fluoropyridin-3-yl)pyrrolidin-1-yl)pyrazolo[1,5-a]pyrimidin-3-yl)(3-hydroxy-3-methylazetidin-1-yl)methanone To a DMF (1.0 mL) solution of (R)-5-(2-(5-fluoropyridin-3-yl)pyrrolidin-1-yl)pyrazolo[1,5-a]pyrimidine-3-carboxylic acid (Preparation I, 85 mg, 0.26 mmol) was added HATU (118 mg, 0.31 mmol) and 3-methylazetidin-3-ol 2,2,2-trifluoroacetate (63 mg, 0.31 mmol) at ambient temperature, followed by addition of DIEA (0.14 mL, 0.78 mmol) at 0° C. After stirring for 5 minutes at ambient temperature, the reaction was directly purified by reverse-phase chromatography (5 to 45% acetonitrile/water) to yield the final product as white solid (84 mg, 82%). LCMS (apci) m/z=397.1 (M+H).

Example 93

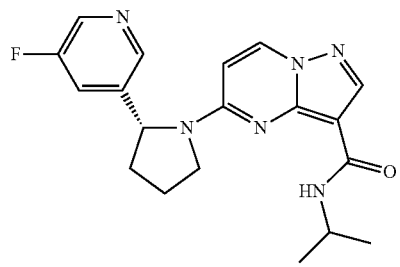 [SMILES: CC(C)NC(=O)c1cnn2ccc(N3CCC[C@@H]3c3cncc(F)c3)nc12]

(R)-5-(2-(5-fluoropyridin-3-yl)pyrrolidin-1-yl)-N-isopropylpyrazolo[1,5-a]pyrimidine-3-carboxamide To a DMF (1.0 mL) solution of (R)-5-(2-(5-fluoropyridin-3-yl)pyrrolidin-1-yl)pyrazolo[1,5-a]pyrimidine-3-carboxylic acid (Preparation I, 80 mg, 0.244 mmol) was added HATU (112 mg, 0.293 mmol) and propan-2-amine (0.0250 ml, 0.293 mmol) at ambient temperature, followed by dropwise addition of DIEA (0.128 ml, 0.733 mmol) at 0° C. After stirring for 5 minutes at ambient temperature, the reaction was poured into 1:1 water/saturated NaHCO₃ (15 mL) and the layers were separated. The aqueous layer was extracted with EtOAc (3×15 mL). The combined organic layers were dried (Na₂SO₄), filtered and concentrated. The crude material was purified by reverse-phase chromatography (5 to 54% acetonitrile/water) to yield the final product as white solid (26 mg, 29%). LCMS (apci) m/z=369.1 (M+H).

Example 94

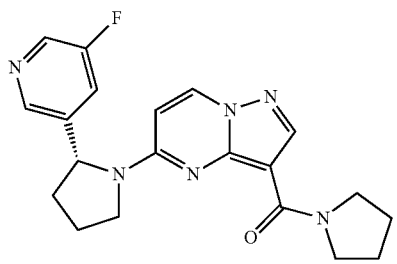 [SMILES: O=C(c1cnn2ccc(N3CCC[C@@H]3c3cncc(F)c3)nc12)N1CCCC1]

(R)-(5-(2-(5-fluoropyridin-3-yl)pyrrolidin-1-yl)pyrazolo[1,5-a]pyrimidin-3-yl)(pyrrolidin-1-yl)methanone To a solution of (R)-5-(2-(5-fluoropyridin-3-yl)pyrrolidin-1-yl)pyrazolo[1,5-a]pyrimidine-3-carboxylic acid (Preparation I, 50 mg, 0.15 mmol) in anhydrous CH₂Cl₂ (2 mL) was added HOBt (41 mg, 0.31 mmol) followed by EDCI (88 mg, 0.46 mmol). The solution was stirred for 15 minutes, then treated with triethylamine (64 µL, 0.46 mmol) followed by pyrrolidine (38 µL, 0.46 mmol). After stirring at ambient temperature overnight, the reaction mixture was partitioned between saturated NH₄Cl (20 mL) and CH₂Cl₂ (20 mL). The aqueous layer was extracted with CH₂Cl₂ (2×10 mL). The combined organic phases were washed with brine (10 mL), dried over Na₂SO₄ and concentrated. The crude material was purified by silica chromatography (2 to 5% MeOH/CH₂Cl₂) to yield the final product as white solid (38 mg, 65%). LCMS (apci) m/z=381.1 (M+H).

Example 95

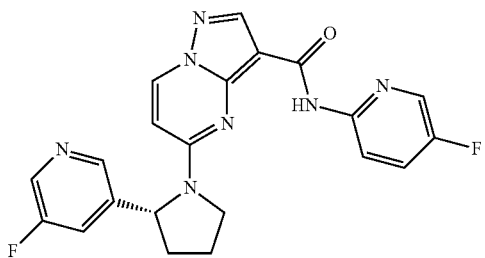 [SMILES: O=C(Nc1ccc(F)cn1)c1cnn2ccc(N3CCC[C@@H]3c3cncc(F)c3)nc12]

(R)—N-(5-fluoropyridin-2-yl)-5-(2-(5-fluoropyridin-3-yl)pyrrolidin-1-yl)pyrazolo[1,5-a]pyrimidine-3-carboxamide To a DMF (0.25 mL) solution of (R)-5-(2-(5-fluoropyridin-3-yl)pyrrolidin-1-yl)pyrazolo[1,5-a]pyrimidine-3-carboxylic acid (Preparation I, 25 mg, 0.076 mmol) and HATU (35 mg, 0.092 mmol) was added 5-fluoropyridin-2-amine (10 mg, 0.092 mmol), followed by drop-wise addition of DIEA (0.040 mL, 0.23 mmol) at ambient temperature. The reaction was heated at 70° C. overnight, cooled, and directly purified by reverse-phase chromatography (5 to 66% acetonitrile/water) to yield the final product as white solid (25 mg, 78%). LCMS (apci) m/z=422.0 (M+H).

Example 96

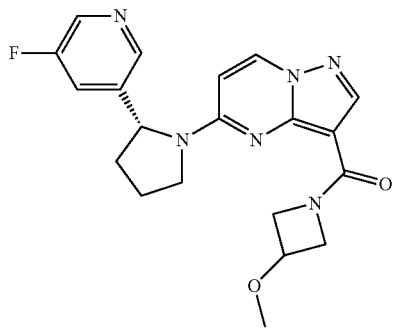 [SMILES: COC1CN(C(=O)c2cnn3ccc(N4CCC[C@@H]4c4cncc(F)c4)nc23)C1]

Step A: Preparation of 3-methoxyazetidine 2,2,2-trifluoroacetate

A solution of tert-butyl 3-methoxyazetidine-1-carboxylate (270 mg, 1.44 mmol) in 1:1 TFA/DCM (1 mL) was stirred at ambient temperature for 1 hour and concentrated. The crude product was directly used in the next step assuming quantitative yield.

Step B: Preparation of (R)-(5-(2-(5-fluoropyridin-3-yl)pyrrolidin-1-yl)pyrazolo[1,5-a]pyrimidin-3-yl)(3-methoxyazetidin-1-yl)methanone To a DMF (0.3 mL) solution of (R)-5-(2-(5-fluoropyridin-3-yl)pyrrolidin-1-yl)pyrazolo[1,5-a]pyrimidine-3-carboxylic acid (Preparation I, 30 mg, 0.092 mmol) and HATU (42 mg, 0.11 mmol) was added 3-methoxyazetidine 2,2,2-trifluoroacetate (22 mg, 0.11 mmol), followed by dropwise addition of DIEA (0.048 mL, 0.27 mmol). After stirring for 30 minutes at ambient temperature, the reaction was directly purified by reverse-phase chromatography (5 to 50% acetonitrile/water) to yield the final product as white solid (25 mg, 69%). LCMS (apci) m/z=397.1 (M+H).

Example 97

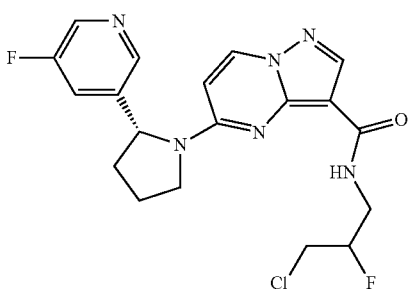 [SMILES: O=C(NCC(F)CCl)c1cnn2ccc(N3CCC[C@@H]3c3cncc(F)c3)nc12]

N-(3-chloro-2-fluoropropyl)-5-((R)-2-(5-fluoropyridin-3-yl)pyrrolidin-1-yl)pyrazolo[1,5-a]pyrimidine-3-carboxamide To a DMF (0.3 mL) solution of (R)-5-(2-(5-fluoropyridin-3-yl)pyrrolidin-1-yl)pyrazolo[1,5-a]pyrimidine-3-carboxylic acid (Preparation I, 30 mg, 0.092 mmol) and HATU (42 mg, 0.11 mmol) was added 3-fluoroazetidine hydrochloride (12 mg, 0.11 mmol), followed by DIEA (0.048 ml, 0.27 mmol) at ambient temperature. After stirring for 2 hours, the reaction was directly purified by reverse-phase chromatography (5 to 58% acetonitrile/water) to yield the product as white solid (8.8 mg, 23%). The isolated product was presumed to result from ring-opening of the azetidine starting material. LCMS (apci) m/z=421.0 (M+H).

Example 98

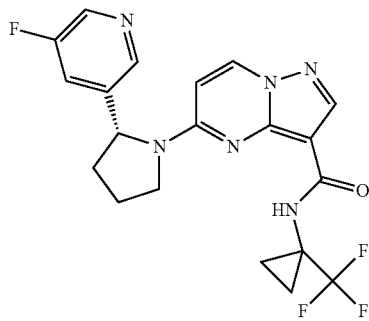 [SMILES: O=C(NC1(C(F)(F)F)CC1)c1cnn2ccc(N3CCC[C@@H]3c3cncc(F)c3)nc12]

(R)-5-(2-(5-fluoropyridin-3-yl)pyrrolidin-1-yl)-N-(1-(trifluoromethyl)cyclopropyl)pyrazolo[1,5-a]pyrimidine-3-carboxamide

Step A: Preparation of tert-butyl 1-(trifluoromethyl)cyclopropylcarbamate

Diphenylphosphoryl azide (0.462 mL, 2.14 mmol) was added drop-wise to a stirred mixture of 1-(trifluoromethyl)cyclopropanecarboxylic acid (300 mg, 1.95 mmol), TEA (0.271 mL, 1.95 mmol) and 4A molecular sieves in anhydrous tert-BuOH (4 mL) under nitrogen at ambient temperature. The reaction was heated to reflux for 18 hours, then cooled, filtered, and concentrated, and the residue was taken up in ether (20 mL). The organic layer was washed with saturated $NaHCO_3$ and water (20 mL each), dried ($Na_2SO_4$), filtered and concentrated, giving the crude product as white solid (0.32 g, 72%). The crude product was used directly in the next step without further purification.

Step B: Preparation of 1-(trifluoromethyl)cyclopropanamine hydrochloride

A solution of tert-butyl 1-(trifluoromethyl)cyclopropylcarbamate (0.3 g, 1.3 mmol) in HCl (4 N dioxane, 6.7 mL, 27 mmol) was stirred at ambient temperature overnight. The reaction was then concentrated to yield the crude product as white solid, which was used directly in the next step assuming quantitative yield.

Step C: Preparation of (R)-5-(2-(5-fluoropyridin-3-yl)pyrrolidin-1-yl)-N-(1-(trifluoromethyl)cyclopropyl)pyrazolo[1,5-a]pyrimidine-3-carboxamide To a DMF (0.4 mL) solution of (R)-5-(2-(5-fluoropyridin-3-yl)pyrrolidin-1-yl)pyrazolo[1,5-a]pyrimidine-3-carboxylic acid (Preparation I, 50 mg, 0.15 mmol) and HATU (87 mg, 0.23 mmol) was charged 1-(trifluoromethyl)cyclopropanamine hydrochloride (37 mg, 0.23 mmol), followed by drop-wise addition of DIEA (0.080 mL, 0.46 mmol). After stirring first at ambient temperature for 15 minutes and then at 85° C. overnight, the reaction was cooled and directly purified by reverse-phase chromatography (5 to 60% acetonitrile/water) to yield the final product as off-white solid (15 mg, 23%). LCMS (apci) m/z=435.0 (M+H).

The compounds listed in Table A were prepared according to the method described in Example 91, 92, 93 or 94, by reacting (R)-5-(2-(5-fluoropyridin-3-yl)pyrrolidin-1-yl)pyrazolo[1,5-a]pyrimidine-3-carboxylic acid (Preparation I) with appropriate amine starting materials in the presence of an amide coupling reagent (e.g. HATU, EDCI/HOBt) and an organic base (e.g. DIEA, TEA) in an appropriate solvent (e.g. DMF, DCM).

TABLE A

| Ex. # | Structure | Chemical Name | Data |
|---|---|---|---|
| 99 | 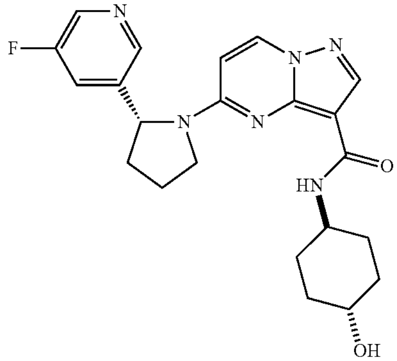 | 5-((R)-2-(5-fluoropyridin-3-yl)pyrrolidin-1-yl)-N-((trans)-4-hydroxycyclohexyl)pyrazolo[1,5-a]pyrimidine-3-carboxamide | LCMS (apci) m/z = 425.1 (M + H) |

TABLE A-continued

| Ex. # | Structure | Chemical Name | Data |
|---|---|---|---|
| 100 | 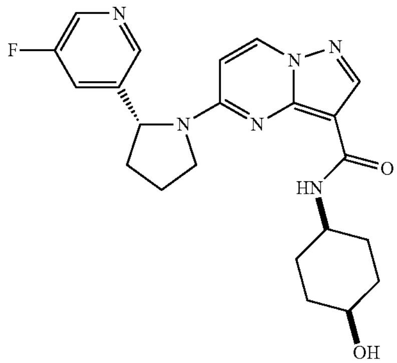 | 5-((R)-2-(5-fluoropyridin-3-yl)pyrrolidin-1-yl)-N-((cis)-4-hydroxycyclohexyl)pyrazolo[1,5-a]pyrimidine-3-carboxamide | LCMS (apci) m/z = 425.1 (M + H) |
| 101 | 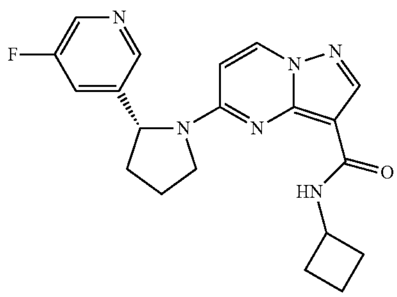 [SMILES: O=C(NC1CCC1)c1cnn2ccc(N3CCC[C@@H]3c3cncc(F)c3)nc12] | (R)-N-cyclobutyl-5-(2-(5-fluoropyridin-3-yl)pyrrolidin-1-yl)pyrazolo[1,5-a]pyrimidine-3-carboxamide | LCMS (apci) m/z = 381.1 (M + H) |
| 102 | 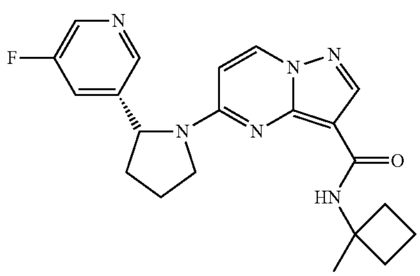 | (R)-5-(2-(5-fluoropyridin-3-yl)pyrrolidin-1-yl)-N-(1-methylcyclobutyl)pyrazolo[1,5-a]pyrimidine-3-carboxamide | LCMS (apci) m/z = 395.1 (M + H) |
| 103 | 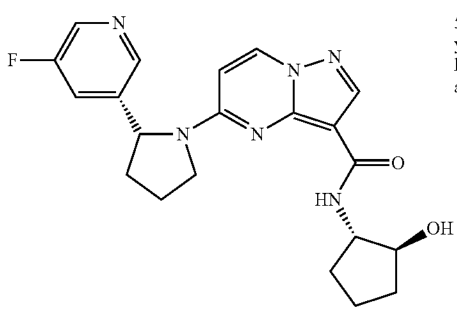 | 5-((R)-2-(5-fluoropyridin-3-yl)pyrrolidin-1-yl)-N-((1S,2S)-2-hydroxycyclopentyl)pyrazolo[1,5-a]pyrimidine-3-carboxamide | LCMS (apci) m/z = 411.1 (M + H) |
| 104 | 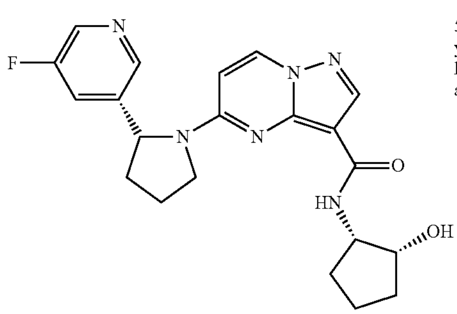 | 5-((R)-2-(5-fluoropyridin-3-yl)pyrrolidin-1-yl)-N-((1S,2R)-2-hydroxycyclopentyl)pyrazolo[1,5-a]pyrimidine-3-carboxamide | LCMS (apci) m/z = 411.1 (M + H) |

TABLE A-continued

| Ex. # | Chemical Name | Data |
|---|---|---|
| 105 | 5-((R)-2-(5-fluoropyridin-3-yl)pyrrolidin-1-yl)-N-((1S,3S)-3-hydroxycyclopentyl)pyrazolo[1,5-a]pyrimidine-3-carboxamide | LCMS (apci) m/z = 411.1 (M + H) |
| 106 | (R)-N-(cyclopropylmethyl)-5-(2-(5-fluoropyridin-3-yl)pyrrolidin-1-yl)pyrazolo[1,5-a]pyrimidine-3-carboxamide | LCMS (apci) m/z = 381.1 (M + H) |
| 107 | (R)-5-(2-(5-fluoropyridin-3-yl)pyrrolidin-1-yl)-N-(1-(hydroxymethyl)cyclopropyl)pyrazolo[1,5-a]pyrimidine-3-carboxamide | LCMS (apci) m/z = 397.1 (M + H) |
| 108 | (R)-(5-(2-(5-fluoropyridin-3-yl)pyrrolidin-1-yl)pyrazolo[1,5-a]pyrimidin-3-yl)(3-hydroxyazetidin-1-yl)methanone | LCMS (apci) m/z = 383.1 (M + H) |
| 109 | 5-((R)-2-(5-fluoropyridin-3-yl)pyrrolidin-1-yl)-N-((S)-2-hydroxypropyl)pyrazolo[1,5-a]pyrimidine-3-carboxamide | LCMS (apci) m/z = 385.1 (M + H) |

TABLE A-continued

| Ex. # | Structure | Chemical Name | Data |
|---|---|---|---|
| 110 | 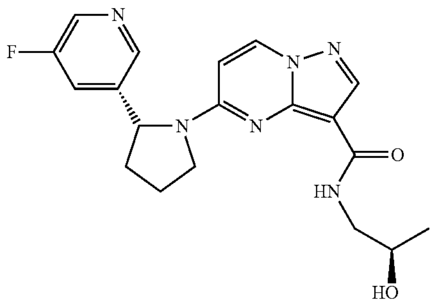 | 5-((R)-2-(5-fluoropyridin-3-yl)pyrrolidin-1-yl)-N-((R)-2-hydroxypropyl)pyrazolo[1,5-a]pyrimidine-3-carboxamide | LCMS (apci) m/z = 385.1 (M + H) |
| 111 | 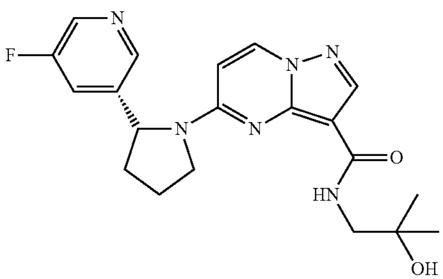 | (R)-5-(2-(5-fluoropyridin-3-yl)pyrrolidin-1-yl)-N-(2-hydroxy-2-methylpropyl)pyrazolo[1,5-a]pyrimidine-3-carboxamide | LCMS (apci) m/z = 399.1 (M + H) |
| 112 | 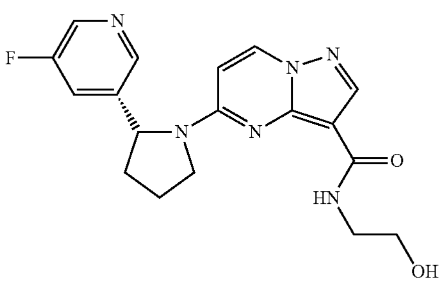 | (R)-5-(2-(5-fluoropyridin-3-yl)pyrrolidin-1-yl)-N-(2-hydroxyethyl)pyrazolo[1,5-a]pyrimidine-3-carboxamide | LCMS (apci) m/z = 371.1 (M + H) |
| 113 | 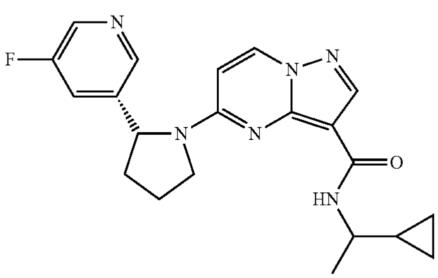 | N-(1-cyclopropylethyl)-5-((R)-2-(5-fluoropyridin-3-yl)pyrrolidin-1-yl)pyrazolo[1,5-a]pyrimidine-3-carboxamide | LCMS (apci) m/z = 395.1 (M + H) |
| 114 | 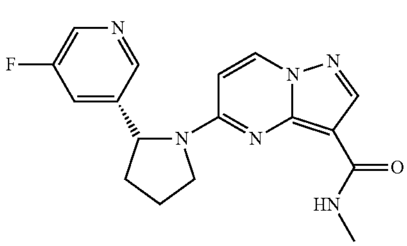 | (R)-5-(2-(5-fluoropyridin-3-yl)pyrrolidin-1-yl)-N-methylpyrazolo[1,5-a]pyrimidine-3-carboxamide | LCMS (apci) m/z = 341.1 (M + H) |

TABLE A-continued

| Ex. # | Structure | Chemical Name | Data |
|---|---|---|---|
| 115 | 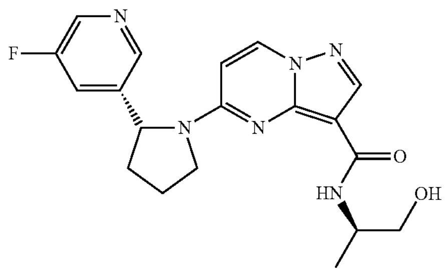 | 5-((R)-2-(5-fluoropyridin-3-yl)pyrrolidin-1-yl)-N-((R)-1-hydroxypropan-2-yl)pyrazolo[1,5-a]pyrimidine-3-carboxamide | LCMS (apci) m/z = 385.1 (M + H) |
| 116 | 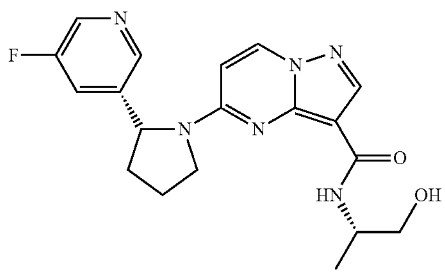 | 5-((R)-2-(5-fluoropyridin-3-yl)pyrrolidin-1-yl)-N-((S)-1-hydroxypropan-2-yl)pyrazolo[1,5-a]pyrimidine-3-carboxamide | LCMS (apci) m/z = 385.1 (M + H) |
| 117 | 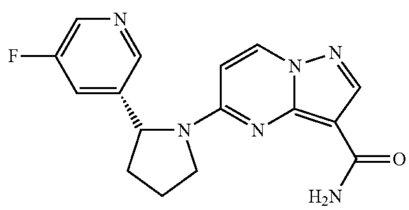 | (R)-5-(2-(5-fluoropyridin-3-yl)pyrrolidin-1-yl)pyrazolo[1,5-a]pyrimidine-3-carboxamide | LCMS (apci) m/z = 327.0 (M + H) |
| 118 | 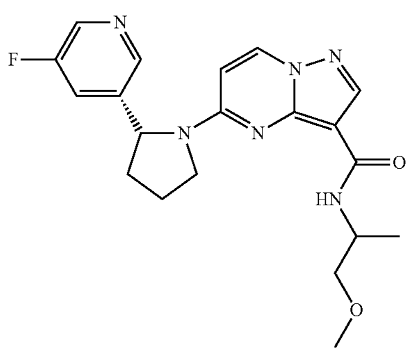 | 5-((R)-2-(5-fluoropyridin-3-yl)pyrrolidin-1-yl)-N-(1-methoxypropan-2-yl)pyrazolo[1,5-a]pyrimidine-3-carboxamide | LCMS (apci) m/z = 399.1 (M + H) |
| 119 | 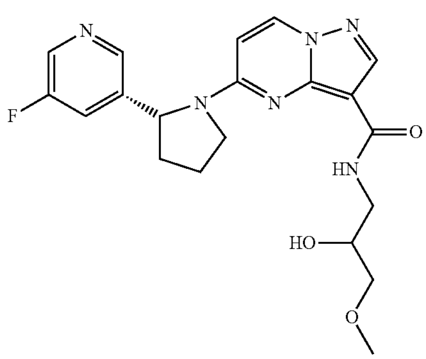 | 5-((R)-2-(5-fluoropyridin-3-yl)pyrrolidin-1-yl)-N-(2-hydroxy-3-methoxypropyl)pyrazolo[1,5-a]pyrimidine-3-carboxamide | LCMS (apci) m/z = 415.1 (M + H) |

| Ex. # | Structure | Chemical Name | Data |
|---|---|---|---|
| 120 | 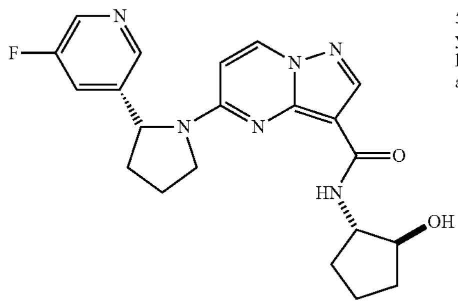 | 5-((R)-2-(5-fluoropyridin-3-yl)pyrrolidin-1-yl)-N-((trans)-2-hydroxycyclopentyl)pyrazolo[1,5-a]pyrimidine-3-carboxamide | LCMS (apci) m/z = 411.1 (M + H) |
| 121 | 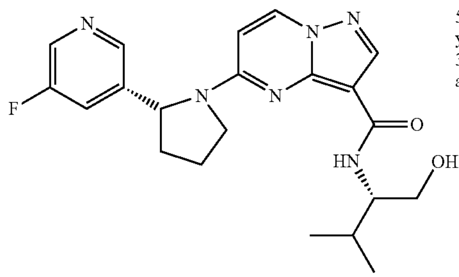 | 5-((R)-2-(5-fluoropyridin-3-yl)pyrrolidin-1-yl)-N-((S)-1-hydroxy-3-methylbutan-2-yl)pyrazolo[1,5-a]pyrimidine-3-carboxamide | LCMS (apci) m/z = 413.1 (M + H) |
| 122 | 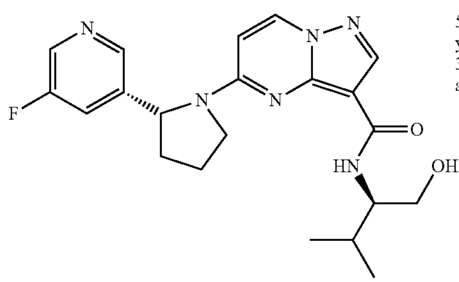 | 5-((R)-2-(5-fluoropyridin-3-yl)pyrrolidin-1-yl)-N-((R)-1-hydroxy-3-methylbutan-2-yl)pyrazolo[1,5-a]pyrimidine-3-carboxamide | LCMS (apci) m/z = 413.1 (M + H) |
| 123 | 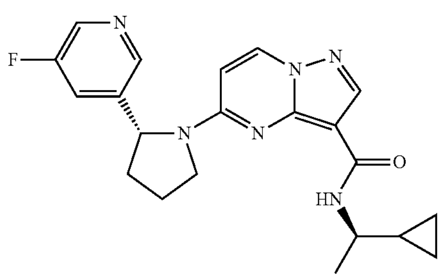 [SMILES: C[C@@H](NC(=O)c1cnn2ccc(N3CCC[C@@H]3c3cncc(F)c3)nc12)C1CC1] | N-((R)-1-cyclopropylethyl)-5-((R)-2-(5-fluoropyridin-3-yl)pyrrolidin-1-yl)pyrazolo[1,5-a]pyrimidine-3-carboxamide | LCMS (apci) m/z = 395.1 (M + H) |
| 124 | 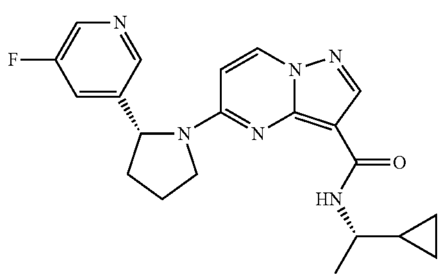 [SMILES: C[C@H](NC(=O)c1cnn2ccc(N3CCC[C@@H]3c3cncc(F)c3)nc12)C1CC1] | N-((S)-1-cyclopropylethyl)-5-((R)-2-(5-fluoropyridin-3-yl)pyrrolidin-1-yl)pyrazolo[1,5-a]pyrimidine-3-carboxamide | LCMS (apci) m/z = 395.1 (M + H) |

TABLE A-continued

| Ex. # | Structure | Chemical Name | Data |
|---|---|---|---|
| 125 | 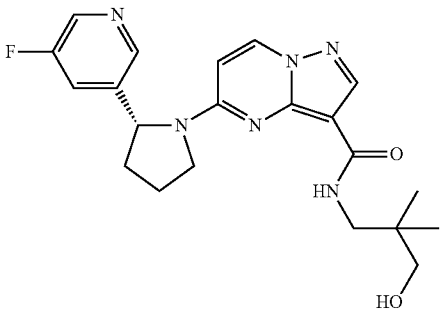 [SMILES: CC(C)(CO)CNC(=O)c1cnn2ccc(N3CCC[C@@H]3c3cncc(F)c3)nc12] | (R)-5-(2-(5-fluoropyridin-3-yl)pyrrolidin-1-yl)-N-(3-hydroxy-2,2-dimethylpropyl)pyrazolo[1,5-a]pyrimidine-3-carboxamide | LCMS (apci) m/z = 413.1 (M + H) |
| 126 | 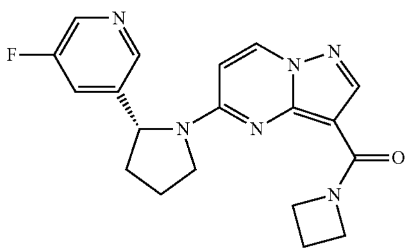 [SMILES: O=C(c1cnn2ccc(N3CCC[C@@H]3c3cncc(F)c3)nc12)N1CCC1] | (R)-azetidin-1-yl(5-(2-(5-fluoropyridin-3-yl)pyrrolidin-1-yl)pyrazolo[1,5-a]pyrimidin-3-yl)methanone | LCMS (apci) m/z = 367.1 (M + H) |
| 127 | 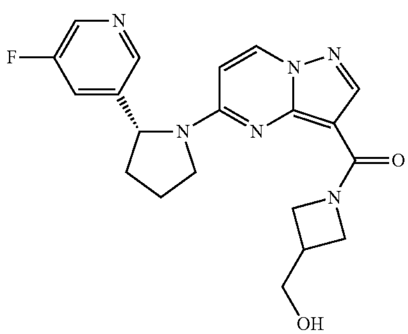 [SMILES: O=C(c1cnn2ccc(N3CCC[C@@H]3c3cncc(F)c3)nc12)N1CC(CO)C1] | (R)-(5-(2-(5-fluoropyridin-3-yl)pyrrolidin-1-yl)pyrazolo[1,5-a]pyrimidin-3-yl)(3-(hydroxymethyl)azetidin-1-yl)methanone | LCMS (apci) m/z = 397.1 (M + H) |
| 128 | 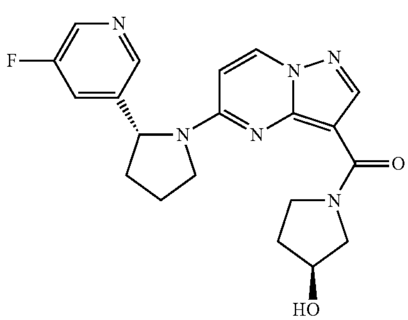 [SMILES: O=C(c1cnn2ccc(N3CCC[C@@H]3c3cncc(F)c3)nc12)N1CC[C@H](O)C1] | (5-((R)-2-(5-fluoropyridin-3-yl)pyrrolidin-1-yl)pyrazolo[1,5-a]pyrimidin-3-yl)((S)-3-hydroxypyrrolidin-1-yl)methanone | LCMS (apci) m/z = 397.1 (M + H) |
| 129 | 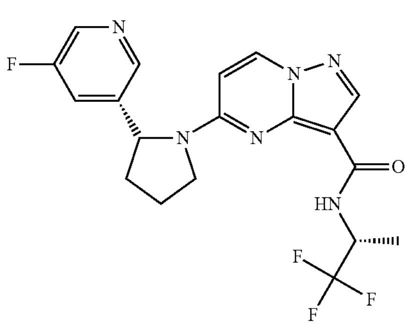 | 5-((R)-2-(5-fluoropyridin-3-yl)pyrrolidin-1-yl)-N-((R)-1,1,1-trifluoropropan-2-yl)pyrazolo[1,5-a]pyrimidine-3-carboxamide | LCMS (apci) m/z = 423.0 (M + H) |

TABLE A-continued

| Ex. # | Structure | Chemical Name | Data |
|---|---|---|---|
| 130 | 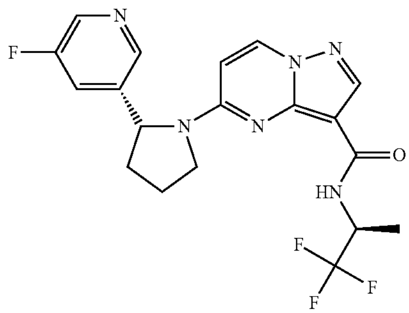 | 5-((R)-2-(5-fluoropyridin-3-yl)pyrrolidin-1-yl)-N-((S)-1,1,1-trifluoropropan-2-yl)pyrazolo[1,5-a]pyrimidine-3-carboxamide | LCMS (apci) m/z = 423.0 (M + H) |
| 131 | 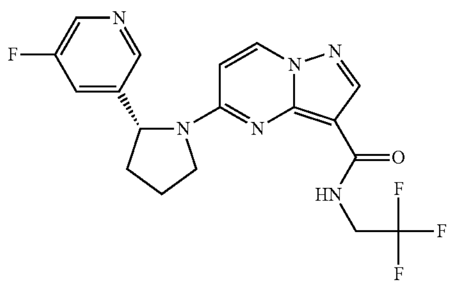 [SMILES: O=C(NCC(F)(F)F)c1cnn2ccc(N3CCC[C@@H]3c3cncc(F)c3)nc12] | (R)-5-(2-(5-fluoropyridin-3-yl)pyrrolidin-1-yl)-N-(2,2,2-trifluoroethyl)pyrazolo[1,5-a]pyrimidine-3-carboxamide | LCMS (apci) m/z = 409.0 (M + H) |
| 132 | 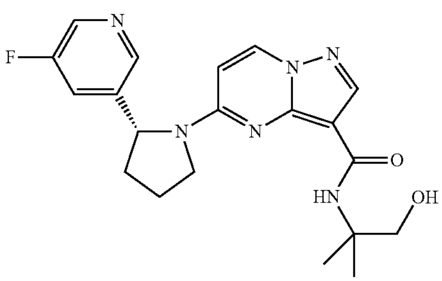 [SMILES: CC(C)(CO)NC(=O)c1cnn2ccc(N3CCC[C@@H]3c3cncc(F)c3)nc12] | (R)-5-(2-(5-fluoropyridin-3-yl)pyrrolidin-1-yl)-N-(1-hydroxy-2-methylpropan-2-yl)pyrazolo[1,5-a]pyrimidine-3-carboxamide | LCMS (apci) m/z = 399.1 (M + H) |
| 133 | 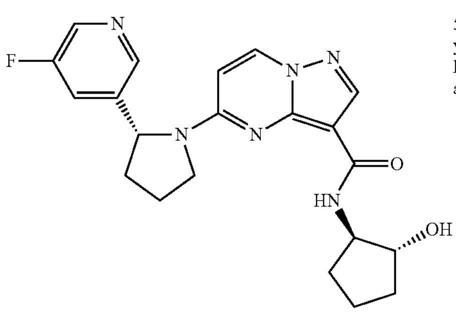 | 5-((R)-2-(5-fluoropyridin-3-yl)pyrrolidin-1-yl)-N-((1R,2R)-2-hydroxycyclopentyl)pyrazolo[1,5-a]pyrimidine-3-carboxamide | LCMS (apci) m/z = 411.1 (M + H) |
| 134 | 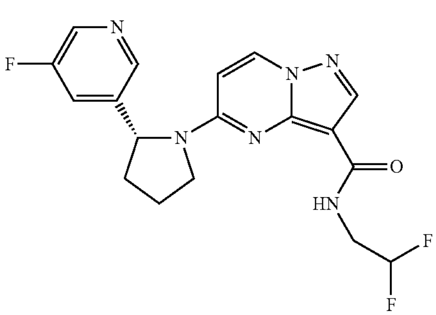 [SMILES: O=C(NCC(F)F)c1cnn2ccc(N3CCC[C@@H]3c3cncc(F)c3)nc12] | (R)-N-(2,2-difluoroethyl)-5-(2-(5-fluoropyridin-3-yl)pyrrolidin-1-yl)pyrazolo[1,5-a]pyrimidine-3-carboxamide | LCMS (apci) m/z = 391.0 (M + H) |

TABLE A-continued

| Ex. # | Structure | Chemical Name | Data |
|---|---|---|---|
| 135 | 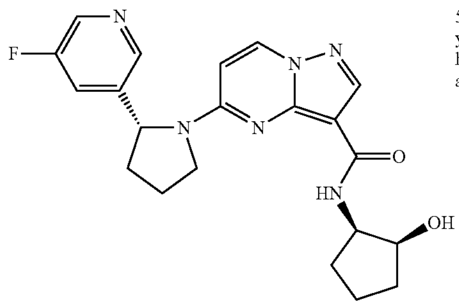 | 5-((R)-2-(5-fluoropyridin-3-yl)pyrrolidin-1-yl)-N-((1R,2S)-2-hydroxycyclopentyl)pyrazolo[1,5-a]pyrimidine-3-carboxamide | LCMS (apci) m/z = 411.1 (M + H) |
| 136 | 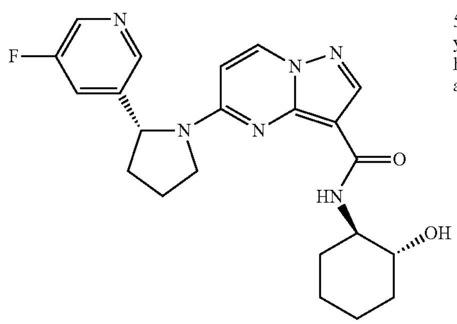 | 5-((R)-2-(5-fluoropyridin-3-yl)pyrrolidin-1-yl)-N-((1R,2R)-2-hydroxycyclohexyl)pyrazolo[1,5-a]pyrimidine-3-carboxamide | LCMS (apci) m/z = 425.1 (M + H) |
| 137 | 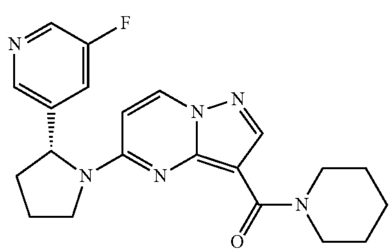 [SMILES: O=C(c1cnn2ccc(N3CCC[C@@H]3c3cncc(F)c3)nc12)N1CCCCC1] | (R)-(5-(2-(5-fluoropyridin-3-yl)pyrrolidin-1-yl)pyrazolo[1,5-a]pyrimidin-3-yl)(piperidin-1-yl)methanone | LCMS (apci) m/z = 395.1 (M + H) |
| 138 | 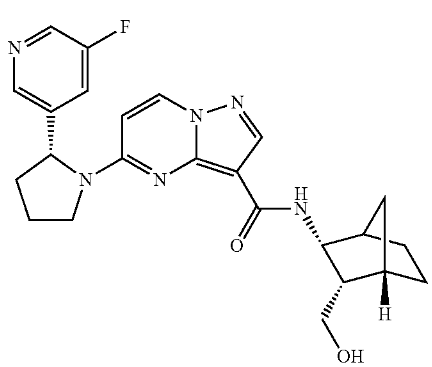 [SMILES: O=C(N[C@@H]1C2CC[C@@H](C2)[C@@H]1CO)c1cnn2ccc(N3CCC[C@@H]3c3cncc(F)c3)nc12] | 5-((R)-2-(5-fluoropyridin-3-yl)pyrrolidin-1-yl)-N-((2R,3S,4S)-3-(hydroxymethyl)bicyclo[2.2.1]heptan-2-yl)pyrazolo[1,5-a]pyrimidine-3-carboxamide | LCMS (apci) m/z = 451.2 (M + H) |

Example 139

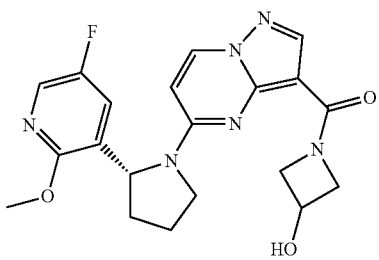 [SMILES: COc1ncc(F)cc1[C@H]1CCCN1c1ccn2ncc(C(=O)N3CC(O)C3)c2n1]

(R)-(5-(2-(5-fluoro-2-methoxypyridin-3-yl)pyrrolidin-1-yl)pyrazolo[1,5-a]pyrimidin-3-yl)(3-hydroxyazetidin-1-yl)methanone To a DMF (0.4 mL) solution of (R)-5-(2-(5-fluoro-2-methoxypyridin-3-yl)pyrrolidin-1-yl)pyrazolo[1,5-a]pyrimidine-3-carboxylic acid (Preparation K, 30 mg, 0.084 mmol) was added HATU (38 mg, 0.10 mmol) and azetidin-3-ol hydrochloride (11 mg, 0.10 mmol) at ambient temperature, followed by dropwise addition of DIEA (0.044 ml, 0.25 mmol) at 0° C. After stirring for 20 minutes at ambient temperature, the reaction was directly purified by reverse-phase chromatography (5 to 50% acetonitrile/water) to yield the final product as white solid (26 mg, 75%). LCMS (apci) m/z=413.1 (M+H).

Example 140

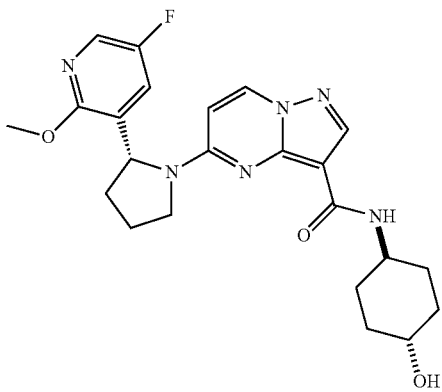

5-((R)-2-(5-fluoro-2-methoxypyridin-3-yl)pyrrolidin-1-yl)-N-((trans)-4-hydroxycyclohexyl)pyrazolo[1,5-a]pyrimidine-3-carboxamide To a solution of (R)-5-(2-(5-fluoro-2-methoxypyridin-3-yl)pyrrolidin-1-yl)pyrazolo[1,5-a]pyrimidine-3-carboxylic acid (Preparation K, 30 mg, 0.084 mmol) in anhydrous CH$_2$Cl$_2$ (2 mL) was added HOBt (34 mg, 0.25 mmol) followed by EDCI (48 mg, 0.25 mmol). The solution was stirred for 30 minutes, then treated with (trans)-4-aminocyclohexanol (29 mg, 0.25 mmol) followed by triethylamine (35 µL, 0.25 mmol). After stirring at ambient temperature for 5 hours, the reaction mixture was diluted with EtOAc, washed with saturated NH$_4$Cl (20 mL), saturated NaHCO$_3$, and brine, then dried (Na$_2$SO$_4$), filtered and concentrated. The crude material was purified by silica chromatography (4% MeOH/CH$_2$Cl$_2$) to yield the final product as white solid (23 mg, 60%). LCMS (apci) m/z=455.1 (M+H).

Example 141

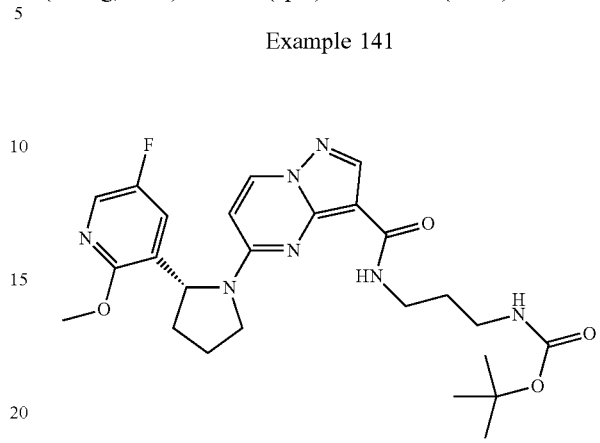

(R)-tert-butyl 3-(5-(2-(5-fluoro-2-methoxypyridin-3-yl)pyrrolidin-1-yl)pyrazolo[1,5-a]pyrimidine-3-carboxamido)propylcarbamate To a mixture of (R)-5-(2-(5-fluoro-2-methoxypyridin-3-yl)pyrrolidin-1-yl)pyrazolo[1,5-a]pyrimidine-3-carboxylic acid (Preparation K, 200 mg, 0.560 mmol) and HATU (255 mg, 0.672 mmol) in DMF (2 mL) was added DIEA (292 µL, 1.68 mmol), followed by dropwise addition of tert-butyl 3-aminopropylcarbamate (117 mg, 0.672 mmol) at ambient temperature. After stirring for 3 hours, the reaction was directly purified by reverse-phase chromatography (5 to 70% acetonitrile/water) to yield the final product as white solid (250 mg, 87%). LCMS (apci) m/z=414.1 (M+H–Boc).

Example 142

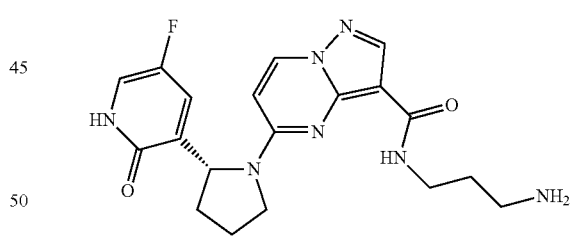

(R)—N-(3-aminopropyl)-5-(2-(5-fluoro-2-oxo-1,2-dihydropyridin-3-yl)pyrrolidin-1-yl)pyrazolo[1,5-a]pyrimidine-3-carboxamide A mixture of (R)-tert-butyl 3-(5-(2-(5-fluoro-2-methoxypyridin-3-yl)pyrrolidin-1-yl)pyrazolo[1,5-a]pyrimidine-3-carboxamido)propylcarbamate (Example 141, 70 mg, 0.14 mmol) and HCl (4 N dioxane, 1.7 mL, 6.8 mmol) in a pressure reaction tube was heated at 85° C. for 12 hours then concentrated under reduced pressure. The crude material was purified by reverse-phase chromatography (5 to 40% acetonitrile/water) to yield the final product as white solid. LCMS (apci) m/z=400.1 (M+H).

Example 143

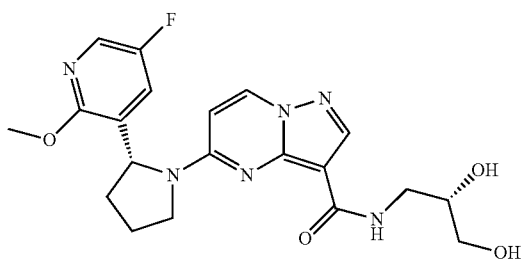 [SMILES: COc1ncc(F)cc1[C@H]1CCCN1c1ccn2ncc(C(=O)NC[C@H](O)CO)c2n1]

N—((S)-2,3-dihydroxypropyl)-5-((R)-2-(5-fluoro-2-methoxypyridin-3-yl)pyrrolidin-1-yl)pyrazolo[1,5-a]pyrimidine-3-carboxamide Step A: Preparation of N—(((S)-2,2-dimethyl-1,3-dioxolan-4-yl)methyl)-5-((R)-2-(5-fluoro-2-methoxypyridin-3-yl)pyrrolidin-1-yl)pyrazolo[1,5-a]pyrimidine-3-carboxamide Prepared according to the method described in Example 140, replacing (trans)-4-aminocyclohexanol with (S)-(2,2-dimethyl-1,3-dioxolan-4-yl)methanamine. LCMS (apci) m/z=471.0 (M+H−Boc).

Step B: Preparation of N—((S)-2,3-dihydroxypropyl)-5-((R)-2-(5-fluoro-2-methoxypyridin-3-yl)pyrrolidin-1-yl)pyrazolo[1,5-a]pyrimidine-3-carboxamide To a solution of N—(((S)-2,2-dimethyl-1,3-dioxolan-4-yl)methyl)-5-((R)-2-(5-fluoro-2-methoxypyridin-3-yl)pyrrolidin-1-yl)pyrazolo[1,5-a]pyrimidine-3-carboxamide (36 mg, 0.077 mmol) in THF (2 mL) was added HCl (3 N aq.) at ambient temperature. The resulting mixture was stirred for 5 hours. The reaction was diluted with EtOAc, washed with saturated NH$_4$Cl and brine, then dried (MgSO$_4$), filtered and concentrated. The crude material was rinsed with ether to yield the final product as white solid (30 mg, 91%). LCMS (apci) m/z=431.1 (M+H).

Example 144

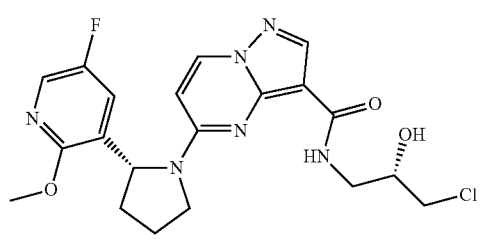 [SMILES: COc1ncc(F)cc1[C@H]1CCCN1c1ccn2ncc(C(=O)NC[C@H](O)CCl)c2n1]

N—((S)-3-chloro-2-hydroxypropyl)-5-((R)-2-(5-fluoro-2-methoxypyridin-3-yl)pyrrolidin-1-yl)pyrazolo[1,5-a]pyrimidine-3-carboxamide Step A: Preparation of (S)-1-amino-3-chloropropan-2-ol hydrochlorid To a solution of benzaldehyde (4.50 g, 42.4 mmol) in EtOH (12 mL) was added aqueous ammonia (4.01 g, 65.9 mmol) in several portions. After stirring for 10 minutes, (S)-2-(chloromethyl)oxirane (3.81 g, 41.2 mmol) was added and the reaction mixture was stirred for 2 hours at ambient temperature. The reaction mixture was then heated at 35-40° C. with a heating mantle for 6 hours, followed by stirring at ambient temperature for 18 hours. The reaction was concentrated to 5 mL and toluene (5 mL) was added. The mixture was heated to 36° C. and a solution of concentrated HCl (6.09 g, 61.8 mmol) and water (5.9 mL) was added slowly over 5 minutes to maintain an internal reaction temperature range of 36-41° C. The biphasic mixture was heated at 42-45° C. for 3 hours. The organic phase was separated and washed with water (10 mL). The aqueous phases were combined and ethanol (10 mL) was added. The mixture was concentrated to 10 mL, and ethanol (6×10 mL) was added, concentrating after each addition. After the last concentration step, the slurry was warmed to reflux, cooled to ambient temperature, and then placed at −20° C. for 18 hours. The product was collected by vacuum filtration, washed with cold ethanol, and vacuum-dried, to provide the product as white solid (3.58 g, 60% yield).

Step B: Preparation of N—((S)-3-chloro-2-hydroxypropyl)-5-((R)-2-(5-fluoro-2-methoxypyridin-3-yl)pyrrolidin-1-yl)pyrazolo[1,5-a]pyrimidine-3-carboxamide Prepared by the method described in Example 139, replacing azetidin-3-ol hydrochloride with (S)-1-amino-3-chloropropan-2-ol hydrochloride. LCMS (apci) m/z=449.0 (M+H)

Example 145

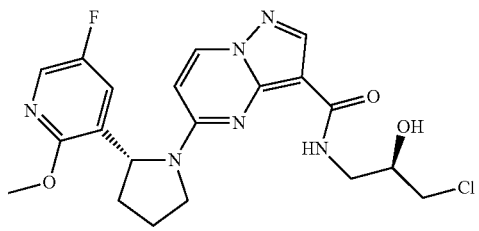 [SMILES: COc1ncc(F)cc1[C@H]1CCCN1c1ccn2ncc(C(=O)NC[C@@H](O)CCl)c2n1]

N—((R)-3-chloro-2-hydroxypropyl)-5-((R)-2-(5-fluoro-2-methoxypyridin-3-yl)pyrrolidin-1-yl)pyrazolo[1,5-a]pyrimidine-3-carboxamide Step A: Preparation of (R)-1-amino-3-chloropropan-2-ol hydrochloride Prepared by the method described in Example 144, Step A, replacing (S)-2-(chloromethyl)oxirane with (R)-2-(chloromethyl)oxirane.

Step B: Preparation of N—((R)-3-chloro-2-hydroxypropyl)-5-((R)-2-(5-fluoro-2-methoxypyridin-3-yl)pyrrolidin-1-yl)pyrazolo[1,5-a]pyrimidine-3-carboxamide Prepared by the method described in Example 139, replacing azetidin-3-ol hydrochloride with (R)-1-amino-3-chloropropan-2-ol hydrochloride. LCMS (apci) m/z=449.0 (M+H)

Example 146

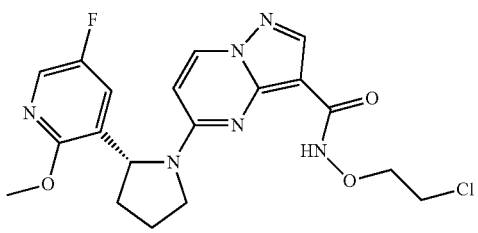 [SMILES: COc1ncc(F)cc1[C@H]1CCCN1c1ccn2ncc(C(=O)NOCCCl)c2n1]

(R)—N-(2-chloroethoxy)-5-(2-(5-fluoro-2-methoxy-pyridin-3-yl)pyrrolidin-1-yl)pyrazolo[1,5-a]pyrimidine-3-carboxamide

Step A: Preparation of 2-(2-chloroethoxy)isoindoline-1,3-dione

A 1 L round-bottomed flask was charged 2-hydroxyisoindoline-1,3-dione (16.6 g, 98.71 mmol), followed by DMF (100 mL), then 1-bromo-2-chloroethane (25.2 mL, 296.1 mmol), and then triethylamine (42.1 mL, 296.1 mmol). After stirring at ambient temperature overnight, the reaction mixture was filtered (GF/F) and rinsed with DMF. The filtrate (250 mL) was poured into ice-water (2 L) while stirring, and the resulting precipitate was filtered, rinsed with water, and dried, yielding the crude product as a white solid (21 g). The crude product was triturated with heptane (3×400 mL), filtered and air-dried, giving the product as white solid (17.6 g, 79%).

Step B: Preparation of O-(2-chloroethyl)hydroxylamine hydrochloride

A 1 L three-necked round-bottomed flask was charged HCl (6 μM aq., 295 mL, 1773 mmol), followed by 2-(2-chloroethoxy)isoindoline-1,3-dione (10 g, 44.3 mmol) with stirring. A water condenser was attached and the reaction was refluxed at 100° C. for 2 hours, then stirred at ambient temperature overnight. The reaction mixture was filtered. Absolute EtOH was added to the filtrate and filtrate was concentrated. The crude material was triturated from hot EtOH to yield the first crop of product as white solid (2.2 g). The mother liquor was concentrated and triturated as described, yielding a second crop of product (1.7) g.

Step C: Preparation of (R)—N-(2-chloroethoxy)-5-(2-(5-fluoro-2-methoxypyridin-3-yl)pyrrolidin-1-yl)pyrazolo[1,5-a]pyrimidine-3-carboxamide Prepared by the method described in Example 139, replacing azetidin-3-ol hydrochloride with O-(2-chloroethyl)hydroxylamine hydrochloride. LCMS (apci) m/z=434.9 (M+H)

The compounds listed in Table B were prepared according to the method described in Example 139 or Example 140, by reacting (R)-5-(2-(5-fluoro-2-methoxypyridin-3-yl)pyrrolidin-1-yl)pyrazolo[1,5-a]pyrimidine-3-carboxylic acid (Preparation K) with an appropriate amine starting material in the presence of an amide coupling reagent (e.g. HATU, EDCI/HOBt) and an organic base (e.g. DIEA, TEA) in an appropriate solvent (e.g. DMF, DCM).

TABLE B

| Ex. # | Structure | Chemical Name | Data |
|---|---|---|---|
| 147 | 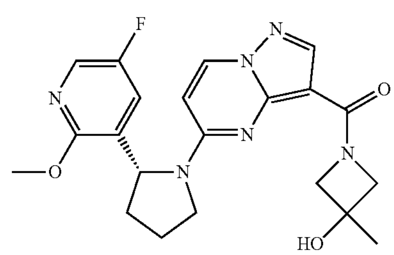 [SMILES: COc1ncc(F)cc1[C@H]1CCCN1c1ccn2ncc(C(=O)N3CC(C)(O)C3)c2n1] | (R)-(5-(2-(5-fluoro-2-methoxypyridin-3-yl)pyrrolidin-1-yl)pyrazolo[1,5-a]pyrimidin-3-yl)(3-hydroxy-3-methylazetidin-1-yl)methanone | LCMS (apci) m/z = 427.1 (M + H) |
| 148 | 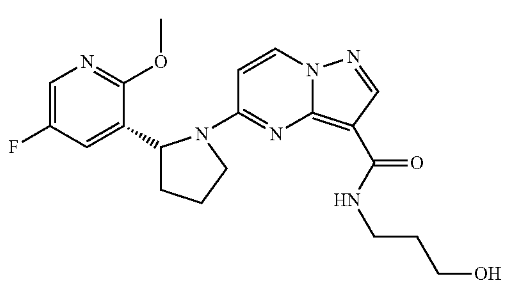 | (R)-5-(2-(5-fluoro-2-methoxypyridin-3-yl)pyrrolidin-1-yl)-N-(3-hydroxypropyl)pyrazolo[1,5-a]pyrimidine-3-carboxamide | LCMS (apci) m/z = 415.1 (M + H) |

TABLE B-continued

| Ex. # | Structure | Chemical Name | Data |
|---|---|---|---|
| 149 | 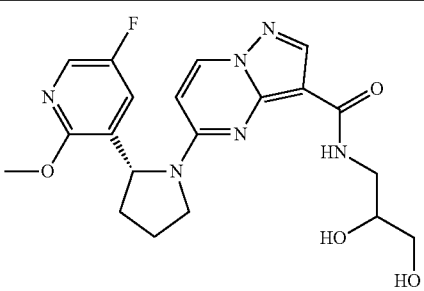 | N-(2,3-dihydroxypropyl)-5-((R)-2-(5-fluoro-2-methoxypyridin-3-yl)pyrrolidin-1-yl)pyrazolo[1,5-a]pyrimidine-3-carboxamide | LCMS (apci) m/z = 431.1 (M + H) |
| 150 | 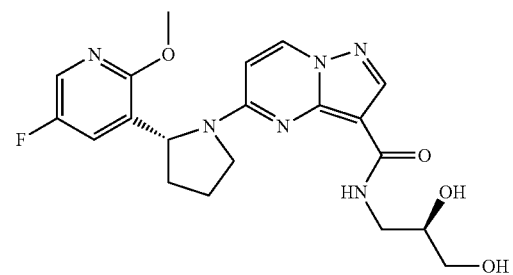 [SMILES: COc1ncc(F)cc1[C@H]1CCCN1c1ccn2ncc(C(=O)NC[C@@H](O)CO)c2n1] | N-((R)-2,3-dihydroxypropyl)-5-((R)-2-(5-fluoro-2-methoxypyridin-3-yl)pyrrolidin-1-yl)pyrazolo[1,5-a]pyrimidine-3-carboxamide | LCMS (apci) m/z = 431.0 (M + H) |
| 151 | 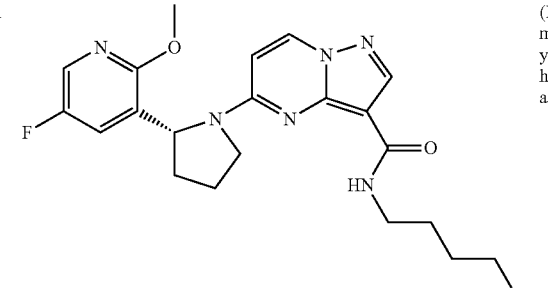 | (R)-5-(2-(5-fluoro-2-methoxypyridin-3-yl)pyrrolidin-1-yl)-N-(4-hydroxybutyl)pyrazolo[1,5-a]pyrimidine-3-carboxamide | LCMS (apci) m/z = 429.1 (M + H) |
| 152 | 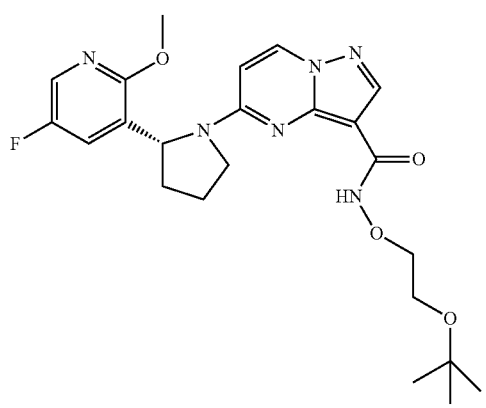 [SMILES: COc1ncc(F)cc1[C@H]1CCCN1c1ccn2ncc(C(=O)NOCCOC(C)(C)C)c2n1] | (R)-N-(2-tert-butoxyethoxy)-5-(2-(5-fluoro-2-methoxypyridin-3-yl)pyrrolidin-1-yl)pyrazolo[1,5-a]pyrimidine-3-carboxamide | LCMS (apci) m/z = 473.0 (M + H) |
| 153 | 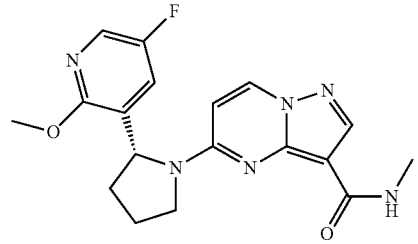 | (R)-5-(2-(5-fluoro-2-methoxypyridin-3-yl)pyrrolidin-1-yl)-N-methylpyrazolo[1,5-a]pyrimidine-3-carboxamide | MS (apci) m/z = 371.1 (M + H) |

TABLE B-continued

| Ex. # | Chemical Name | Data |
|---|---|---|
| 154 | 5-((R)-2-(5-fluoro-2-methoxypyridin-3-yl)pyrrolidin-1-yl)-N-((1S,3S)-3-hydroxycyclopentyl)pyrazolo[1,5-a]pyrimidine-3-carboxamide | MS (apci) m/z = 441.1 (M + H) |
| 155 | (R)-5-(2-(5-fluoro-2-methoxypyridin-3-yl)pyrrolidin-1-yl)-N-(2-hydroxyethyl)pyrazolo[1,5-a]pyrimidine-3-carboxamide | MS (apci) m/z = 401.1 (M + H) |
| 156 | 5-((R)-2-(5-fluoro-2-methoxypyridin-3-yl)pyrrolidin-1-yl)-N-((S)-2-hydroxypropyl)pyrazolo[1,5-a]pyrimidine-3-carboxamide | MS (apci) m/z = 415.1 (M + H) |
| 157 | 5-((R)-2-(5-fluoro-2-methoxypyridin-3-yl)pyrrolidin-1-yl)-N-((R)-2-hydroxypropyl)pyrazolo[1,5-a]pyrimidine-3-carboxamide | MS (apci) m/z = 415.1 (M + H) |
| 158 | (R)-5-(2-(5-fluoro-2-methoxypyridin-3-yl)pyrrolidin-1-yl)-N-(2-hydroxy-2-methylpropyl)pyrazolo[1,5-a]pyrimidine-3-carboxamide | MS (apci) m/z = 429.1 (M + H) |

TABLE B-continued

| Ex. # | Structure | Chemical Name | Data |
|---|---|---|---|
| 159 | 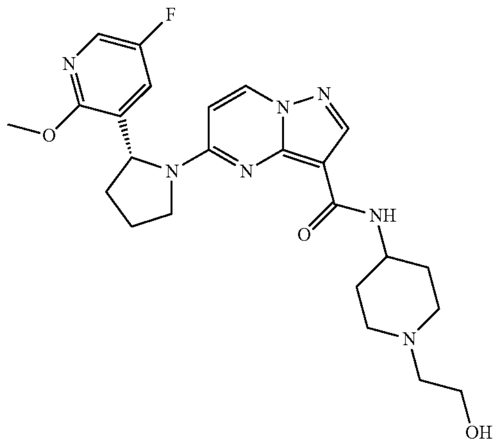 [SMILES: COc1ncc(F)cc1[C@H]1CCCN1c1ccn2ncc(C(=O)NC3CCN(CCO)CC3)c2n1] | (R)-5-(2-(5-fluoro-2-methoxypyridin-3-yl)pyrrolidin-1-yl)-N-(1-(2-hydroxyethyl)piperidin-4-yl)pyrazolo[1,5-a]pyrimidine-3-carboxamide | MS (apci) m/z = 484.2 (M + H) |
| 160 | 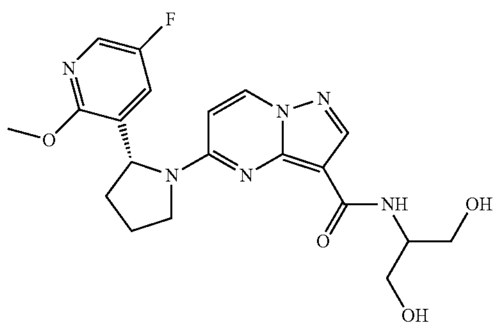 [SMILES: COc1ncc(F)cc1[C@H]1CCCN1c1ccn2ncc(C(=O)NC(CO)CO)c2n1] | (R)-N-(1,3-dihydroxypropan-2-yl)-5-(2-(5-fluoro-2-methoxypyridin-3-yl)pyrrolidin-1-yl)pyrazolo[1,5-a]pyrimidine-3-carboxamide | MS (apci) m/z = 431.1 (M + H) |
| 161 | 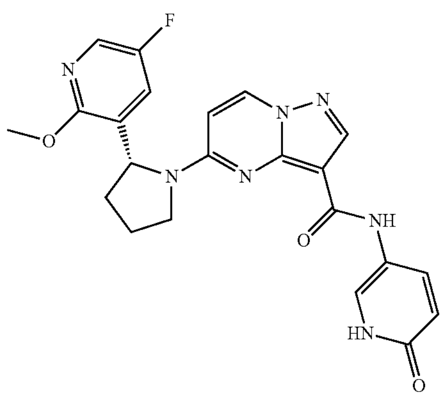 [SMILES: COc1ncc(F)cc1[C@H]1CCCN1c1ccn2ncc(C(=O)Nc3ccc(=O)[nH]c3)c2n1] | (R)-5-(2-(5-fluoro-2-methoxypyridin-3-yl)pyrrolidin-1-yl)-N-(6-oxo-1,6-dihydropyridin-3-yl)pyrazolo[1,5-a]pyrimidine-3-carboxamide | MS (apci) m/z = 450.0 (M + H) |
| 162 | 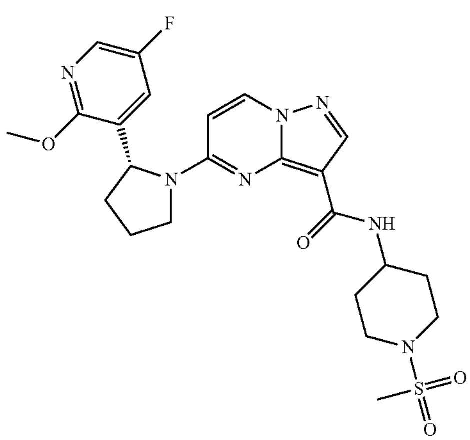 [SMILES: COc1ncc(F)cc1[C@H]1CCCN1c1ccn2ncc(C(=O)NC3CCN(S(C)(=O)=O)CC3)c2n1] | (R)-5-(2-(5-fluoro-2-methoxypyridin-3-yl)pyrrolidin-1-yl)-N-(1-(methylsulfonyl)piperidin-4-yl)pyrazolo[1,5-a]pyrimidine-3-carboxamide | MS (apci) m/z = 518.1 (M + H) |

TABLE B-continued

| Ex. # | Structure | Chemical Name | Data |
|---|---|---|---|
| 163 | 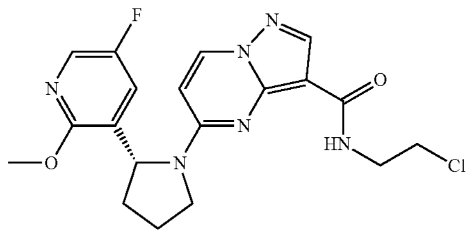 [SMILES: COc1ncc(F)cc1[C@H]1CCCN1c1ccn2ncc(C(=O)NCCCl)c2n1] | (R)-N-(2-chloroethyl)-5-(2-(5-fluoro-2-methoxypyridin-3-yl)pyrrolidin-1-yl)pyrazolo[1,5-a]pyrimidine-3-carboxamide | LCMS (apci) m/z = 419.1 (M + H) |
| 164 | 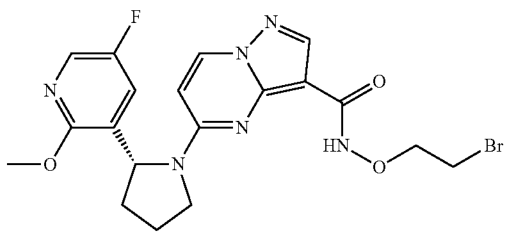 [SMILES: COc1ncc(F)cc1[C@H]1CCCN1c1ccn2ncc(C(=O)NOCCBr)c2n1] | (R)-N-(2-bromoethoxy)-5-(2-(5-fluoro-2-methoxypyridin-3-yl)pyrrolidin-1-yl)pyrazolo[1,5-a]pyrimidine-3-carboxamide | LCMS (apci) m/z = 479.0 (M + H) |

The compounds listed Table C were prepared by the method described in Examples 1, 139 or 140, by reacting (R)-5-(2-(2,5-difluorophenyl)pyrrolidin-1-yl)pyrazolo[1,5-a]pyrimidine-3-carboxylic acid (Preparation C) with an appropriate amine starting material in the presence of an amide coupling reagent (e.g. HATU, EDCI/HOBt) and an organic base (e.g. DIEA, TEA) in an appropriate solvent (e.g. DMF, DCM).

TABLE C

| Ex. # | Structure | Chemical Name | Data |
|---|---|---|---|
| 165 | 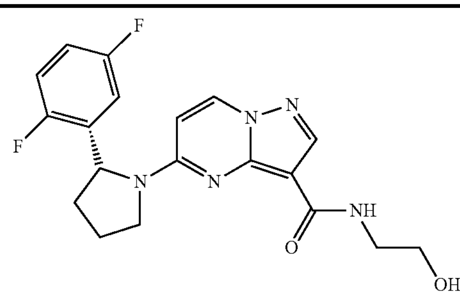 | 5-(2-(2,5-difluorophenyl)pyrrolidin-1-yl)-N-(2-hydroxyethyl)pyrazolo[1,5-a]pyrimidine-3-carboxamide | LCMS (apci) m/z = 388.1 (M + H) |
| 166 | 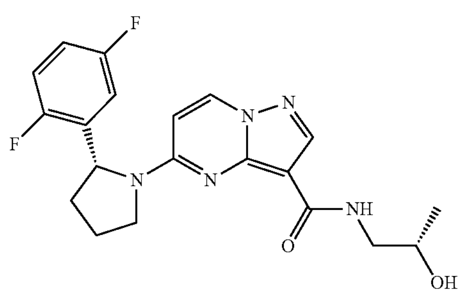 [SMILES: C[C@H](O)CNC(=O)c1cnn2ccc(N3CCC[C@@H]3c3cc(F)ccc3F)nc12] | 5-((R)-2-(2,5-difluorophenyl)pyrrolidin-1-yl)-N-(2-hydroxypropyl)pyrazolo[1,5-a]pyrimidine-3-carboxamide | LCMS (apci) m/z = 402.1 (M + H) |
| 167 | 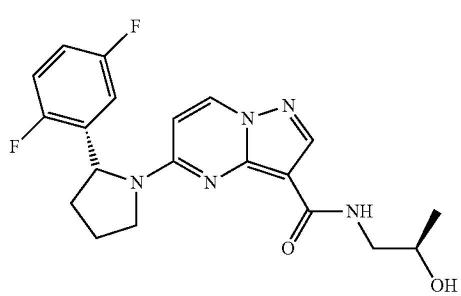 | 5-((R)-2-(2,5-difluorophenyl)pyrrolidin-1-yl)-N-(2-hydroxypropyl)pyrazolo[1,5-a]pyrimidine-3-carboxamide | LCMS (apci) m/z = 402.1 (M + H) |

TABLE C-continued

| Ex. # | Structure | Chemical Name | Data |
|---|---|---|---|
| 168 | 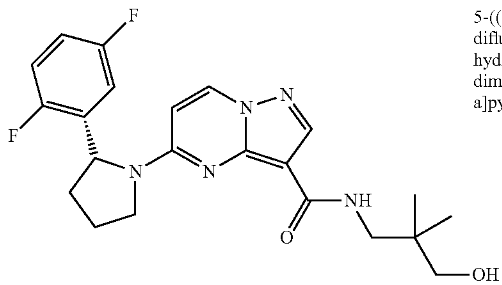 | 5-((R)-2-(2,5-difluorophenyl)pyrrolidin-1-yl)-N-(3-hydroxy-2,2-dimethylpropyl)pyrazolo[1,5-a]pyrimidine-3-carboxamide | LCMS (apci) m/z = 430.2 (M + H) |
| 169 | 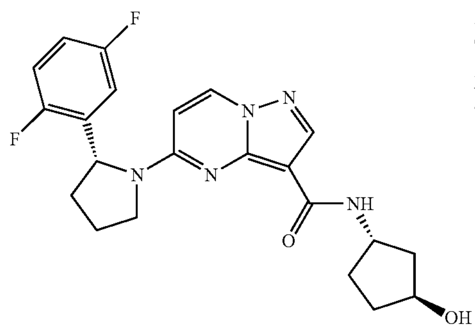 [SMILES: O=C(N[C@H]1CC[C@H](O)C1)c1cnn2ccc(N3CCC[C@@H]3c3cc(F)ccc3F)nc12] | 5-((R)-2-(2,5-difluorophenyl)pyrrolidin-1-yl)-N-((1S,3S)-3-hydroxycyclopentyl)pyrazolo[1,5-a]pyrimidine-3-carboxamide | LCMS (apci) m/z = 428.1 (M + H) |
| 170 | 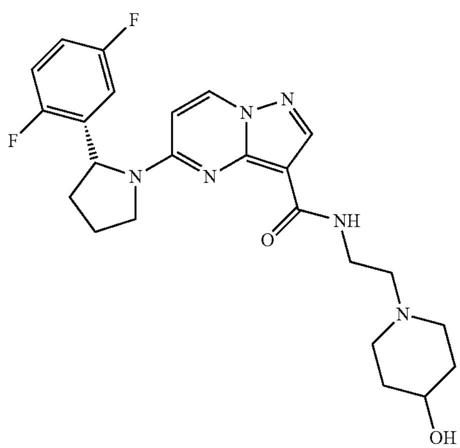 | 5-((R)-2-(2,5-difluorophenyl)pyrrolidin-1-yl)-N-(2-(4-hydroxypiperidin-1-yl)ethyl)pyrazolo[1,5-a]pyrimidine-3-carboxamide | LCMS (apci) m/z = 471.2 (M + H) |
| 171 | 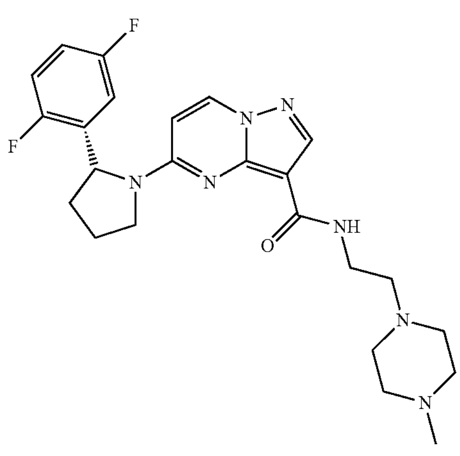 | 5-((R)-2-(2,5-difluorophenyl)pyrrolidin-1-yl)-N-(2-(4-methylpiperazin-1-yl)ethyl)pyrazolo[1,5-a]pyrimidine-3-carboxamide | LCMS (apci) m/z = 470.2 (M + H) |

TABLE C-continued

| Ex. # | Structure | Chemical Name | Data |
|---|---|---|---|
| 172 | 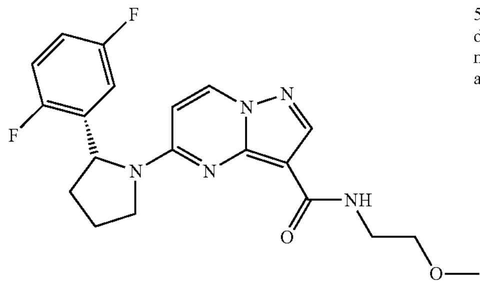 | 5-((R)-2-(2,5-difluorophenyl)pyrrolidin-1-yl)-N-(2-methoxyethyl)pyrazolo[1,5-a]pyrimidine-3-carboxamide | LCMS (apci) m/z = 402.1 (M + H) |
| 173 | 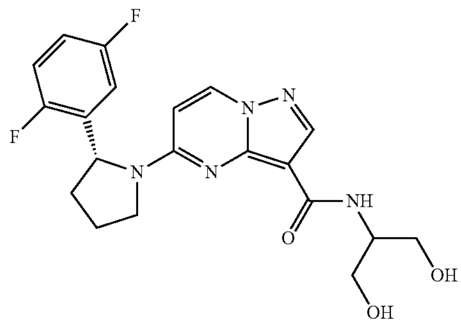 [SMILES: O=C(NC(CO)CO)c1cnn2ccc(N3CCC[C@@H]3c3cc(F)ccc3F)nc12] | 5-((R)-2-(2,5-difluorophenyl)pyrrolidin-1-yl)-N-(1,3-dihydroxypropan-2-yl)pyrazolo[1,5-a]pyrimidine-3-carboxamide | LCMS (apci) m/z = 418.1 (M + H) |
| 174 | 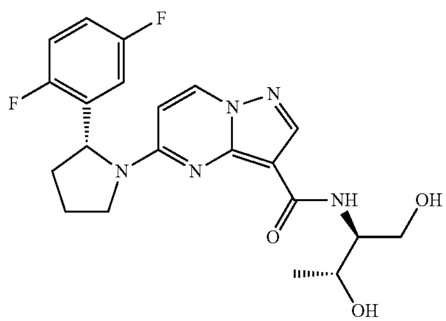 [SMILES: C[C@@H](O)[C@H](CO)NC(=O)c1cnn2ccc(N3CCC[C@@H]3c3cc(F)ccc3F)nc12] | 5-((R)-2-(2,5-difluorophenyl)pyrrolidin-1-yl)-N-((2S,3R)-1,3-dihydroxybutan-2-yl)pyrazolo[1,5-a]pyrimidine-3-carboxamide | LCMS (apci) m/z = 432.1 (M + H) |
| 175 | 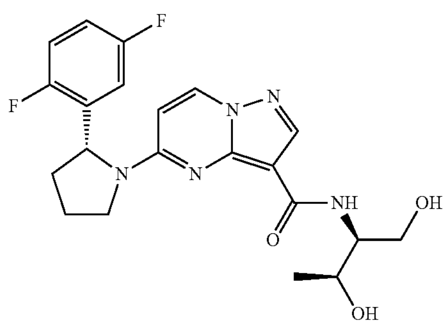 [SMILES: C[C@H](O)[C@H](CO)NC(=O)c1cnn2ccc(N3CCC[C@@H]3c3cc(F)ccc3F)nc12] | 5-((R)-2-(2,5-difluorophenyl)pyrrolidin-1-yl)-N-((2S,3S)-1,3-dihydroxybutan-2-yl)pyrazolo[1,5-a]pyrimidine-3-carboxamide | LCMS (apci) m/z = 432.1 (M + H) |
| 176 | 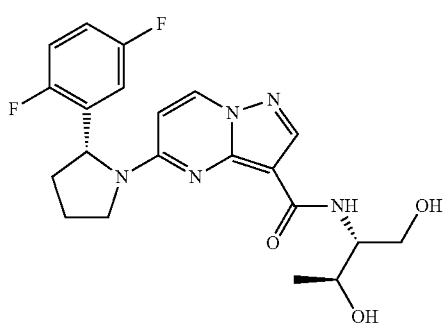 [SMILES: C[C@H](O)[C@@H](CO)NC(=O)c1cnn2ccc(N3CCC[C@@H]3c3cc(F)ccc3F)nc12] | 5-((R)-2-(2,5-difluorophenyl)pyrrolidin-1-yl)-N-((2R,3S)-1,3-dihydroxybutan-2-yl)pyrazolo[1,5-a]pyrimidine-3-carboxamide | LCMS (apci) m/z = 432.1 (M + H) |

TABLE C-continued

| Ex. # | Structure | Chemical Name | Data |
|---|---|---|---|
| 177 | 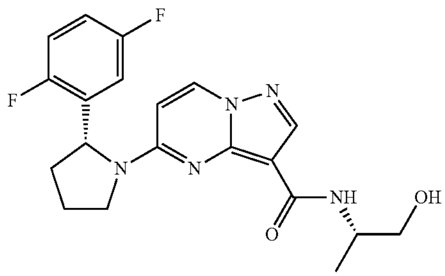 [SMILES: C[C@@H](CO)NC(=O)c1cnn2ccc(N3CCC[C@@H]3c3cc(F)ccc3F)nc12] | 5-((R)-2-(2,5-difluorophenyl)pyrrolidin-1-yl)-N-((S)-1-hydroxypropan-2-yl)pyrazolo[1,5-a]pyrimidine-3-carboxamide | LCMS (apci) m/z = 402.1 (M + H) |
| 178 | 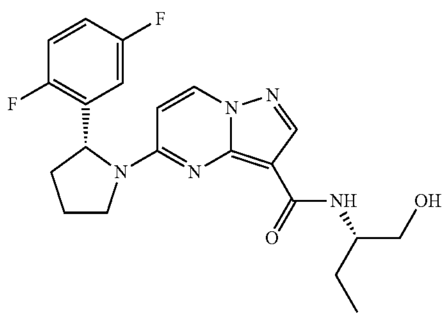 [SMILES: CC[C@@H](CO)NC(=O)c1cnn2ccc(N3CCC[C@@H]3c3cc(F)ccc3F)nc12] | 5-((R)-2-(2,5-difluorophenyl)pyrrolidin-1-yl)-N-((S)-1-hydroxybutan-2-yl)pyrazolo[1,5-a]pyrimidine-3-carboxamide | LCMS (apci) m/z = 416.1 (M + H) |
| 179 | 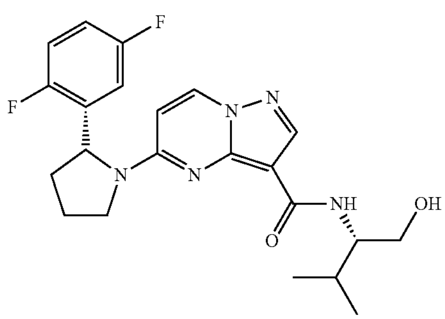 | 5-((R)-2-(2,5-difluorophenyl)pyrrolidin-1-yl)-N-((S)-1-hydroxy-3-methylbutan-2-yl)pyrazolo[1,5-a]pyrimidine-3-carboxamide | LCMS (apci) m/z = 430.1 (M + H) |
| 180 | 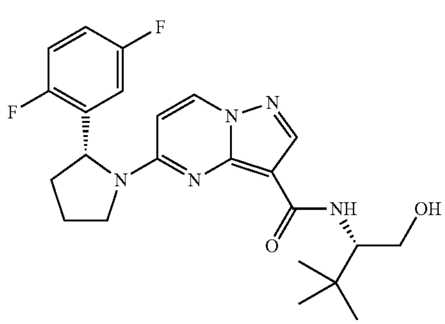 [SMILES: CC(C)(C)[C@@H](CO)NC(=O)c1cnn2ccc(N3CCC[C@@H]3c3cc(F)ccc3F)nc12] | 5-((R)-2-(2,5-difluorophenyl)pyrrolidin-1-yl)-N-((S)-1-hydroxy-3,3-dimethylbutan-2-yl)pyrazolo[1,5-a]pyrimidine-3-carboxamide | LCMS (apci) m/z = 444.2 (M + H) |

Example 181

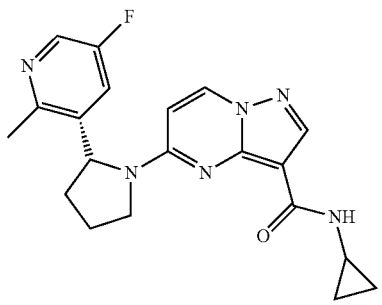

N-cyclopropyl-5-(2-(5-fluoro-2-methylpyridin-3-yl)pyrrolidin-1-yl)pyrazolo[1,5-a]pyrimidine-3-carboxamide To a solution of (R)-5-(2-(5-fluoro-2-methylpyridin-3-yl)pyrrolidin-1-yl)pyrazolo[1,5-a]pyrimidine-3-carboxylic acid (Preparation O, 50 mg, 0.15 mmol) in DCM (2 mL) was added HOBt (40 mg, 0.29 mmol) followed by EDCI (84 mg, 0.44 mmol). The solution was stirred at ambient temperature for 15 minutes, then treated with triethylamine (61 μL, 0.44 mmol) followed by cyclopropylamine (31 μL, 0.44 mmol). After stirring for 16 hours the mixture was partitioned between saturated NH$_4$Cl solution (20 mL) and DCM (20 mL) and the aqueous layer was extracted with DCM (2×10 mL). The combined organic phases were washed with brine (10 mL), dried over Na$_2$SO$_4$, filtered and concentrated. The residue was purified by silica gel column chromatography, eluting with 2-4% MeOH/DCM, to afford the title product as white solid (44 mg, 79%). MS (apci) m/z=381.1 (M+H).

Example 182

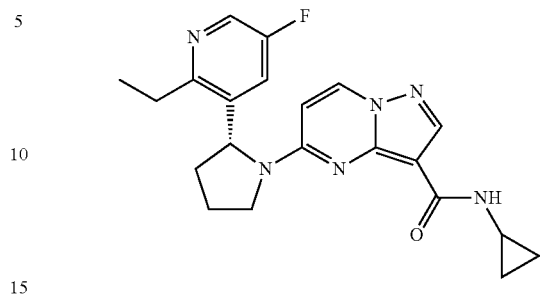

N-cyclopropyl-5-(2-(2-ethyl-5-fluoropyridin-3-yl)pyrrolidin-1-yl)pyrazolo[1,5-a]pyrimidine-3-carboxamide Prepared according to the method of Example 181, substituting (R)-5-(2-(5-fluoro-2-methylpyridin-3-yl)pyrrolidin-1-yl)pyrazolo[1,5-a]pyrimidine-3-carboxylic acid with (R)-5-(2-(2-ethyl-5-fluoropyridin-3-yl)pyrrolidin-1-yl)pyrazolo[1,5-a]pyrimidine-3-carboxylic acid (Preparation Q). MS (apci) m/z=395.1 (M+H).

The compounds listed in Table D were prepared by the method described in Example 181 or 182, by reacting (R)-5-(2-(5-fluoro-2-methylpyridin-3-yl)pyrrolidin-1-yl)pyrazolo[1,5-a]pyrimidine-3-carboxylic acid (Preparation O) or (R)-5-(2-(2-ethyl-5-fluoropyridin-3-yl)pyrrolidin-1-yl)pyrazolo[1,5-a]pyrimidine-3-carboxylic acid (Preparation Q) with an appropriate amine starting material in the presence of an amide coupling reagent (e.g. EDCI/HOBt) and an organic base (e.g. TEA) in an appropriate solvent (e.g. DCM).

TABLE D

| Ex. # | Structure | Chemical Name | Data |
|---|---|---|---|
| 183 | 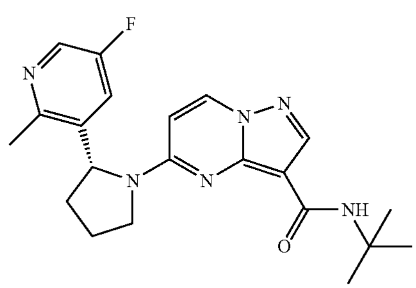 [SMILES: Cc1ncc(F)cc1[C@H]1CCCN1c1ccn2ncc(C(=O)NC(C)(C)C)c2n1] | (R)-N-tert-butyl-5-(2-(5-fluoro-2-methylpyridin-3-yl)pyrrolidin-1-yl)pyrazolo[1,5-a]pyrimidine-3-carboxamide | LCMS (apci) m/z = 397.1 (M + H) |
| 184 | 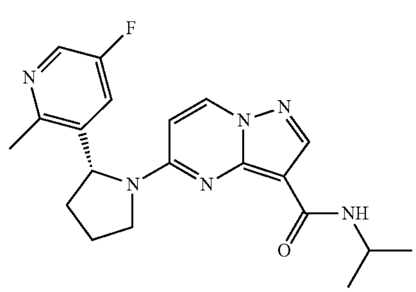 [SMILES: Cc1ncc(F)cc1[C@H]1CCCN1c1ccn2ncc(C(=O)NC(C)C)c2n1] | (R)-5-(2-(5-fluoro-2-methylpyridin-3-yl)pyrrolidin-1-yl)-N-isopropylpyrazolo[1,5-a]pyrimidine-3-carboxamide | LCMS (apci) m/z = 383.1 (M + H) |

TABLE D-continued

| Ex. # | Structure | Chemical Name | Data |
|---|---|---|---|
| 185 | 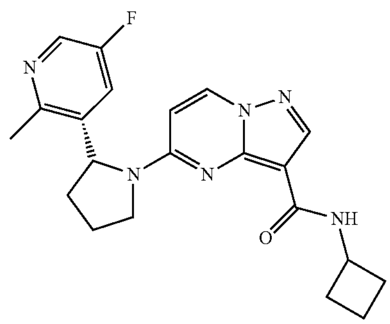 | (R)-N-cyclobutyl-5-(2-(5-fluoro-2-methylpyridin-3-yl)pyrrolidin-1-yl)pyrazolo[1,5-a]pyrimidine-3-carboxamide | LCMS (apci) m/z = 395.1 (M + H) |
| 186 | 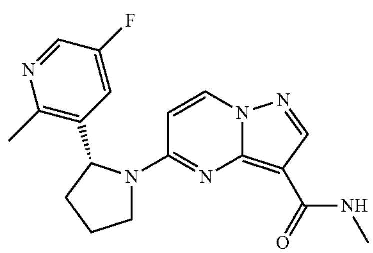 | (R)-5-(2-(5-fluoro-2-methylpyridin-3-yl)pyrrolidin-1-yl)-N-methylpyrazolo[1,5-a]pyrimidine-3-carboxamide | LCMS (apci) m/z = 355.1 (M + H) |
| 187 | 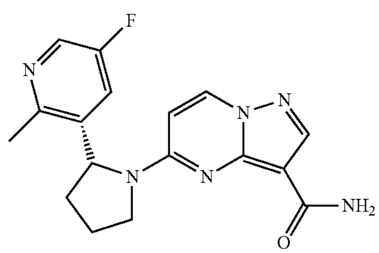 | (R)-5-(2-(5-fluoro-2-methylpyridin-3-yl)pyrrolidin-1-yl)pyrazolo[1,5-a]pyrimidine-3-carboxamide | LCMS (apci) m/z = 341.0 (M + H) |
| 188 | 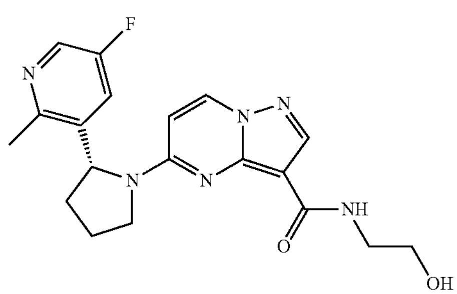 [SMILES: Cc1ncc(F)cc1[C@H]1CCCN1c1ccn2ncc(C(=O)NCCO)c2n1] | (R)-5-(2-(5-fluoro-2-methylpyridin-3-yl)pyrrolidin-1-yl)-N-(2-hydroxyethyl)pyrazolo[1,5-a]pyrimidine-3-carboxamide | LCMS (apci) m/z = 385.1 (M + H) |
| 189 | 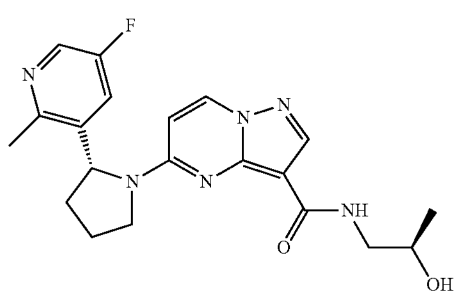 [SMILES: Cc1ncc(F)cc1[C@H]1CCCN1c1ccn2ncc(C(=O)NC[C@@H](C)O)c2n1] | (R)-5-(2-(5-fluoro-2-methylpyridin-3-yl)pyrrolidin-1-yl)-N-((R)-2-hydroxypropyl)pyrazolo[1,5-a]pyrimidine-3-carboxamide | LCMS (apci) m/z = 399.1 (M + H) |

TABLE D-continued

| Ex. # | Structure | Chemical Name | Data |
|---|---|---|---|
| 190 | 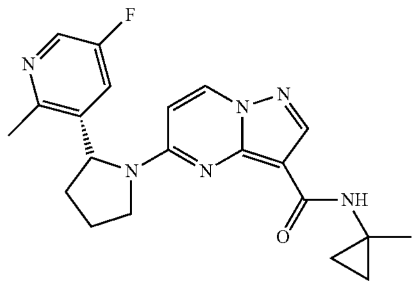 | (R)-5-(2-(5-fluoro-2-methylpyridin-3-yl)pyrrolidin-1-yl)-N-(1-methylcyclopropyl)pyrazolo[1,5-a]pyrimidine-3-carboxamide | LCMS (apci) m/z = 395.1 (M + H) |
| 191 | 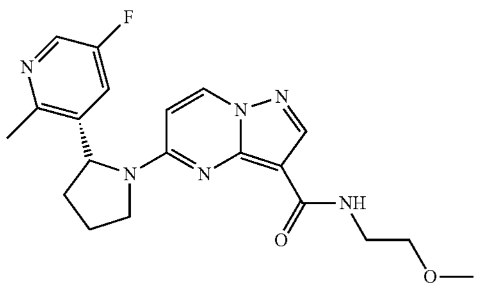 | (R)-5-(2-(5-fluoro-2-methylpyridin-3-yl)pyrrolidin-1-yl)-N-(2-methoxyethyl)pyrazolo[1,5-a]pyrimidine-3-carboxamide | LCMS (apci) m/z = 399.1 (M + H) |
| 192 | 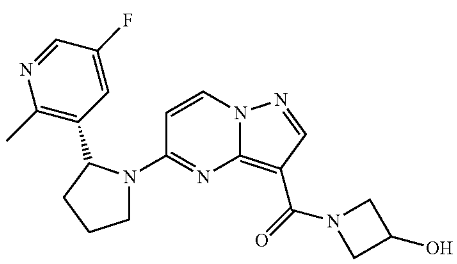 | (R)-(5-(2-(5-fluoro-2-methylpyridin-3-yl)pyrrolidin-1-yl)pyrazolo[1,5-a]pyrimidin-3-yl)(3-hydroxyazetidin-1-yl)methanone | LCMS (apci) m/z = 397.1 (M + H) |
| 193 | 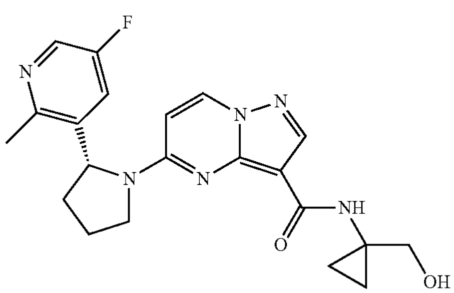 [SMILES: Cc1ncc(F)cc1[C@H]1CCCN1c1ccn2ncc(C(=O)NC3(CO)CC3)c2n1] | (R)-5-(2-(5-fluoro-2-methylpyridin-3-yl)pyrrolidin-1-yl)-N-(1-(hydroxymethyl)cyclopropyl)pyrazolo[1,5-a]pyrimidine-3-carboxamide | LCMS (apci) m/z = 411.1 (M + H) |
| 194 | 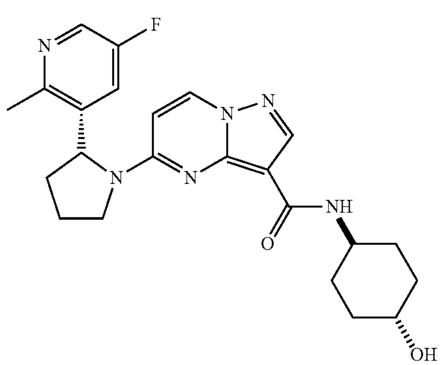 | 5-((R)-2-(5-fluoro-2-methylpyridin-3-yl)pyrrolidin-1-yl)-N-((trans)-4-hydroxycyclohexyl)pyrazolo[1,5-a]pyrimidine-3-carboxamide | LCMS (apci) m/z = 439.1 (M + H) |

TABLE D-continued

| Ex. # | Structure | Chemical Name | Data |
|---|---|---|---|
| 195 | 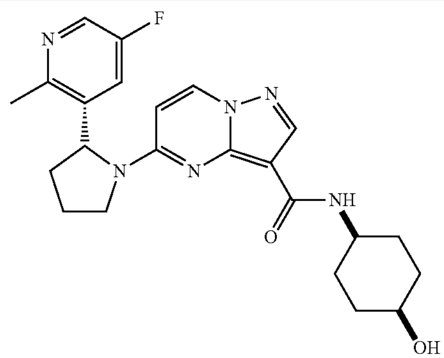 | 5-((R)-2-(5-fluoro-2-methylpyridin-3-yl)pyrrolidin-1-yl)-N-((cis)-4-hydroxycyclohexyl)pyrazolo[1,5-a]pyrimidine-3-carboxamide | LCMS (apci) m/z = 439.2 (M + H) |
| 196 | 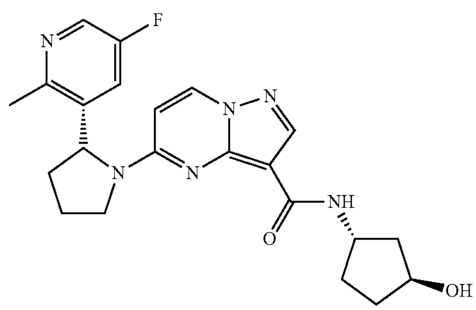 | 5-((R)-2-(5-fluoro-2-methylpyridin-3-yl)pyrrolidin-1-yl)-N-((1S,3S)-3-hydroxycyclopentyl)pyrazolo[1,5-a]pyrimidine-3-carboxamide | LCMS (apci) m/z = 425.1 (M + H) |
| 197 | 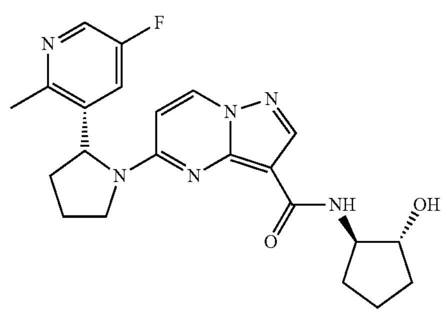 | 5-((R)-2-(5-fluoro-2-methylpyridin-3-yl)pyrrolidin-1-yl)-N-((1R,2R)-2-hydroxycyclopentyl)pyrazolo[1,5-a]pyrimidine-3-carboxamide | LCMS (apci) m/z = 425.1 (M + H) |
| 198 | 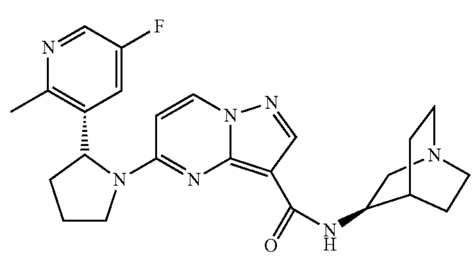 | 5-((R)-2-(5-fluoro-2-methylpyridin-3-yl)pyrrolidin-1-yl)-N-((R)-quinuclidin-3-yl)pyrazolo[1,5-a]pyrimidine-3-carboxamide | LCMS (apci) m/z = 450.2 (M + H) |
| 199 | 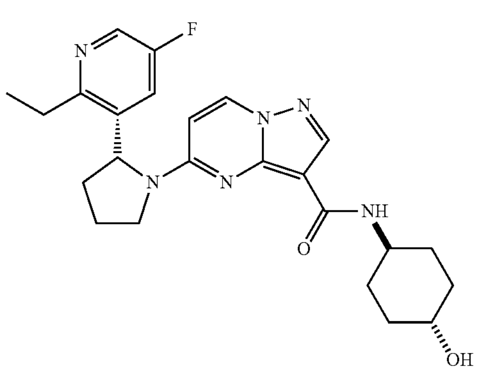 | 5-((R)-2-(2-ethyl-5-fluoropyridin-3-yl)pyrrolidin-1-yl)-N-((trans)-4-hydroxycyclohexyl)pyrazolo[1,5-a]pyrimidine-3-carboxamide | LCMS (apci) m/z = 453.2 (M + H) |

TABLE D-continued

| Ex. # | Structure | Chemical Name | Data |
|---|---|---|---|
| 200 | 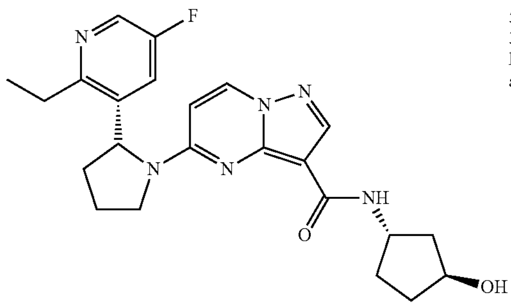 | 5-((R)-2-(2-ethyl-5-fluoropyridin-3-yl)pyrrolidin-1-yl)-N-((1S,3S)-3-hydroxycyclopentyl)pyrazolo[1,5-a]pyrimidine-3-carboxamide | LCMS (apci) m/z = 439.1 (M + H) |
| 201 | 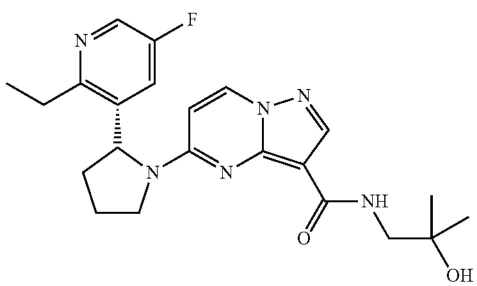 | (R)-5-(2-(2-ethyl-5-fluoropyridin-3-yl)pyrrolidin-1-yl)-N-(2-hydroxy-2-methylpropyl)pyrazolo[1,5-a]pyrimidine-3-carboxamide | LCMS (apci) m/z = 427.1 (M + H) |

Example 202

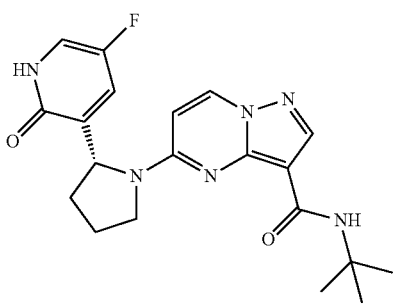 [SMILES: CC(C)(C)NC(=O)c1cnn2ccc(N3CCC[C@@H]3c3cc(F)c[nH]c3=O)nc12]

(R)—N-tert-butyl-5-(2-(5-fluoro-2-oxo-1,2-dihydropyridin-3-yl)pyrrolidin-1-yl)pyrazolo[1,5-a]pyrimidine-3-carboxamide A pressure flask was charged with (R)—N-tert-butyl-5-(2-(5-fluoro-2-methoxypyridin-3-yl)pyrrolidin-1-yl)pyrazolo[1,5-a]pyrimidine-3-carboxamide (Example 80, 10 mg, 0.024 mmol), dioxane (0.7 mL) and 2M HCl (0.100 mL, 0.200 mmol). The flask was sealed and the reaction mixture was stirred at 80° C. for 5 days. The mixture was cooled to ambient temperature and concentrated. The residue was purified by reverse-phase column chromatography (0-50% acetonitrile/water) to afford the title compound (8.2 mg, 85%). MS (apci) m/z=399.1 (M+H).

Example 203

(R)—N-(2-chloroethyl)-5-(2-(5-fluoro-2-oxo-1,2-dihydropyridin-3-yl)pyrrolidin-1-yl)pyrazolo[1,5-a]pyrimidine-3-carboxamide Prepared by the method described in Example 202, replacing (R)—N-tert-butyl-5-(2-(5-fluoro-2-methoxypyridin-3-yl)pyrrolidin-1-yl)pyrazolo[1,5-a]pyrimidine-3-carboxamide with (R)—N-(2-chloroethyl)-5-(2-(5-fluoro-2-methoxypyridin-3-yl)pyrrolidin-1-yl)pyrazolo[1,5-a]pyrimidine-3-carboxamide (Example 163, 100 mg, 0.239 mmol), replacing 2 M HCl with 4 M HCl dioxane solution, and reaction was conducted at 100° C. for 90 minutes. LCMS (apci) m/z=405.0 (M+H).

Example 204

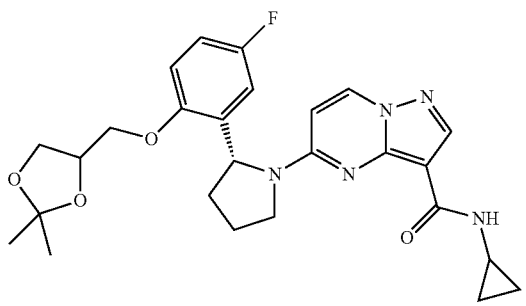 [SMILES: CC1(C)OCC(COc2ccc(F)cc2[C@H]2CCCN2c2ccn3ncc(C(=O)NC4CC4)c3n2)O1]

N-cyclopropyl-5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxamide

Step A: Preparation of ethyl 5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxylate A mixture of (R)-ethyl 5-(2-(5-fluoro-2-hydroxyphenyl)pyrrolidin-1-yl)pyrazolo[1,5-a]pyrimidine-3-carboxylate (Example 86, Step C, 140 mg, 0.378 mmol), 4-(chloromethyl)-2,2-dimethyl-1,3-dioxolane (114 mg, 0.756 mmol), potassium carbonate (261 mg, 1.89 mmol) and sodium bromide (77.8 mg, 0.756 mmol) in dry DMF (5 mL) was heated at 100° C. for 14 days. The mixture was concentrated and the residue purified by chromatography to afford the title compound (45 mg, 25% yield). MS (apci) m/z=485.0 (M+H).

Step B: Preparation of 5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxylic acid The compound was prepared according to the method of Example 86, Step E, using ethyl 5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxylate (47 mg, 100%). MS (apci) m/z=457.0 (M+H).

Step C: Preparation of N-cyclopropyl-5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxamide Prepared according to the method of Example 86, Step F, using 5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxylic acid and cyclopropyl amine to yield the title compound as a white solid (33.0 mg, 99% yield.). MS (apci) m/z=496.1 (M+H).

Example 205

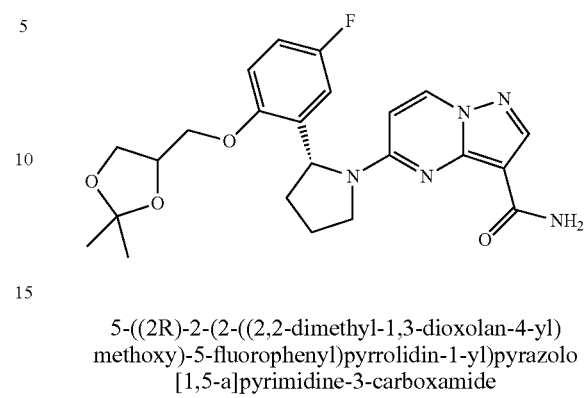

5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxamide Prepared according to the procedure described in Example 204 using ammonium chloride in place of cyclopropyl amine in Step C (white solid, 13 mg, 85% yield.). MS (apci) m/z=456.0 (M+H).

Example 206

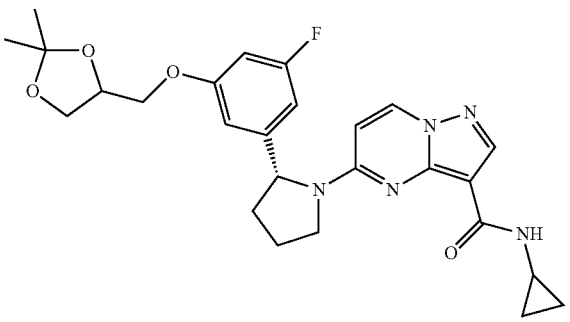 [SMILES: CC1(C)OCC(COc2cc(F)cc([C@H]3CCCN3c3ccn4ncc(C(=O)NC5CC5)c4n3)c2)O1]

N-cyclopropyl-5-((2R)-2-(3-((2,2-dimethyl-1,3-dioxolan-4-yl)methoxy)-5-fluorophenyl)pyrrolidin-1-yl)pyrazolo[1,5-a]pyrimidine-3-carboxamide Prepared according to the method of Example 204 using (R)-ethyl 5-(2-(3-fluoro-5-hydroxyphenyl)pyrrolidin-1-yl)pyrazolo[1,5-a]pyrimidine-3-carboxylate (Example 76, Step C) in Step A (36 mg, 82% yield). MS (apci) m/z=496.1 (M+H).

Example 207

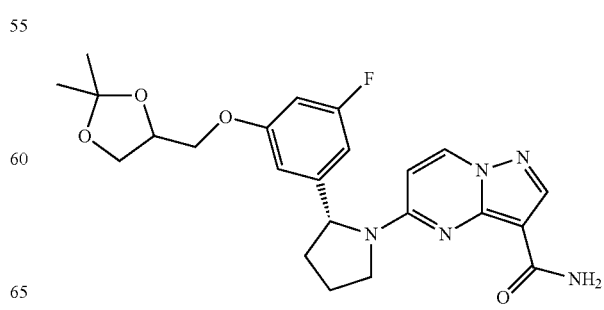

5-((2R)-2-(3-((2,2-dimethyl-1,3-dioxolan-4-yl)
methoxy)-5-fluorophenyl)pyrrolidin-1-yl)pyrazolo
[1,5-a]pyrimidine-3-carboxamide Prepared according to the method of Example 204, using (R)-ethyl 5-(2-(3-fluoro-5-hydroxyphenyl)pyrrolidin-1-yl)pyrazolo[1,5-a]pyrimidine-3-carboxylate (Example 76, Step C) in Step A and ammonium chloride in Step C to yield the title compound as a white solid (19 mg, 55% yield.). MS (apci) m/z=456.0 (M+H).

Example 208

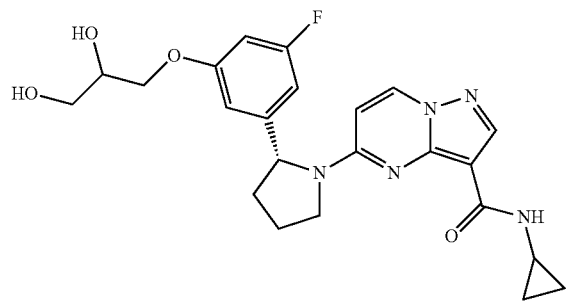 [SMILES: O=C(NC1CC1)c1cnn2ccc(N3CCC[C@@H]3c3cc(F)cc(OCC(O)CO)c3)nc12]

N-cyclopropyl-5-((2R)-2-(3-(2,3-dihydroxy-
propoxy)-5-fluorophenyl)pyrrolidin-1-yl)pyrazolo[1,
5-a]pyrimidine-3-carboxamide A solution of N-cyclopropyl-5-((2R)-2-(3-((2,2-dimethyl-1,3-dioxolan-4-yl)methoxy)-5-fluorophenyl)pyrrolidin-1-yl)pyrazolo[1,5-a]pyrimidine-3-carboxamide (Example 206, 30 mg, 0.061 mmol) in dioxane (0.5 mL) was charged with two drops of 6N HCl and shaken for two minutes. DIEA (5 drops) was added and the mixture directly purified by reverse phase column chromatography (0-50% acetonitrile/water) to afford N-cyclopropyl-5-((2R)-2-(3-(2,3-dihydroxypropoxy)-5-fluorophenyl)pyrrolidin-1-yl)pyrazolo[1,5-a]pyrimidine-3-carboxamide (23 mg, 83% yield) as a clear film. MS (apci) m/z=456.1 (M+H).

Example 209

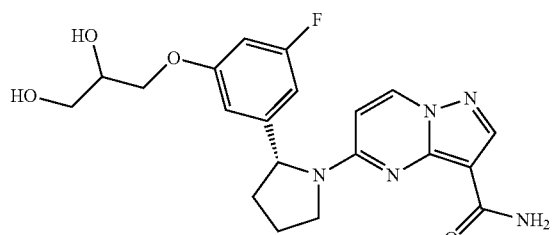

5-((2R)-2-(3-(2,3-dihydroxypropoxy)-5-fluorophe-
nyl)pyrrolidin-1-yl)pyrazolo[1,5-a]pyrimidine-3-
carboxamide Prepared from 5-((2R)-2-(3-((2,2-dimethyl-1,3-dioxolan-4-yl)methoxy)-5-fluorophenyl)pyrrolidin-1-yl)pyrazolo[1,5-a]pyrimidine-3-carboxamide (Example 207) according to the procedure of Example 208 (8.5 mg, 55% yield). MS (apci) m/z=416.0 (M+H).

Example 210

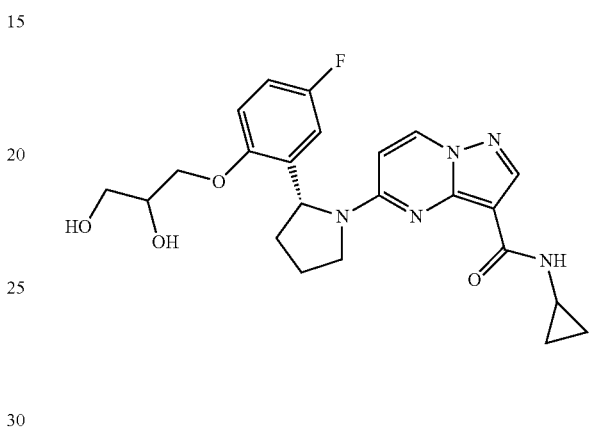

N-cyclopropyl-5-((2R)-2-(2-(2,3-dihydroxy-
propoxy)-5-fluorophenyl)pyrrolidin-1-yl)pyrazolo[1,
5-a]pyrimidine-3-carboxamide Prepared from N-cyclopropyl-5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxamide (Example 204) using the procedure of Example 208 (19 mg, 65% yield). MS (apci) m/z=456.1 (M+H).

Example 211

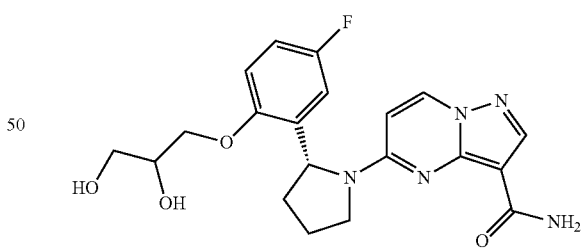

5-((2R)-2-(2-(2,3-dihydroxypropoxy)-5-fluorophe-
nyl)pyrrolidin-1-yl)pyrazolo[1,5-a]pyrimidine-3-
carboxamide Prepared from 5-((2R)-2-(3-((2,2-dimethyl-1,3-dioxolan-4-yl)methoxy)-5-fluorophenyl)pyrrolidin-1-yl)pyrazolo[1,5-a]pyrimidine-3-carboxamide (Example 205) using the procedure of Example 208 (10 mg, 95% yield). MS (apci) m/z=416.0 (M+H).

Example 212

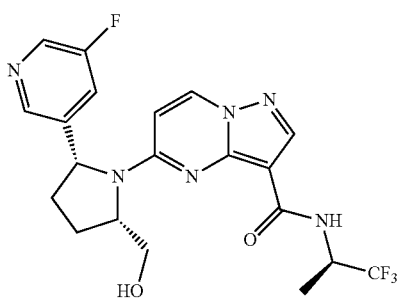 [SMILES: C[C@@H](NC(=O)c1cnn2ccc(N3[C@H](CO)CC[C@@H]3c3cncc(F)c3)nc12)C(F)(F)F]

5-((2R,5S)-2-(5-fluoropyridin-3-yl)-5-(hydroxymethyl)pyrrolidin-1-yl)-N—((R)-1,1,1-trifluoropropan-2-yl)pyrazolo[1,5-a]pyrimidine-3-carboxamide

Step A: Preparation of (S)-ethyl 2-(tert-butoxycarbonylamino)-5-(5-fluoropyridin-3-yl)-5-oxopentanoate A solution of 3-bromo-5-fluoropyridine (4.28 g, 24.3 mmol) in dry THF (25 mL) was cooled to −40 to −50° C. and 2M isopropylmagnesium chloride in THF (10.2 mL, 20.4 mmol) was added. The mixture was allowed to warm to 0° C. and was stirred for 30 minutes. The mixture was cooled to −20° C. and a solution of (S)-1-tert-butyl 2-ethyl 5-oxopyrrolidine-1,2-dicarboxylate (5.00 g, 19.4 mmol) in dry THF (15 mL) was added. The mixture was allowed to reach ambient temperature over 30 minutes and was stirred at ambient temperature for 30 minutes. The reaction was slowly quenched with 2M HCl (10 mL, 20.0 mmol) followed by 10% aqueous NH$_4$Cl (10 mL). The mixture was stirred for 10 minutes and was transferred to a separatory funnel using MTBE rinses (10 mL). Heptane (15 mL) was added and the organic layer was removed. The organic layer was washed 10% aqueous NH$_4$Cl (25 mL) and DI H$_2$O (25 mL). The organic layer was concentrated to provide the crude product as a yellow oil (7.03 g, 102%).

Step B: Preparation of (2S,5R)-ethyl 5-(5-fluoropyridin-3-yl)pyrrolidine-2-carboxylate (S)-ethyl 2-(tert-butoxycarbonylamino)-5-(5-fluoropyridin-3-yl)-5-oxopentanoate (4.80 g, 13.55 mmol) was treated with TFA (24 mL) and the mixture was stirred at ambient temperature for 45 minutes. The mixture was concentrated and the residue was dissolved in H$_2$O (10 mL) and EtOAc (50 mL) was added. The mixture was treated slowly with saturated aqueous K$_2$CO$_3$ (15 mL). The aqueous layer was separated and the organic layer was washed with 10% aqueous NH$_4$Cl. The EtOAc layer was concentrated to give crude (S)-ethyl 5-(5-fluoropyridin-3-yl)-3,4-dihydro-2H-pyrrole-2-carboxylate as an amber oil (2.67 g, 83% yield). The oil was dissolved in isopropyl alcohol (20 mL) and was treated with 10% Pd/C (0.266 g, 0.250 mmol). The reaction vessel was purged with hydrogen gas (3×) and mixture was stirred at ambient temperature under 1 atm of hydrogen for 16 hours. The reaction was purged with nitrogen and filtered through a Celite pad. The filtrate was concentrated to furnish the title compound as an amber oil that began to solidify upon standing (2.58 g, 96%).

Step C: Preparation of ((2S,5R)-5-(5-fluoropyridin-3-yl)pyrrolidin-2-yl)methanol To a solution of (2S,5R)-ethyl 5-(5-fluoropyridin-3-yl)pyrrolidine-2-carboxylate (1.10 g, 4.62 mmol) in dry THF (20 mL) was added 2M LiAlH$_4$ in THF (3.00 mL, 6.00 mmol). The reaction was stirred at ambient temperature for 30 minutes and Na$_2$SO$_4$ 10H$_2$O (3.00 g, 9.31 mmol) was added in small portions. The mixture was stirred for 3 hours at ambient temperature and was filtered. The collected solid was washed with EtOAc and the washes combined with the filtrate. The solution was concentrated to provide crude ((2S,5R)-5-(5-fluoropyridin-3-yl)pyrrolidin-2-yl)methanol (0.95 g, 105% yield) that was used directly in the next step. MS (apci) m/z=197.1 (M+H).

Step D: Preparation of ethyl 5-((2R,5S)-2-(5-fluoropyridin-3-yl)-5-(hydroxymethyl)pyrrolidin-1-yl)pyrazolo[1,5-a]pyrimidine-3-carboxylate A mixture of ((2S,5R)-5-(5-fluoropyridin-3-yl)pyrrolidin-2-yl)methanol (0.910 g, 4.64 mmol), ethyl 5-chloropyrazolo[1,5-a]pyrimidine-3-carboxylate (Preparation B, 1.05 g, 4.64 mmol) and DIEA (1.10 mL, 6.00 mmol) in isopropyl alcohol (1.0 mL) was heated at 90° C. for 16 hours. The reaction mixture was concentrated and the residue was purified by reverse phase column chromatography (0-50% acetonitrile/water) followed by normal phase column chromatography (2-5% MeOH/DCM) to afford ethyl 5-((2R,5S)-2-(5-fluoropyridin-3-yl)-5-(hydroxymethyl)pyrrolidin-1-yl)pyrazolo[1,5-a]pyrimidine-3-carboxylate (0.250 g, 14% yield) as a viscous, clear oil. MS (apci) m/z=386.0 (M+H).

Step E: Preparation of 5-((2R,5S)-2-(5-fluoropyridin-3-yl)-5-(hydroxymethyl)pyrrolidin-1-yl)pyrazolo[1,5-a]pyrimidine-3-carboxylic acid A mixture of ethyl 5-((2R,5S)-2-(5-fluoropyridin-3-yl)-5-(hydroxymethyl)pyrrolidin-1-yl)pyrazolo[1,5-a]pyrimidine-3-carboxylate (0.250 g, 0.649 mmol) and 2M sodium hydroxide (3.24 mL, 6.48 mmol) in MeOH (10 mL) was stirred at ambient temperature for 4 days followed by 50° C. for 5 hours. The reaction was cooled to ambient temperature and 4M HCl in dioxane (1.78 mL, 7.14 mmol) was added. The mixture was concentrated and the residue was purified by reverse phase column chromatography (0-40% acetonitrile/water) to afford 5-((2R,5S)-2-(5-fluoropyridin-3-yl)-5-(hydroxymethyl)pyrrolidin-1-yl)pyrazolo[1,5-a]pyrimidine-3-carboxylic acid (210 mg, 90% yield) as a white solid. MS (apci) m/z=358.0 (M+H).

Step F: Preparation of 5-((2R,5S)-2-(5-fluoropyridin-3-yl)-5-(hydroxymethyl)pyrrolidin-1-yl)-N—((R)-1,1,1-trifluoropropan-2-yl)pyrazolo[1,5-a]pyrimidine-3-carboxamide To a mixture of 5-((2R,5S)-2-(5-fluoropyridin-3-yl)-5-(hydroxymethyl)pyrrolidin-1-yl)pyrazolo[1,5-a]pyrimidine-3-carboxylic acid (10.0 mg, 0.028 mmol), (R)-1,1,1-trifluoropropan-2-amine (6.33 mg, 0.056 mmol) and HATU (10.5 mg, 0.045 mmol) in dry DMF (0.2 mL) was added DIEA (15.0 µL, 0.084 mmol). The reaction vessel was flushed with nitrogen, sealed, and the reaction stirred at ambient temperature for 16 hours. The reaction mixture was directly purified by reverse phase column chromatography (0-50%

CH₃CN/H₂O) to provide the title compound (6.50 mg, 51% yield) as a white solid. MS (apci) m/z=453.0 (M+H).

Example 213

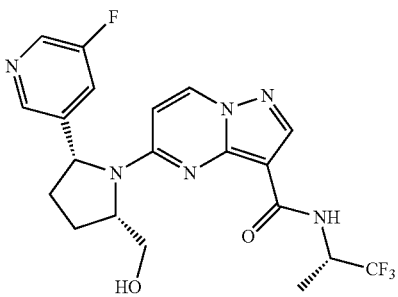 [SMILES: C[C@H](NC(=O)c1cnn2ccc(N3[C@H](CO)CC[C@@H]3c3cncc(F)c3)nc12)C(F)(F)F]

5-((2R,5S)-2-(5-fluoropyridin-3-yl)-5-(hydroxymethyl)pyrrolidin-1-yl)-N—((S)-1,1,1-trifluoropropan-2-yl)pyrazolo[1,5-a]pyrimidine-3-carboxamide Prepared according to the method of Example 212, Step F, using (S)-1,1,1-trifluoropropan-2-amine (white solid; 5.5 mg, 43%). MS (apci) m/z=453.0 (M+H).

Example 214

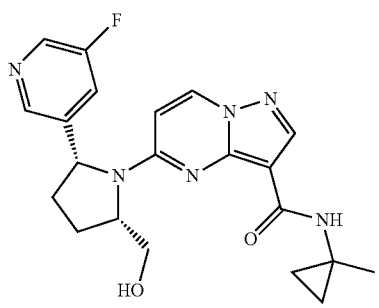 [SMILES: CC1(NC(=O)c2cnn3ccc(N4[C@H](CO)CC[C@@H]4c4cncc(F)c4)nc23)CC1]

5-((2R,5S)-2-(5-fluoropyridin-3-yl)-5-(hydroxymethyl)pyrrolidin-1-yl)-N-(1-methylcyclopropyl)pyrazolo[1,5-a]pyrimidine-3-carboxamide Prepared according to the method of Example 212, Step F, using 1-methylcyclopropane amine (white solid; 2.5 mg, 22%). MS (apci) m/z=411.1 (M+H).

Example 215

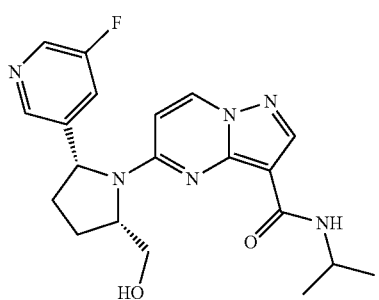 [SMILES: CC(C)NC(=O)c1cnn2ccc(N3[C@H](CO)CC[C@@H]3c3cncc(F)c3)nc12]

5-((2R,5S)-2-(5-fluoropyridin-3-yl)-5-(hydroxymethyl)pyrrolidin-1-yl)-N-isopropylpyrazolo[1,5-a]pyrimidine-3-carboxamide Prepared according to the method of Example 212, Step F, using isopropyl amine (white solid; 2.5 mg, 12%). MS (apci) m/z=399.1 (M+H).

Example 216

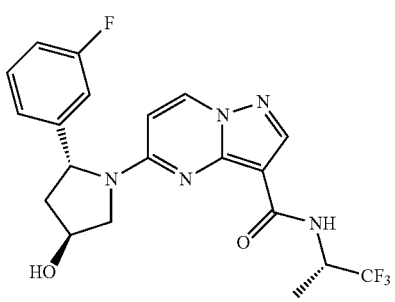 [SMILES: C[C@H](NC(=O)c1cnn2ccc(N3C[C@@H](O)C[C@@H]3c3cccc(F)c3)nc12)C(F)(F)F]

5-((2R,4S)-2-(3-fluorophenyl)-4-hydroxypyrrolidin-1-yl)-N—((S)-1,1,1-trifluoropropan-2-yl)pyrazolo[1,5-a]pyrimidine-3-carboxamide Step A: Preparation of (ethyl 5-((2R,4S)-4-acetoxy-2-(3-fluorophenyl)pyrrolidin-1-yl)pyrazolo[1,5-a]pyrimidine-3-carboxylate To a mixture of ethyl 5-((2R,4R)-2-(3-fluorophenyl)-4-hydroxypyrrolidin-1-yl)pyrazolo[1,5-a]pyrimidine-3-carboxylate (Example 41, Step E, 260 mg, 0.702 mmol) and PPh₃ (460 mg, 1.75 mmol) in THF (10.0 mL) was added DIAD (276 μL, 1.40 mmol) followed by acetic acid (80.4 μL, 1.40 mmol). The reaction was stirred at ambient temperature for 48 hours and then concentrated. The residue was purified by reverse phase column chromatography (0-70% acetonitrile/water) to afford ethyl 5-((2R,4S)-4-acetoxy-2-(3-fluorophenyl)pyrrolidin-1-yl)pyrazolo[1,5-a]pyrimidine-3-carboxylate (228 mg, 79% yield). MS (apci) m/z=413.0 (M+H).

Step B: Preparation of 5-((2R,4S)-2-(3-fluorophenyl)-4-hydroxypyrrolidin-1-yl)pyrazolo[1,5-a]pyrimidine-3-carboxylic acid A mixture of ethyl 5-((2R,4S)-4-acetoxy-2-(3-fluorophenyl)pyrrolidin-1-yl)pyrazolo[1,5-a]pyrimidine-3-carboxylate (225 mg, 0.546 mmol) and NaOH (131 mg, 1.64 mmol) in MeOH (1.0 mL) was stirred at ambient temperature for 60 hours followed by 3 hours at 60° C. The mixture was cooled to ambient temperature and 4M HCl in dioxane (1 mL) was added. The mixture was concentrated and the residue was treated with DCM. The mixture was filtered through Celite and concentrated to afford 5-((2R,4S)-2-(3-fluorophenyl)-4-hydroxypyrrolidin-1-yl)pyrazolo[1,5-a]pyrimidine-3-carboxylic acid (188 mg, 10% yield) as a white solid. MS (apci) m/z=343.0 (M+H).

Step C: Preparation of 5-((2R,4S)-2-(3-fluorophenyl)-4-hydroxypyrrolidin-1-yl)-N—((S)-1,1,1-trifluoropropan-2-yl)pyrazolo[1,5-a]pyrimidine-3-carboxamide Prepared according to the method of Example 212, Step F, using 5-((2R,4S)-2-(3-fluorophenyl)-4-hydroxypyrrolidin-1-yl)pyrazolo[1,5-a]pyrimidine-3-carboxylic acid and (S)-1,1,1-trifluoropropan-2-amine (white solid; 2.1 mg, 16% yield). MS (apci) m/z=438.0 (M+H).

Example 217

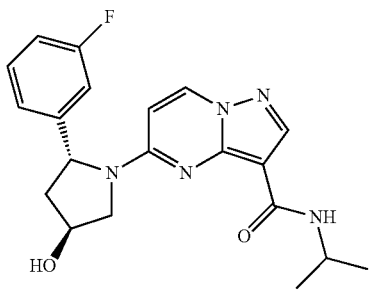 [SMILES: CC(C)NC(=O)c1cnn2ccc(N3C[C@@H](O)C[C@@H]3c3cccc(F)c3)nc12]

5-((2R,4S)-2-(3-fluorophenyl)-4-hydroxypyrrolidin-1-yl)-N-isopropylpyrazolo[1,5-a]pyrimidine-3-carboxamide Prepared according to the method of Example 212, Step F, using 5-((2R,4S)-2-(3-fluorophenyl)-4-hydroxypyrrolidin-1-yl)pyrazolo[1,5-a]pyrimidine-3-carboxylic acid (Example 216, Step B) and isopropyl amine. The title compound was obtained as a white solid (5.5 mg, 49% yield). MS (apci) m/z=384.1 (M+H).

Example 218

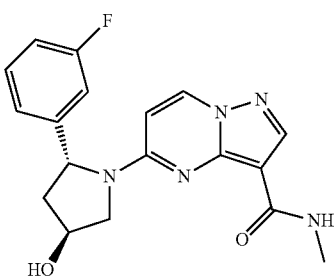 [SMILES: CNC(=O)c1cnn2ccc(N3C[C@@H](O)C[C@@H]3c3cccc(F)c3)nc12]

5-((2R,4S)-2-(3-fluorophenyl)-4-hydroxypyrrolidin-1-yl)-N-methylpyrazolo[1,5-a]pyrimidine-3-carboxamide Prepared according to the method of Example 212, Step F, using 5-((2R,4S)-2-(3-fluorophenyl)-4-hydroxypyrrolidin-1-yl)pyrazolo[1,5-a]pyrimidine-3-carboxylic acid (Example 216, Step B) and methyl amine. The title compound was obtained as a white solid (6.1 mg, 29% yield). MS (apci) m/z=356.1 (M+H).

Example 219

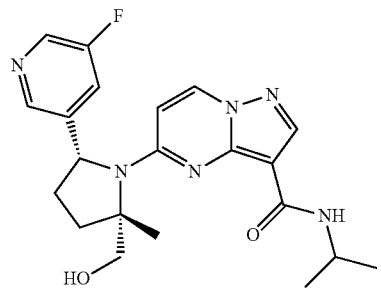 [SMILES: CC(C)NC(=O)c1cnn2ccc(N3[C@@H](c4cncc(F)c4)CC[C@@]3(C)CO)nc12]

5-((2S,5R)-5-(5-fluoropyridin-3-yl)-2-(hydroxymethyl)-2-methylpyrrolidin-1-yl)-N-isopropylpyrazolo[1,5-a]pyrimidine-3-carboxamide Step A: Preparation of (2S,5R)-1-tert-butyl 2-ethyl 5-(5-fluoropyridin-3-yl)pyrrolidine-1,2-dicarboxylate A mixture of (2S,5R)-ethyl 5-(5-fluoropyridin-3-yl)pyrrolidine-2-carboxylate (Example 212, Step B, 1.00 g, 4.20 mmol), di-tert-butyl dicarbonate (0.962 g, 4.41 mmol) and PS-DMAP (0.210 g, 0.210 mmol, 1.00 mmol/g load) in dry DCM (20 mL) was mixed at ambient temperature for 18 hours. The reaction mixture was filtered and the filtrate was concentrated. The residue was purified on a silica gel column (2-10% MeOH/DCM) to afford (2S,5R)-1-tert-butyl 2-ethyl 5-(5-fluoropyridin-3-yl)pyrrolidine-1,2-dicarboxylate (1.36 g, 96% yield) as a yellow oil. MS (apci) m/z=339.0 (M+H).

Step B: Preparation of (2S,5R)-1-tert-butyl 2-ethyl 5-(5-fluoropyridin-3-yl)-2-methylpyrrolidine-1,2-dicarboxylate A solution of (2S,5R)-1-tert-butyl 2-ethyl 5-(5-fluoropyridin-3-yl)pyrrolidine-1,2-dicarboxylate (250 mg, 0.739 mmol) in THF (10 mL) was cooled to −78° C. and 0.5 µM KHMDS in toluene (1.77 mL, 0.885 mmol) was added dropwise. The reaction was stirred for 1 hour at −78° C. and MeI (59.9 µL, 0.960 mmol) was added. The reaction was allowed to warm to ambient temperature and saturated aqueous NaCl (20 mL) was added. The mixture was extracted with EtOAc (2×50 mL) and the combined organic extracts were filtered and concentrated to afford (2S,5R)-1-tert-butyl 2-ethyl 5-(5-fluoropyridin-3-yl)-2-methylpyrrolidine-1,2-dicarboxylate (255 mg, 98% yield) as a clear oil. MS (apci) m/z=353.1 (M+H).

Step C: Preparation of (2S,5R)-tert-butyl 5-(5-fluoropyridin-3-yl)-2-(hydroxymethyl)-2-methylpyrrolidine-1-carboxylate A solution of (2S,5R)-1-tert-butyl 2-ethyl 5-(5-fluoropyridin-3-yl)-2-methylpyrrolidine-1,2-dicarboxylate (240 mg, 0.681 mmol) in THF (10 mL) was cooled to −78° C. and 1M LiAlH₄ in THF (1.50 mL, 1.50 mmol) was added dropwise. The reaction was allowed to warm to 0° C. and was quenched with small portions of Na₂SO₄-10H₂O (967 mg, 6.81 mmol). The mixture was filtered and concentrated to afford (2S,5R)-tert-butyl 5-(5-fluoropyridin-3-yl)-2-(hydroxymethyl)-2-methylpyrrolidine-1-carboxylate (200 mg, 95% yield). MS (apci) m/z=311.1 (M+H).

Step D: Preparation of ((2S,5R)-5-(5-fluoropyridin-3-yl)-2-methylpyrrolidin-2-yl)methanol hydrochloride To a solution of (2S,5R)-tert-butyl 5-(5-fluoropyridin-3-yl)-2-(hydroxymethyl)-2-methylpyrrolidine-1-carboxylate (200 mg, 0.644 mmol) in DCM (5 mL) was added 4M HCl in dioxane (1.61 mL, 6.44 mmol). The reaction was stirred at ambient temperature for 16 hours and then concentrated to afford ((2S,5R)-5-(5-fluoropyridin-3-yl)-2-methylpyrrolidin-2-yl)methanol hydrochloride (130 mg, 96% yield). MS (apci) m/z=211.1 (M+H).

Step E: Preparation of ethyl 5-((2S,5R)-5-(5-fluoropyridin-3-yl)-2-(hydroxymethyl)-2-methylpyrrolidin-1-yl)pyrazolo[1,5-a]pyrimidine-3-carboxylate A sealed reaction vessel was charged with ((2S,5R)-5-(5-fluoropyridin-3-yl)-2-methylpyrrolidin-2-yl)methanol hydrochloride (0.135 g, 0.547 mmol), ethyl 5-chloropyrazolo[1,5-a]pyrimidine-3-carboxylate (Preparation B, 0.136 g, 0.602 mmol), DIEA (0.124 mL, 0.711 mmol) and isopropyl alcohol (1 mL). The vessel was sealed and the mixture was heated at 190° C. for 48 hours. The reaction was cooled to ambient temperature and concentrated. The residue was purified by reverse phase column chromatography (0-50% acetonitrile/water) to afford ethyl 5-((2S,5R)-5-(5-fluoropyridin-3-yl)-2-(hydroxymethyl)-2-methylpyrrolidin-1-yl)pyrazolo[1,5-a]pyrimidine-3-carboxylate (55 mg, 25% yield) as a viscous clear oil. MS (apci) m/z=400.1 (M+H).

Step F: Preparation of 5-((2S,5R)-5-(5-fluoropyridin-3-yl)-2-(hydroxymethyl)-2-methylpyrrolidin-1-yl)pyrazolo[1,5-a]pyrimidine-3-carboxylic acid A mixture of ethyl 5-((2S,5R)-5-(5-fluoropyridin-3-yl)-2-(hydroxymethyl)-2-methylpyrrolidin-1-yl)pyrazolo[1,5-a]pyrimidine-3-carboxylate (52.0 mg, 0.130 mmol) and NaOH (26.0 mg, 0.325 mmol) in MeOH (1.0 mL) was stirred at ambient temperature for 60 hours. The reaction was treated with HCl (4 N dioxane, 163 µL, 0.651 mmol) and concentrated. The residue was treated with DCM and filtered through Celite. The solution was concentrated to afford 5-((2S,5R)-5-(5-fluoropyridin-3-yl)-2-(hydroxymethyl)-2-methylpyrrolidin-1-yl)pyrazolo[1,5-a]pyrimidine-3-carboxylic acid (29 mg, 60% yield) as a white solid. MS (apci) m/z=372.0 (M+H).

Step G: Preparation of 5-((2S,5R)-5-(5-fluoropyridin-3-yl)-2-(hydroxymethyl)-2-methylpyrrolidin-1-yl)-N-isopropylpyrazolo[1,5-a]pyrimidine-3-carboxamide Prepared according to the method of Example 212, Step F, using 5-((2S,5R)-5-(5-fluoropyridin-3-yl)-2-(hydroxymethyl)-2-methylpyrrolidin-1-yl)pyrazolo[1,5-a]pyrimidine-3-carboxylic acid and isopropyl amine. The title compound was obtained as a white solid (7.2 mg, 46% yield). MS (apci) m/z=413.1 (M+H).

Example 220

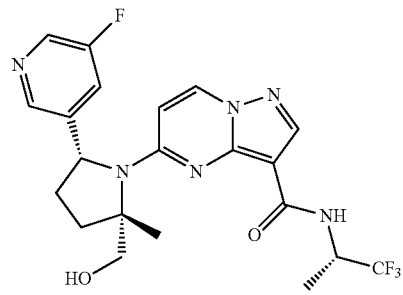 [SMILES: C[C@H](NC(=O)c1cnn2ccc(N3[C@@H](c4cncc(F)c4)CC[C@@]3(C)CO)nc12)C(F)(F)F]

5-((2S,5R)-5-(5-fluoropyridin-3-yl)-2-(hydroxymethyl)-2-methylpyrrolidin-1-yl)-N—((S)-1,1,1-trifluoropropan-2-yl)pyrazolo[1,5-a]pyrimidine-3-carboxamide Prepared according to the method of Example 212, Step F, using 5-((2S,5R)-5-(5-fluoropyridin-3-yl)-2-(hydroxymethyl)-2-methylpyrrolidin-1-yl)pyrazolo[1,5-a]pyrimidine-3-carboxylic acid (Example 219, Step F) and (S)-1,1,1-trifluoropropan-2-amine. The title compound was obtained as a white solid (5.4 mg, 31% yield). MS (apci) m/z=467.1 (M+H).

Example 221

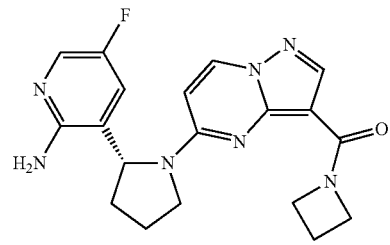 [SMILES: Nc1ncc(F)cc1[C@H]1CCCN1c1ccn2ncc(C(=O)N3CCC3)c2n1]

(R)-(5-(2-(2-amino-5-fluoropyridin-3-yl)pyrrolidin-1-yl)pyrazolo[1,5-a]pyrimidin-3-yl)(azetidin-1-yl)methanone A mixture of (R)—N-(3-aminopropyl)-5-(2-(5-fluoro-2-oxo-1,2-dihydropyridin-3-yl)pyrrolidin-1-yl)pyrazolo[1,5-a]pyrimidine-3-carboxamide hydrochloride (Example 142, 83 mg, 0.190 mmol) and POCl₃ (697 µL, 7.62 mmol) was sealed and heated at 100° C. for 5 minutes. The reaction mixture was diluted with 1 mL heptane and azeotroped twice to yield the crude product. The crude material was purified by reverse-phase chromatography (5 to 40% acetonitrile/water) to yield the title product as white solid (2 mg, 3%). LCMS (apci) m/z=382.3 (M+H).

Example 222

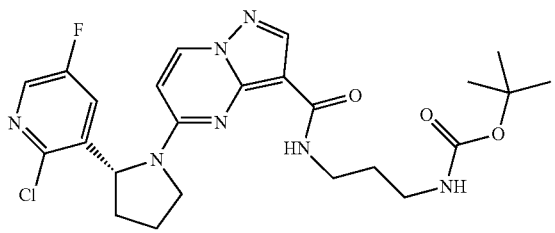 [SMILES: CC(C)(C)OC(=O)NCCCNC(=O)c1cnn2ccc(N3CCC[C@@H]3c3cc(F)cnc3Cl)nc12]

(R)-tert-butyl 3-(5-(2-(2-chloro-5-fluoropyridin-3-yl)pyrrolidin-1-yl)pyrazolo[1,5-a]pyrimidine-3-carboxamido)propylcarbamate

Step A: Preparation of (R)-tert-butyl 2-(2-chloro-5-fluoropyridin-3-yl)pyrrolidine-1-carboxylate A solution of tert-butyl pyrrolidine-1-carboxylate (1 mL 5.70 mmol) and (−)-sparteine (1.31 mL, 5.70 mmol) in anhydrous MTBE (30 mL) was first cooled to −78° C. under nitrogen, followed by addition of sec-butyl lithium (4.07 mL, 1.4M, 5.70 mmol) drop-wise over 15 minutes with a syringe, maintaining the temperature below −75° C. The pale yellowish solution was stirred at −78° C. for 3 hours before being treated with zinc chloride (3.80 mL, 1.0 M, 3.80 mmol) dropwise over 15 minutes while maintaining the temperature below −73° C. The mixture was stirred at −78° C. for 30 minutes, then placed into an ambient temperature water bath and stirred for another hour. At this point a large amount of white precipitate was present. The mixture was treated with 3-bromo-2-chloro-5-fluoropyridine (1.00 g, 4.75 mmol) in MTBE (5 mL), followed by addition of palladium acetate (53 mg, 0.24 mmol) and tri-t-butylphosphine tetrafluoroborate (83 mg, 0.28 mmol). The mixture was allowed to stir at ambient temperature overnight to reach completion. The mixture was treated with NH$_4$OH (1 mL), stirred for 30 minutes and filtered through GF/F paper, washing with MTBE. The filtrate was washed with 10% citric acid (30 mL) and the aqueous layer was back-washed with MTBE (2×30 mL). The combined organic phases were washed with brine (20 mL), dried (MgSO$_4$), and concentrated to afford the crude product as dark yellowish oil. This crude material was purified on a silica 50 g Biotage SNAP cartridge eluting with 10% EtOAc in hexanes to afford the desired product as colorless oil (0.5 g, 35%). MS (apci pos) m/z=201.1 (M+H−Boc).

Step B: Preparation of (R)-2-chloro-5-fluoro-3-(pyrrolidin-2-yl)pyridine dihydrochloride To a dioxane (5 mL) solution of (R)-tert-butyl 2-(2-chloro-5-fluoropyridin-3-yl)pyrrolidine-1-carboxylate (500 mg, 1.66 mmol) was added HCl (4 N dioxane, 20 mL), followed by stirring at ambient temperature overnight. The mixture was concentrated and treated with Et$_2$O, then vacuum-dried, to provide the product as a white solid (0.36 g, 80%). MS (apci pos) m/z=201.1 (M+H). The enantiomeric excess (ee %) of the product was determined to be >92% according to the method described in Preparation A.

Step C: Preparation of (R)-ethyl 5-(2-(2-chloro-5-fluoropyridin-3-yl)pyrrolidin-1-yl)pyrazolo[1,5-a]pyrimidine-3-carboxylate To a solution of ethyl 5-hydroxypyrazolo[1,5-a]pyrimidine-3-carboxylate (Preparation B, Step A, 275 mg, 1.33 mmol) in anhydrous DMF (5 mL) was added (Benzotriazol-1-yloxy)tris(dimethylamino)phosphonium hexafluorophosphate (BOP) (646 mg, 1.46 mmol). The heterogeneous mixture was stirred for 10 minutes before adding DIEA (1.16 mL, 6.6 mmol), followed by addition of (R)-2-chloro-5-fluoro-3-(pyrrolidin-2-yl)pyridine dihydrochloride (363 mg, 1.33 mmol). The reaction was stirred at ambient temperature overnight to reach completion. The mixture was partitioned between 10% citric acid (30 mL) and EtOAc (30 mL), and the aqueous layer was extracted with EtOAc (2×20 mL). The combined organic phases were washed successively with water (20 mL), saturated NaHCO$_3$ (20 mL), water (20 mL) and brine (3×20 mL), then dried (Na$_2$SO$_4$) and concentrated to afford the crude product as an orange foam. The crude material was purified on a 25 g Biotage SNAP silica cartridge eluting with 1% MeOH/DCM to afford the desired product as cream-colored foam (0.35 g, 68%). MS (apci pos) m/z=390.0 (M+H).

Step D: Preparation of (R)-5-(2-(2-chloro-5-fluoropyridin-3-yl)pyrrolidin-1-yl)pyrazolo[1,5-a]pyrimidine-3-carboxylic acid Prepared by the method described in Preparation C, Step B, replacing (R)-ethyl 5-(2-(2,5-difluorophenyl)pyrrolidin-1-yl)pyrazolo[1,5-a]pyrimidine-3-carboxylate with (R)-ethyl 5-(2-(2-chloro-5-fluoropyridin-3-yl)pyrrolidin-1-yl)pyrazolo[1,5-a]pyrimidine-3-carboxylate. MS (apci pos) m/z=361.9 (M+H).

Step E: Preparation of (R)-tert-butyl 3-(5-(2-(2-chloro-5-fluoropyridin-3-yl)pyrrolidin-1-yl)pyrazolo[1,5-a]pyrimidine-3-carboxamido)propylcarbamate Prepared according to the method described in Example 141, replacing (R)-5-(2-(5-fluoro-2-methoxypyridin-3-yl)pyrrolidin-1-yl)pyrazolo[1,5-a]pyrimidine-3-carboxylic acid with (R)-5-(2-(2-chloro-5-fluoropyridin-3-yl)pyrrolidin-1-yl)pyrazolo[1,5-a]pyrimidine-3-carboxylic acid to yield the title product as white solid. LCMS (apci pos) m/z=418.2 (M+H−Boc).

Example 223

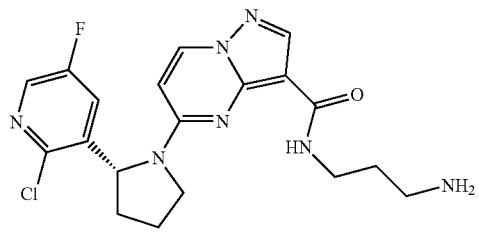 [SMILES: NCCCNC(=O)c1cnn2ccc(N3CCC[C@@H]3c3cc(F)cnc3Cl)nc12]

(R)—N-(3-aminopropyl)-5-(2-(2-chloro-5-fluoropyridin-3-yl)pyrrolidin-1-yl)pyrazolo[1,5-a]pyrimidine-3-carboxamide A mixture of (R)-tert-butyl 3-(5-(2-(2-chloro-5-fluoropyridin-3-yl)pyrrolidin-1-yl)pyrazolo[1,5-a]pyrimidine-3-carboxamido)propylcarbamate (Example 222, 6 mg, 0.012 mmol) and HCl (4 N dioxane, 145 μL, 0.58 mmol) was stirred at ambient temperature for 2 hours and concentrated to yield the product as white solid. LCMS (apci pos) m/z=418.1 (M+H).

Example 224

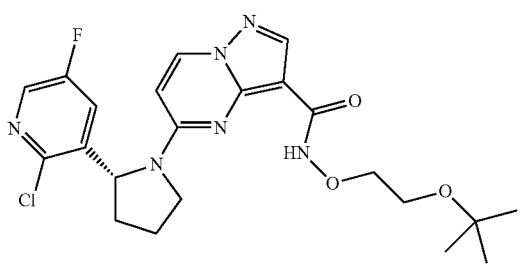 [SMILES: CC(C)(C)OCCONC(=O)c1cnn2ccc(N3CCC[C@@H]3c3cc(F)cnc3Cl)nc12]

(R)—N-(2-tert-butoxyethoxy)-5-(2-(2-chloro-5-fluoropyridin-3-yl)pyrrolidin-1-yl)pyrazolo[1,5-a]pyrimidine-3-carboxamide Prepared according to the method described in Example 222, Step E, replacing tert-butyl 3-aminopropylcarbamate with O-(2-tert-butoxyethyl)hydroxylamine hydrochloride to yield the title product as white solid (58 mg, 87%). LCMS (apci) m/z=476.9 (M+H).

Example 225

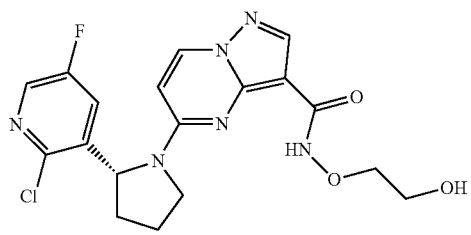 [SMILES: O=C(NOCCO)c1cnn2ccc(N3CCC[C@@H]3c3cc(F)cnc3Cl)nc12]

(R)-5-(2-(2-chloro-5-fluoropyridin-3-yl)pyrrolidin-1-yl)-N-(2-hydroxyethoxy)pyrazolo[1,5-a]pyrimidine-3-carboxamide (R)—N-(2-tert-butoxyethoxy)-5-(2-(2-chloro-5-fluoropyridin-3-yl)pyrrolidin-1-yl)pyrazolo[1,5-a]pyrimidine-3-carboxamide (Example 224, 57 mg, 0.120 mmol) was treated with HCl (4 N dioxane, 1.49 mL, 5.98 mmol), followed by two drops of MeOH to make a clear colorless solution. After stirring 30 minutes at ambient temperature, the reaction was concentrated and dried to yield the title product as white solid, assuming quantitative yield. LCMS (apci) m/z=421.0 (M+H)

Example 226

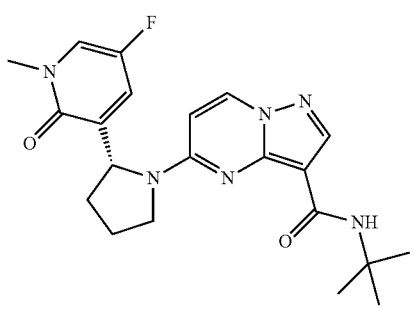 [SMILES: Cn1cc(F)cc([C@H]2CCCN2c2ccn3ncc(C(=O)NC(C)(C)C)c3n2)c1=O]

(R)—N-tert-butyl-5-(2-(5-fluoro-1-methyl-2-oxo-1,2-dihydropyridin-3-yl)pyrrolidin-1-yl)pyrazolo[1,5-a]pyrimidine-3-carboxamide Prepared by the method described in Example 140, using (R)-5-(2-(5-fluoro-1-methyl-2-oxo-1,2-dihydropyridin-3-yl)pyrrolidin-1-yl)pyrazolo[1,5-a]pyrimidine-3-carboxylic acid (Preparation R) and 2-methylpropan-2-amine. The residue was purified by silica column chromatography, eluting with 3% MeOH/DCM to yield the title compound (26 mg, 75% yield). MS (apci) m/z=413.1 (M+H).

The compounds listed in the following Table were also prepared according to the method described in Example 140, by reacting (R)-5-(2-(5-fluoro-1-methyl-2-oxo-1,2-dihydropyridin-3-yl)pyrrolidin-1-yl)pyrazolo[1,5-a]pyrimidine-3-carboxylic acid (Preparation R) with the appropriate amine starting material in the presence of an amide coupling reagent (e.g. EDCI/HOBt), an organic base (for example, TEA) in a solvent (for example, DCM).

TABLE E

| Ex. # | Structure | Chemical Name | Data |
|---|---|---|---|
| 227 | 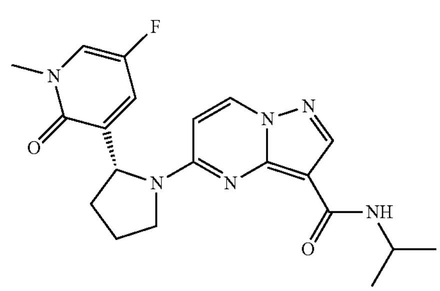 [SMILES: CC(C)NC(=O)c1cnn2ccc(N3CCC[C@@H]3c3cc(F)cn(C)c3=O)nc12] | (R)-5-(2-(5-fluoro-1-methyl-2-oxo-1,2-dihydropyridin-3-yl)pyrrolidin-1-yl)-N-isopropylpyrazolo[1,5-a]pyrimidine-3-carboxamide | MS (apci) m/z = 399.1 (M + H) |

TABLE E-continued

| Ex. # | Structure | Chemical Name | Data |
|---|---|---|---|
| 228 | 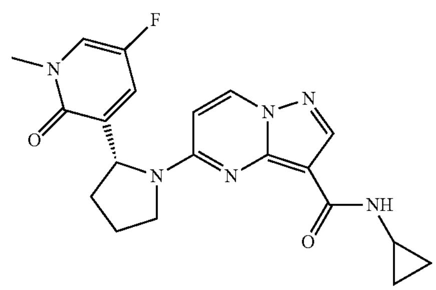 [SMILES: Cn1cc(F)cc([C@H]2CCCN2c2ccn3ncc(C(=O)NC4CC4)c3n2)c1=O] | (R)-N-cyclopropyl-5-(2-(5-fluoro-1-methyl-2-oxo-1,2-dihydropyridin-3-yl)pyrrolidin-1-yl)pyrazolo[1,5-a]pyrimidine-3-carboxamide | MS (apci) m/z = 397.1 (M + H) |
| 229 | 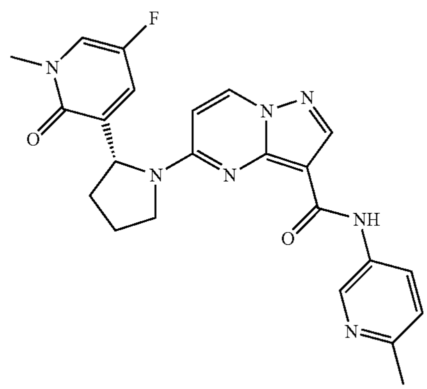 [SMILES: Cc1ccc(NC(=O)c2cnn3ccc(N4CCC[C@@H]4c4cc(F)cn(C)c4=O)nc23)cn1] | (R)-5-(2-(5-fluoro-1-methyl-2-oxo-1,2-dihydropyridin-3-yl)pyrrolidin-1-yl)-N-(6-methylpyridin-3-yl)pyrazolo[1,5-a]pyrimidine-3-carboxamide | MS (apci) m/z = 448.1 (M + H) |
| 230 | 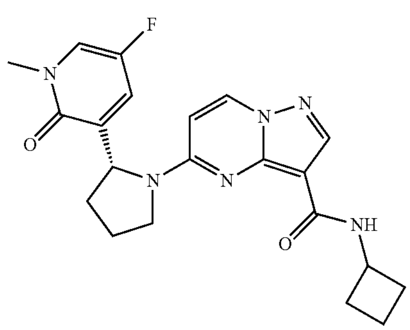 [SMILES: Cn1cc(F)cc([C@H]2CCCN2c2ccn3ncc(C(=O)NC4CCC4)c3n2)c1=O] | (R)-N-cyclobutyl-5-(2-(5-fluoro-1-methyl-2-oxo-1,2-dihydropyridin-3-yl)pyrrolidin-1-yl)pyrazolo[1,5-a]pyrimidine-3-carboxamide | MS (apci) m/z = 411.1 (M + H) |
| 231 | 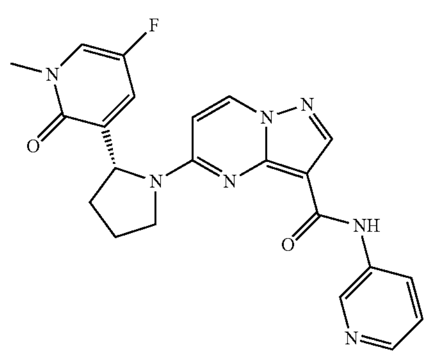 [SMILES: Cn1cc(F)cc([C@H]2CCCN2c2ccn3ncc(C(=O)Nc4cccnc4)c3n2)c1=O] | (R)-5-(2-(5-fluoro-1-methyl-2-oxo-1,2-dihydropyridin-3-yl)pyrrolidin-1-yl)-N-(pyridin-3-yl)pyrazolo[1,5-a]pyrimidine-3-carboxamide | MS (apci) m/z = 434.1 (M + H) |

TABLE E-continued

| Ex. # | Structure | Chemical Name | Data |
|---|---|---|---|
| 232 | 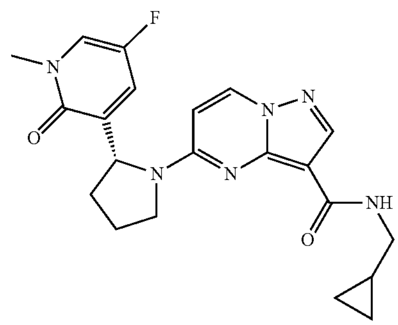 [SMILES: Cn1cc(F)cc([C@H]2CCCN2c2ccn3ncc(C(=O)NCC4CC4)c3n2)c1=O] | (R)-N-(cyclopropylmethyl)-5-(2-(5-fluoro-1-methyl-2-oxo-1,2-dihydropyridin-3-yl)pyrrolidin-1-yl)pyrazolo[1,5-a]pyrimidine-3-carboxamide | MS (apci) m/z = 411.1 (M + H) |
| 233 | 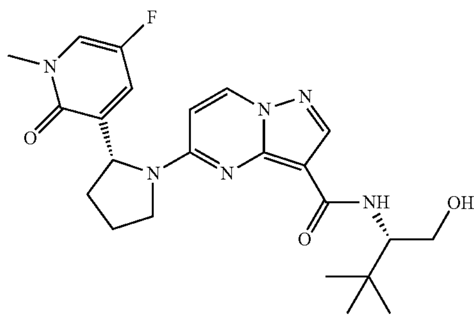 [SMILES: Cn1cc(F)cc([C@H]2CCCN2c2ccn3ncc(C(=O)N[C@H](CO)C(C)(C)C)c3n2)c1=O] | 5-((R)-2-(5-fluoro-1-methyl-2-oxo-1,2-dihydropyridin-3-yl)pyrrolidin-1-yl)-N-((S)-1-hydroxy-3,3-dimethylbutan-2-yl)pyrazolo[1,5-a]pyrimidine-3-carboxamide | MS (apci) m/z = 457.1 (M + H) |
| 234 | 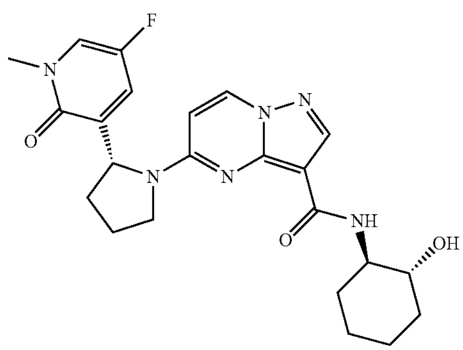 [SMILES: Cn1cc(F)cc([C@H]2CCCN2c2ccn3ncc(C(=O)N[C@@H]4CCCC[C@H]4O)c3n2)c1=O] | 5-((R)-2-(5-fluoro-1-methyl-2-oxo-1,2-dihydropyridin-3-yl)pyrrolidin-1-yl)-N-((1R,2R)-2-hydroxycyclohexyl)pyrazolo[1,5-a]pyrimidine-3-carboxamide | MS (apci) m/z = 455.1 (M + H) |
| 235 | 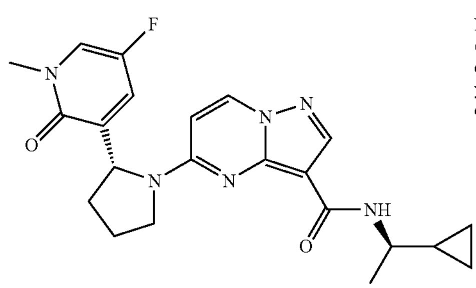 [SMILES: C[C@@H](NC(=O)c1cnn2ccc(N3CCC[C@@H]3c3cc(F)cn(C)c3=O)nc12)C1CC1] | N-((R)-1-cyclopropylethyl)-5-((R)-2-(5-fluoro-1-methyl-2-oxo-1,2-dihydropyridin-3-yl)pyrrolidin-1-yl)pyrazolo[1,5-a]pyrimidine-3-carboxamide | MS (apci) m/z = 425.1 (M + H) |
| 236 | 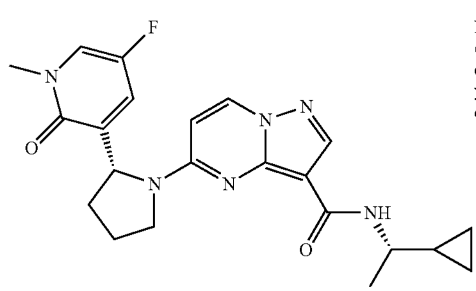 [SMILES: C[C@H](NC(=O)c1cnn2ccc(N3CCC[C@@H]3c3cc(F)cn(C)c3=O)nc12)C1CC1] | N-((S)-1-cyclopropylethyl)-5-((R)-2-(5-fluoro-1-methyl-2-oxo-1,2-dihydropyridin-3-yl)pyrrolidin-1-yl)pyrazolo[1,5-a]pyrimidine-3-carboxamide | MS (apci) m/z = 425.1 (M + H) |

TABLE E-continued

| Ex. # | Structure | Chemical Name | Data |
|---|---|---|---|
| 237 | 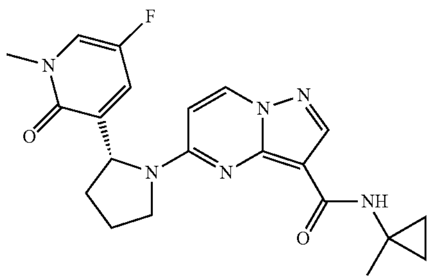 [SMILES: Cn1cc(F)cc([C@H]2CCCN2c2ccn3ncc(C(=O)NC4(C)CC4)c3n2)c1=O] | (R)-5-(2-(5-fluoro-1-methyl-2-oxo-1,2-dihydropyridin-3-yl)pyrrolidin-1-yl)-N-(1-methylcyclopropyl)pyrazolo[1,5-a]pyrimidine-3-carboxamide | MS (apci) m/z = 411.1 (M + H) |
| 238 | 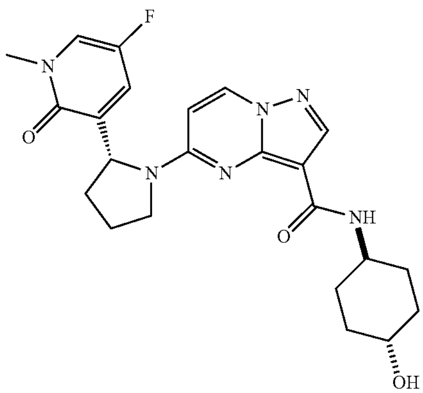 | 5-((R)-2-(5-fluoro-1-methyl-2-oxo-1,2-dihydropyridin-3-yl)pyrrolidin-1-yl)-N-((trans)-4-hydroxycyclohexyl)pyrazolo[1,5-a]pyrimidine-3-carboxamide | MS (apci) m/z = 455.1 (M + H) |
| 239 | 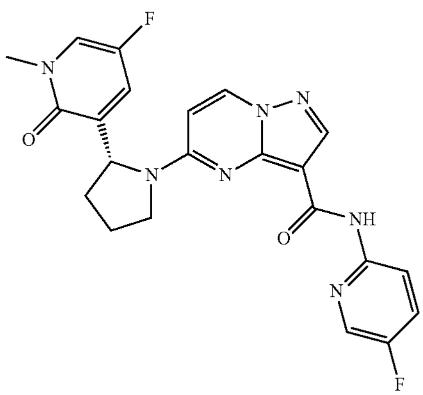 [SMILES: Cn1cc(F)cc([C@H]2CCCN2c2ccn3ncc(C(=O)Nc4ccc(F)cn4)c3n2)c1=O] | (R)-5-(2-(5-fluoro-1-methyl-2-oxo-1,2-dihydropyridin-3-yl)pyrrolidin-1-yl)-N-(5-fluoropyridin-2-yl)pyrazolo[1,5-a]pyrimidine-3-carboxamide | MS (apci) m/z = 452.1 (M + H) |

Example 240

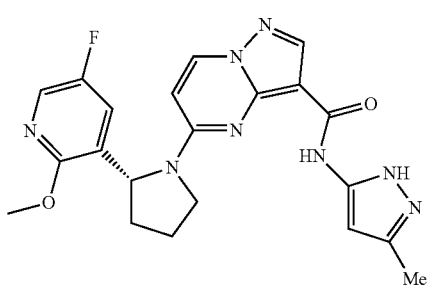 [SMILES: COc1ncc(F)cc1[C@H]1CCCN1c1ccn2ncc(C(=O)Nc3cc(C)n[nH]3)c2n1]

(R)-5-(2-(5-fluoro-2-methoxypyridin-3-yl)pyrrolidin-1-yl)-N-(3-methyl-1H-pyrazol-5-yl)pyrazolo[1,5-a]pyrimidine-3-carboxamide To a suspension of (R)-5-(2-(5-fluoro-2-methoxypyridin-3-yl)pyrrolidin-1-yl)pyrazolo[1,5-a]pyrimidine-3-carboxylic acid (Preparation K, 101 mg, 0.283 mmol) in THF (5 mL) was added triethylamine (34.3 mg, 0.339 mmol), followed by the addition of 2,4,6-trichlorobenzoyl chloride (75.8 mg, 0.311 mmol). The suspension was stirred for 2 hours and then 3-methyl-1H-pyrazol-5-amine (35.7 mg, 0.367 mmol) was introduced. The reaction was heated at 60° C. for 3 hours. After cooling to room temperature, the reaction was partitioned between EtOAc (20 mL) and saturated aqueous NaHCO₃ (10 mL). After phase-separation, the aqueous layer was extracted with EtOAc (2×10 mL). The combined organics were dried (Na₂SO₄), filtered and concentrated. The residue was purified via silica chromatography (EtOAc/MeOH 20:1) to yield the title product (23 mg, 19%). LCMS (apci) m/z=437.0 (M+H).

The compounds listed in Table F were also prepared according to the method described in Example 240, using (R)-5-(2-(5-fluoro-2-methoxypyridin-3-yl)pyrrolidin-1-yl)pyrazolo[1,5-a]pyrimidine-3-carboxylic acid, Preparation K) and an appropriate amine.

TABLE F

| Ex. # | Structure | Chemical Name | Data |
|---|---|---|---|
| 241 | 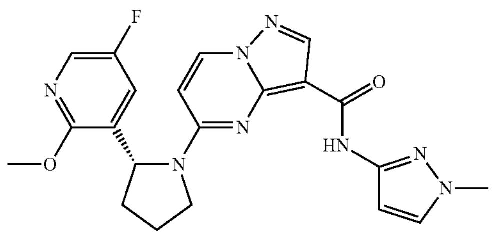 | (R)-5-(2-(5-fluoro-2-methoxypyridin-3-yl)pyrrolidin-1-yl)-N-(1-methyl-1H-pyrazol-3-yl)pyrazolo[1,5-a]pyrimidine-3-carboxamide | LCMS (apci) m/z = 437.0 (M + H) |
| 242 | 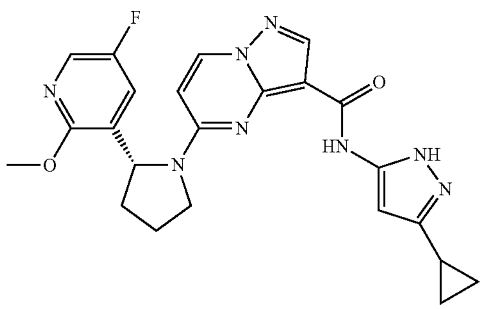 [SMILES: COc1ncc(F)cc1[C@H]1CCCN1c1ccn2ncc(C(=O)Nc3cc(C4CC4)n[nH]3)c2n1] | (R)-N-(3-cyclopropyl-1H-pyrazol-5-yl)-5-(2-(5-fluoro-2-methoxypyridin-3-yl)pyrrolidin-1-yl)pyrazolo[1,5-a]pyrimidine-3-carboxamide | LCMS (apci) m/z = 463.0 (M + H) |
| 243 | 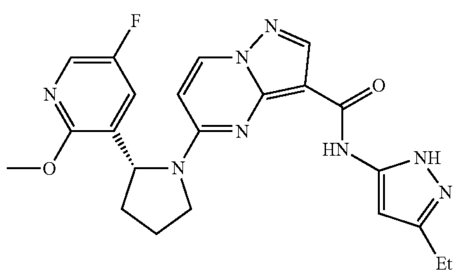 [SMILES: CCc1cc(NC(=O)c2cnn3ccc(N4CCC[C@@H]4c4cc(F)cnc4OC)nc23)[nH]n1] | (R)-N-(3-ethyl-1H-pyrazol-5-yl)-5-(2-(5-fluoro-2-methoxypyridin-3-yl)pyrrolidin-1-yl)pyrazolo[1,5-a]pyrimidine-3-carboxamide | LCMS (apci) m/z = 451.0 (M + H) |
| 244 | 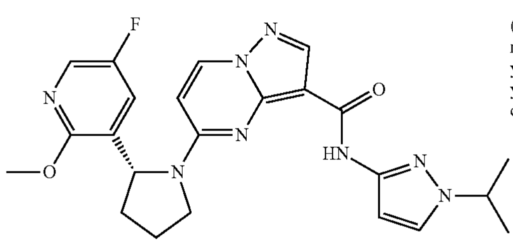 [SMILES: COc1ncc(F)cc1[C@H]1CCCN1c1ccn2ncc(C(=O)Nc3ccn(C(C)C)n3)c2n1] | (R)-5-(2-(5-fluoro-2-methoxypyridin-3-yl)pyrrolidin-1-yl)-N-(1-isopropyl-1H-pyrazol-3-yl)pyrazolo[1,5-a]pyrimidine-3-carboxamide | LCMS (apci) m/z = 465.0 (M + H) |

The compounds in Table G can also be prepared according to the method of Example 240.

TABLE G

| Ex. # | Structure | Name |
|---|---|---|
| 245 | 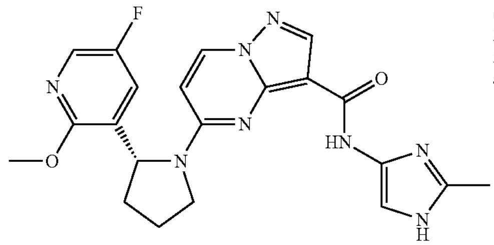 | (R)-5-(2-(5-fluoro-2-methoxypyridin-3-yl)pyrrolidin-1-yl)-N-(2-methyl-1H-imidazol-4-yl)pyrazolo[1,5-a]pyrimidine-3-carboxamide |
| 246 | 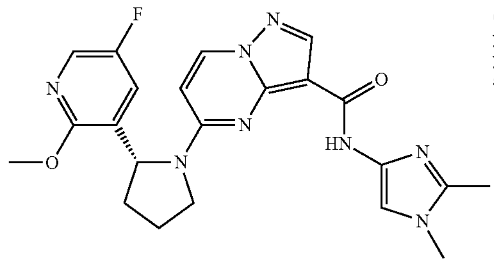 | (R)-N-(1,2-dimethyl-1H-imidazol-4-yl)-5-(2-(5-fluoro-2-methoxypyridin-3-yl)pyrrolidin-1-yl)pyrazolo[1,5-a]pyrimidine-3-carboxamide |

What is claimed is:

1. A compound selected from the group consisting of:
5-((R)-2-(2,5-difluorophenyl)pyrrolidin-1-yl)-N-((trans)-4-hydroxycyclohexyl)pyrazolo[1,5-a]pyrimidine-3-carboxamide;
(R)-5-(2-(2,5-difluorophenyl)pyrrolidin-1-yl)-N-(1-(hydroxymethyl)cyclopropyl)pyrazolo[1,5-a]pyrimidine-3-carboxamide;
(R)—N-(2-(1H-imidazol-4-yl)ethyl)-5-(2-(2,5-difluorophenyl)pyrrolidin-1-yl)pyrazolo[1,5-a]pyrimidine-3-carboxamide;
5-((R)-2-(2,5-difluorophenyl)pyrrolidin-1-yl)-N—((S)-2,3-dihydroxypropyl)pyrazolo[1,5-a]pyrimidine-3-carboxamide;
(R)-5-(2-(2,5-difluorophenyl)pyrrolidin-1-yl)pyrazolo[1,5-a]pyrimidine-3-carboxamide;
(R)—N-cyclopropyl-5-(2-(5-fluoropyridin-3-yl)pyrrolidin-1-yl)pyrazolo[1,5-a]pyrimidine-3-carboxamide;
(R)-5-(2-(2,5-difluorophenyl)pyrrolidin-1-yl)-N-(2-methyl-1-(methylsulfonamido)propan-2-yl)pyrazolo[1,5-a]pyrimidine-3-carboxamide;
(R)—N-cyclopropyl-5-(2-(3-fluoro-5-(2-methoxyethoxy)phenyl)pyrrolidin-1-yl)pyrazolo[1,5-a]pyrimidine-3-carboxamide;
5-((R)-2-(5-fluoropyridin-3-yl)pyrrolidin-1-yl)-N-((cis)-4-hydroxycyclohexyl)pyrazolo[1,5-a]pyrimidine-3-carboxamide;
N-(1-cyclopropylethyl)-5-((R)-2-(5-fluoropyridin-3-yl)pyrrolidin-1-yl)pyrazolo[1,5-a]pyrimidine-3-carboxamide;
5-((R)-2-(2-ethyl-5-fluoropyridin-3-yl)pyrrolidin-1-yl)-N-((trans)-4-hydroxycyclohexyl)pyrazolo[1,5-a]pyrimidine-3-carboxamide; and
(R)—N-(cyclopropylmethyl)-5-(2-(5-fluoro-1-methyl-2-oxo-1,2-dihydropyridin-3-yl)pyrrolidin-1-yl)pyrazolo[1,5-a]pyrimidine-3-carboxamide,
or a pharmaceutically acceptable salt thereof.

2. The compound of claim 1, wherein the compound is 5-((R)-2-(2,5-difluorophenyl)pyrrolidin-1-yl)-N-((trans)-4-hydroxycyclohexyl)pyrazolo[1,5-a]pyrimidine-3-carboxamide, or a pharmaceutically acceptable salt thereof.

3. The compound of claim 1, wherein the compound is (R)-5-(2-(2,5-difluorophenyl)pyrrolidin-1-yl)-N-(1-(hydroxymethyl)cyclopropyl)pyrazolo[1,5-a]pyrimidine-3-carboxamide, or a pharmaceutically acceptable salt thereof.

4. The compound of claim 1, wherein the compound is (R)—N-(2-(1H-imidazol-4-yl)ethyl)-5-(2-(2,5-difluorophenyl)pyrrolidin-1-yl)pyrazolo[1,5-a]pyrimidine-3-carboxamide, or a pharmaceutically acceptable salt thereof.

5. The compound of claim 1, wherein the compound is 5-((R)-2-(2,5-difluorophenyl)pyrrolidin-1-yl)-N—((S)-2,3-dihydroxypropyl)pyrazolo[1,5-a]pyrimidine-3-carboxamide, or a pharmaceutically acceptable salt thereof.

6. The compound of claim 1, wherein the compound is (R)-5-(2-(2,5-difluorophenyl)pyrrolidin-1-yl)pyrazolo[1,5-a]pyrimidine-3-carb oxamide, or a pharmaceutically acceptable salt thereof.

7. The compound of claim 1, wherein the compound is (R)—N-cyclopropyl-5-(2-(5-fluoropyridin-3-yl)pyrrolidin-1-yl)pyrazolo[1,5-a]pyrimidine-3-carboxamide, or a pharmaceutically acceptable salt thereof.

8. The compound of claim 1, wherein the compound is (R)-5-(2-(2,5-difluorophenyl)pyrrolidin-1-yl)-N-(2-methyl-1-(methylsulfonamido)propan-2-yl)pyrazolo[1,5-a]pyrimidine-3-carboxamide, or a pharmaceutically acceptable salt thereof.

9. The compound of claim 1, wherein the compound is (R)—N-cyclopropyl-5-(2-(3-fluoro-5-(2-methoxyethoxy)phenyl)pyrrolidin-1-yl)pyrazolo[1,5-a]pyrimidine-3-carboxamide, or a pharmaceutically acceptable salt thereof.

10. The compound of claim 1, wherein the compound is 5-((R)-2-(5-fluoropyridin-3-yl)pyrrolidin-1-yl)-N-((cis)-4-hydroxycyclohexyl)pyrazolo[1,5-a]pyrimidine-3-carboxamide, or a pharmaceutically acceptable salt thereof.

11. The compound of claim 1, wherein the compound is N-(1-cyclopropylethyl)-5-((R)-2-(5-fluoropyridin-3-yl)pyrrolidin-1-yl)pyrazolo[1,5-a]pyrimidine-3-carboxamide, or a pharmaceutically acceptable salt thereof.

12. The compound of claim 1, wherein the compound is 5-((R)-2-(2-ethyl-5-fluoropyridin-3-yl)pyrrolidin-1-yl)-N—((trans)-4-hydroxycyclohexyl)pyrazolo[1,5-a]pyrimidine-3-carboxamide, or a pharmaceutically acceptable salt thereof.

13. The compound of claim 1, wherein the compound is (R)—N-(cyclopropylmethyl)-5-(2-(5-fluoro-1-methyl-2-oxo-1,2-dihydropyridin-3-yl)pyrrolidin-1-yl)pyrazolo[1,5-a]pyrimidine-3-carboxamide, or a pharmaceutically acceptable salt thereof.

14. The compound of claim 1, wherein the compound is selected from the group consisting of:
    5-((R)-2-(2,5-difluorophenyl)pyrrolidin-1-yl)-N-((trans)-4-hydroxycyclohexyl)pyrazolo[1,5-a]pyrimidine-3-carboxamide;
    (R)-5-(2-(2,5-difluorophenyl)pyrrolidin-1-yl)-N-(1-(hydroxymethyl)cyclopropyl)pyrazolo[1,5-a]pyrimidine-3-carboxamide;
    (R)—N-(2-(1H-imidazol-4-yl)ethyl)-5-(2-(2,5-difluorophenyl)pyrrolidin-1-yl)pyrazolo[1,5-a]pyrimidine-3-carboxamide;
    5-((R)-2-(2,5-difluorophenyl)pyrrolidin-1-yl)-N—((S)-2,3-dihydroxypropyl)pyrazolo[1,5-a]pyrimidine-3-carboxamide;
    (R)-5-(2-(2,5-difluorophenyl)pyrrolidin-1-yl)pyrazolo[1,5-a]pyrimidine-3-carboxamide;
    (R)—N-cyclopropyl-5-(2-(5-fluoropyridin-3-yl)pyrrolidin-1-yl)pyrazolo[1,5-a]pyrimidine-3-carboxamide;
    (R)-5-(2-(2,5-difluorophenyl)pyrrolidin-1-yl)-N-(2-methyl-1-(methylsulfonamido)propan-2-yl)pyrazolo[1,5-a]pyrimidine-3-carboxamide;
    (R)—N-cycloppropyl-5-(2-(3-fluoro-5-(2-methoxyethoxy)phenyl)pyrrolidin-1-yl)pyrazolo[1,5-a]pyrimidine-3-carboxamide;
    5-((R)-2-(5-fluoropyridin-3-yl)pyrrolidin-1-yl)-N-((cis)-4-hydroxycyclohexyl)pyrazolo[1,5-a]pyrimidine-3-carboxamide;
    N-(1-cyclopropylethyl)-5-((R)-2-(5-fluoropyridin-3-yl)pyrrolidin-1-yl)pyrazolo[1,5-a]pyrimidine-3-carboxamide;
    5-((R)-2-(2-ethyl-5-fluoropyridin-3-yl)pyrrolidin-1-yl)-N-((trans)-4-hydroxycyclohexyl)pyrazolo[1,5-a]pyrimidine-3-carboxamide; and
    (R)—N-(cyclopropylmethyl)-5-(2-(5-fluoro-1-methyl-2-oxo-1,2-dihydropyridin-3-yl)pyrrolidin-1-yl)pyrazolo[1,5-a]pyrimidine-3-carboxamide.

15. The compound of claim 1, wherein the compound is in the form of a pharmaceutically acceptable salt.

16. A pharmaceutical composition comprising a compound selected from the group consisting of:
    5-((R)-2-(2,5-difluorophenyl)pyrrolidin-1-yl)-N-((trans)-4-hydroxycyclohexyl)pyrazolo[1,5-a]pyrimidine-3-carboxamide;
    (R)-5-(2-(2,5-difluorophenyl)pyrrolidin-1-yl)-N-(1-(hydroxymethyl)cyclopropyl)pyrazolo[1,5-a]pyrimidine-3-carboxamide;
    (R)—N-(2-(1H-imidazol-4-yl)ethyl)-5-(2-(2,5-difluorophenyl)pyrrolidin-1-yl)pyrazolo[1,5-a]pyrimidine-3-carboxamide;
    5-((R)-2-(2,5-difluorophenyl)pyrrolidin-1-yl)-N—((S)-2,3-dihydroxypropyl)pyrazolo[1,5-a]pyrimidine-3-carboxamide;
    (R)-5-(2-(2,5-difluorophenyl)pyrrolidin-1-yl)pyrazolo[1,5-a]pyrimidine-3-carboxamide;
    (R)—N-cyclopropyl-5-(2-(5-fluoropyridin-3-yl)pyrrolidin-1-yl)pyrazolo[1,5-a]pyrimidine-3-carboxamide;
    (R)-5-(2-(2,5-difluorophenyl)pyrrolidin-1-yl)-N-(2-methyl-1-(methylsulfonamido)propan-2-yl)pyrazolo[1,5-a]pyrimidine-3-carboxamide;
    (R)—N-cyclopropyl-5-(2-(3-fluoro-5-(2-methoxyethoxy)phenyl)pyrrolidin-1-yl)pyrazolo[1,5-a]pyrimidine-3-carboxamide;
    5-((R)-2-(5-fluoropyridin-3-yl)pyrrolidin-1-yl)-N-((cis)-4-hydroxycyclohexyl)pyrazolo[1,5-a]pyrimidine-3-carboxamide;
    N-(1-cyclopropylethyl)-5-((R)-2-(5-fluoropyridin-3-yl)pyrrolidin-1-yl)pyrazolo[1,5-a]pyrimidine-3-carboxamide;
    5-((R)-2-(2-ethyl-5-fluoropyridin-3-yl)pyrrolidin-1-yl)-N-((trans)-4-hydroxycyclohexyl)pyrazolo[1,5-a]pyrimidine-3-carboxamide; and
    (R)—N-(cyclopropylmethyl)-5-(2-(5-fluoro-1-methyl-2-oxo-1,2-dihydropyridin-3-yl)pyrrolidin-1-yl)pyrazolo[1,5-a]pyrimidine-3-carboxamide,
    or a pharmaceutically acceptable salt thereof; and a pharmaceutically acceptable diluent or carrier.

17. The pharmaceutical composition of claim 16, wherein the compound is
    5-((R)-2-(2,5-difluorophenyl)pyrrolidin-1-yl)-N-((trans)-4-hydroxycyclohexyl)pyrazolo[1,5-a]pyrimidine-3-carboxamide, or a pharmaceutically acceptable salt thereof.

18. The pharmaceutical composition of claim 16, wherein the compound is
    (R)-5-(2-(2,5-difluorophenyl)pyrrolidin-1-yl)-N-(1-(hydroxymethyl)cyclopropyl)pyrazolo[1,5-a]pyrimidine-3-carboxamide, or a pharmaceutically acceptable salt thereof.

19. The pharmaceutical composition of claim 16, wherein the compound is
    (R)—N-(2-(1H-imidazol-4-yl)ethyl)-5-(2-(2,5-difluorophenyl)pyrrolidin-1-yl)pyrazolo[1,5-a]pyrimidine-3-carboxamide, or a pharmaceutically acceptable salt thereof.

20. The pharmaceutical composition of claim 16, wherein the compound is
    5-((R)-2-(2,5-difluorophenyl)pyrrolidin-1-yl)-N—((S)-2,3-dihydroxypropyl)pyrazolo[1,5-a]pyrimidine-3-carboxamide, or a pharmaceutically acceptable salt thereof.

21. The pharmaceutical composition of claim 16, wherein the compound is
    (R)-5-(2-(2,5-difluorophenyl)pyrrolidin-1-yl)pyrazolo[1,5-a]pyrimidine-3-carb oxamide, or a pharmaceutically acceptable salt thereof.

22. The pharmaceutical composition of claim 16, wherein the compound is
    (R)—N-cyclopropyl-5-(2-(5-fluoropyridin-3-yl)pyrrolidin-1-yl)pyrazolo[1,5-a]pyrimidine-3-carboxamide, or a pharmaceutically acceptable salt thereof.

23. The pharmaceutical composition of claim 16, wherein the compound is
    (R)-5-(2-(2,5-difluorophenyl)pyrrolidin-1-yl)-N-(2-methyl-1-(methylsulfonamido)propan-2-yl)pyrazolo[1,5-a]pyrimidine-3-carboxamide, or a pharmaceutically acceptable salt thereof.

24. The pharmaceutical composition of claim 16, wherein the compound is (R)—N-cyclopropyl-5-(2-(3-fluoro-5-(2-methoxyethoxy)phenyl)pyrrolidin-1-yl)pyrazolo[1,5-a]pyrimidine-3-carboxamide, or a pharmaceutically acceptable salt thereof.

25. The pharmaceutical composition of claim 16, wherein the compound is 5-((R)-2-(5-fluoropyridin-3-yl)pyrrolidin-1-yl)-N-((cis)-4-hydroxycyclohexyl)pyrazolo[1,5-a]pyrimidine-3-carboxamide, or a pharmaceutically acceptable salt thereof.

26. The pharmaceutical composition of claim 16, wherein the compound is

N-(1-cyclopropylethyl)-5-((R)-2-(5-fluoropyridin-3-yl)pyrrolidin-1-yl)pyrazolo[1,5-a]pyrimidine-3-carboxamide, or a pharmaceutically acceptable salt thereof.

27. The pharmaceutical composition of claim 16, wherein the compound is 5-((R)-2-(2-ethyl-5-fluoropyridin-3-yl)pyrrolidin-1-yl)-N-((trans)-4-hydroxycyclohexyl)pyrazolo[1,5-a]pyrimidine-3-carboxamide, or a pharmaceutically acceptable salt thereof.

28. The pharmaceutical composition of claim 16, wherein the compound is (R)—N-(cyclopropylmethyl)-5-(2-(5-fluoro-1-methyl-2-oxo-1,2-dihydropyridin-3-yl)pyrrolidin-1-yl)pyrazolo[1,5-a]pyrimidine-3-carboxamide, or a pharmaceutically acceptable salt thereof.

29. The pharmaceutical composition of claim 16, wherein the compound is selected from the group consisting of:

5-((R)-2-(2,5-difluorophenyl)pyrrolidin-1-yl)-N-((trans)-4-hydroxycyclohexyl)pyrazolo[1,5-a]pyrimidine-3-carboxamide;

(R)-5-(2-(2,5-difluorophenyl)pyrrolidin-1-yl)-N-(1-(hydroxymethyl)cyclopropyl)pyrazolo[1,5-a]pyrimidine-3-carboxamide;

(R)—N-(2-(1H-imidazol-4-yl)ethyl)-5-(2-(2,5-difluorophenyl)pyrrolidin-1-yl)pyrazolo[1,5-a]pyrimidine-3-carboxamide;

5-((R)-2-(2,5-difluorophenyl)pyrrolidin-1-yl)-N—((S)-2,3-dihydroxypropyl)pyrazolo[1,5-a]pyrimidine-3-carboxamide;

(R)-5-(2-(2,5-difluorophenyl)pyrrolidin-1-yl)pyrazolo[1,5-a]pyrimidine-3-carboxamide;

(R)—N-cyclopropyl-5-(2-(5-fluoropyridin-3-yl)pyrrolidin-1-yl)pyrazolo[1,5-a]pyrimidine-3-carboxamide;

(R)-5-(2-(2,5-difluorophenyl)pyrrolidin-1-yl)-N-(2-methyl-1-(methylsulfonamido)propan-2-yl)pyrazolo[1,5-a]pyrimidine-3-carboxamide;

(R)—N-cyclopropyl-5-(2-(3-fluoro-5-(2-methoxyethoxy)phenyl)pyrrolidin-1-yl)pyrazolo[1, 5-a]pyrimidine-3-carboxamide;

5-((R)-2-(5-fluoropyridin-3-yl)pyrrolidin-1-yl)-N-((cis)-4-hydroxycyclohexyl)pyrazolo[1,5-a]pyrimidine-3-carboxamide;

N-(1-cyclopropylethyl)-5-((R)-2-(5-fluoropyridin-3-yl)pyrrolidin-1-yl)pyrazolo[1,5-a]pyrimidine-3-carboxamide;

5-((R)-2-(2-ethyl-5-fluoropyridin-3-yl)pyrrolidin-1-yl)-N-((trans)-4-hydroxycyclohexyl)pyrazolo[1,5-a]pyrimidine-3-carboxamide; and (R)—N-(cyclopropylmethyl)-5-(2-(5-fluoro-1-methyl-2-oxo-1,2-dihydropyridin-3-yl)pyrrolidin-1-yl)pyrazolo[1,5-a]pyrimidine-3-carboxamide.

30. The composition of claim 1, wherein the compound is in the form of a pharmaceutically acceptable salt.

* * * * *